US010835234B2

(12) United States Patent
Harari et al.

(10) Patent No.: US 10,835,234 B2
(45) Date of Patent: *Nov. 17, 2020

(54) ARTHROSCOPIC SURGICAL DEVICE

(71) Applicant: MININVASIVE LTD., Magal (IL)

(72) Inventors: Boaz Harari, Haifa (IL); Ronen Raz, Magal (IL); Dror Rosner, Holon (IL); Paul Mraz, Duxbury, MA (US)

(73) Assignee: MININVASIVE LTD., Magal (IL)

( * ) Notice: Subject to any disclaimer, the term of this patent is extended or adjusted under 35 U.S.C. 154(b) by 162 days.

This patent is subject to a terminal disclaimer.

(21) Appl. No.: 16/066,171

(22) PCT Filed: Dec. 25, 2016

(86) PCT No.: PCT/IL2016/051379
§ 371 (c)(1),
(2) Date: Jun. 26, 2018

(87) PCT Pub. No.: WO2017/115355
PCT Pub. Date: Jul. 6, 2017

(65) Prior Publication Data
US 2019/0117214 A1 Apr. 25, 2019

Related U.S. Application Data

(60) Provisional application No. 62/273,632, filed on Dec. 31, 2015.

(51) Int. Cl.
*A61B 17/04* (2006.01)
*A61B 17/06* (2006.01)

(52) U.S. Cl.
CPC ...... *A61B 17/0469* (2013.01); *A61B 17/0482* (2013.01); *A61B 2017/06042* (2013.01)

(58) Field of Classification Search
CPC ............ A61B 17/0469; A61B 17/0482; A61B 17/0483; A61B 17/16; A61B 17/1642;
(Continued)

(56) References Cited

U.S. PATENT DOCUMENTS 2,579,192 A 12/1951 Kohl
5,250,055 A 10/1993 Moore et al.
(Continued)

FOREIGN PATENT DOCUMENTS

CN 101193600 9/2010
CN 102292033 12/2011
(Continued)

OTHER PUBLICATIONS

U.S. Appl. No. 61/636,751, filed Apr. 23, 2012.
(Continued)

*Primary Examiner* — Eric S Gibson
(74) *Attorney, Agent, or Firm* — Sughrue Mion, PLLC

(57) ABSTRACT

An arthroscopic bone channel forming and suturing system useful following formation of a first and a second generally straight channel in a bone, the second channel not intersecting the first channel, the system including a curved bone puncture needle configured to be insertable into the first channel, a curved needle driving assembly configured to manipulate the curved needle to form a curved junction between the first channel and the second channel, a suture snare wire assembly configured to insert a suture snare wire to a suture snare wire pick-up location via the second channel in the bone and a coordinated multi-function driving assembly operative to operate the curved needle driving assembly and the suture snare wire assembly in coordinated operation to cause the suture snare wire to be pulled from the suture pick up location and through the first channel via the junction.

18 Claims, 158 Drawing Sheets

(58) Field of Classification Search
CPC ........... A61B 2017/06028; A61B 2017/06042; A61B 2017/0608

See application file for complete search history.

(56) References Cited

U.S. PATENT DOCUMENTS

| | | | |
|---|---|---|---|
| 5,330,479 A | | 7/1994 | Whitmore |
| 5,387,221 A | * | 2/1995 | Bisgaard ............ A61B 17/0469 112/169 |
| 5,499,991 A | | 3/1996 | Garman et al. |
| 5,656,605 A | | 8/1997 | Hansson et al. |
| 5,665,096 A | | 9/1997 | Yoon |
| 5,681,333 A | | 10/1997 | Burkhart et al. |
| 5,961,530 A | | 10/1999 | Moore |
| 6,328,744 B1 | | 12/2001 | Harari |
| 6,443,963 B1 | | 9/2002 | Baldwin |
| 6,523,417 B1 | | 2/2003 | Donahue |
| 7,029,479 B2 | | 4/2006 | Tallarida |
| 7,097,648 B1 | | 8/2006 | Globerman et al. |
| 7,166,116 B2 | | 1/2007 | Lizardi et al. |
| 7,494,496 B2 | | 2/2009 | Swain et al. |
| 7,662,171 B2 | | 2/2010 | West et al. |
| 8,088,130 B2 | | 1/2012 | Kaiser et al. |
| 8,282,643 B2 | | 10/2012 | Dross |
| 8,282,657 B2 | | 10/2012 | McClurg et al. |
| 9,763,659 B2 | * | 9/2017 | Sholev ............... A61B 17/0483 |
| 2002/0040227 A1 | | 4/2002 | Harari |
| 2003/0078599 A1 | | 4/2003 | O'Quinn |
| 2006/0195121 A1 | | 8/2006 | Chu |
| 2006/0271060 A1 | | 11/2006 | Gordon |
| 2007/0005067 A1 | | 1/2007 | Dross |
| 2007/0179509 A1 | | 8/2007 | Nagata et al. |
| 2008/0109015 A1 | | 5/2008 | Chu et al. |
| 2008/0228224 A1 | | 9/2008 | Sauer |
| 2009/0012538 A1 | | 1/2009 | Saliman et al. |
| 2009/0062819 A1 | | 3/2009 | Burkhart |
| 2009/0069823 A1 | | 3/2009 | Foerster |
| 2009/0105729 A1 | | 4/2009 | Zentgraf |
| 2009/0105743 A1 | | 4/2009 | Chu |
| 2009/0131956 A1 | * | 5/2009 | Dewey ............... A61B 17/0401 606/144 |
| 2009/0138029 A1 | * | 5/2009 | Saliman ............ A61B 17/0469 606/144 |
| 2009/0157076 A1 | | 6/2009 | Athas et al. |
| 2009/0206128 A1 | | 8/2009 | Hueil et al. |
| 2009/0270862 A1 | | 10/2009 | Arcenio |
| 2009/0312782 A1 | | 12/2009 | Park |
| 2010/0076436 A1 | | 3/2010 | Hajianpour |
| 2010/0106194 A1 | * | 4/2010 | Bonutti .................. A61B 17/17 606/279 |
| 2010/0152751 A1 | | 6/2010 | Meade et al. |
| 2010/0191248 A1 | | 7/2010 | Mehta et al. |
| 2010/0198258 A1 | | 8/2010 | Heaven et al. |
| 2010/0318139 A1 | | 12/2010 | Beauchamp |
| 2011/0022063 A1 | * | 1/2011 | McClurg ............ A61B 17/0482 606/145 |
| 2011/0040301 A1 | | 2/2011 | Blain et al. |
| 2011/0106124 A1 | | 5/2011 | Beauchamp |
| 2011/0301577 A1 | * | 12/2011 | Simmen ................ A61B 17/16 606/1 |
| 2012/0239085 A1 | | 9/2012 | Schlotterback et al. |
| 2012/0323248 A1 | | 12/2012 | Dross |
| 2013/0123810 A1 | | 5/2013 | Brown et al. |
| 2013/0144337 A1 | | 6/2013 | Stone et al. |
| 2013/0144338 A1 | | 6/2013 | Stone et al. |
| 2013/0178854 A1 | * | 7/2013 | Sholev ............ A61B 17/06066 606/79 |
| 2013/0296931 A1 | | 11/2013 | Sengun |
| 2014/0214038 A1 | * | 7/2014 | Sholev ............... A61B 17/0483 606/79 |
| 2014/0219483 A1 | | 8/2014 | Hong |
| 2014/0249577 A1 | | 9/2014 | Pilgeram |
| 2014/0303625 A1 | * | 10/2014 | Sholev ............... A61B 17/8861 606/80 |
| 2015/0045795 A1 | * | 2/2015 | Sholev ............... A61B 17/8861 606/79 |
| 2015/0258332 A1 | | 9/2015 | Bentley et al. |
| 2015/0351743 A1 | | 12/2015 | Stiggelbout |
| 2015/0351759 A1 | | 12/2015 | Bennett et al. |
| 2016/0015380 A1 | * | 1/2016 | Sholev ............ A61B 17/06166 606/80 |
| 2017/0252031 A1 | | 9/2017 | Harari et al. |
| 2018/0014825 A1 | * | 1/2018 | Sholev ............... A61B 17/0482 |
| 2018/0036016 A1 | | 2/2018 | Sholev et al. |
| 2018/0098775 A1 | | 4/2018 | Sholev et al. |
| 2018/0242983 A1 | * | 8/2018 | Rosner ............... A61B 17/0469 |
| 2018/0256147 A1 | | 9/2018 | Rosner et al. |
| 2019/0117214 A1 | * | 4/2019 | Harari ............... A61B 17/0469 |

FOREIGN PATENT DOCUMENTS

| | | |
|---|---|---|
| EP | 1898812 | 3/2008 |
| EP | 1970016 | 9/2008 |
| EP | 2698128 | 2/2014 |
| GB | 2154484 | 9/1985 |
| JP | 1996-033635 | 2/1996 |
| JP | 1996-509918 | 10/1996 |
| JP | H10-52431 | 2/1998 |
| JP | 2003-501132 | 1/2003 |
| JP | 2008-546489 | 12/2008 |
| JP | 2011-512937 | 4/2011 |
| JP | 5474996 | 4/2014 |
| WO | 96/27331 | 9/1996 |
| WO | 97/47246 | 12/1997 |
| WO | 2000/74578 | 12/2000 |
| WO | 2002/007609 | 1/2002 |
| WO | 2008-510526 | 4/2008 |
| WO | 2009/107121 | 9/2009 |
| WO | 10/056785 | 5/2010 |
| WO | 10/056786 | 5/2010 |
| WO | 10/056787 | 5/2010 |
| WO | 2011/160166 | 12/2011 |
| WO | 2012/007941 | 1/2012 |
| WO | 2013/027209 | 2/2013 |
| WO | 2013/027210 | 2/2013 |
| WO | 2013/071234 | 5/2013 |
| WO | 2013/102909 | 7/2013 |
| WO | 2014/147619 | 9/2014 |
| WO | 2016/038614 | 3/2016 |
| WO | 2017/051404 | 3/2017 |
| WO | 2017/115355 | 7/2017 |

OTHER PUBLICATIONS

U.S. Appl. No. 61/584,267, filed Jan. 8, 2012.
U.S. Appl. No. 61/526,717, filed Aug. 24, 2011.
U.S. Appl. No. 61/363,247, filed Jul. 11, 2010.
U.S. Appl. No. 61/714,813, filed Oct. 17, 2012.
An International Search Report and a Written Opinion both dated Jan. 23, 2013, which issued during the prosecution of Applicant's PCT/IL2012/000318.
An International Search Report and a Written Opinion both dated Dec. 5, 2011, which issued during the prosecution of Applicant's PCT/IL2011/000549.
An International Search Report and a Written Opinion both dated May 10, 2013 which issued during the prosecution of Applicant's PCT/IL2013/050030.
An International Search Report dated Jan. 8, 2013 which issued during the prosecution of Applicant's PCT/IL2012/000319.
An English translation of an Office Action dated Mar. 24, 2015, which issued during the prosecution of Japanese Patent Application No. 519213/2013.
An English translation of an Office Action dated Jul. 3, 2014 which issued during the prosecution of Chinese Patent Application 2011800437287.
An International Search Report and Written Opinion both dated Jul. 11, 2014, which issued during the prosecution of Applicant's PCT/IL 14/50299.
An International Preliminary Search Report dated Aug. 26, 2014, which issued during the prosecution of Applicant's PCT/IL2013/050030.

(56) References Cited

OTHER PUBLICATIONS

An International Preliminary Report dated Feb. 25, 2014 which issued during the prosecution of Applicant'S PCT/IL2012/000319.
Written Opinion dated Jan. 8, 2013 which issued during the prosecution of Applicant's PCT/IL2012/000319.
An International Preliminary Report dated Feb. 25, 2014 which issued during the prosecution of Applicant's PCT/IL2012/000318.
An Office Action dated Apr. 5, 2014 which issued during the prosecution of Australian Patent Application No. 2011277949.
An Office Action dated Jul. 11, 2016 which issued during the prosecution of Australian Patent Application No. 2012298197.
An International Search Report and a Written Opinion both dated Jun. 9, 2016, which issued during the prosecution of Applicant's PCT/IL2015/050978.
An Office Action dated Jun. 27, 2016 which issued during the prosecution of Australian Patent Application No. 2015202032.
An Office Action dated May 24, 2016 which issued during the prosecution of Chinese Patent Application No. 2013800124154.
European Search Report dated Jun. 19, 2015 which issued during the prosecution of Applicant's European App No. 12826407.
European Search Report dated Jan. 27, 2016 which issued during the prosecution of Applicant's European App No. 13733888.
An Invitation to pay additional fees dated Dec. 23, 2015, which issued during the prosecution of Applicant's PCT/IL2015/050923.
Notice of Allowance dated Jan. 7, 2016, which issued during the prosecution of Japanese Patent Application No. 519213/2013.
An Office Action dated Feb. 25, 2016, which issued during the prosecution of U.S. Appl. No. 13/809,562.
An Office Action dated Sep. 1, 2016, which issued during the prosecution of U.S. Appl. No. 14/240,227.
An Invitation to pay additional fees dated Mar. 30, 2016, which issued during the prosecution of Applicant's PCT/IL2015/050978.
An English translation of an Office Action dated Oct. 13, 2015, which issued during the prosecution of Chinese Patent Application 2012800518842.
An English translation of an Office Action dated May 16, 2016, which issued during the prosecution of Japanese Patent Application 5265972014.
U.S. Appl. No. 61/802,958, filed Mar. 18, 2013.
U.S. Appl. No. 61/887,561, filed Oct. 7, 2013.
An International Preliminary Report dated Sep. 22, 2016, which issued during the prosecution of Applicant's PCT/IL2014/050299.
U.S. Appl. No. 62/273,632, filed Dec. 31, 2015.
An Office Action dated Feb. 18, 2016 which issued during the prosecution of Australian Patent Application No. 2012298197.
An International Search Report and a Written Opinion both dated Mar. 10, 2016, which issued during the prosecution of Applicant's PCT/IL2015/050923.
An International Search Report and a Written Opinion both dated Aug. 23, 2017, which issued during the prosecutin of Applicant's PCT/IL2016/051379.
An English translation of an Office Action dated Sep. 6, 2016, which issued during the prosecution of Japanese Patent Application No. 526597/2014.
An Office Action dated Aug. 3, 2016, which issued during the prosecution of U.S. Appl. No. 14/240,082.
An English translation of an Office Action dated May 16, 2017, which issued during the prosecution of Japenese Patent Application No. 526597/2014.
An Office Action dated Nov. 29, 2016 which issued during the prosecution of Japanese Patent Application No. 550801/2014.
An Office Action dated Oct. 13, 2016, which issued during the prosecution of U.S. Appl. No. 14/240,082.
An Office Action dated Mar. 21, 2017, which issued during the prosecution of U.S. Appl. No. 14/240,227.
An Office Action dated Mar. 20, 2017, which issued during the prosecution of U.S. Appl. No. 14/240,082.
European Search Report dated May 11, 2017, which issued during the prosecution of Applicant's European App. No. 11806391.6.
European Search Report dated Jan. 17, 2017, which issued during the prosecution of Applicant's European App. No. 14769413.7.
Notice of Allowance dated May 26, 2017, which issued during the prosecution of U.S. Appl. No. 13/809,562.
An Office Action dated Apr. 6, 2017, which issued during the prosecution of U.S. Appl. No. 14/370,884.
An Office Action dated Jul. 13, 2017, which issued during the prosecution of U.S. Appl. No. 14/370,884.
An Office Action dated Dec. 2, 2016, which issued during the prosecution of U.S. Appl. No. 13/809,562.
An International Preliminary Report dated Mar. 26, 2013, which issued during the prosecution of Applicant's PCT/IL2011/000549.
An International Preliminary Report dated Mar. 14, 2017, which issued during the prosecution of Applicant's PCT/IL2015/050923.
Notice of Allowance dated Sep. 1, 2017, which issued during the prosecution of U.S. Appl. No. 14/240,082.
Notice of Allowance dated Aug. 11, 2017, which issued during the prosecution of U.S. Appl. No. 13/809,562.
Notice of Allowance dated May 26, 2017, which issued during the prosecution of U.S. Appl. No. 14/240,227.
An Office Action dated Jul. 5, 2017, which issued during the prosecution of Australian Patent Application No. 2013207071.
An Office Action dated Mar. 31, 2017, which issued during the prosecution of Canadian Patent Application No. 2804255.
An English translation of an Office Action dated Feb. 9, 2016, which issued during the prosecution of Israel Patent Application No. 224079.
An English translation of an Office Action dated May 31, 2017, which issued during the prosecution of Chinese Patent Application 201480016633.X.
Notice of Allowance together with the English translation dated Nov. 1, 2017, which issued during the prosecution of Korean Patent Application No. 10-2013-7003093.
An Office Action dated May 8, 2018, which issued during the prosecution of U.S. Appl. No. 15/665,838.
An International Search Report and a Written Opinion both dated May 24, 2018, which issued during the prosecution of Applicant's PCT/IL2018/050180.
An Advisory Action dated Apr. 4, 2018, which issued during the prosecution of U.S. Appl. No. 14/370,884.
An Advisory Action dated Mar. 1, 2018, which issued during the prosecution of U.S. Appl. No. 14/370,884.
An Advisory Action dated Aug. 29, 2018, which issued during the prosecution of U.S. Appl. No. 14/370,884.
An Office Action dated Nov. 14, 2017, which issued during the prosecution of U.S. Appl. No. 14/370,884.
An Office Action dated May 7, 2018, which issued during the prosecution of U.S. Appl. No. 14/370,884.
An Office Action dated Aug. 31, 2018, which issued during the prosecution of U.S. Appl. No. 15/509,066.
An Office Action dated Mar. 5, 2018, which issued during the prosecution of U.S. Appl. No. 14/766,490.
An Office Action dated Aug. 1, 2018, which issued during the prosecution of U.S. Appl. No. 15/451,733.
An International Preliminary Report dated Mar. 27, 2018, which issued during the prosecution of Applicant's PCT/IL2015/050978.
An English translation of an Office Action dated Feb. 24, 2018, which issued during the prosecution of Chinese Patent Application 201480016633.X.
An English translation of an Office Action dated Aug. 21, 2018, which issued during the prosecution of Japanese Patent Application No. 526597/2014.
An English translation of an Office Action dated Nov. 28, 2017, which issued during the prosecution of Japanese Patent Application No. 503779/2016.
Notice of Allowance dated Sep. 24, 2018, which issued during the prosecution of U.S. Appl. No. 14/766,490.
Notice of Allowance dated Jun. 29, 2018, which issued during the prosecution of U.S. Appl. No. 15/665,838.
An English translation of an Office Action dated Jul. 31, 2018, which issued during the prosecution of Japanese Patent Application No. 503779/2016.

(56) References Cited

OTHER PUBLICATIONS

An Office Action dated Jan. 31, 2018, which issued during the prosecution of U.S. Appl. No. 15/665,838.
An Office Action dated Apr. 16, 2018, which issued during the prosecution of U.S. Appl. No. 15/784,590.
An Office Action dated May 18, 2018, which issued during the prosecution of U.S. Appl. No. 15/684,367.
An English translation of a Pre-Appeal Report dated Jan. 24, 2018, which issued during the prosecution of Japanese Patent Application No. 526597/2014.
An Office Action dated Mar. 15, 2018, which issued during the prosecution of Australian Patent Application No. 2013207071.
An Office Action dated Jan. 3, 2018, which issued during the prosecution of Australian Patent Application No. 2014233765.
An Office Action dated Mar. 15, 2018, which issued during the prosecution of Australian Patent Application No. 2014233765.
An English translation of an Office Action dated Feb. 9, 2018, which issued during the prosecution of Korean Patent Application No. 10-2014-7007475.
An Office Action dated Jan. 22, 2018, which issued during the prosecution of Canadian Patent Application No. 2846004.
An English translation of an Office Action dated Nov. 16, 2018 which issued during the prosecution of Chinese Patent Application No. 201710176362X.
An Office Action dated Mar. 6, 2019, which issued during the prosecution of U.S. Appl. No. 15/684,367.

\* cited by examiner

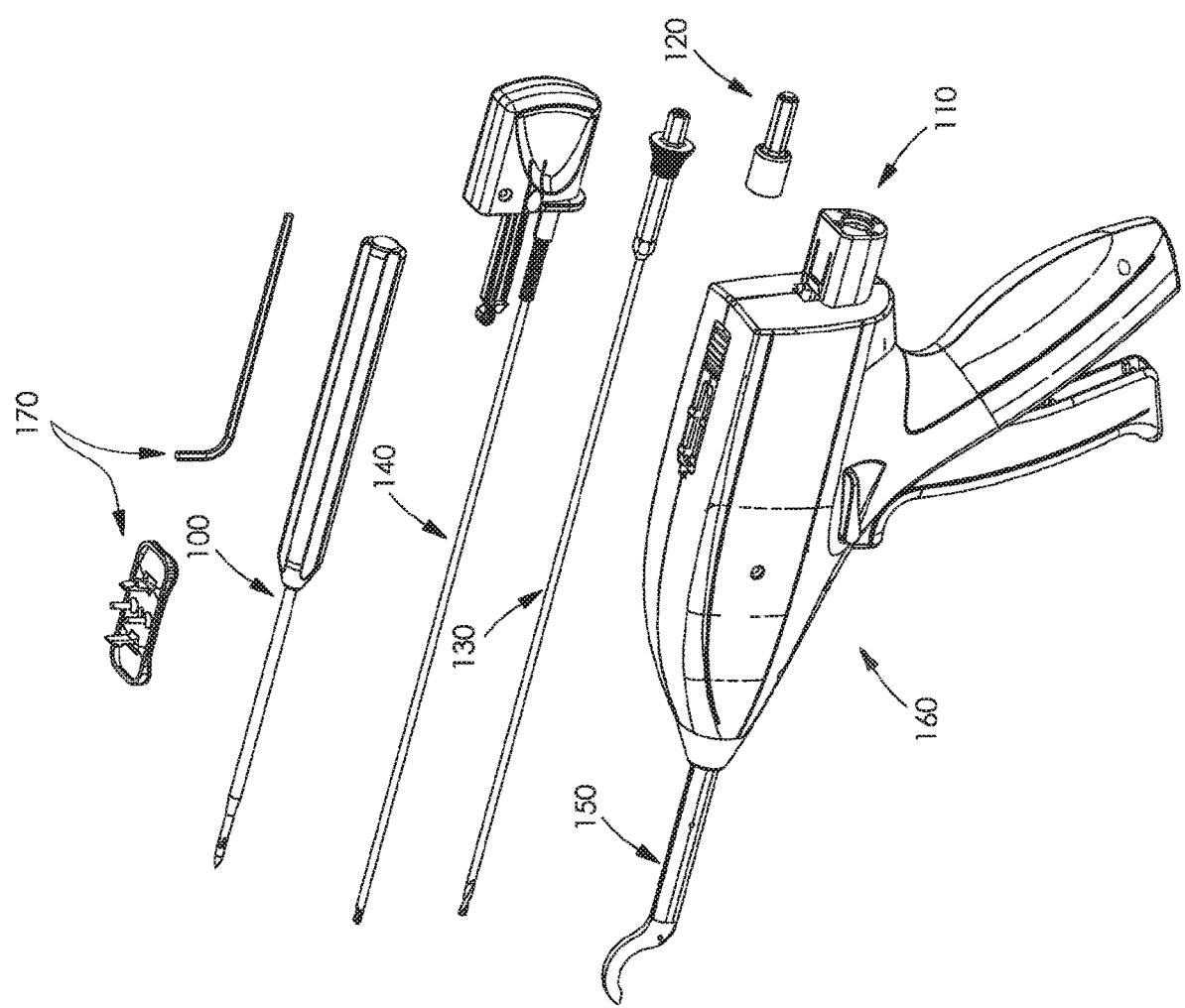

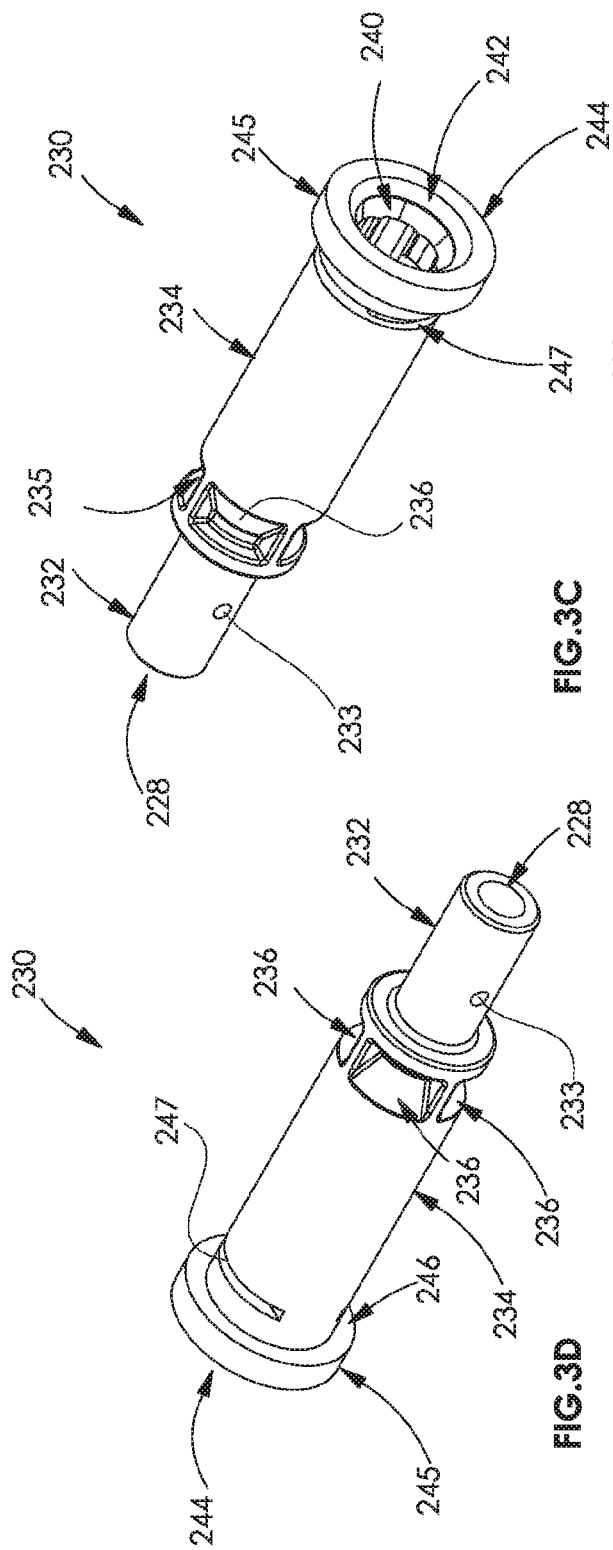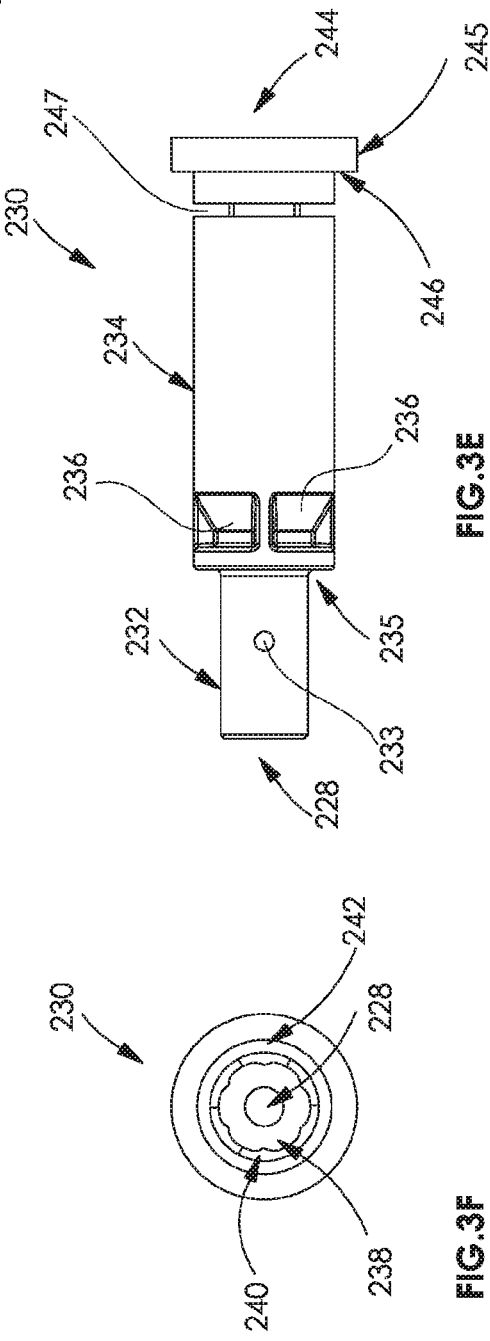

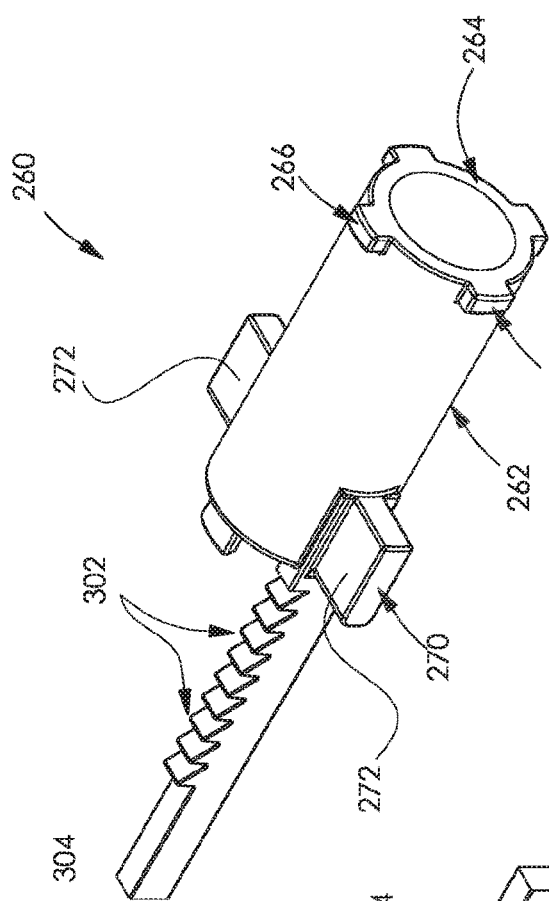
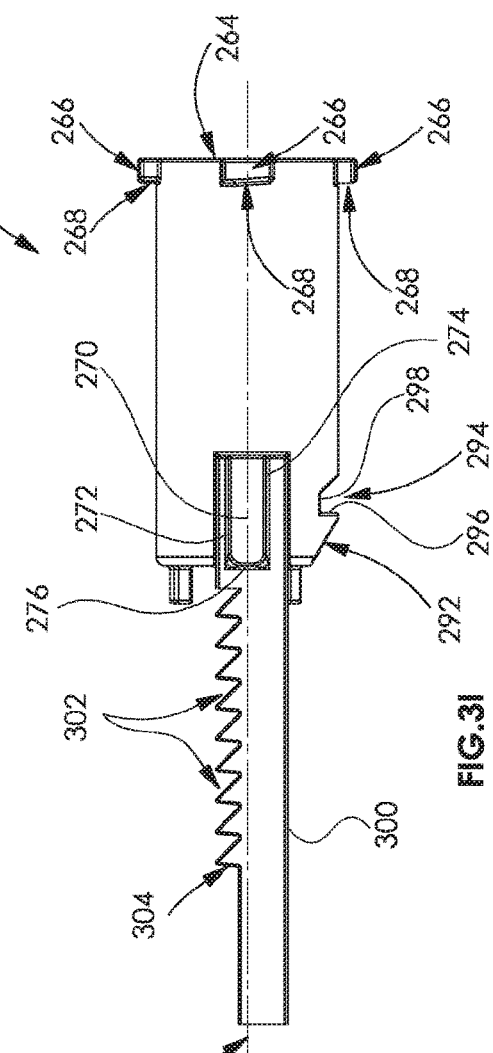
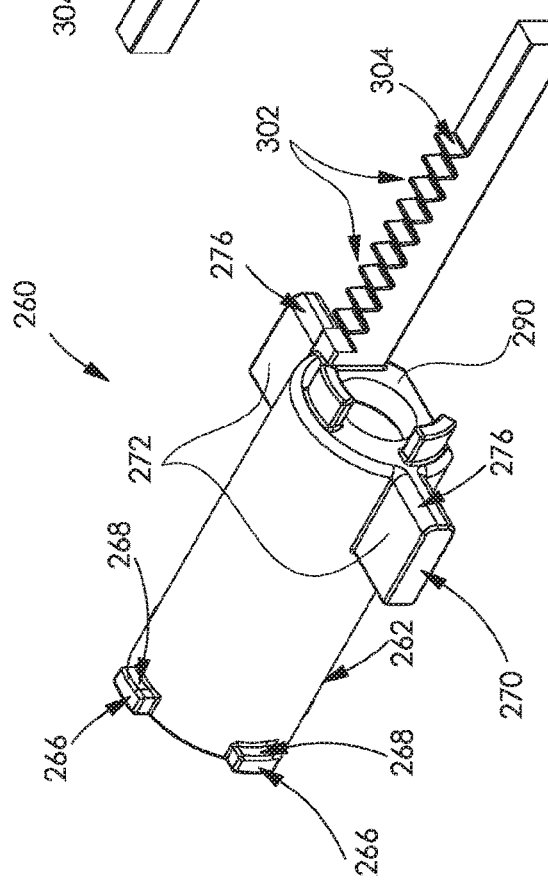
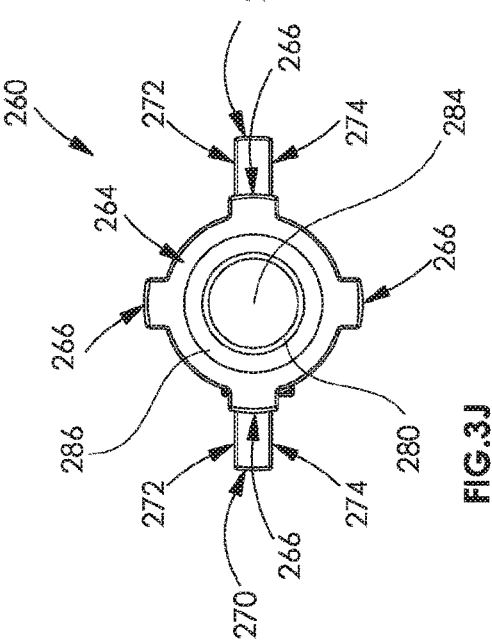

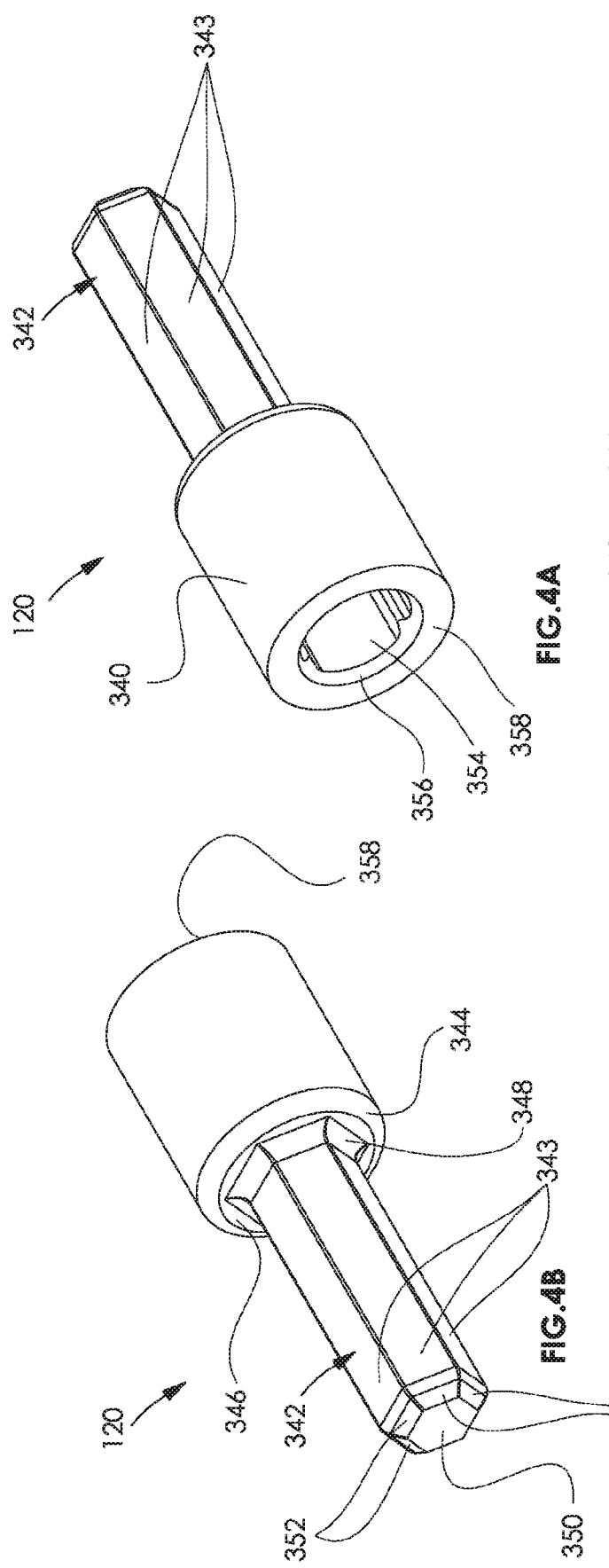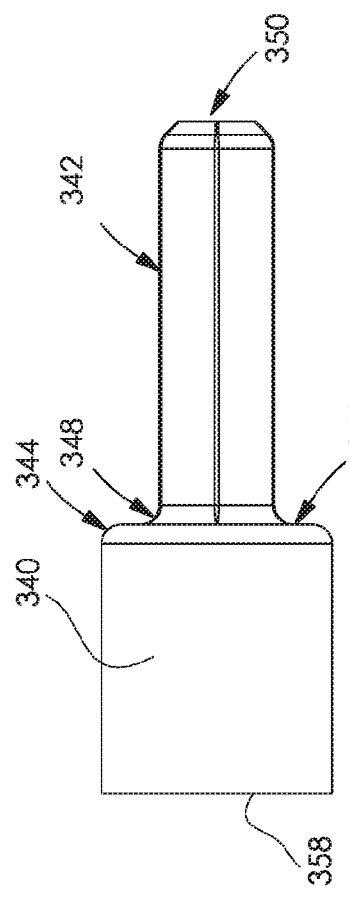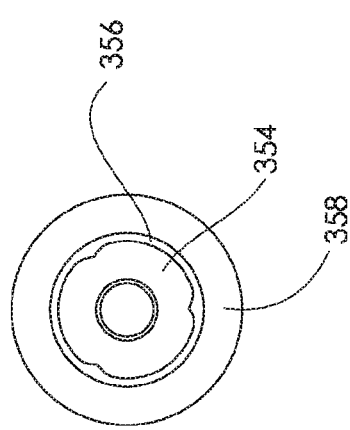

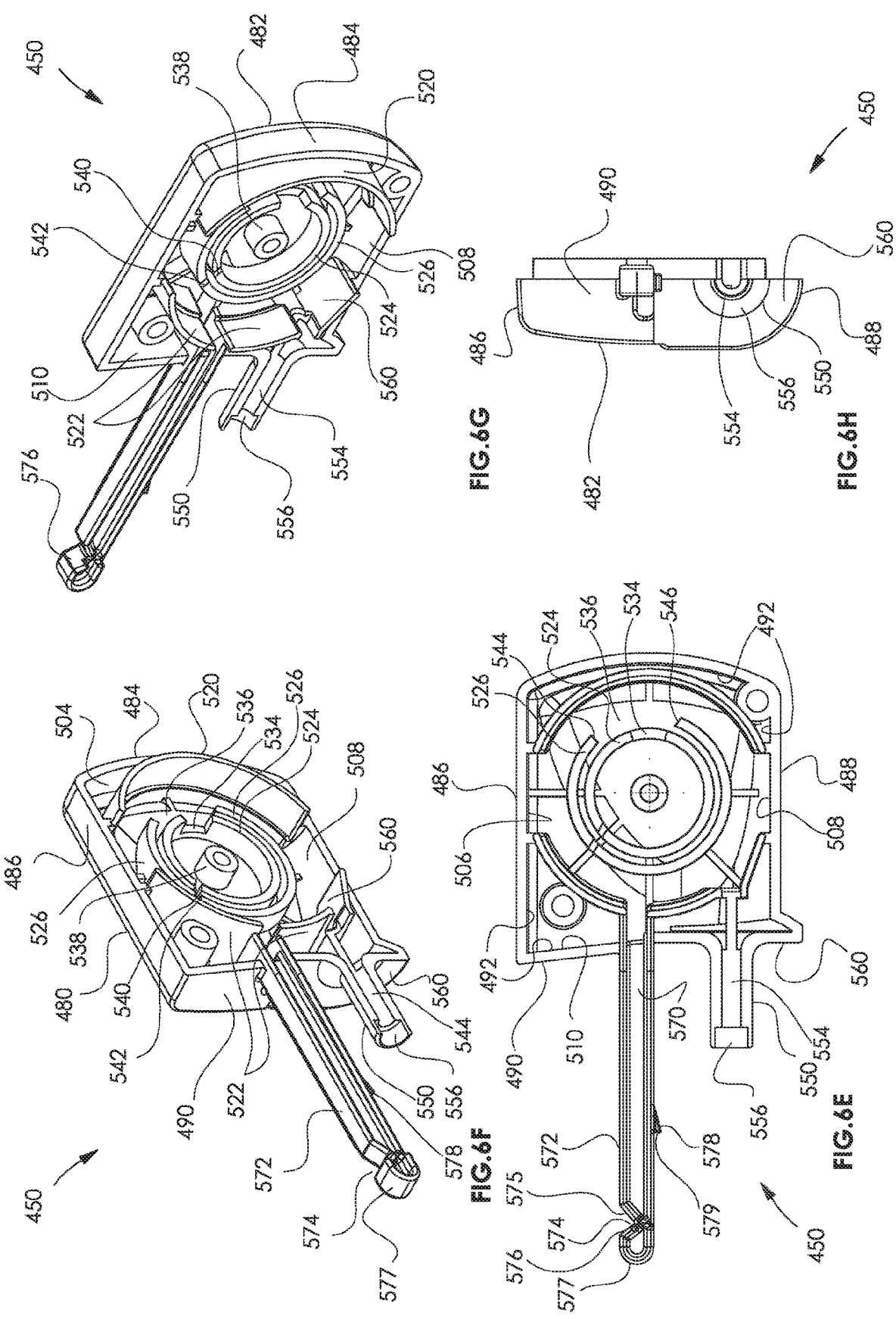

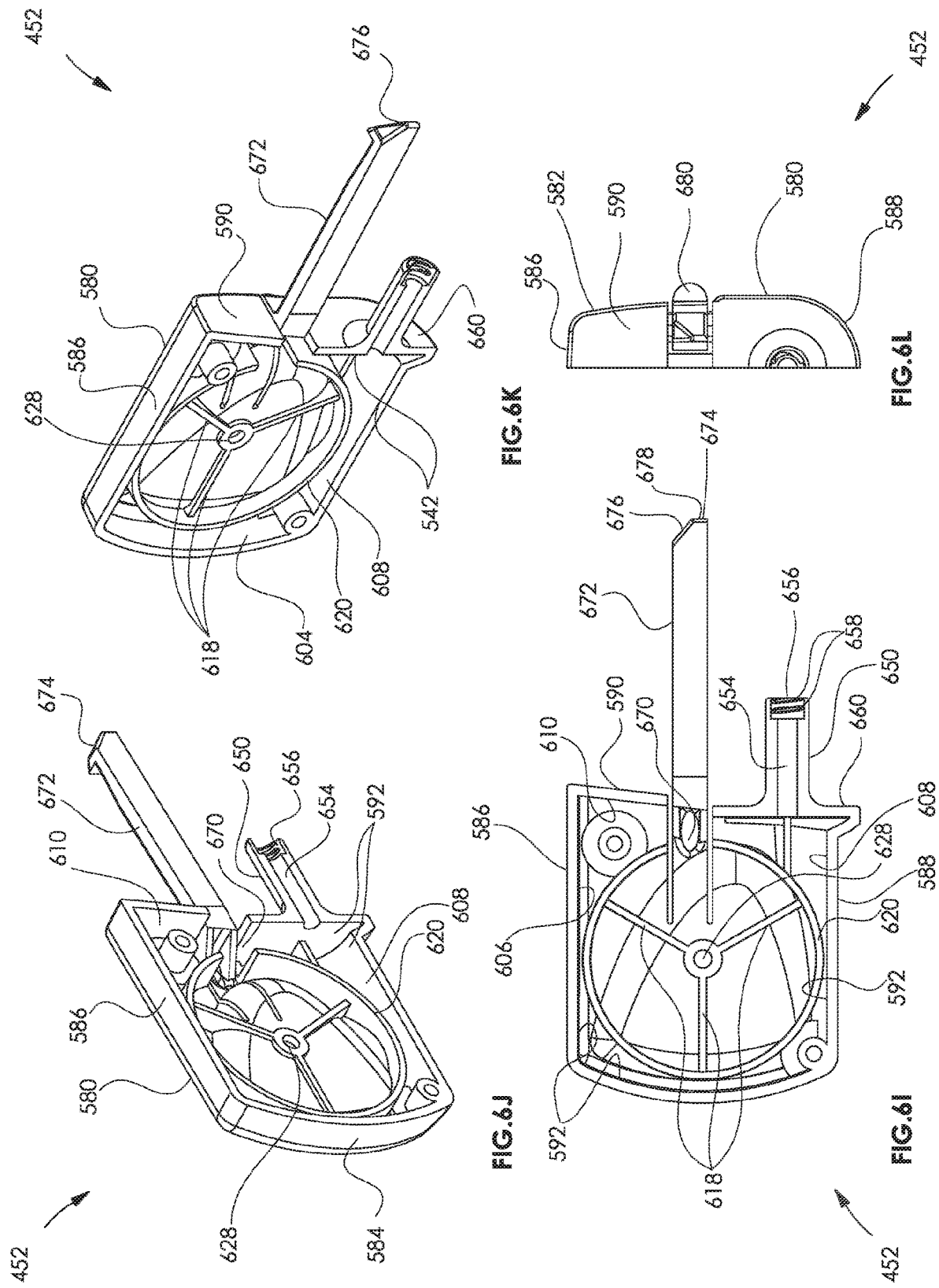

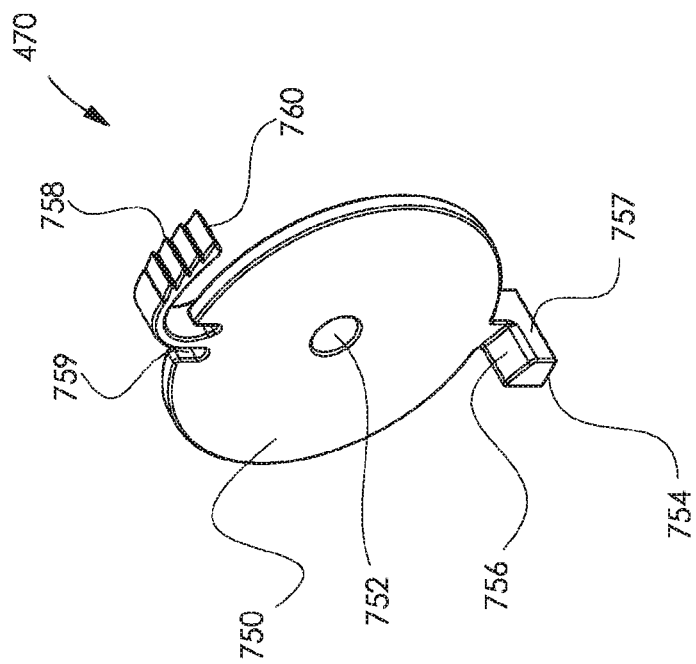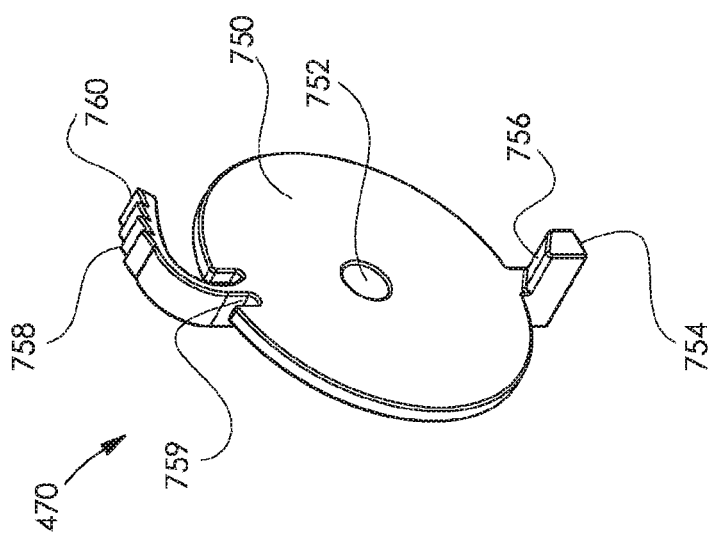

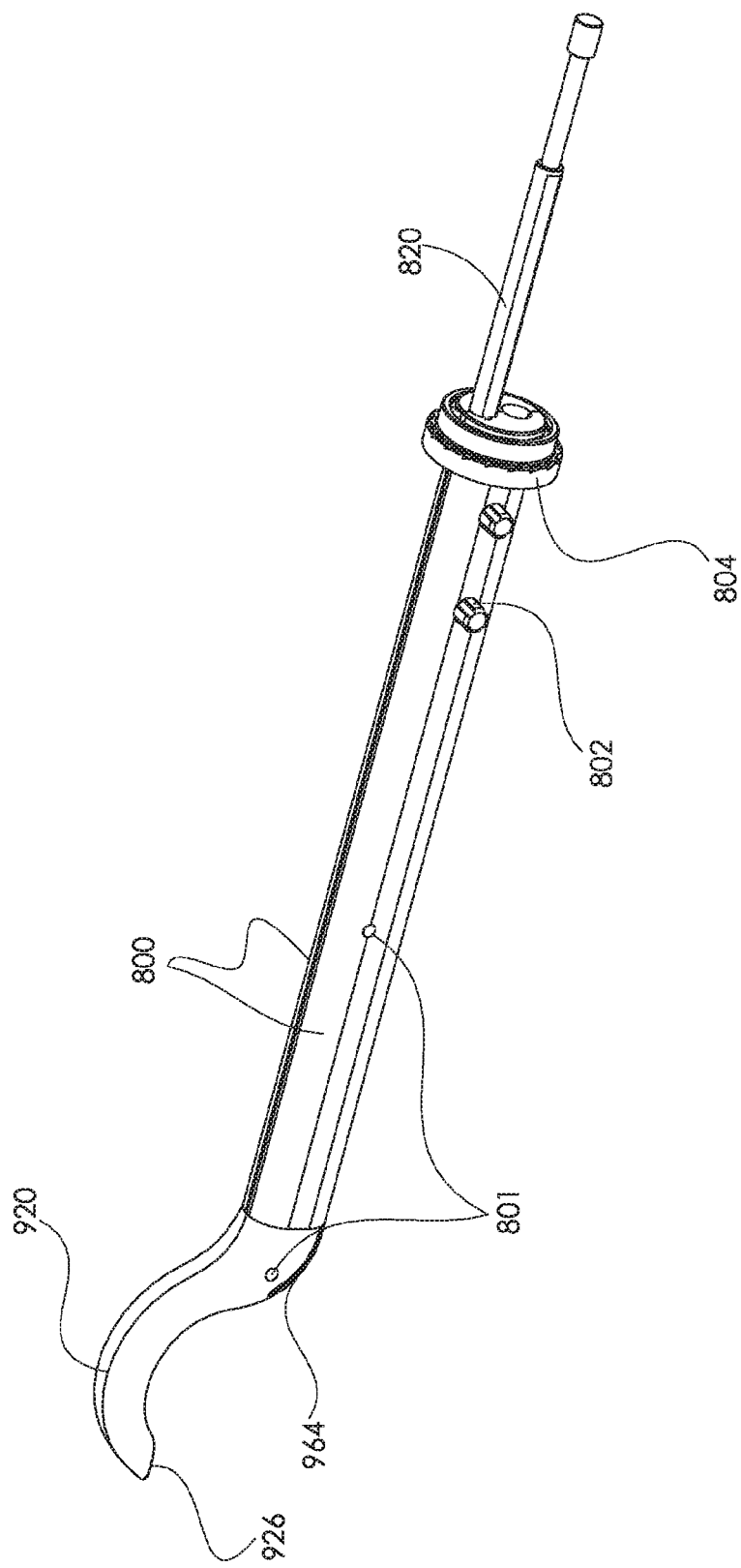

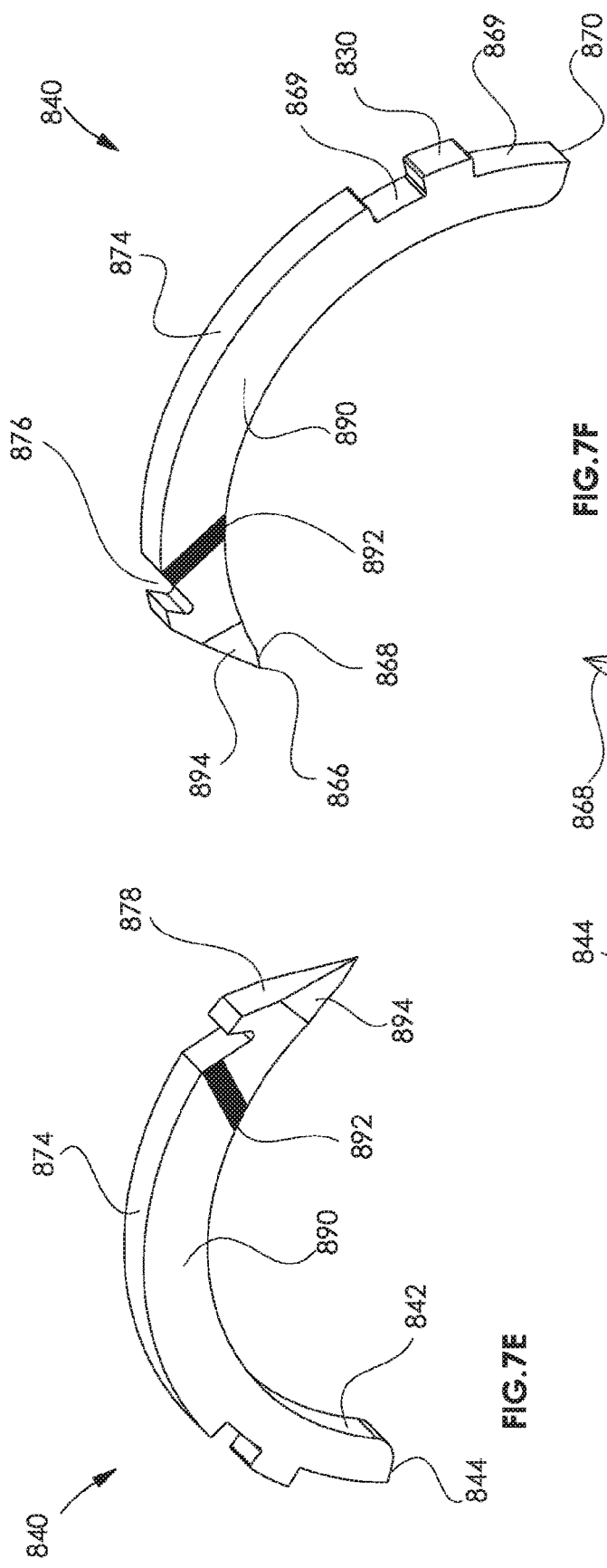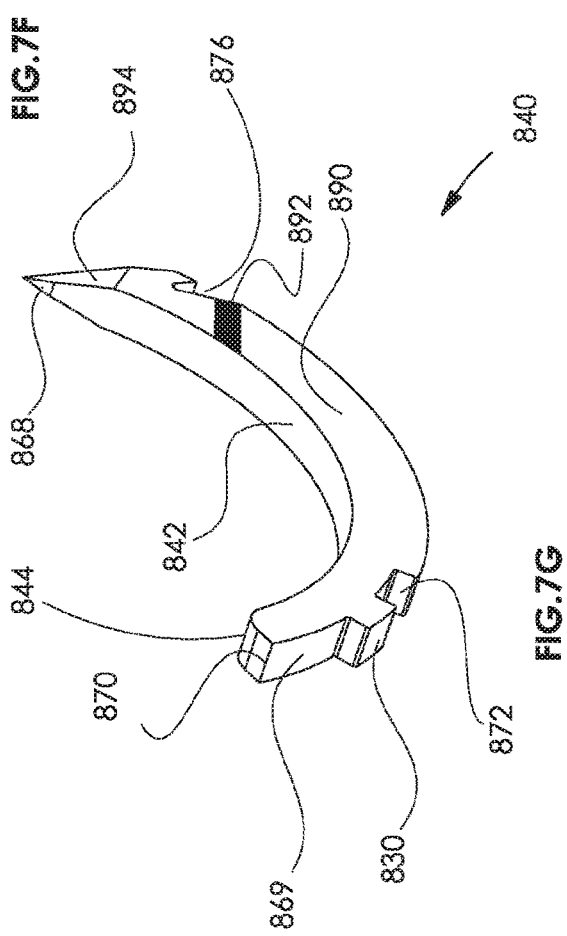

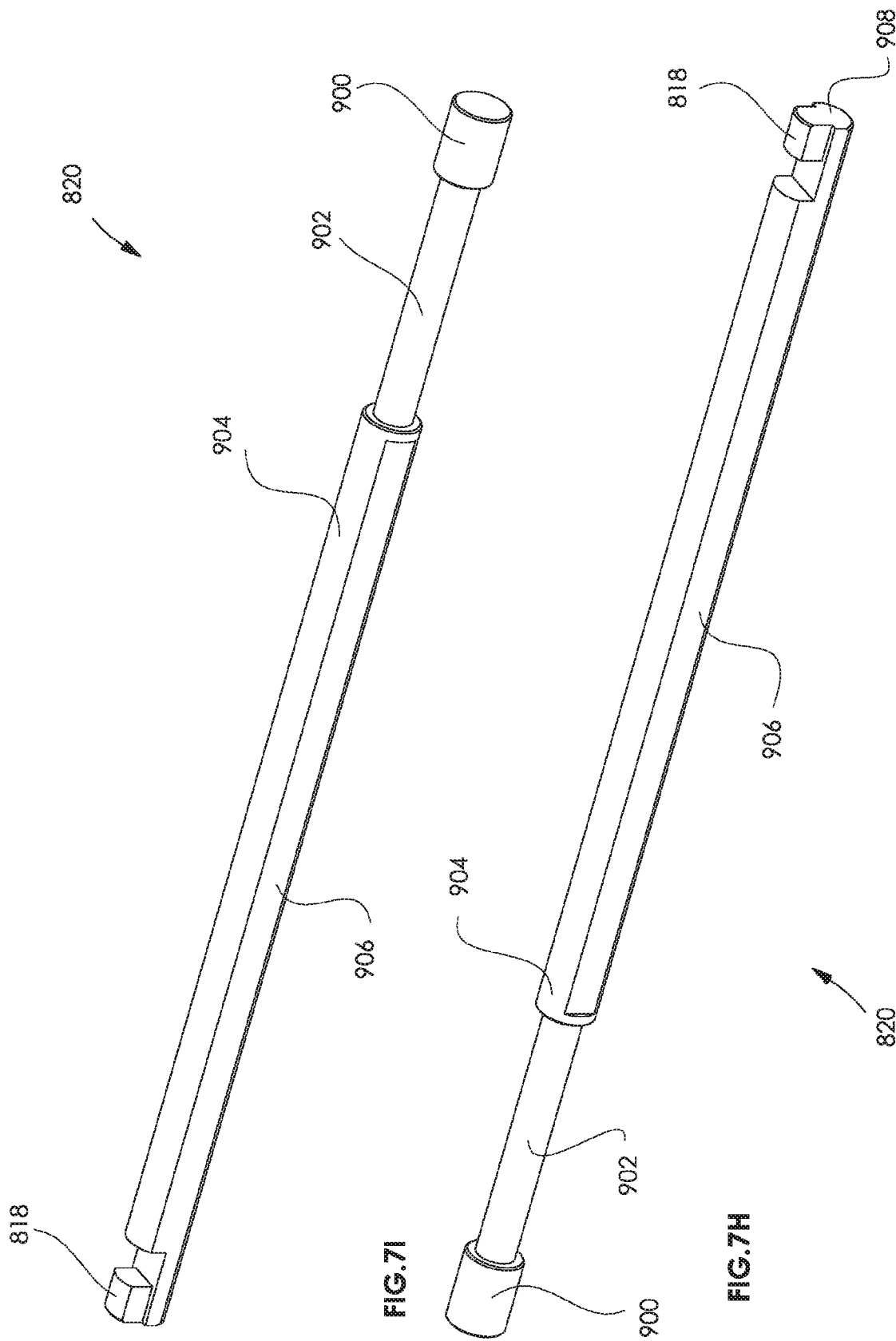

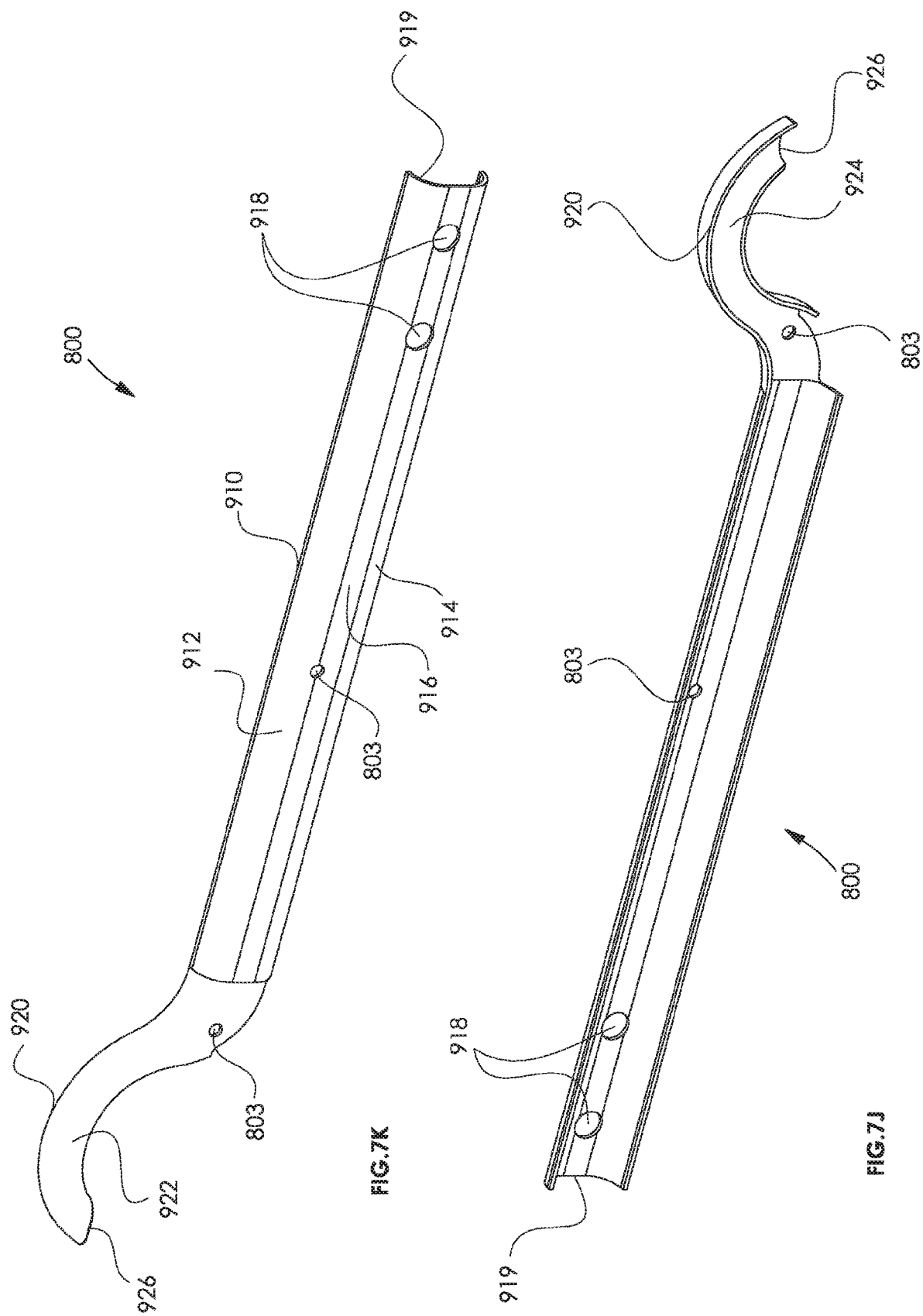

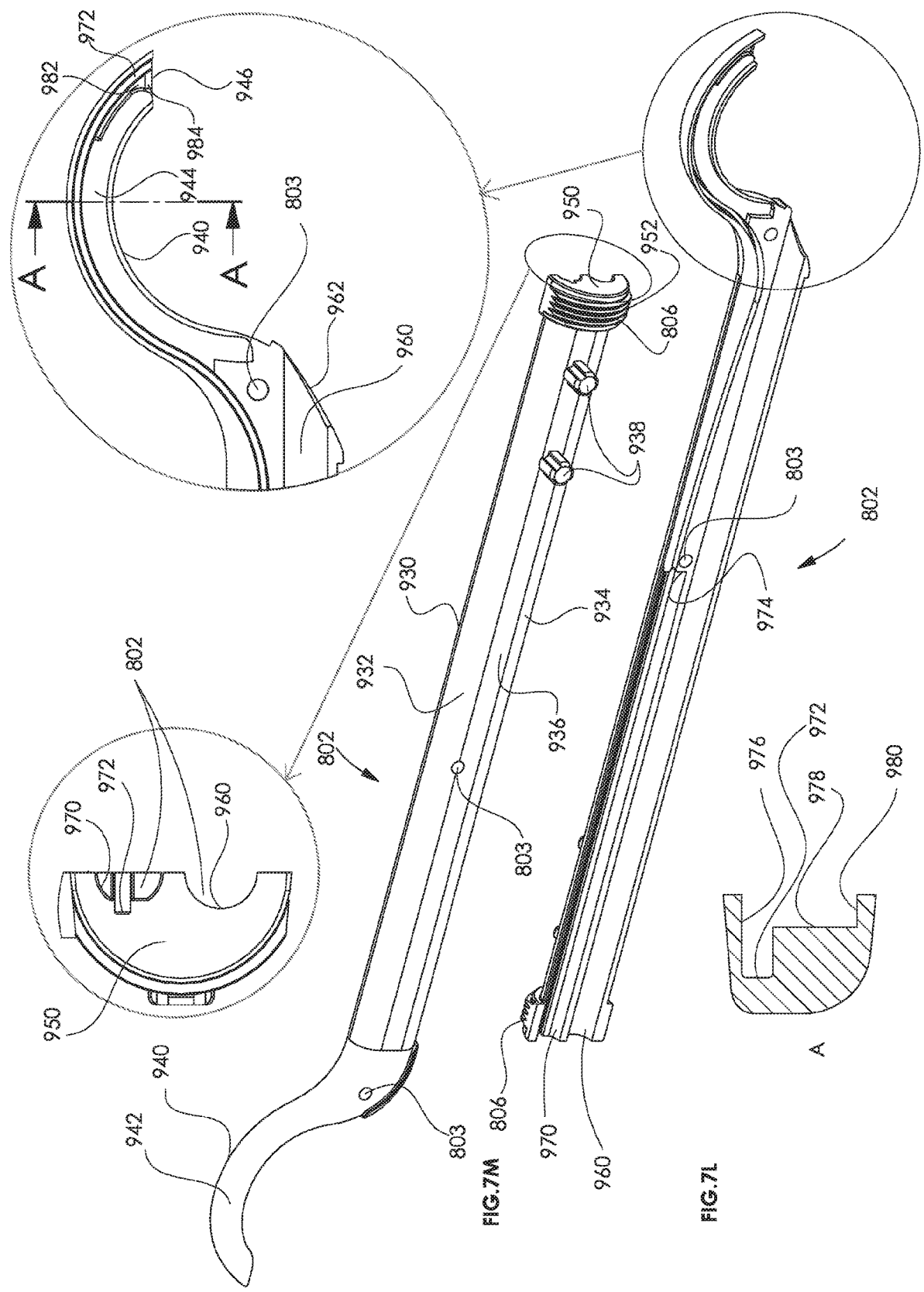

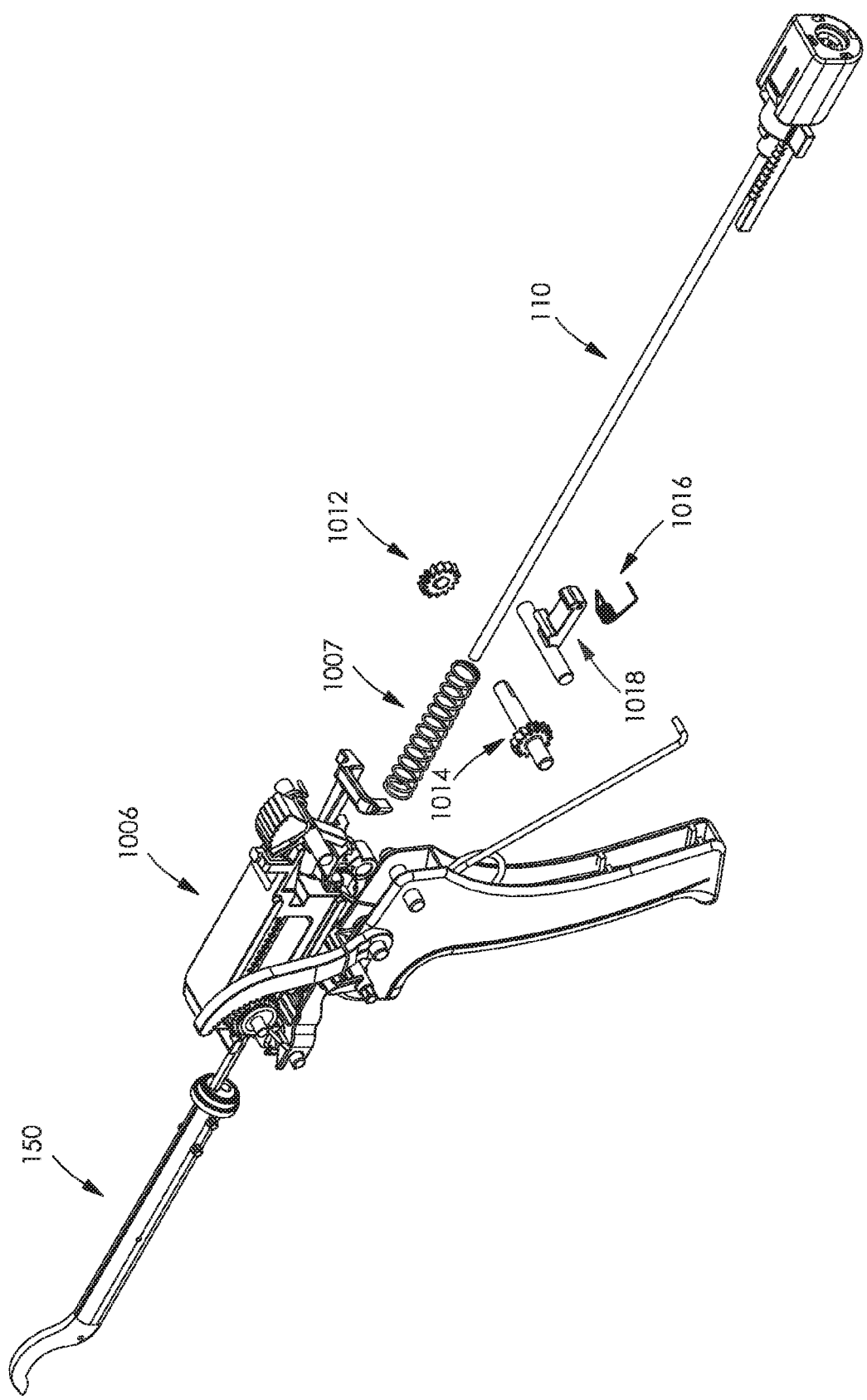

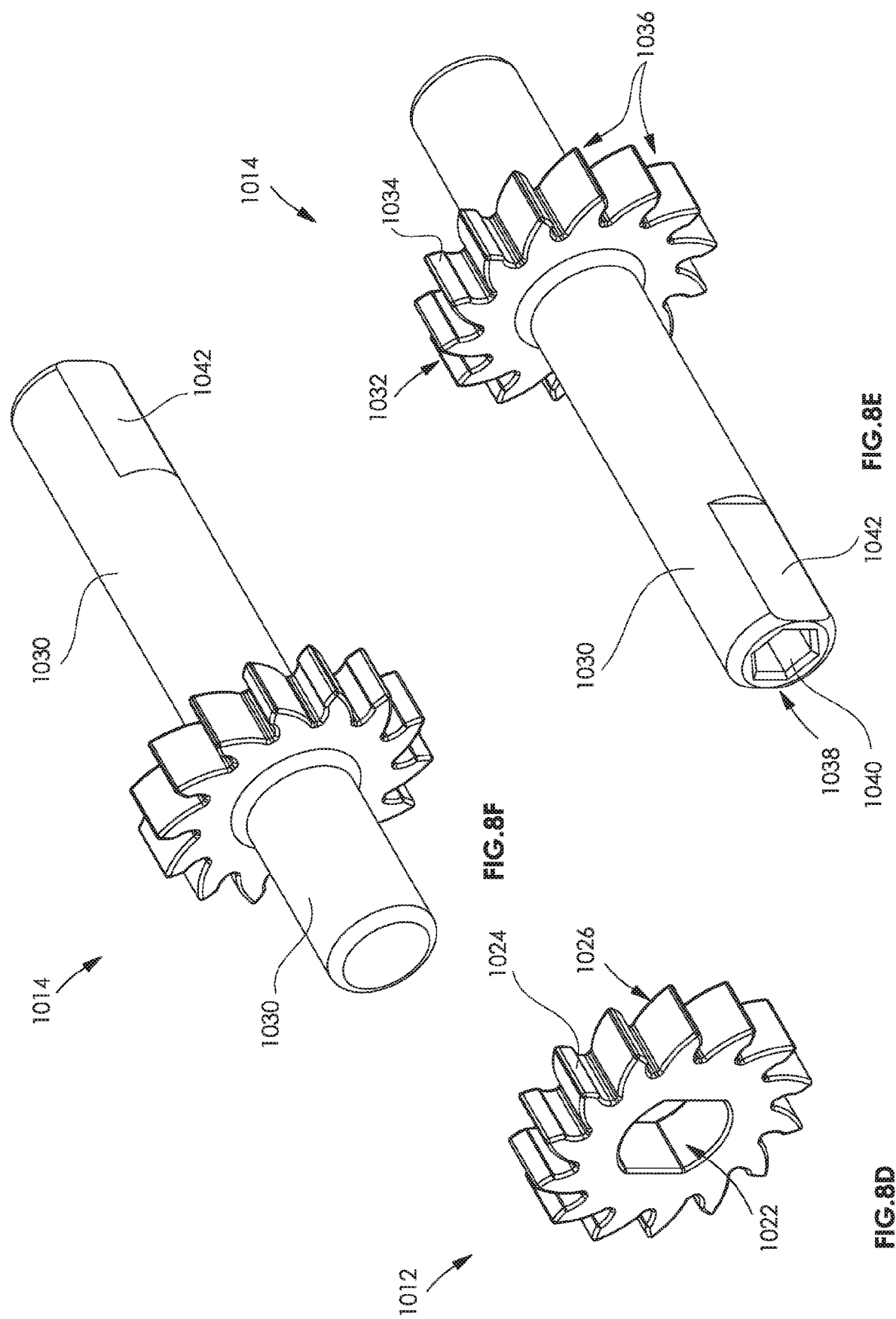

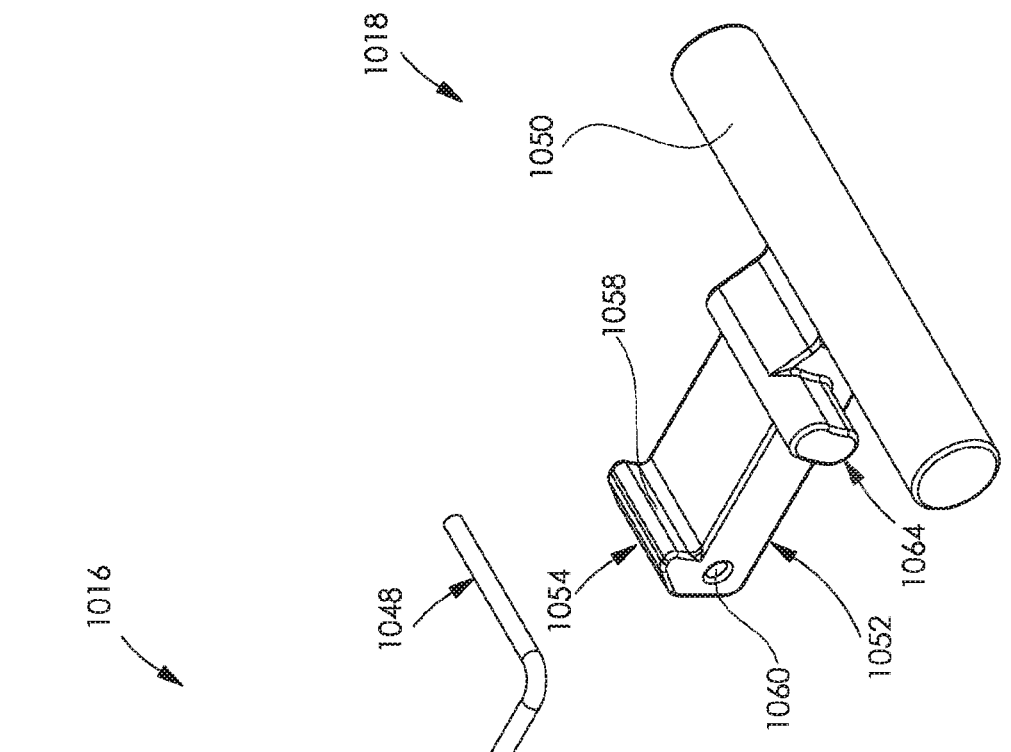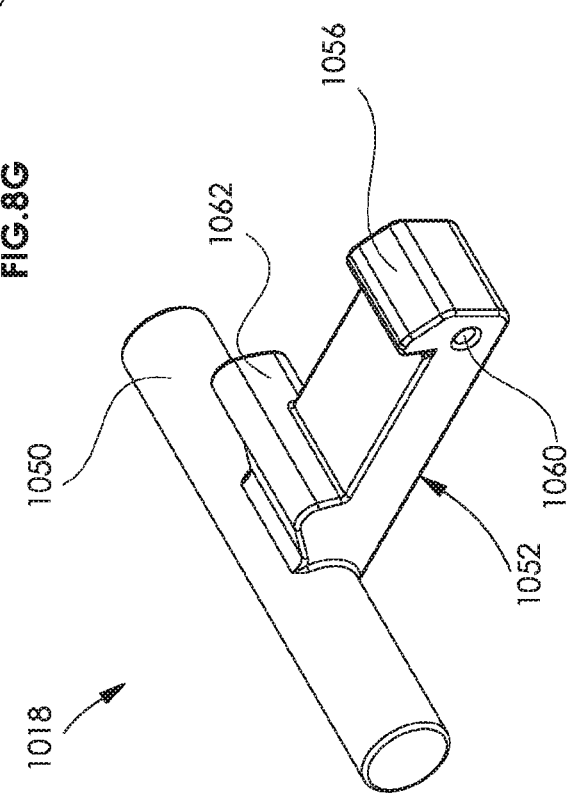

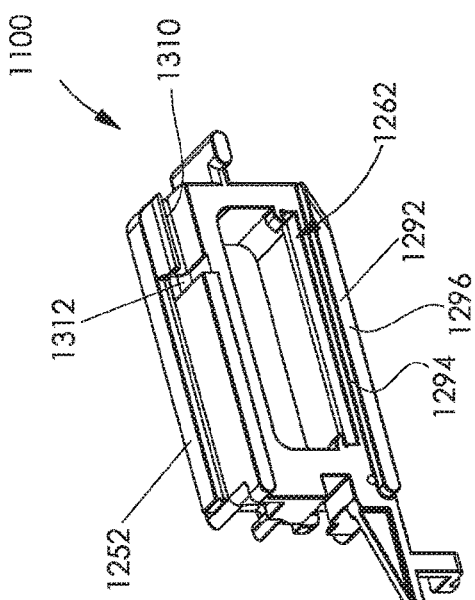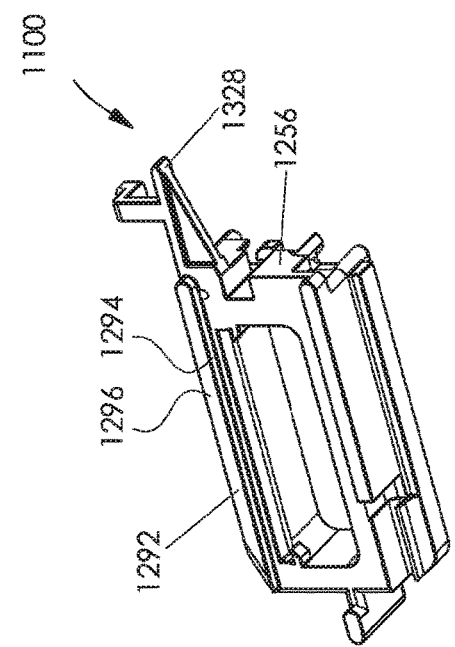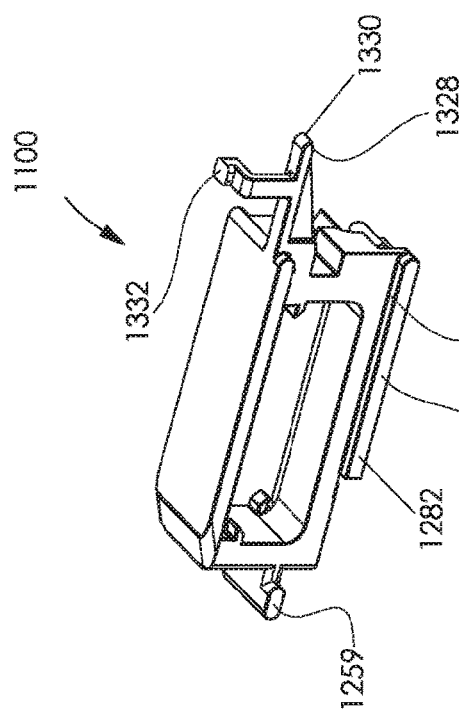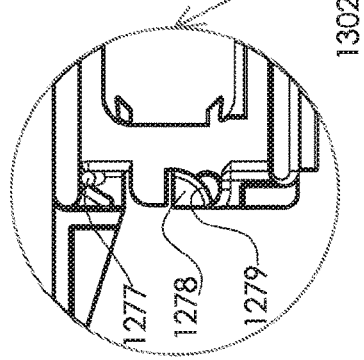

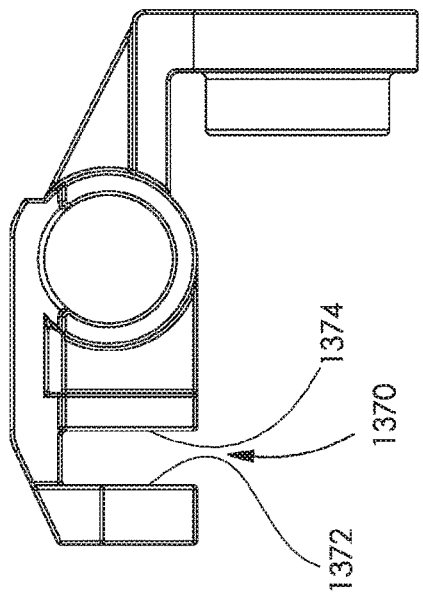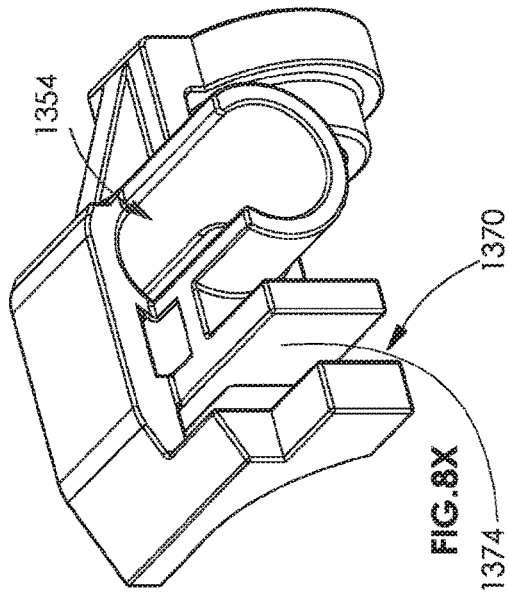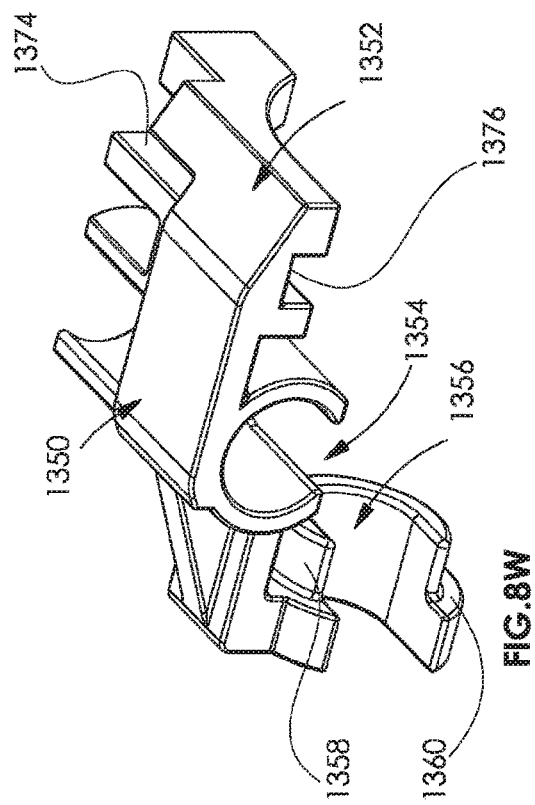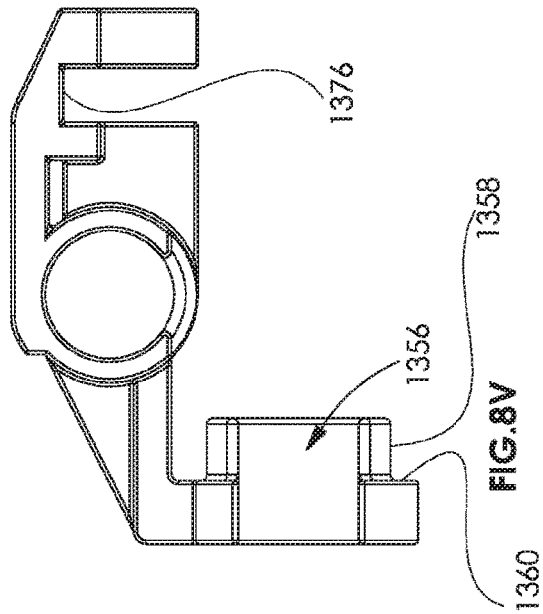

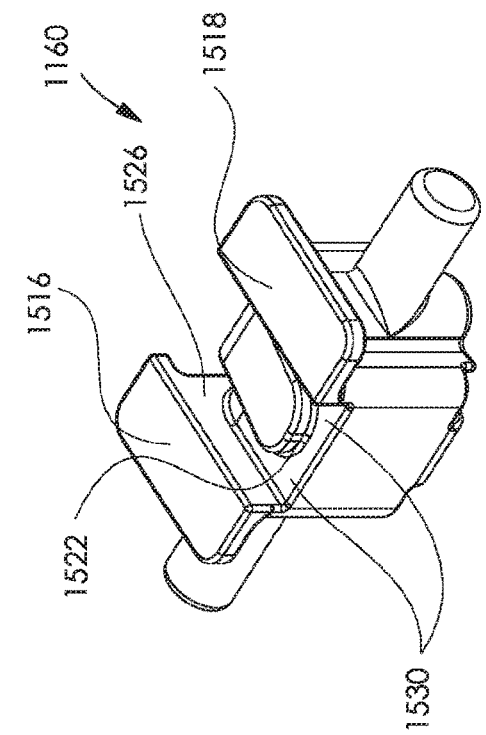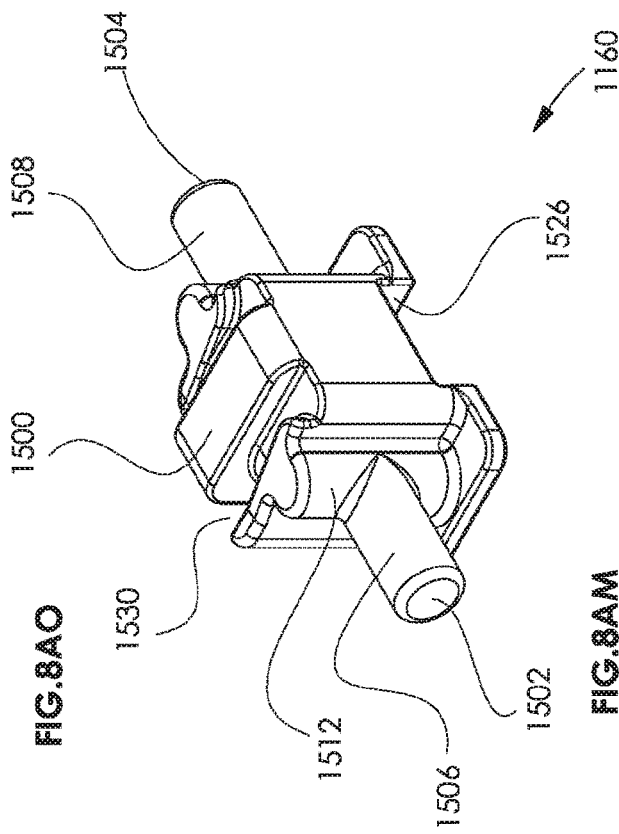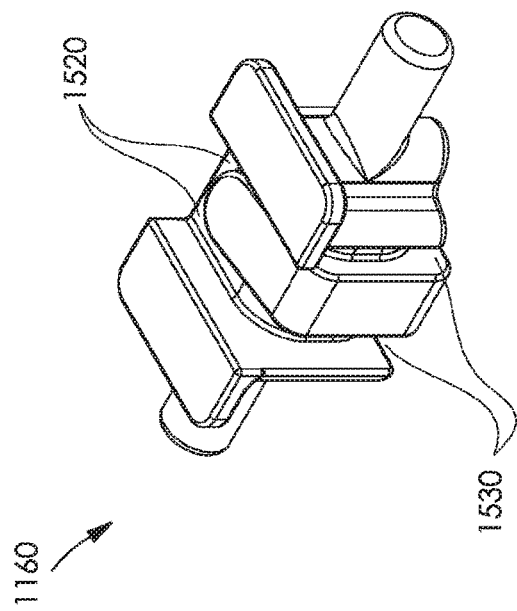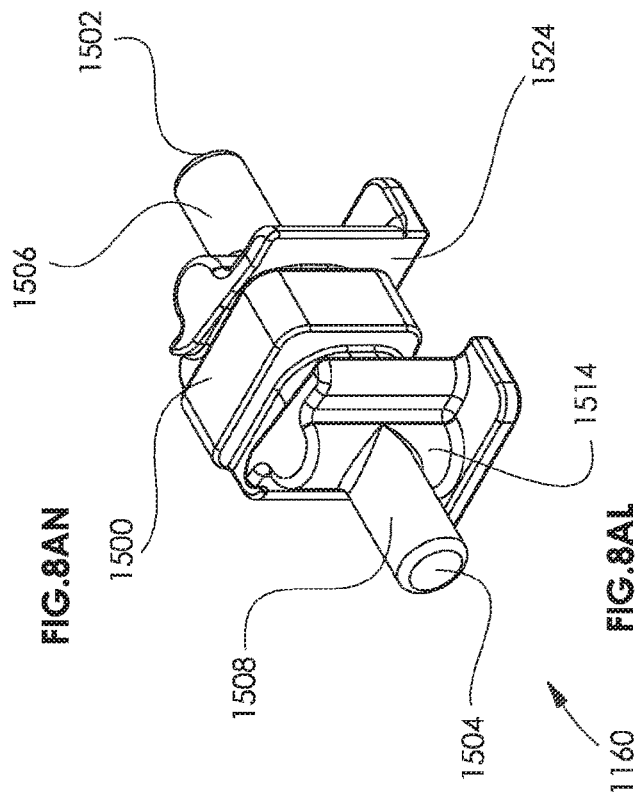

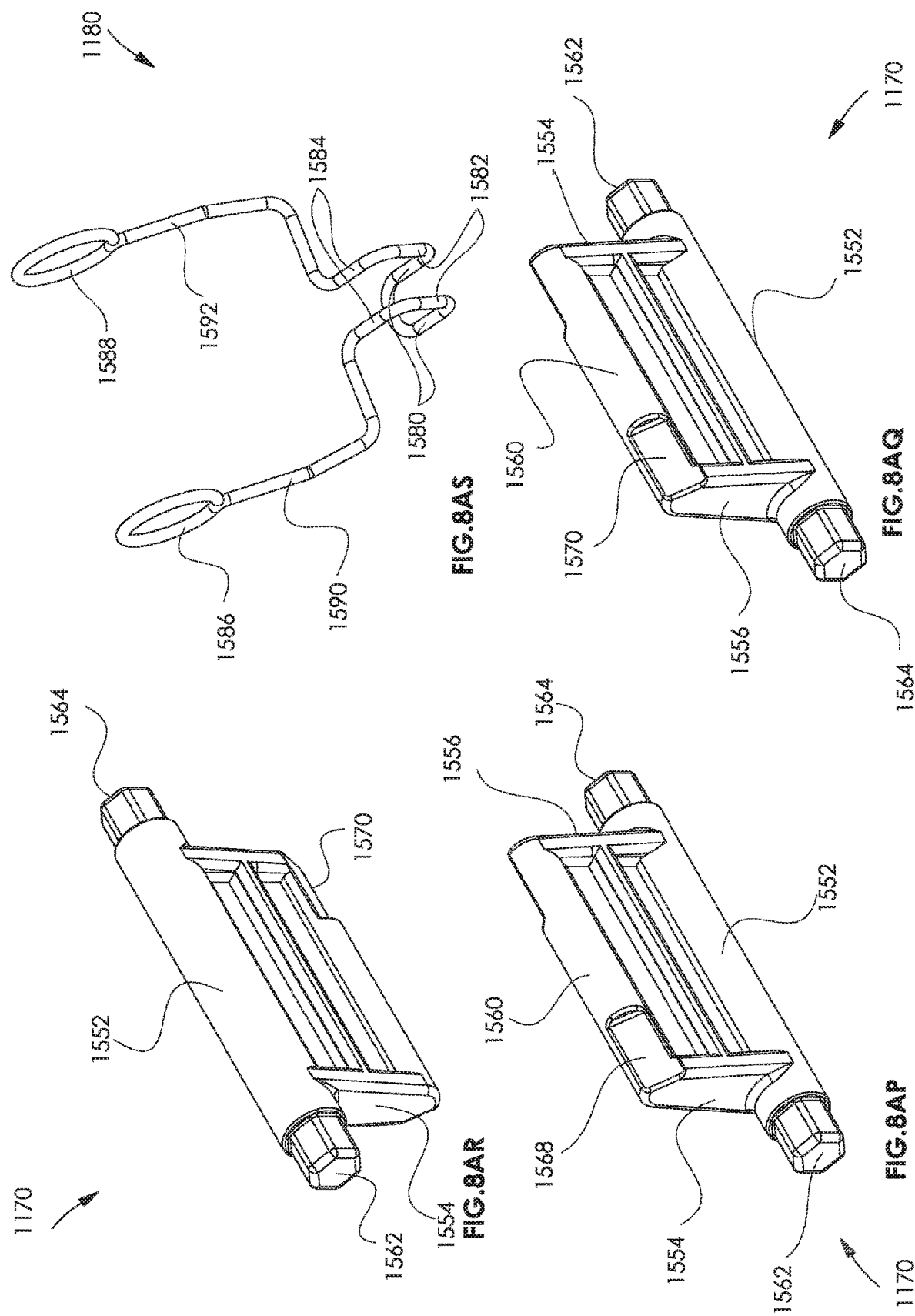

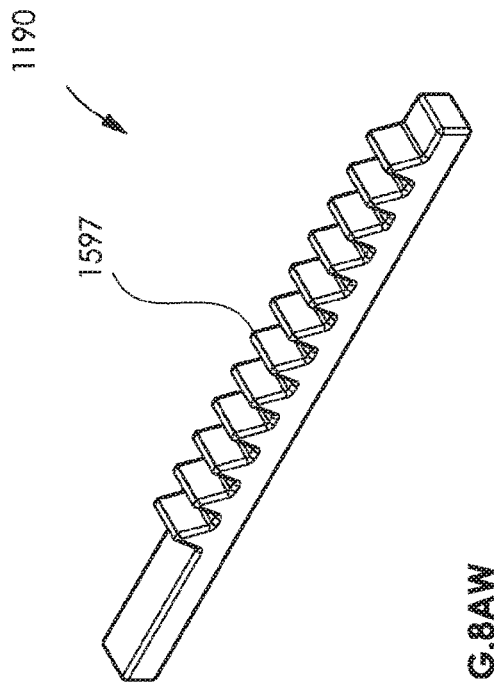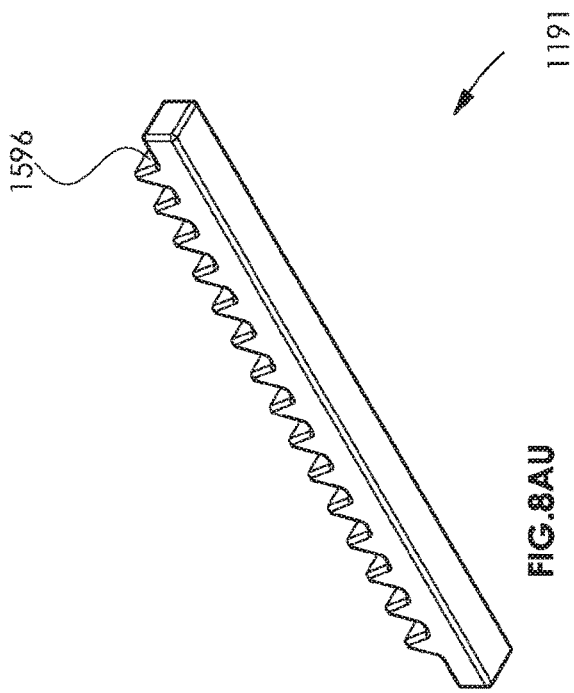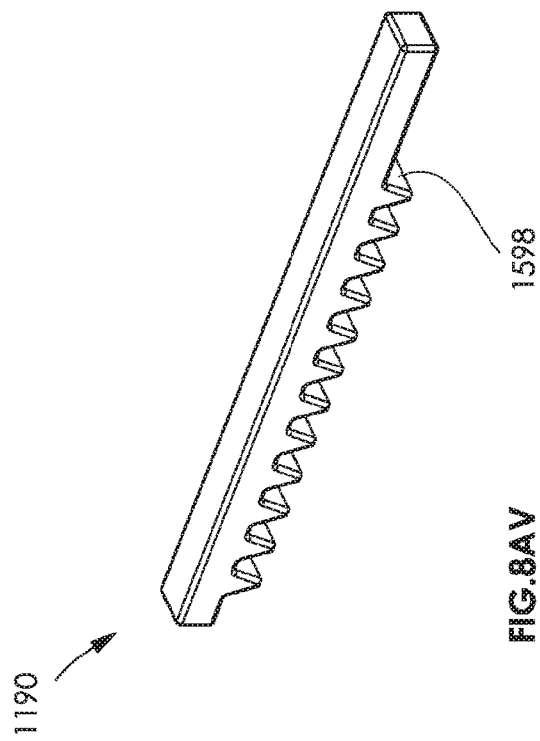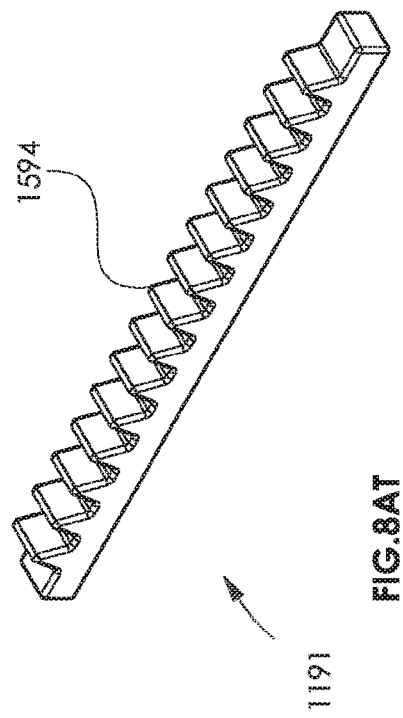

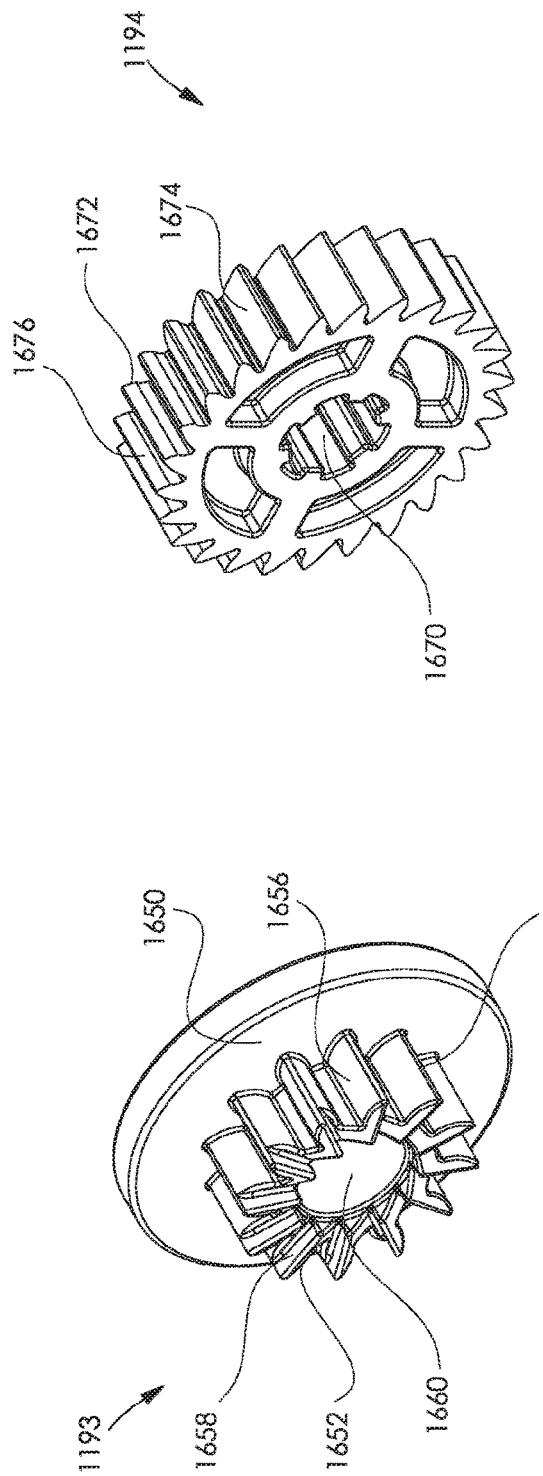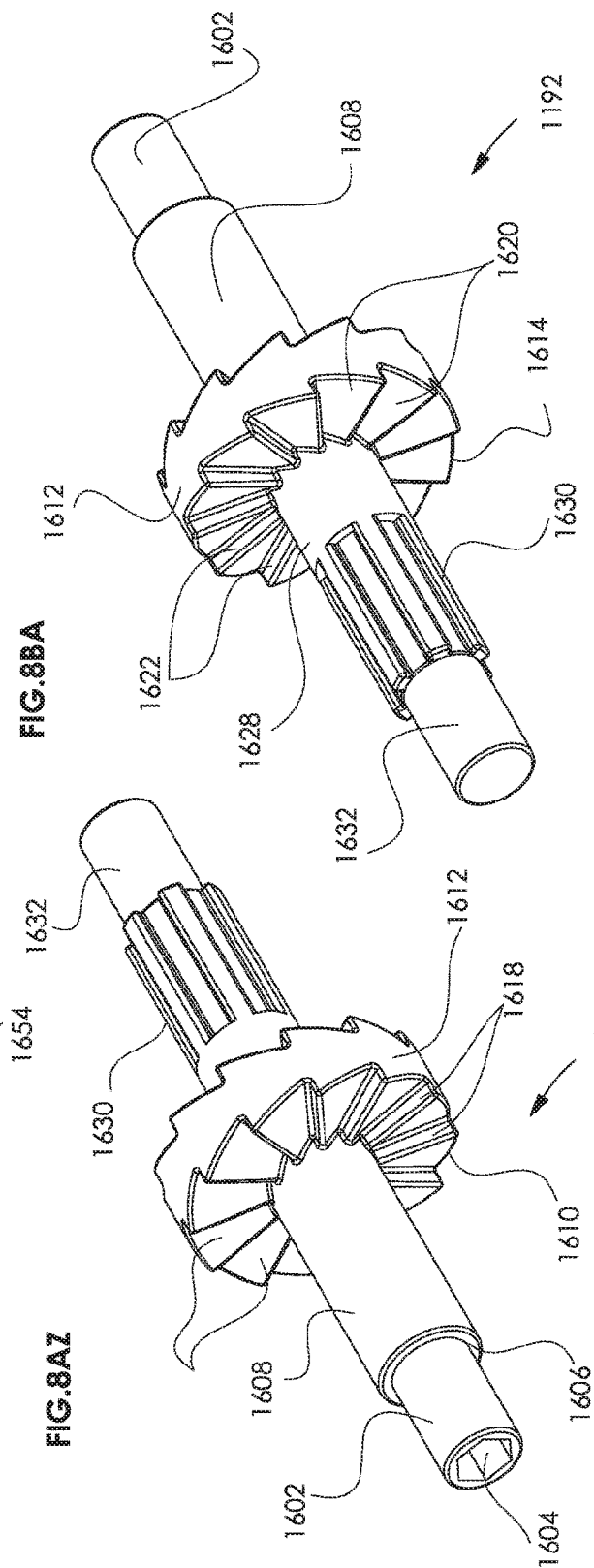

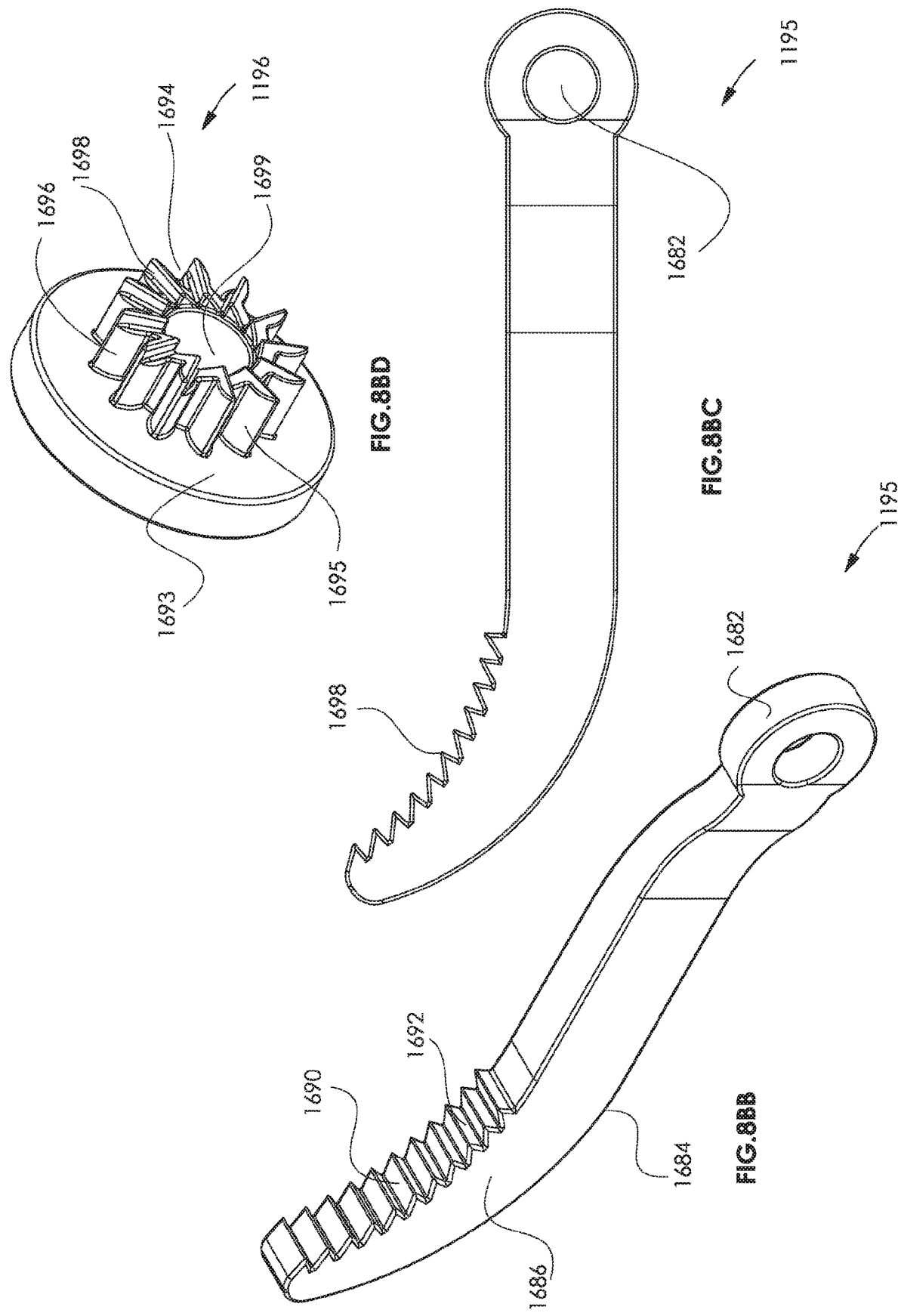

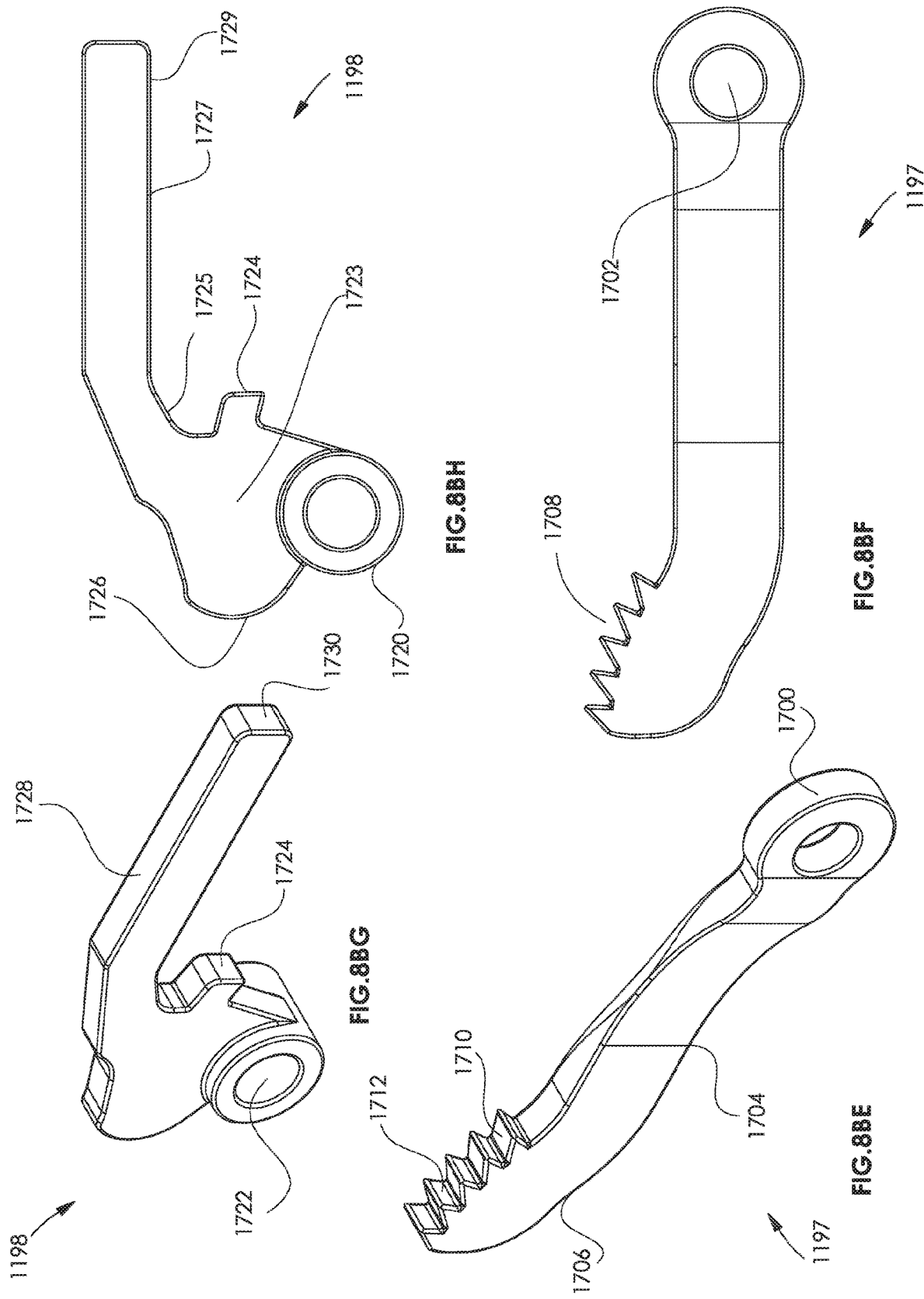

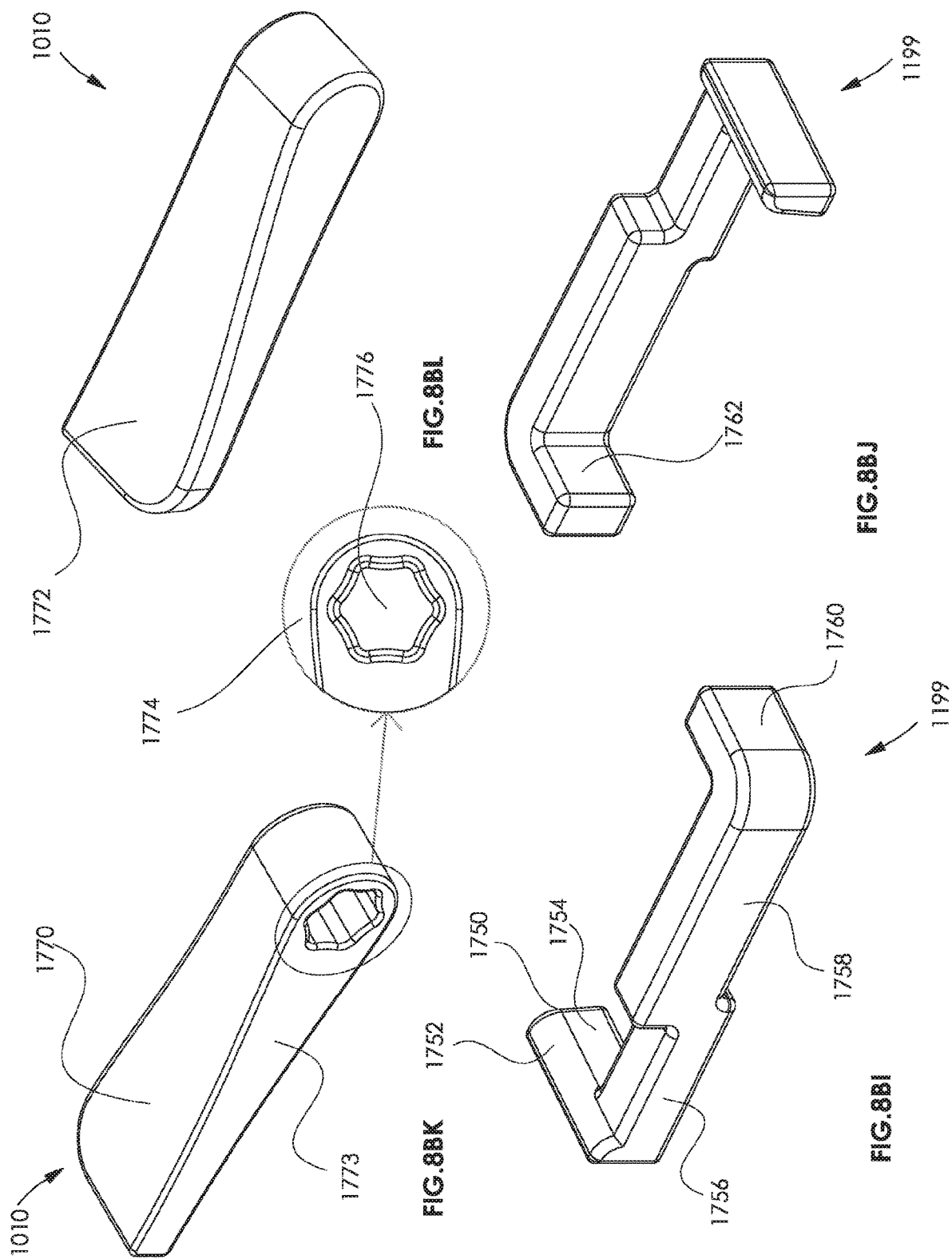

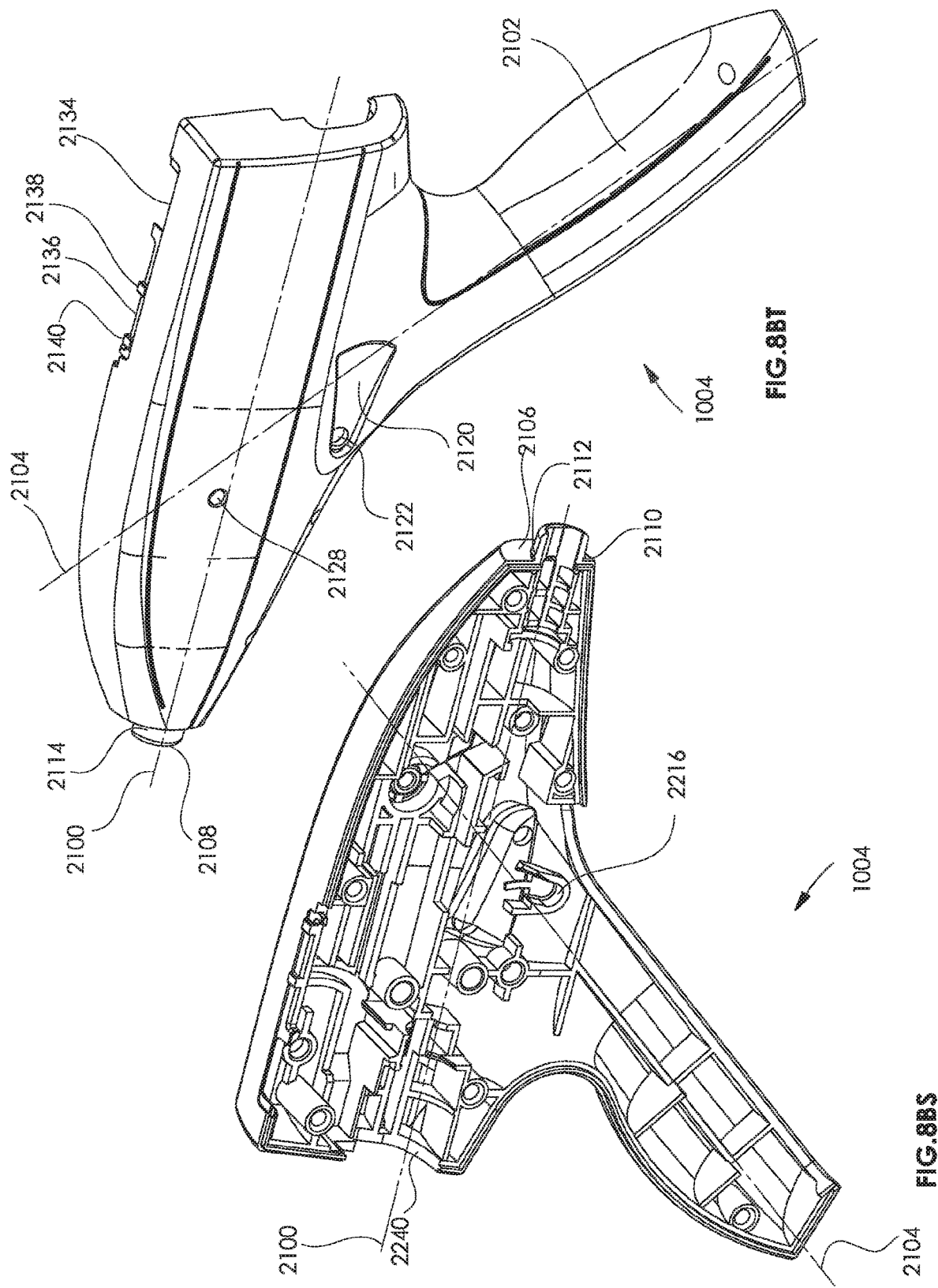

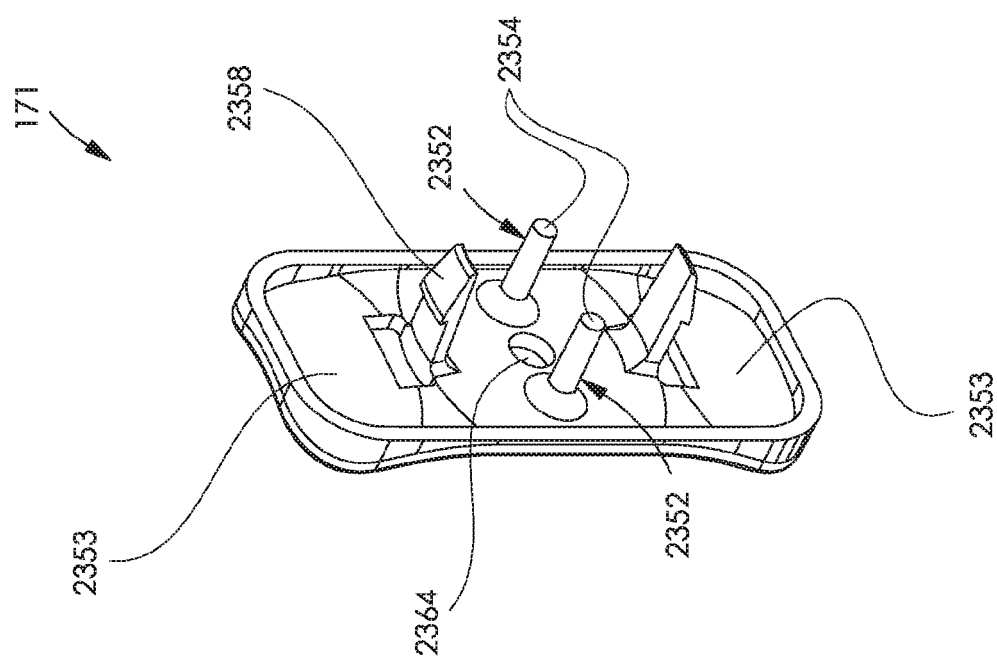
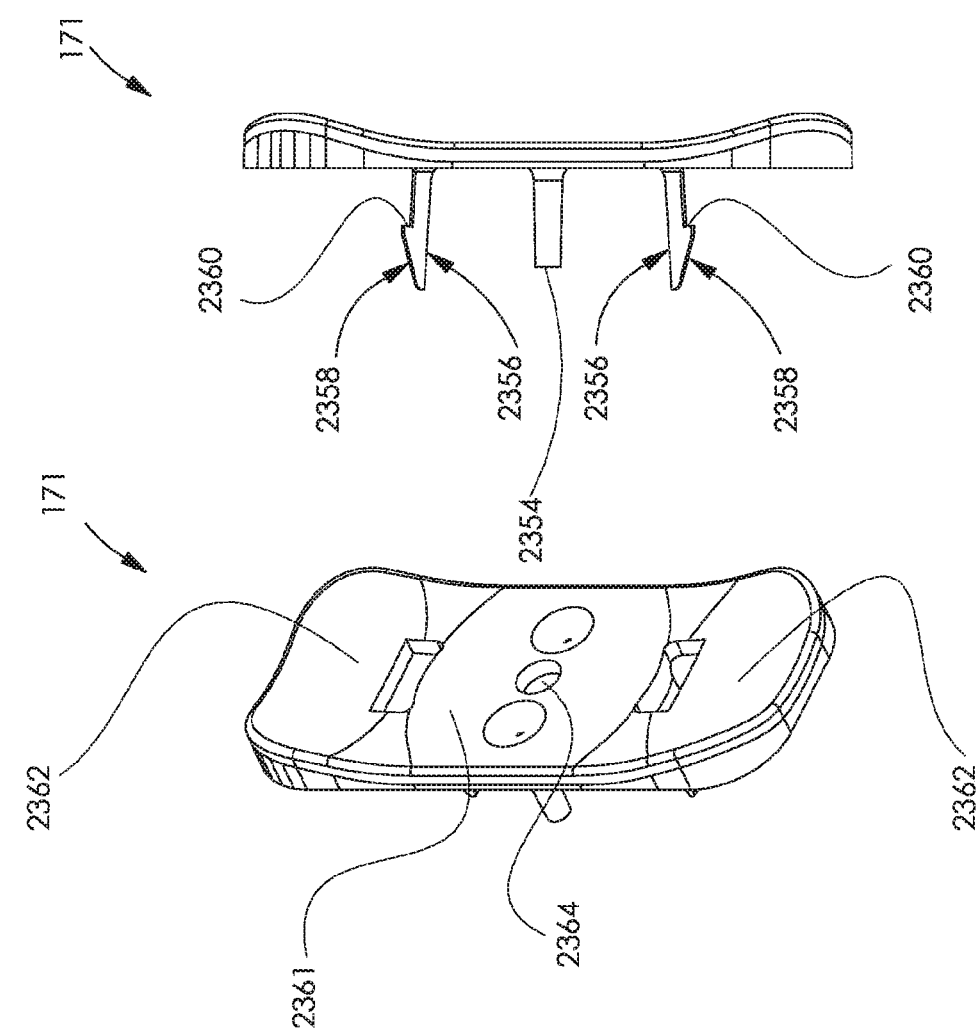
Fig. 9A.
Fig. 9B.
Fig. 9C.

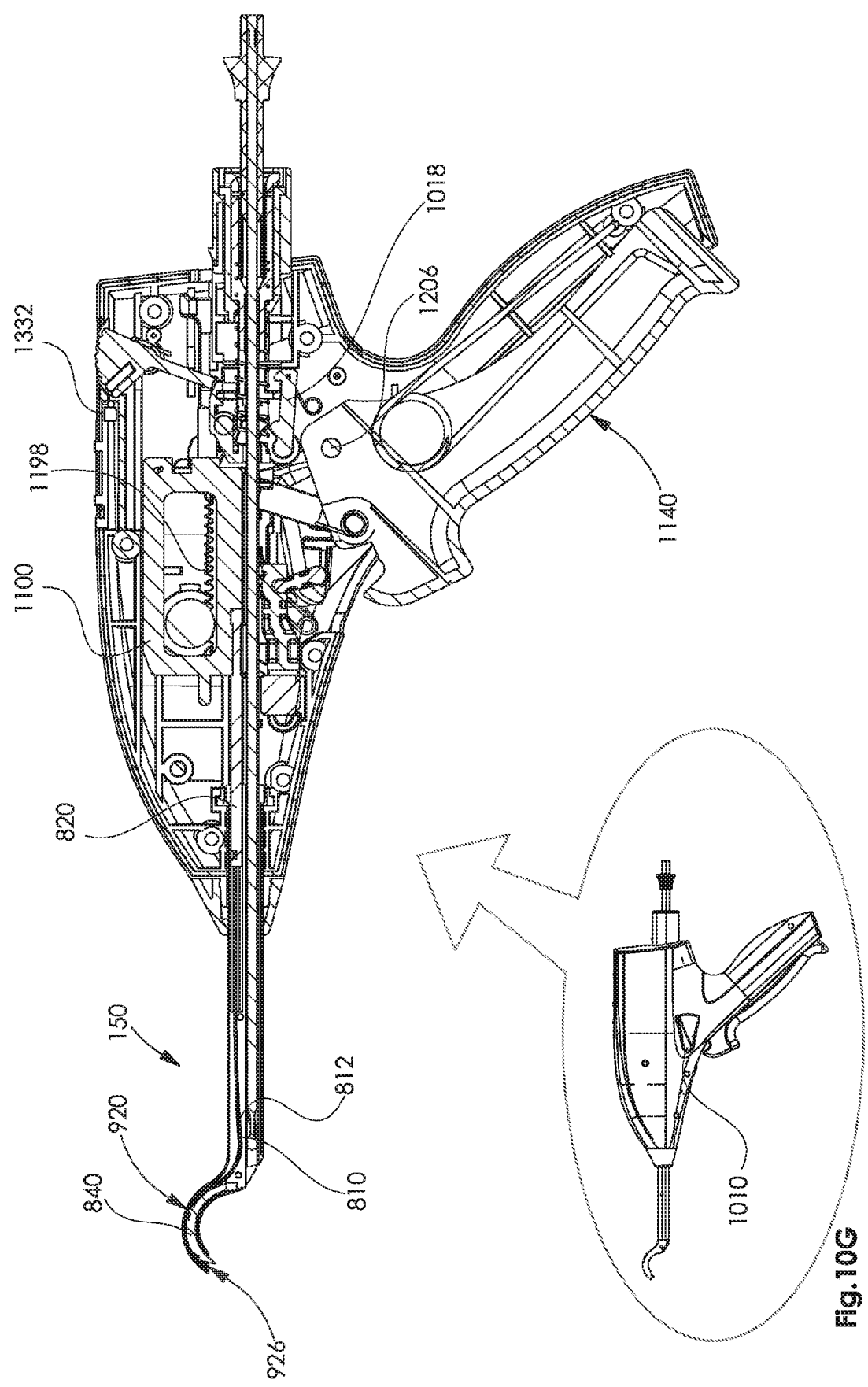

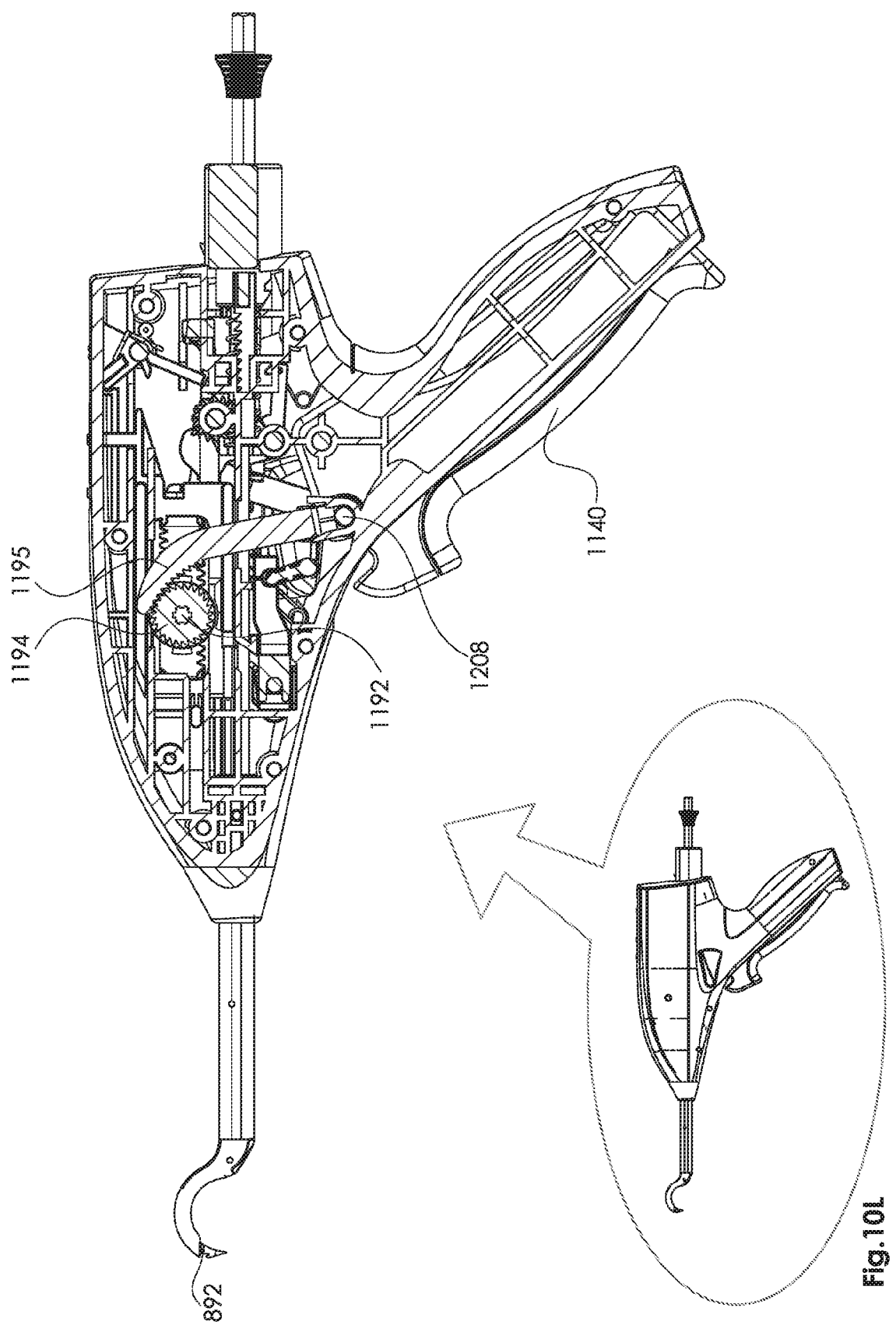

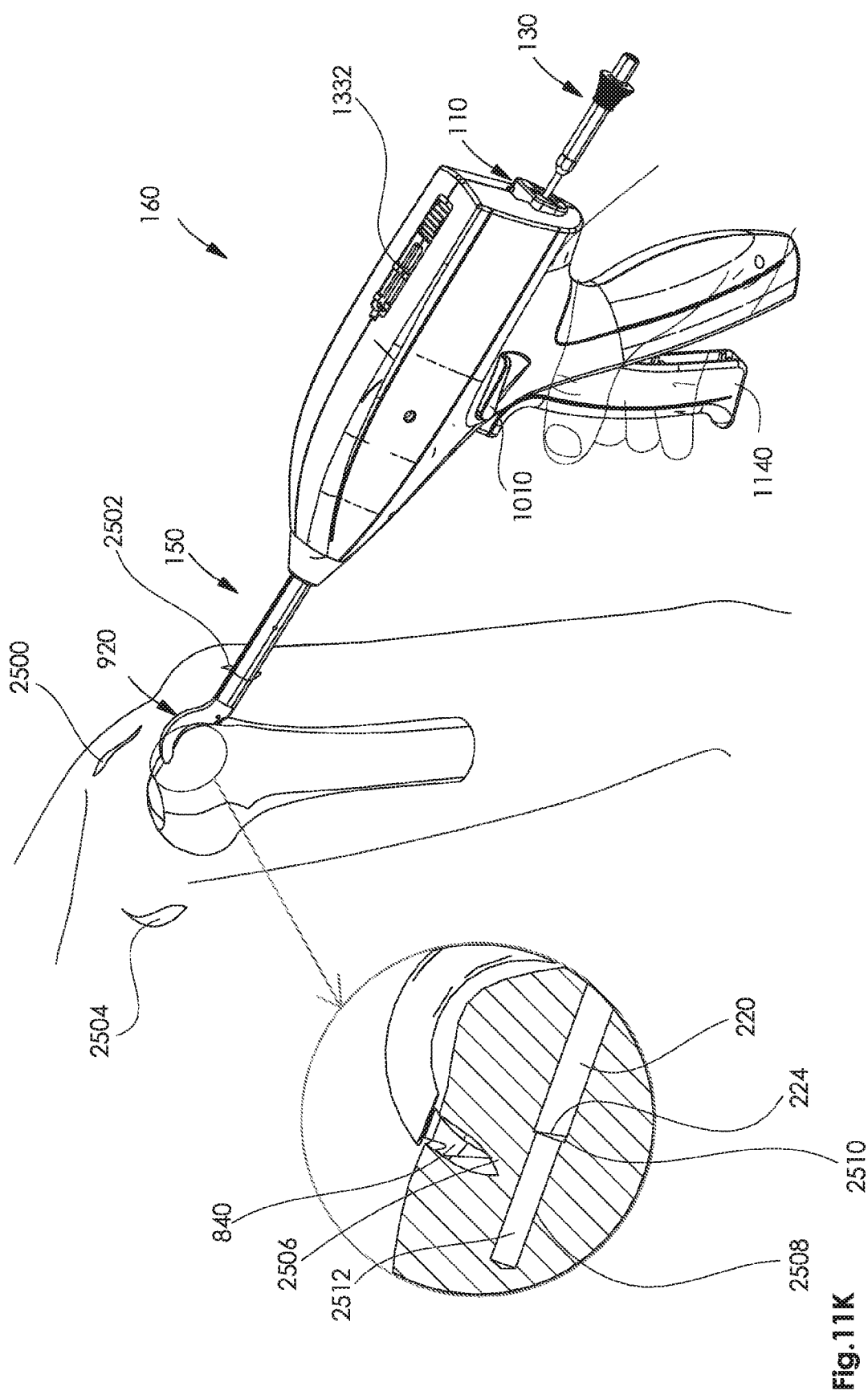

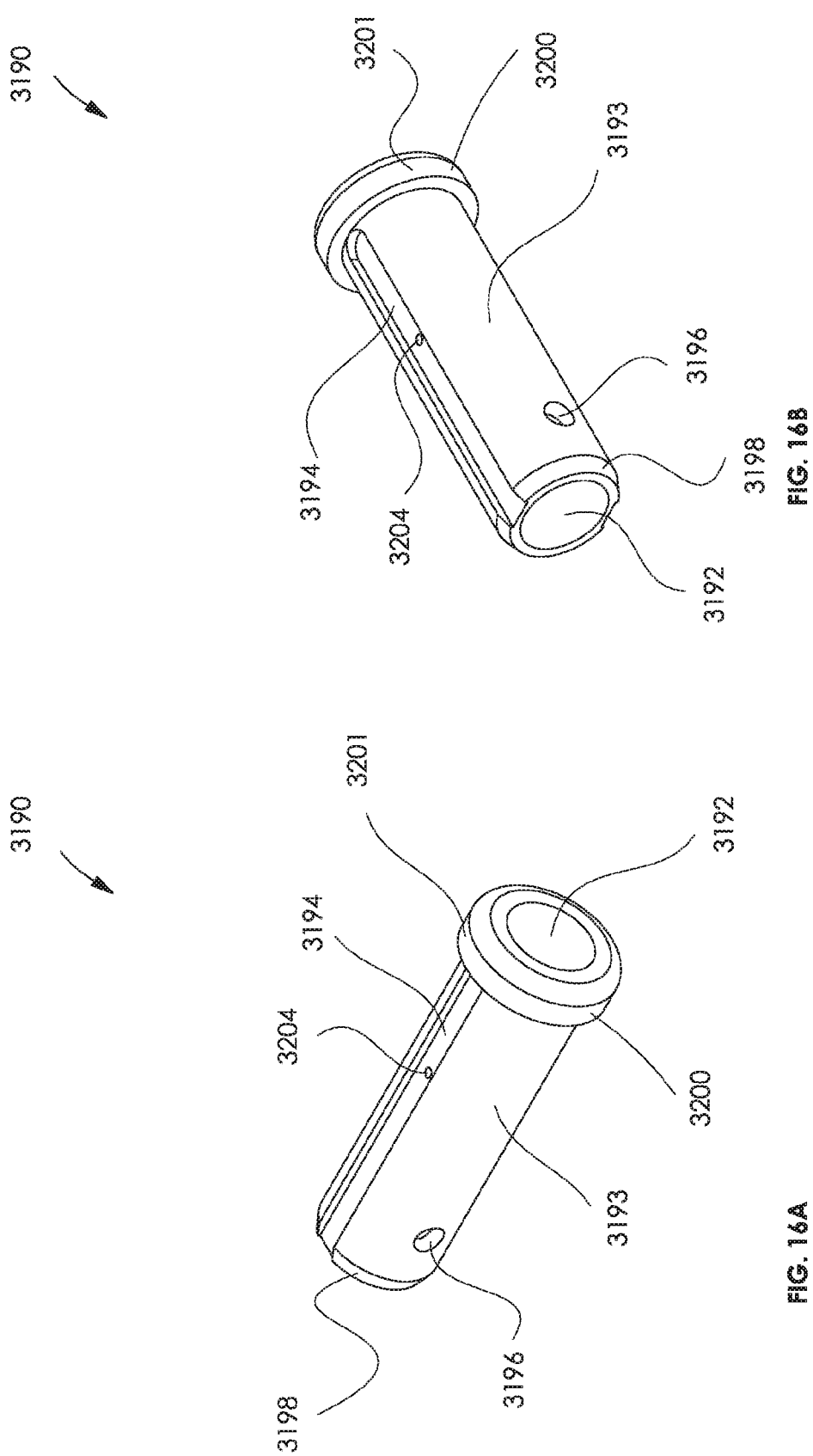

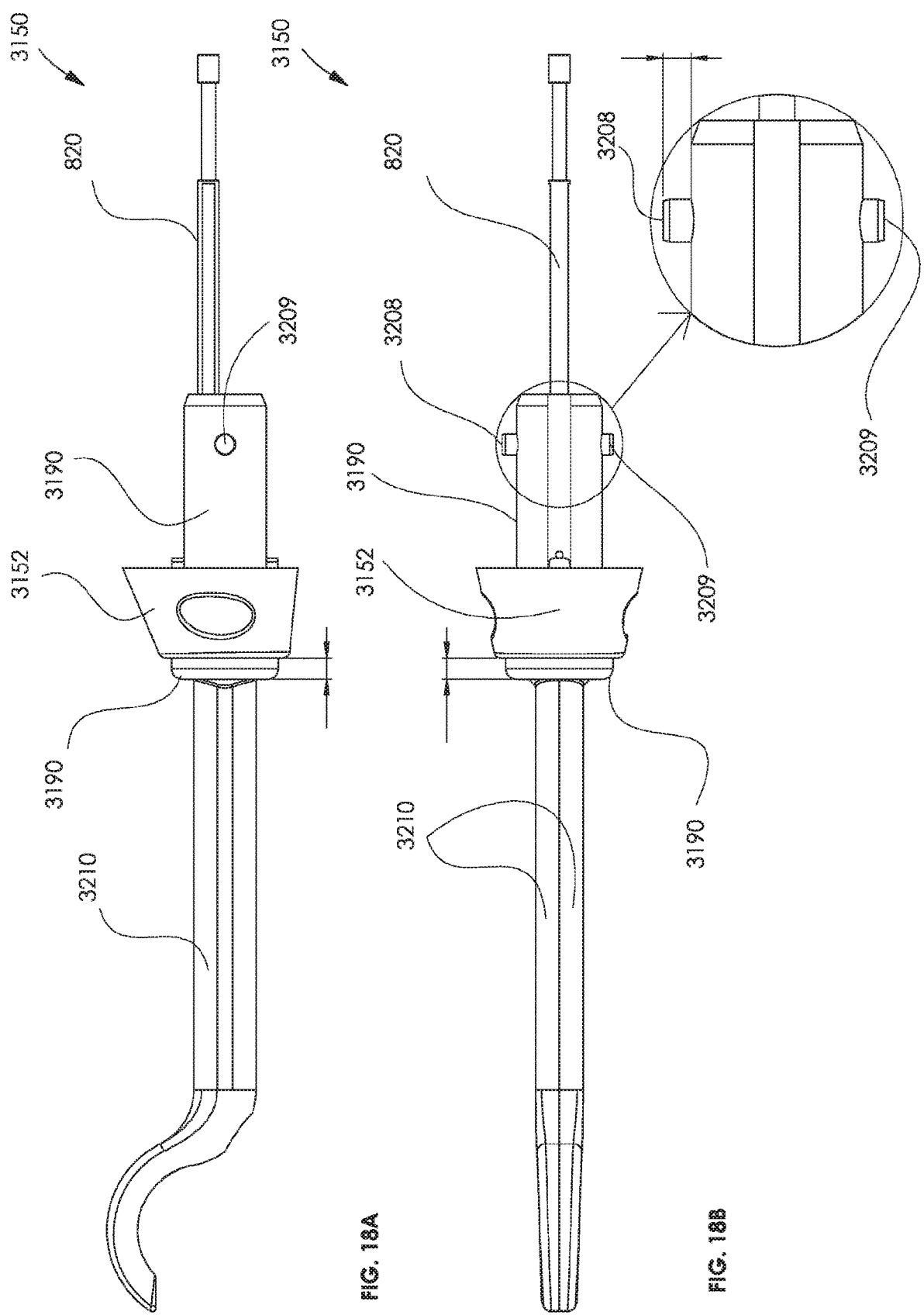

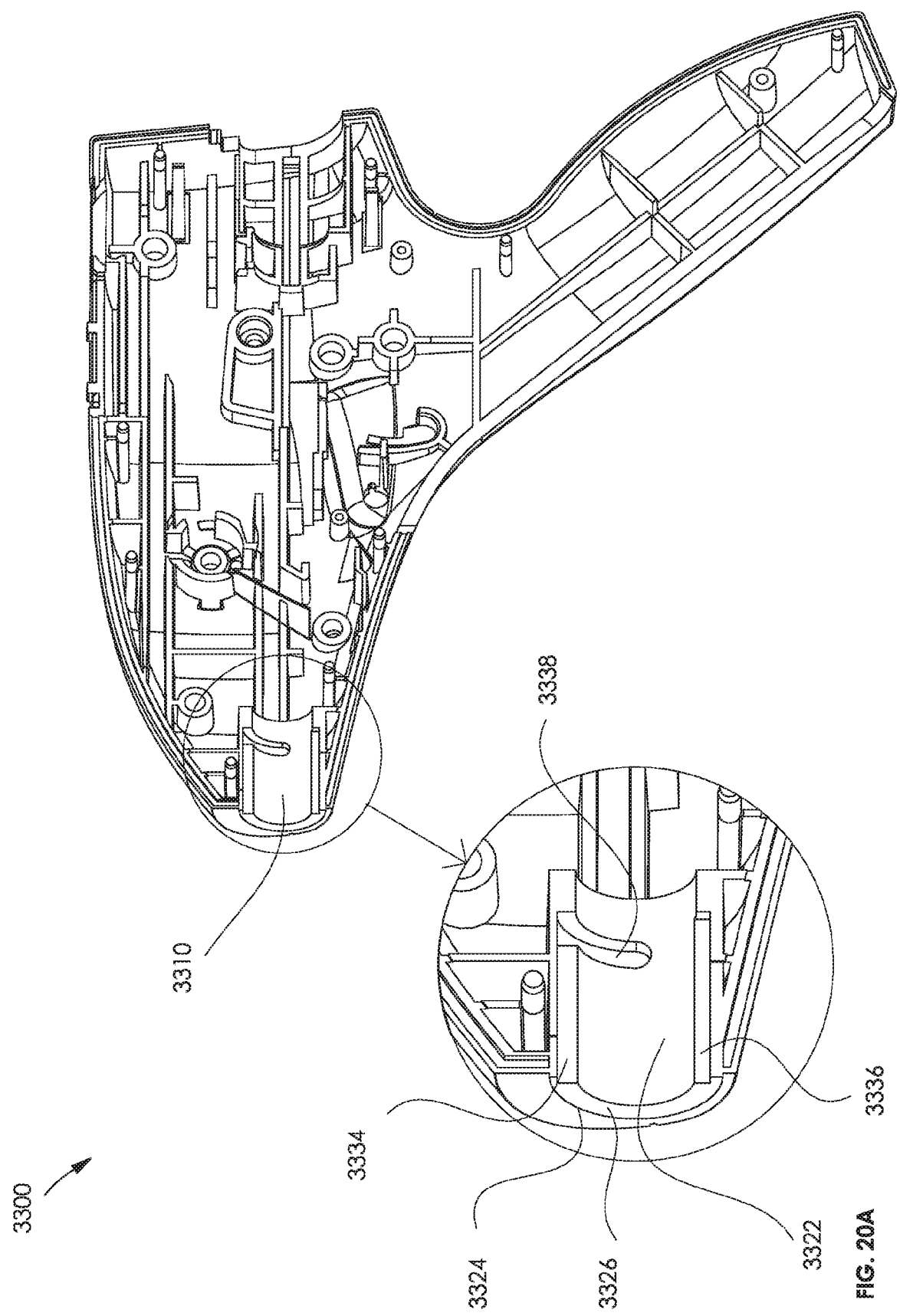

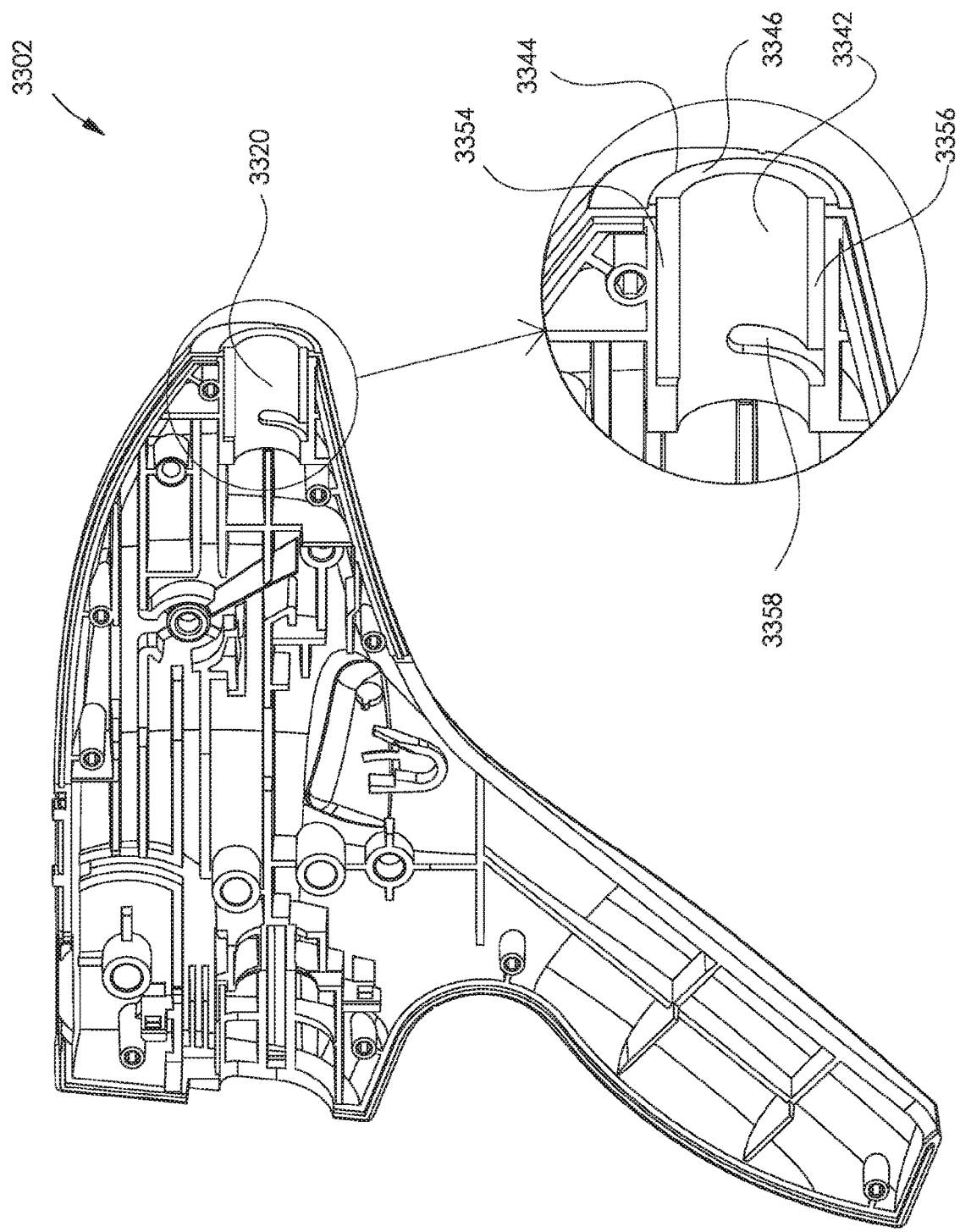

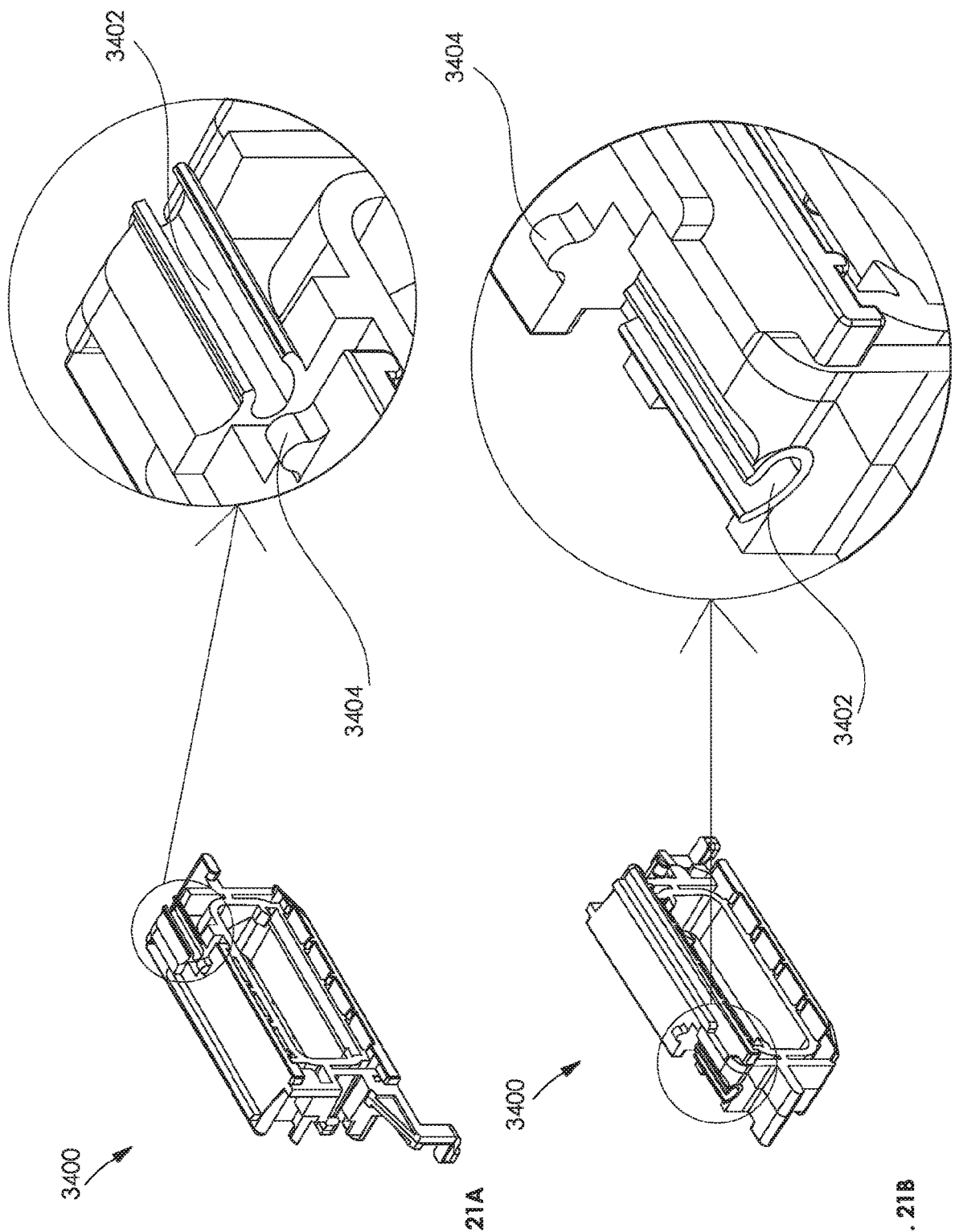

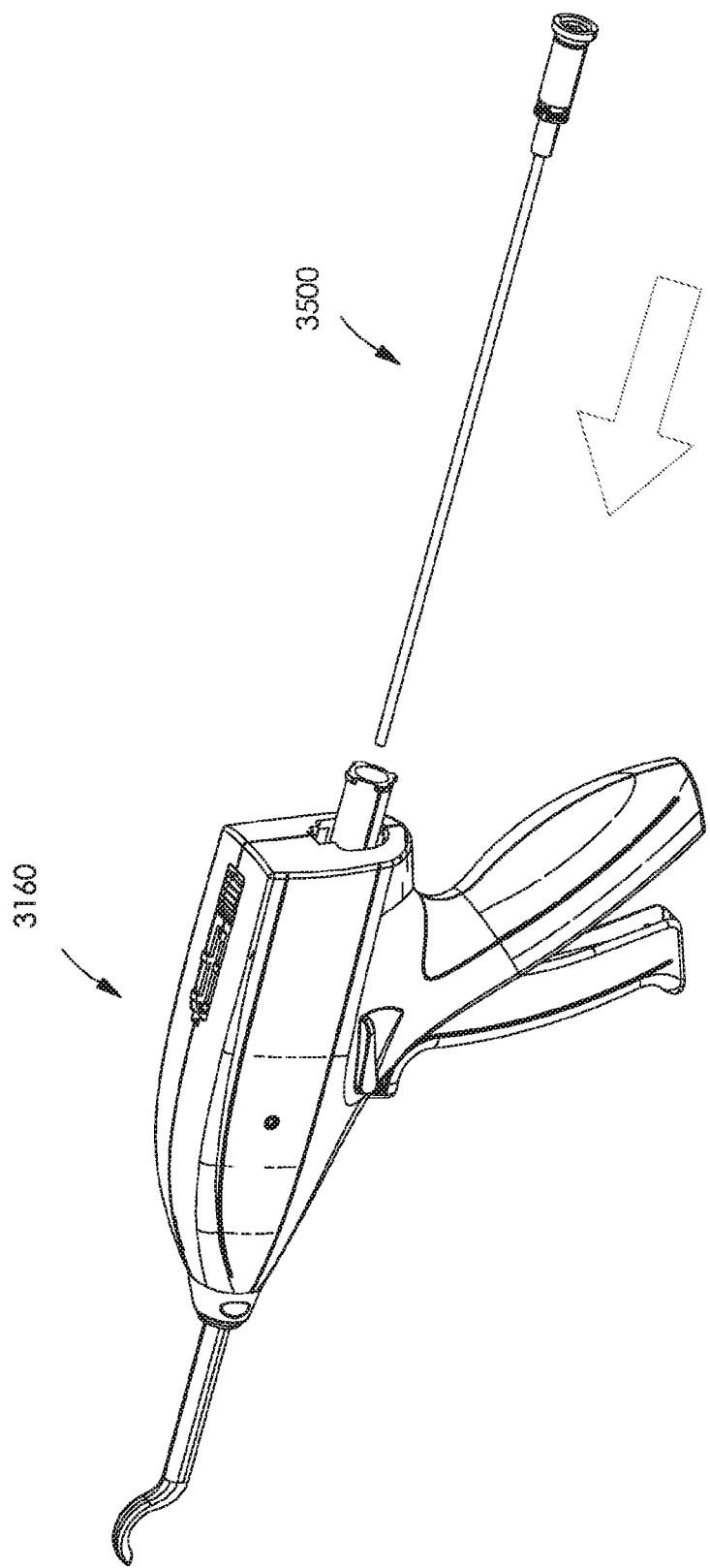

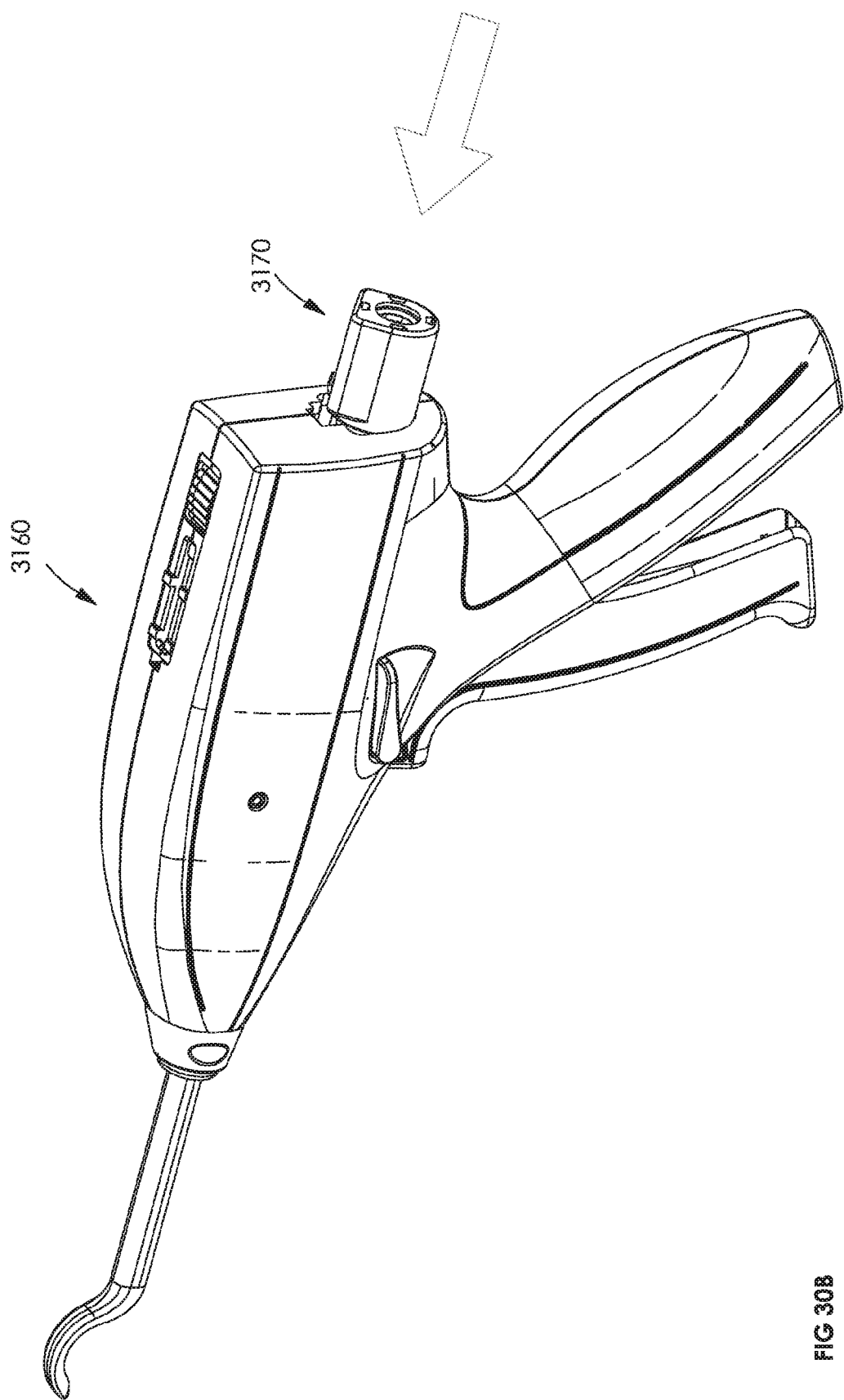

ARTHROSCOPIC SURGICAL DEVICE

REFERENCE TO RELATED APPLICATIONS

Reference is hereby made to U.S. Provisional Patent Application Ser. No. 62/273,632, filed Dec. 31, 2015 and entitled ARTHROSCOPIC SURGICAL DEVICE, the disclosure of which is hereby incorporated by reference and priority of which is hereby claimed pursuant to 37 C.F.R. 1.78(a)(1).

Reference is also made to the following PCT Patent Applications and U.S. Provisional Applications which are believed to be related to the present application, the contents of which are hereby incorporated by reference herein:

Published PCT Patent Application No. WO/2014/147619, entitled "Arthroscopic Surgical Device" and published Sep. 9, 2014;

Published PCT Patent Application No. WO/2013/102909, entitled "Arthroscopic Surgical Device" and published Jul. 11, 2013.

Published PCT Patent Application No. WO/2013/027209, entitled "Arthroscopic Surgical Device" and published Feb. 28, 2013.

Published PCT Patent Application No. WO/2013/027210, entitled "Circular Bone Tunneling Device Employing a Stabilizing Element" and published Feb. 28, 2013.

Published PCT Patent Application No. WO 2012/007941, entitled "Circular Bone Tunneling Device" and published Jul. 11, 2011;

U.S. Provisional Patent Application Ser. No. 61/802,958, entitled "Arthroscopic Surgical Device" and filed Mar. 18, 2013.

U.S. Provisional Patent Application Ser. No. 61/887,561, entitled "Arthroscopic Surgical Device" and filed Oct. 7, 2013.

U.S. Provisional Patent Application Ser. No. 61/636,751, entitled "Circular Bone Tunneling Device Employing a Stabilizing Element" and filed Apr. 23, 2012;

U.S. Provisional Patent Application Ser. No. 61/526,717, entitled "Circular Bone Tunneling Device" and filed Aug. 24, 2011;

U.S. Provisional Patent Application Ser. No. 61/714,813, entitled "Arthroscopic Surgical Device" and filed Oct. 17, 2012; and U.S. Provisional Patent Application Ser. No. 61/584,267, entitled "Circular Bone Tunneling Device" and filed Jan. 8, 2012.

Reference is also made to the PCT Patent Application PCT/112015/050978 filed Sep. 24, 2015 and entitled ARTHROSCOPIC SURGICAL DEVICE, which is believed to be related to the present application, the contents of which are hereby incorporated by reference herein.

FIELD OF THE INVENTION

The present invention relates generally to arthroscopic surgical devices and more particularly to arthroscopic bone tunneling devices.

BACKGROUND OF THE INVENTION

Various types of arthroscopic surgical instruments are known for various applications including orthopedic surgery.

SUMMARY OF THE INVENTION

It is appreciated that the terms 'tunnel' and 'channel' are used interchangeably in the description of the present invention and refer to a hollow bore, such as a cylindrically circular hollow bore, formed in a bone. It is also appreciated that the terms 'tunneling' and 'channeling' are used interchangeably in the description of the present invention and refer to a method of forming a hollow bore, such as a cylindrically circular hollow bore, in a bone.

It is further appreciated that the term "suture" as used throughout the description of the present invention refers to any suitable suture and also refers to a transfer wire which is used to pull a suture through the bone and that use of the term "snare wire" as used throughout the description of the present invention refers to either a transfer wire or a suture. Typically, a transfer wire is used with the system and method of the present invention and is formed of Nitinol. Typically, a transfer wire used with the system and method of the present invention is folded over to form a loop at one end.

It is yet further appreciated that the term "hexagonal wrench" as used throughout the description of the present invention refers to any suitable wrench with an hexagonal longitudinal shape, usually formed in a "L" shape. Hexagonal wrenches are also sometimes referred to as Allen wrenches or hexagonal keys.

The present invention seeks to provide an improved arthroscopic bone tunneling and suturing device.

There is thus provided in accordance with a preferred embodiment of the present invention an arthroscopic bone channel forming and suturing system useful with a punch configured to form a first generally straight channel in a bone and a drill configured to form a second generally straight channel in the bone, the second generally straight channel not intersecting the first generally straight channel, the system including a curved bone puncture needle configured to be insertable into the first generally straight channel, a curved needle driving assembly configured to manipulate the curved needle to form a curved junction between the first generally straight channel and the second generally straight channel, a suture snare wire assembly configured to insert a suture snare wire to a suture snare wire pick-up location via the second generally straight channel in the bone and a coordinated multi-function driving assembly operative to operate the curved needle driving assembly and the suture snare wire assembly in coordinated operation to cause the suture snare wire to be pulled from the suture pick up location and through the first generally straight channel via the junction.

Preferably, the coordinated multi-function driving assembly operates automatically in response to repeated manual actuations. Additionally or alternatively, the coordinated multi-function driving assembly includes an override sub-assembly which is selectably operative to withdraw the curved needle after the curved needle has begun to be inserted into the first generally straight channel but before the curved needle begins to pull the suture through the junction.

In accordance with a preferred embodiment of the present invention the arthroscopic bone channel forming and suturing system also includes an arthroscopic surgical device, a work channel assembly, a snare wire cartridge assembly and a curved shaft assembly. Additionally or alternatively, the arthroscopic bone channel forming and suturing system also includes at least one of a bone punch assembly, a quick connection element, a drill bit assembly and a manual override gear shifter.

Preferably, the work channel assembly includes a hollow elongate tube, a work channel hub, a rack-defining intermediate element in which the work channel hub is at least partially seated and a retaining cap element, the hollow elongate tube extending along a longitudinal axis and having an inclined forward edge and a rearward end fixedly mounted within a socket formed in the work channel hub. Additionally, the work channel hub is an integrally formed element including a forward socket-defining portion having a transverse bore, a main cylindrical portion disposed rearwardly of the forward socket-defining portion and an axial central bore and a flange disposed at a rear end.

In accordance with a preferred embodiment of the present invention the rack-defining intermediate element includes a main cylindrical portion formed with an axial bore which extends along a longitudinal axis and a linear ratchet gear rack. Additionally or alternatively, the snare wire cartridge assembly includes a main housing portion, a secondary housing portion, an elongate hollow shaft, which is mounted onto the main and secondary housing portions, a compression spring mounted over the elongate hollow shaft, a tension spring mounted within the main housing portion, a snare wire winding drum located within the main housing portion and having circularly symmetric array of gear teeth, a folded over length of snare wire, which defines a pre-formed loop and is partially located within the elongate hollow, with the with loop being located at a forward end of the elongate hollow shaft and partially wound about the snare wire winding drum and a snare wire tensioning element, cooperating with the snare wire winding drum.

In accordance with a preferred embodiment of the present invention the tensioning element includes a disc portion having a central aperture and a spring engaging protrusion which defines an inclined spring engaging surface and an abutment engaging surface and a flexible ratchet gear engaging portion, extending radially outwardly from the disc portion generally in a direction opposite to the spring engaging protrusion and including a curved linear array of gear teeth that are configured for ratchet-like engagement with the circularly symmetric array of gear teeth of the snare wire winding drum. Additionally, pulling of the snare wire, which is wound under tension on the snare wire winding drum rotates the snare wire winding drum against the urging of a spring until the snare wire winding drum can no longer rotate due to engagement of an abutment engaging surface of the spring engaging protrusion with an abutment of the main housing portion, whereby continued pulling on the snare wire enables the snare wire to be freely unwound from the snare wire winding drum and drawn forwardly through the elongate hollow shaft.

Preferably, the curved shaft assembly includes a pair of curved shaft assembly outer elements, a pair of curved shaft assembly inner elements and a curved shaft assembly location ring which engages corresponding ends of the pair of curved shaft assembly inner elements and is retained at a fixed axial location within the arthroscopic surgical device and provides axial adjustability of the position of the curved shaft assembly relative to the arthroscopic surgical device.

In accordance with a preferred embodiment of the present invention the curved bone puncture needle is formed to have a radially inward-facing generally curved edge surface which extends from a slightly rounded back end surface to a tapered tip, a rearward radially outward-facing generally curved surface portion which extends from a generally non-rounded corner at a back end surface to a top protrusion and therebeyond to a shoulder from which extends a forward radially outward-facing generally curved surface portion and a pair of curved side surfaces each including a tapered tip side surface.

Preferably, the arthroscopic surgical device includes first and second housing portions, an arthroscopic surgical mechanism enclosed by the first and second housing portions, a driving direction selector lever and a retaining cone, which is operative for retaining the first and second housing portions together over and in engagement with the curved shaft assembly. Additionally, the arthroscopic surgical mechanism includes the following elements, which are operative for retraction of the work channel assembly: a ratchet gear defining driving surfaces on each of a multiplicity of gear teeth, which, in turn, engage a linear ratchet gear track forming part of the work channel assembly, axle-mounted gear, which is preferably integrally formed and includes a cylindrical axle onto a first end of which is mounted the ratchet gear, a rotation urging spring having a coil a pair of spring end arms and a work channel assembly retaining hook element, which selectably locks and releases the work channel assembly with respect to the arthroscopic surgical device.

In accordance with a preferred embodiment of the present invention driving direction selector lever has rearwardly and forwardly-tilted operative orientations.

In accordance with preferred embodiment of the present invention the arthroscopic surgical mechanism also includes a cartridge assembly retaining element, a cartridge assembly retaining spring which defines a retaining arm and a manually actuable driving engine assembly. Additionally, the manually actuable driving engine assembly includes at least five of the following elements: a main chassis, an auxiliary chassis, a cartridge pusher, a cartridge pusher connector, a hand-engageable driving handle, a main driving direction shifting element, a shiftable element, a driving direction selector lever responsive toggle element, a direction-shifting spring, a rearward driving gear rack, a forward driving gear rack, a clutch, a main driving gear, a needle driving ratchet arm, a forward driving gear, a work channel retracting ratchet arm, a pivotable arm and a shiftable link. Additionally or alternatively, the manually actuable driving engine assembly includes at least one of the following elements: a driving handle spring, a main driving direction shifting element spring, a handle pivot axle, a driving pin and a ratchet arm urging spring.

In accordance with a preferred embodiment of the present invention disengagement of the cartridge assembly retaining element produces immediate partial axial retraction of the snare wire cartridge assembly from the work channel assembly.

Preferably, the coordinated multi-function driving assembly defines a main driving axis and includes a hand engageable driving handle portion, which is angled with respect to the main driving axis of between 120 and 140 degrees. Additionally or alternatively, the coordinated multi-function driving assembly defines a main driving axis and includes a hand engageable, driving handle portion, which is angled with respect to the main driving axis of 132.5 degrees.

In accordance with a preferred embodiment of the present invention the work channel assembly includes a hollow elongate tube and a work channel hub, the hollow elongate tube extending along a longitudinal axis and having an inclined forward edge and a rearward end fixedly mounted within a socket formed in the work channel hub. Additionally, the work channel assembly also includes a rack-defining intermediate element including a main cylindrical portion formed with an axial bore which extends along a longitudinal axis and a linear ratchet gear rack.

In accordance with a preferred embodiment of the present invention the curved shaft assembly includes a pair of curved shaft assembly elements, a generally conical mounting portion, a compression spring and a generally hollow cylindrical element.

Preferably, the arthroscopic surgical device includes first and second housing portions, an arthroscopic surgical mechanism enclosed by the first and second housing portions, a driving direction selector lever and a detachably retaining cone, which is operative for detachably retaining the first and second housing portions together over and in engagement with the curved shaft assembly.

There is also provided in accordance with another preferred embodiment of the present invention a snare wire cartridge assembly including a main housing portion, a secondary housing portion, an elongate hollow shaft, which is mounted onto the main and secondary housing portions, a compression spring mounted over the elongate hollow shaft, a tension spring mounted within the main housing portion, a snare wire winding drum located within the main housing portion and having circularly symmetric array of gear teeth, a folded over length of snare wire, which defines a pre-formed loop and is partially located within the elongate hollow, with the with loop being located at a forward end of the elongate hollow shaft and partially wound about the snare wire winding drum and a snare wire tensioning element, cooperating with the snare wire winding drum.

Preferably, the tensioning element includes a disc portion having a central aperture and a spring engaging protrusion which defines an inclined spring engaging surface and an abutment engaging surface and a flexible ratchet gear engaging portion, extending radially outwardly from the disc portion generally in a direction opposite to the spring engaging protrusion and including a curved linear array of gear teeth that are configured for ratchet-like engagement with the circularly symmetric array of gear teeth of the snare wire winding drum.

In accordance with a preferred embodiment of the present invention pulling of the snare wire, which is wound under tension on the snare wire winding drum rotates the snare wire winding drum against the urging of a spring until the snare wire winding drum can no longer rotate due to engagement of an abutment engaging surface of the spring engaging protrusion with an abutment of the main housing portion, whereby continued pulling on the snare wire enables the snare wire to be freely unwound from the snare wire winding drum and drawn forwardly through the elongate hollow shaft.

There is further provided in accordance with yet another preferred embodiment of the present invention a curved shaft assembly including a pair of curved shaft assembly outer elements, a pair of curved shaft assembly inner elements and a curved shaft assembly location ring which engages corresponding ends of the pair of curved shaft assembly inner elements and is retained at a fixed axial location within an arthroscopic surgical device and provides axial adjustability of the position of the curved shaft assembly relative to the arthroscopic surgical device.

Preferably, the outer elements are formed of metal and the inner elements are formed of plastic.

There is even further provided in accordance with still another preferred embodiment of the present invention a curved bone puncture needle including a radially inward-facing generally curved edge surface which extends from a slightly rounded back end surface to a tapered tip, a rearward radially outward-facing generally curved surface portion which extends from a generally non-rounded corner at a back end surface to a top protrusion and therebeyond to a shoulder from which extends a forward radially outward-facing generally curved surface portion and a pair of curved side surfaces each including a tapered tip side surface.

There is still further provided in accordance with yet another preferred embodiment of the present invention an arthroscopic surgical device including first and second housing portions, an arthroscopic surgical mechanism enclosed by the first and second housing portions, a driving direction selector lever and a retaining cone, which is operative for retaining the first and second housing portions together over and in engagement with the curved shaft assembly.

Preferably, the arthroscopic surgical mechanism includes the following elements which are operative for retraction of a work channel assembly a ratchet gear defining driving surfaces on each of a multiplicity of gear teeth, which, in turn, engage a linear ratchet gear track forming part of the work channel assembly, axle-mounted gear, which is preferably integrally formed and includes a cylindrical axle onto a first end of which is mounted the ratchet gear, a rotation urging spring having a coil a pair of spring end arms and a work channel assembly retaining hook element, which selectably locks and releases the work channel assembly with respect to the arthroscopic surgical device.

In accordance with a preferred embodiment of the present invention the arthroscopic surgical mechanism also includes a cartridge assembly retaining element, a cartridge assembly retaining spring which defines a retaining arm; and a manually actuable driving engine assembly.

There is also provided in accordance with still another preferred embodiment of the present invention an arthroscopic surgical device including a housing defining a main driving axis and including a hand engageable driving handle portion, which is angled with respect to the main driving axis at an angle of between 120 and 140 degrees.

Preferably, the hand engageable driving handle portion is angled with respect to the main driving axis at an angle of 132.5 degrees.

There is further provided in accordance with another preferred embodiment of the present invention an arthroscopic bone channel forming and suturing method useful following formation of a first generally straight channel and a second generally straight channel in a bone, the second generally straight channel not intersecting the first generally straight channel, the method including inserting a curved bone puncture needle into the first generally straight channel, manipulating the curved needle to form a curved junction between the first generally straight channel and the second generally straight channel, inserting a suture snare wire to a suture snare wire pick-up location via the second generally straight channel in the bone and causing the suture snare wire to be pulled from the suture pick up location and through the first generally straight channel via the junction.

Preferably, the causing step operates in response to repeated manual actuations. Additionally or alternatively, the arthroscopic bone channel forming and suturing method also includes withdrawing the curved needle after the curved needle has begun to be inserted into the first generally straight channel but before the curved needle begins to pull the suture through the junction.

There is yet further provided in accordance with still another preferred embodiment of the present invention a detachable curved shaft assembly including a pair of curved shaft assembly elements, a generally conical mounting portion, a compression spring and a generally hollow cylindrical element.

BRIEF DESCRIPTION OF THE DRAWINGS

The present invention will be understood and appreciated from the following detailed description, taken in conjunction with the drawings in which:

FIGS. 3C, 3D, 3E & 3F are respectively a forwardly-facing pictorial illustration; a rearwardly-facing pictorial illustration, a side view illustration and a forwardly-facing rear end view illustration of a work channel hub, forming part of the work channel assembly of FIGS. 3A & 3B;

FIGS. 3G, 3H, 3I & 3J are respectively a forwardly-facing pictorial illustration; a rearwardly-facing pictorial illustration, a side view illustration and a forwardly-facing rear end view illustration of a rack-defining intermediate element, forming part of the work channel assembly of FIGS. 3A & 3B;

FIGS. 4A, 4B, 4C & 4D are simplified illustrations of a quick connection element forming part of the arthroscopic surgical assembly of FIGS. 1A & 1B;

FIGS. 6E, 6F, 6G & 6H are simplified respective interior plan view, first and second interior pictorial view and rearward facing end view illustrations of a main housing portion of the snare wire cartridge assembly;

FIGS. 6I, 6J, 6K & 6L are simplified respective interior plan view, first and second interior pictorial view and rearward facing end view illustrations of a secondary housing portion of the snare wire cartridge assembly;

FIGS. 6Q & 6R are simplified first and second interior pictorial view illustrations of a tensioning element cooperating with the snare wire winding drum;

FIGS. 7A, 7B, 7C, 7D, 7E, 7F, 7G, 7H, 7I, 7J, 7K, 7L, 7M, 7N, 7O & 7P are simplified illustrations of a curved shaft assembly forming part of the arthroscopic surgical assembly of FIGS. 1A & 1B;

FIGS. 8A, 8B, 8C, 8D, 8E, 8F, 8G, 8H, 8I, 8J, 8K, 8L, 8M, 8N, 8O, 8P, 8Q, 8R, 8S, 8T, 8U, 8V, 8W, 8X, 8Y, 8Z, 8AA, 8AB, 8AC, 8AD, 8AE, 8AF, 8AG, 8AH, 8AI, 8AJ, 8AK, 8AL, 8AM, 8AN, 8AO, 8AP, 8AQ, 8AR, 8AS, 8AT, 8AU, 8AV, 8AW, 8AX, 8AY, 8AZ, 8BA, 8BB, 8BC, 8BD, 8BE, 8BF, 8BG, 8BH, 8BI, 8BJ, 8BK, 8BL, 8BM, 8BN, 8BO, 8BP, 8BQ, 8BR, 8BS, 8BT, & 8BU are simplified illustrations of the arthroscopic surgical device forming part of the arthroscopic surgical assembly of FIGS. 1A & 1B;

FIGS. 9A, 9B & 9C are simplified respective top view, side view and bottom view illustrations of a manual override element useful in the operation of the arthroscopic surgical assembly of FIGS. 1A & 1B;

FIGS. 10A, 10B, 10C, 10D, 10E, 10F, 10G, 10H, 10I, 10J, 10K, 10L, 10M, 10N, 10O, 10P, 10Q, 10R, 10S, 10T, 10U, 10V, 10W, 10X, 10Y, 10Z, 10AA, 10AB, 10AC, 10AD, 10AE, 10AF, 10AG, 10AH, 10AI, 10AJ, 10AK, 10AL, 10AM & 10AN are simplified illustrations of details of the operation of the arthroscopic surgical assembly of FIGS. 1A-9F;

FIGS. 11A, 11B, 11C, 11D,11E, 11F, 11G, 11H, 11I, 11J, 11K, 11L, 11M, 11N, 11O, 11P, 11Q, 11R, 11S & 11T are simplified illustrations of operation of the arthroscopic surgical device of FIGS. 1A-10AN in a clinical context;

FIGS. 16A & 16B are simplified opposite view illustrations of a hollow generally cylindrical guide element forming part of the curved shaft assembly of FIGS. 15A-15D;

FIGS. 18A and 18B are simplified side view illustrations of the curved shaft assembly of FIGS. 15A-15F in a first operative orientation, showing opposite views;

FIGS. 20A & 20B are simplified illustrations of part of the arthroscopic surgical device forming part of the arthroscopic surgical assembly of FIGS. 1A & 1B showing opposite facing views and corresponding to FIGS. 8BP, 8BQ and 8BR and FIGS. 8BS, 8BT and 8BU respectively;

FIGS. 21A & 21B are simplified illustrations of the main chassis, forming part of the arthroscopic surgical assembly of FIGS. 1A & 1B and showing opposite facing views and corresponding to FIG. 8T;

FIGS. 27A & 27B are simplified illustrations of the arthroscopic surgical assembly of FIGS. 12A-26B in a sixth operative orientation, showing opposite facing views;

FIGS. 28A & 289 are simplified illustrations of the arthroscopic surgical assembly of FIGS. 12A-27B in a seventh operative orientation, showing opposite facing views;

FIGS. 30A & 30B are simplified illustrations of the arthroscopic surgical assembly of FIGS. 12A-29B in a ninth operative orientation, showing opposite facing views.

DETAILED DESCRIPTION OF PREFERRED EMBODIMENTS

It is appreciated that the terms 'tunnel' and 'channel' are used interchangeably in the description of the present invention and refer to a hollow bore, such as a cylindrically circular hollow bore, formed in a bone. It is also appreciated that the terms 'tunneling' and 'channeling' are used interchangeably in the description of the present invention and refer to a method of forming a hollow bore, such as a cylindrically circular hollow bore, in a bone.

It is further appreciated that the term "suture" as used throughout the description of the present invention refers to any suitable suture and also refers to a transfer wire which is used to pull a suture through the bone and that use of the term "snare wire" as used throughout the description of the present invention refers to either a transfer wire or a suture. Typically, a snare wire is used with the system and method of the present invention and is formed of Nitinol. Typically, a snare wire used with the system and method of the present invention is folded over to form a loop at one end thereof.

Figure 1A:
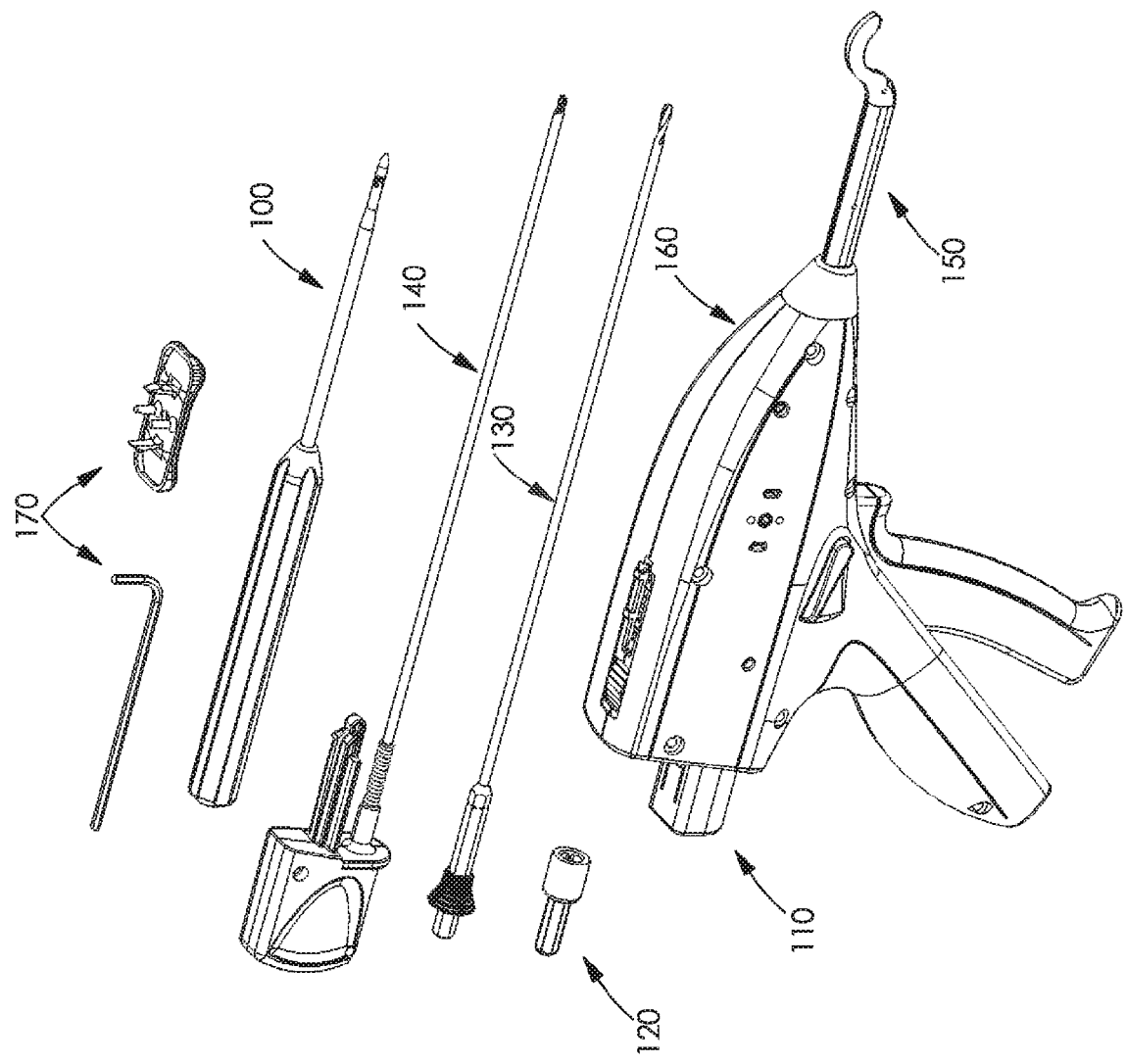
FIGS. 1A & 1B are simplified pictorial illustrations of an arthroscopic surgical assembly constructed and operative in accordance with a preferred embodiment of the present invention, showing opposite views.

Reference is now made to FIGS. 1A & 1B, which are simplified pictorial illustrations of an arthroscopic surgical assembly, constructed and operative in accordance with a preferred embodiment of the present invention, showing opposite views, and to various additional drawings which are specifically referenced hereinbelow.

Figures 2A, 2B:
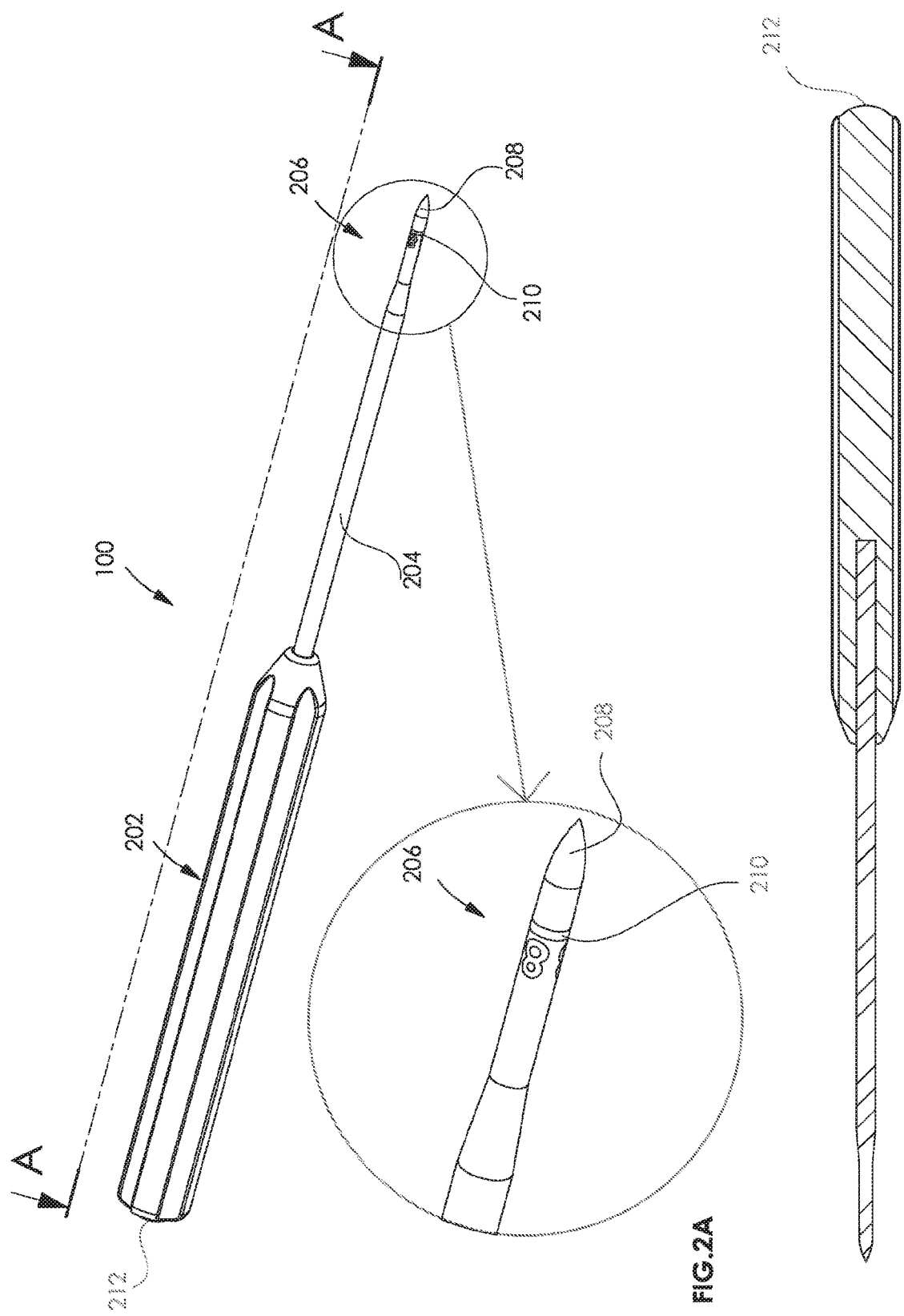
FIGS. 2A & 2B are simplified illustrations of a punch assembly forming part of the arthroscopic surgical assembly of FIGS. 1A & 1B.
Figure 3A:
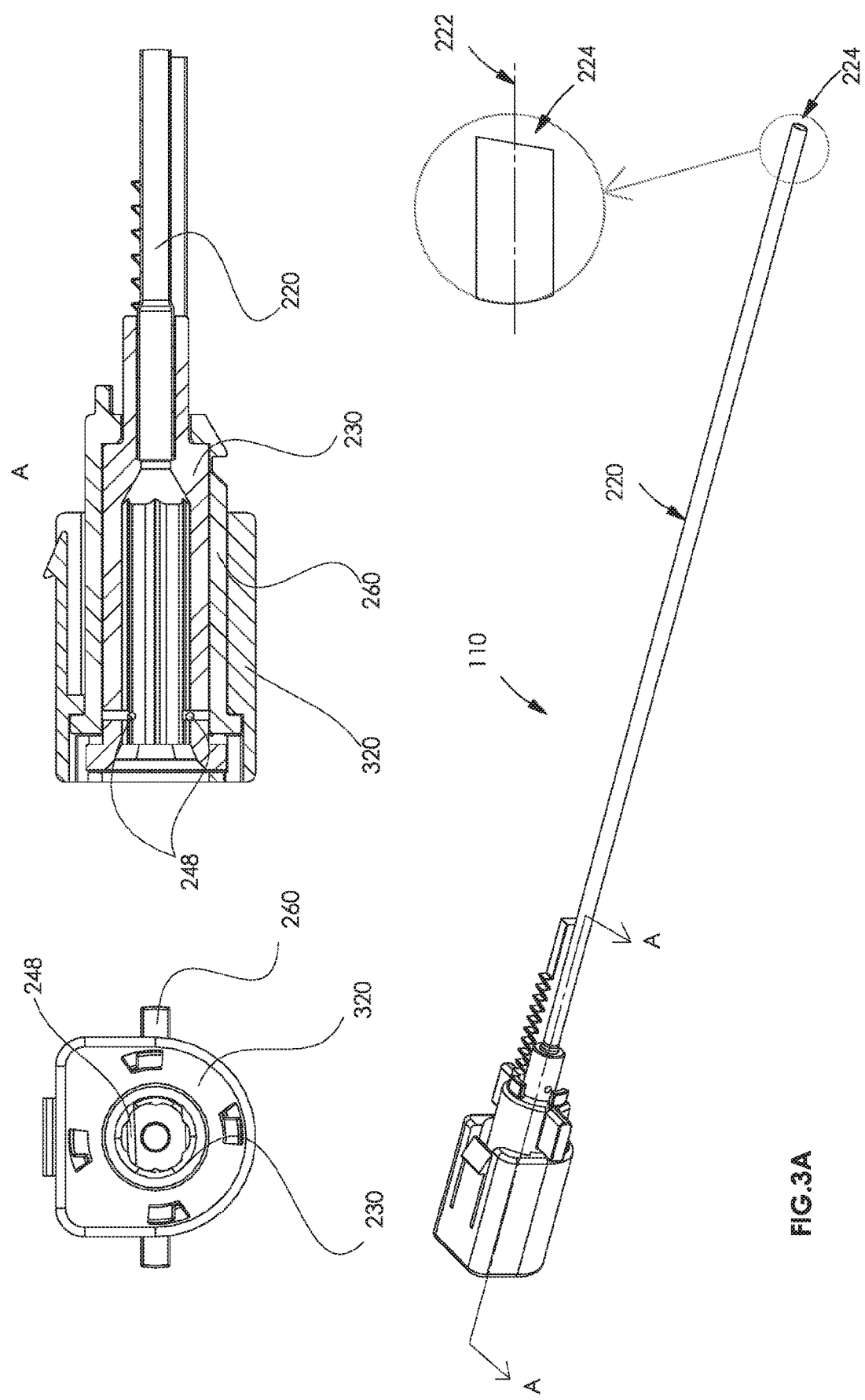
FIGS. 3A & 3B are simplified illustrations of a work channel assembly forming part of the arthroscopic surgical assembly of FIGS. 1A & 1B.
Figure 3B:
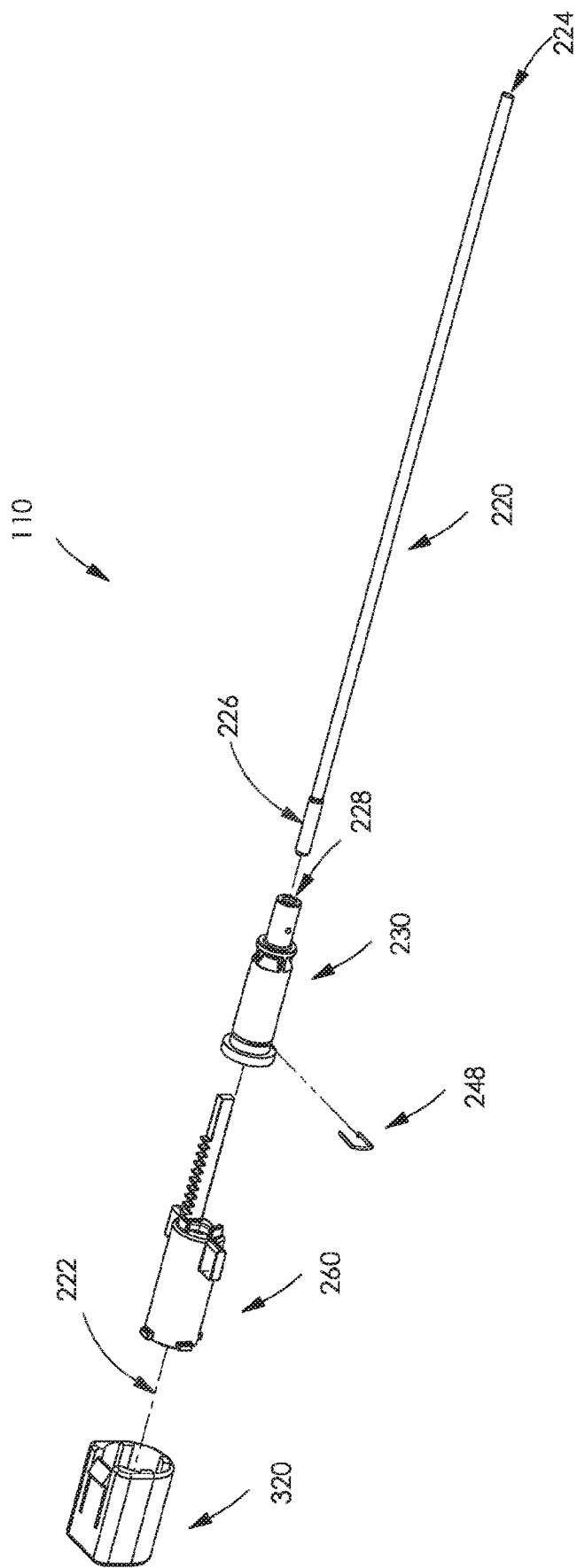
Figure 3K:
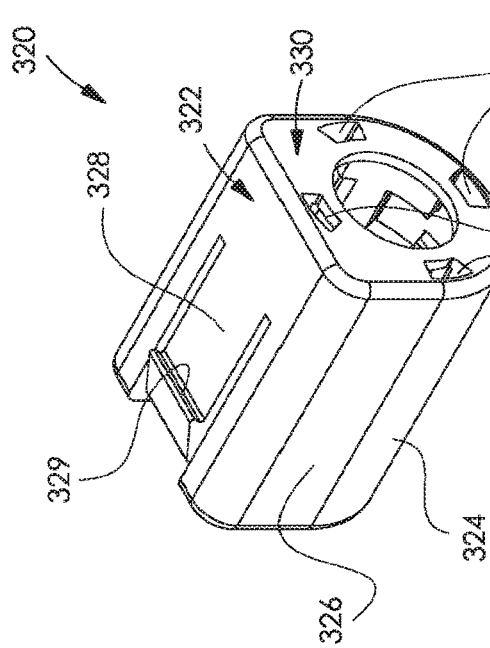
FIGS. 3K, 3L, 3M, 3N, 3O & 3P are respectively a forwardly-facing pictorial illustration; a top rearwardly-facing pictorial illustration, a bottom rearwardly-facing pictorial illustration, a rearwardly-facing front end view illustration, and first and second interior side view illustrations of a retaining cap element, forming part of the work channel assembly of FIGS. 3A & 3B.
Figure 3L:
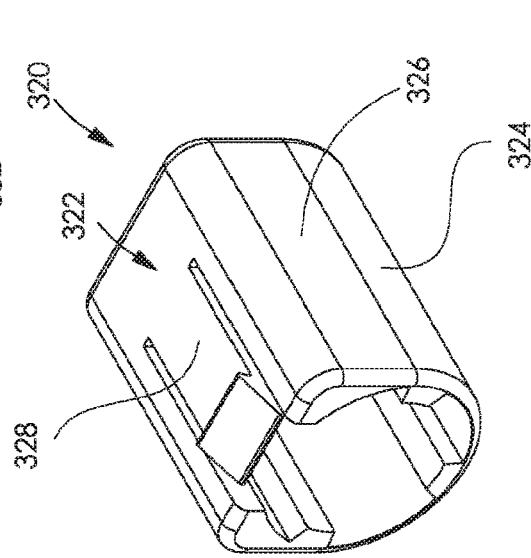
Figure 5A:
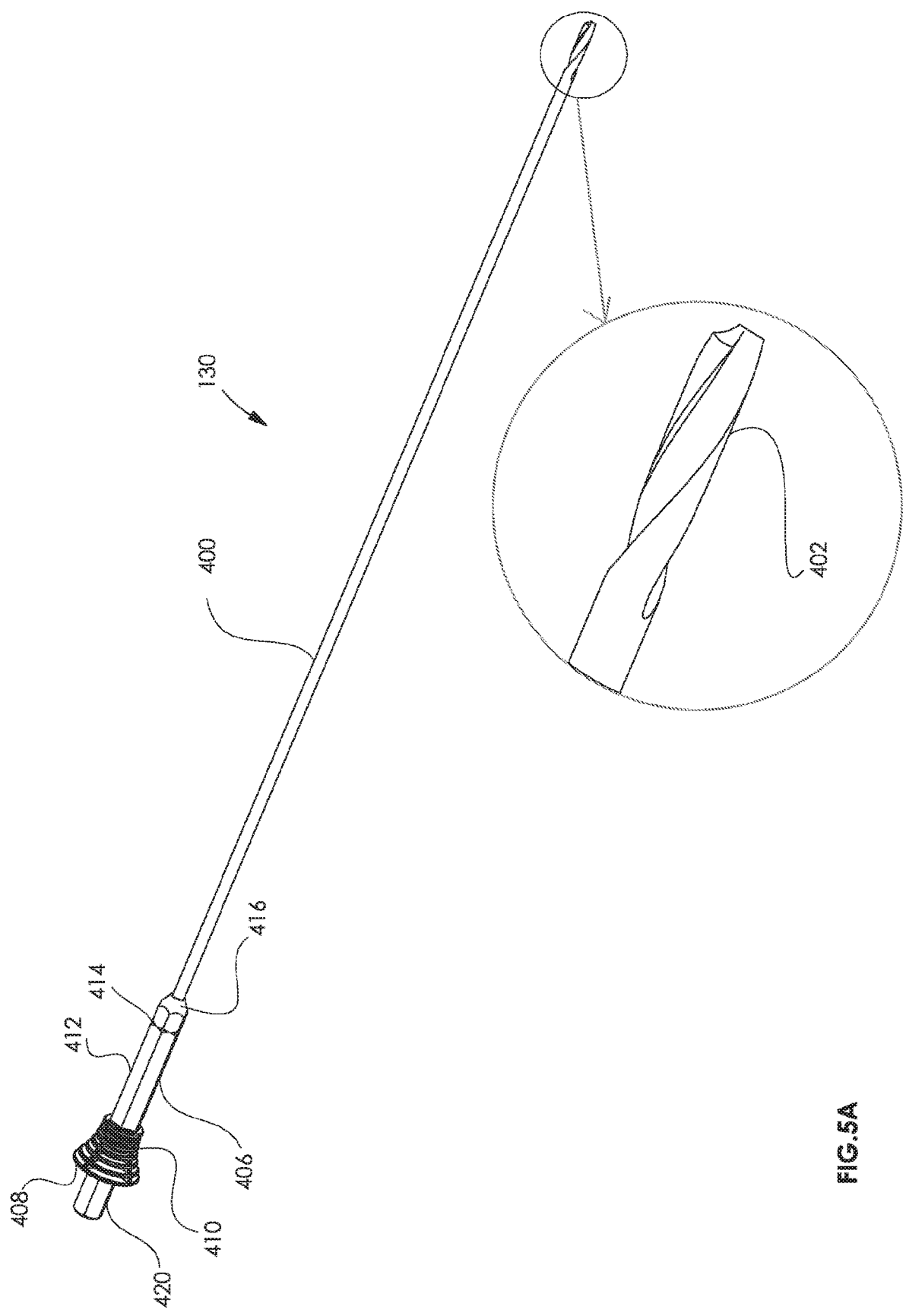
FIGS. 5A & 5B are simplified illustrations of a drill bit assembly forming part of the arthroscopic surgical assembly of FIGS. 1A & 1B.
Figure 5B:
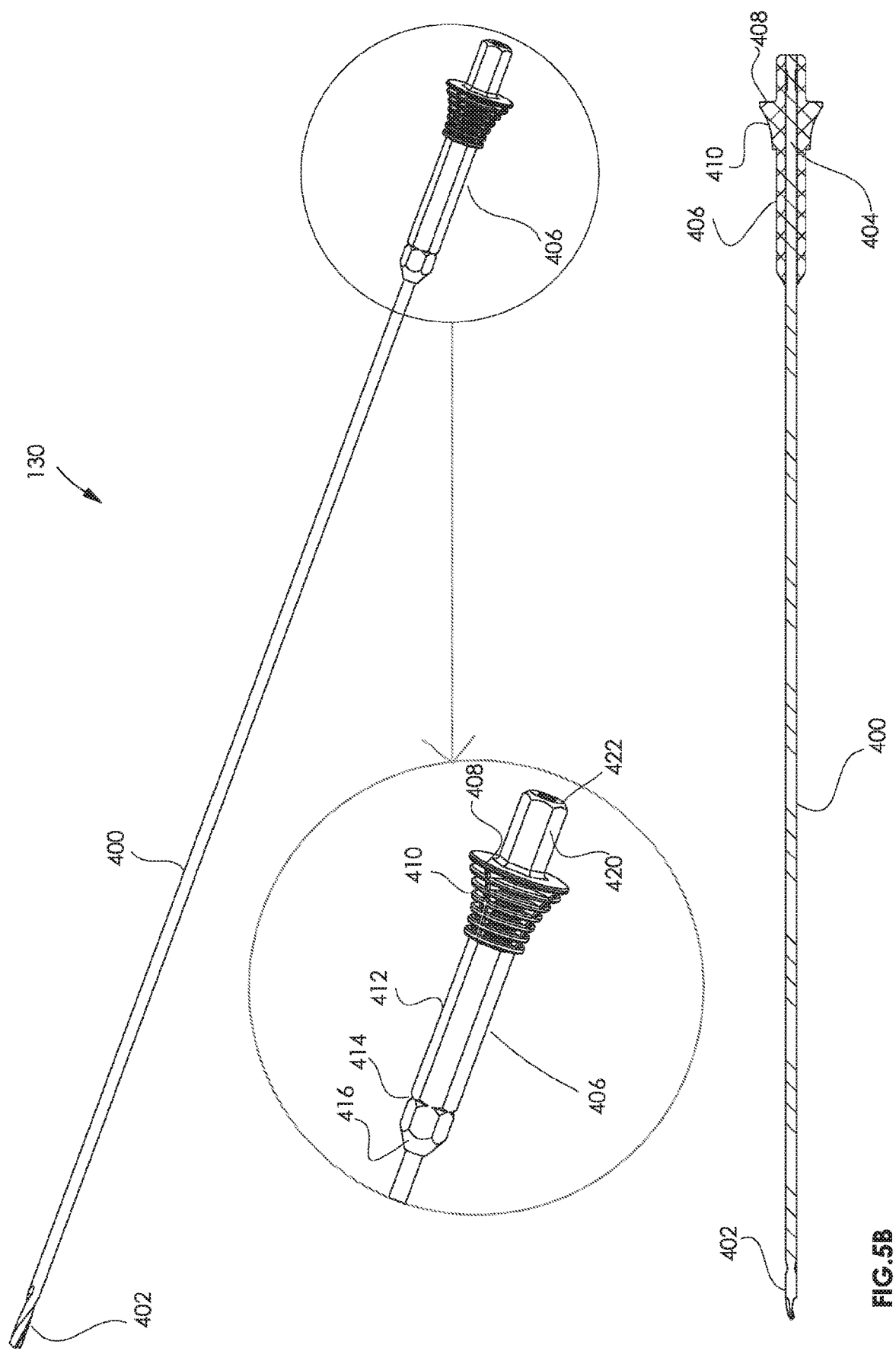
Figure 6A:
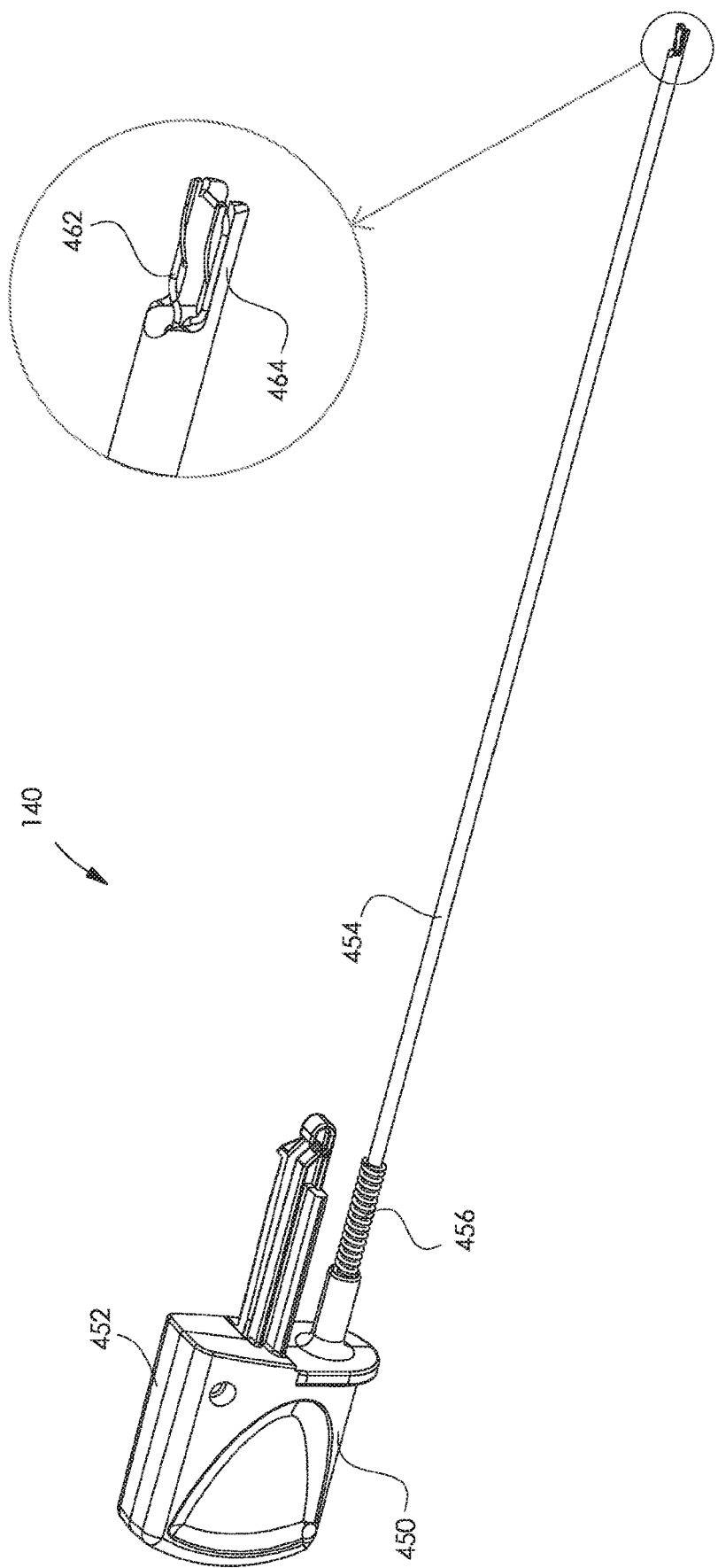
FIGS. 6A, 6B, 6C & 6D are simplified respective rearward-facing and forward-facing pictorial illustrations and rearward-facing and forward-facing exploded view illustrations of a snare wire cartridge assembly forming part of the arthroscopic surgical assembly of FIGS. 1A & 1B.
Figure 6B:
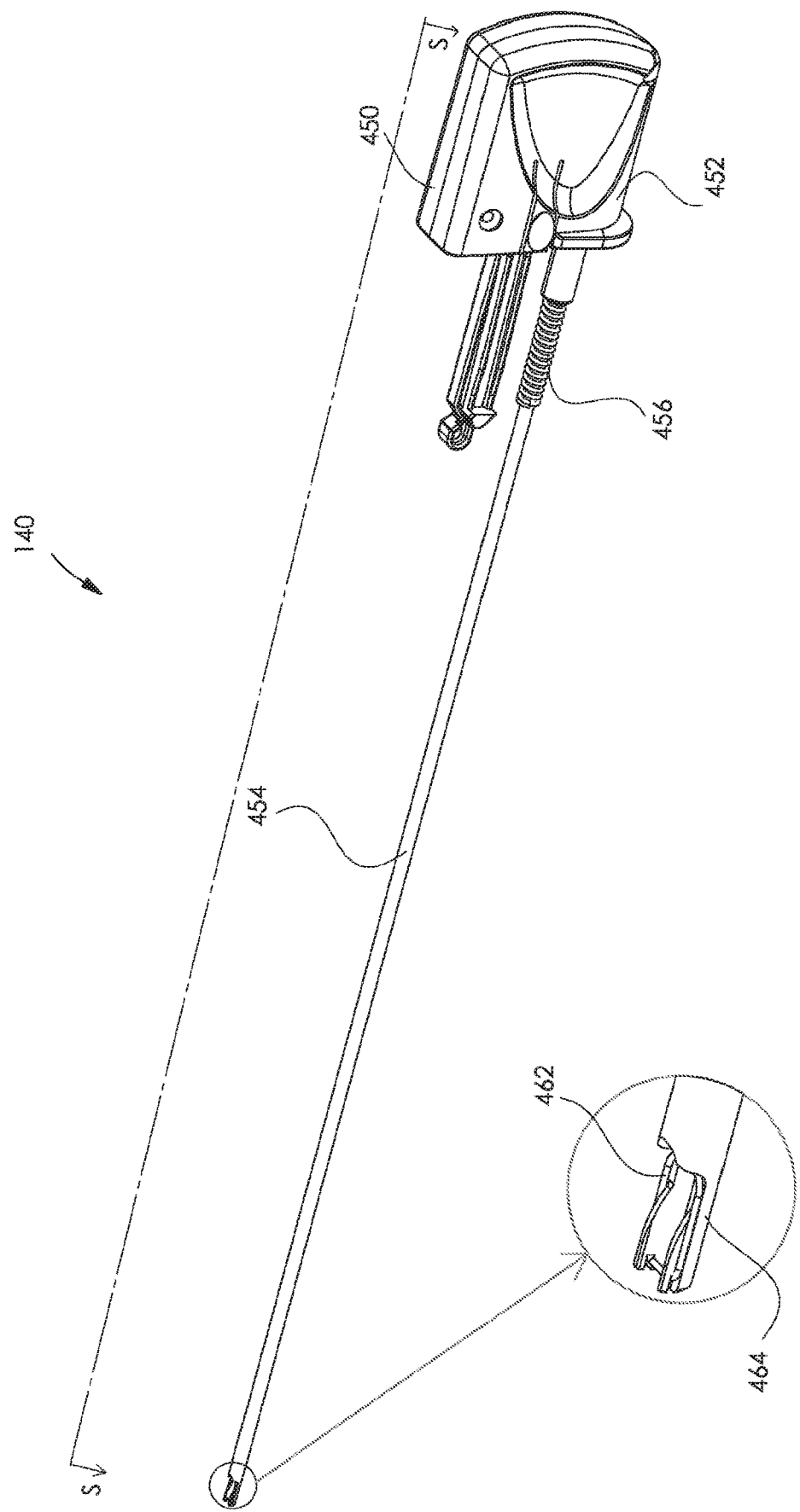
Figure 6C:
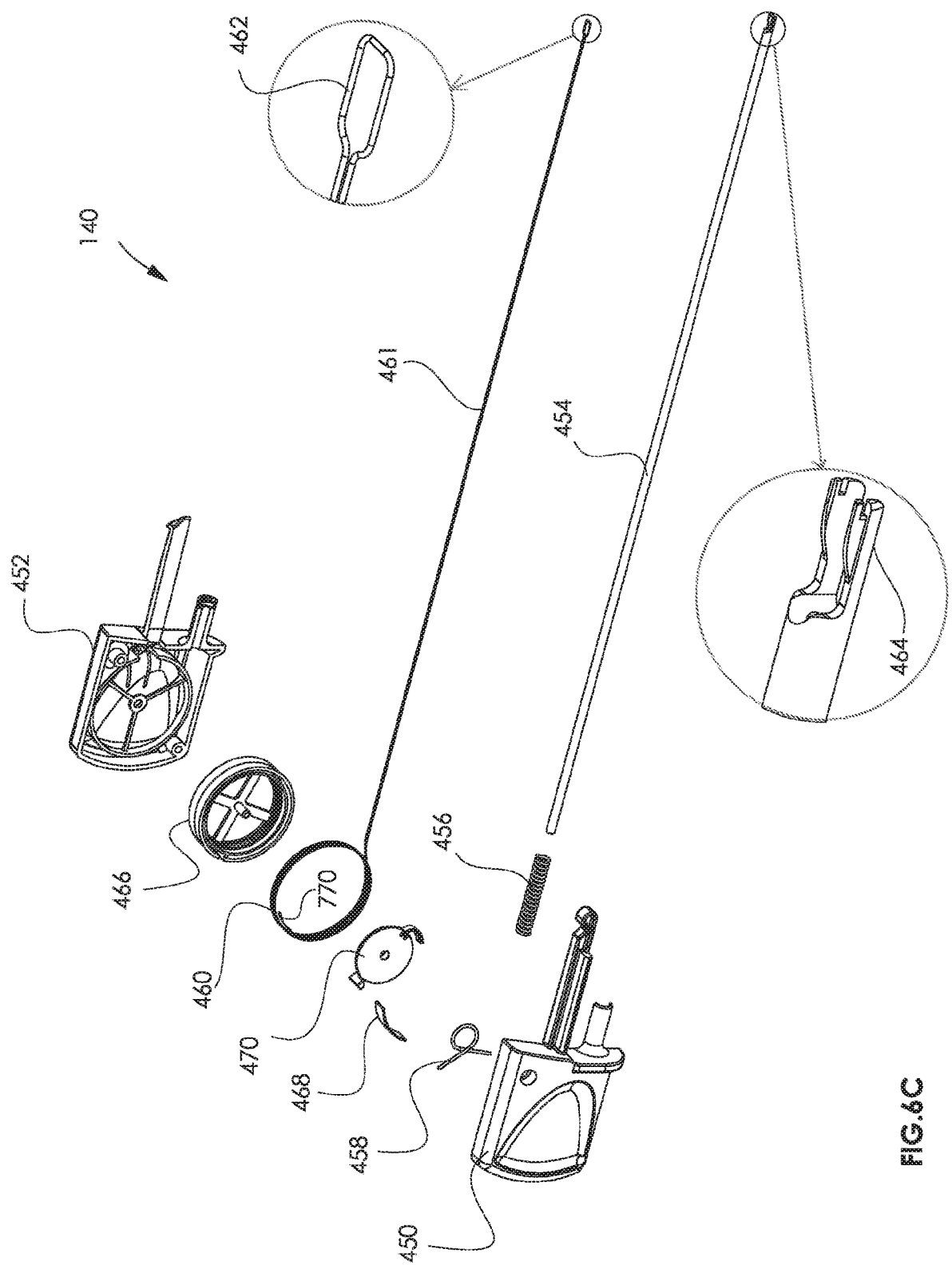
Figure 6D:
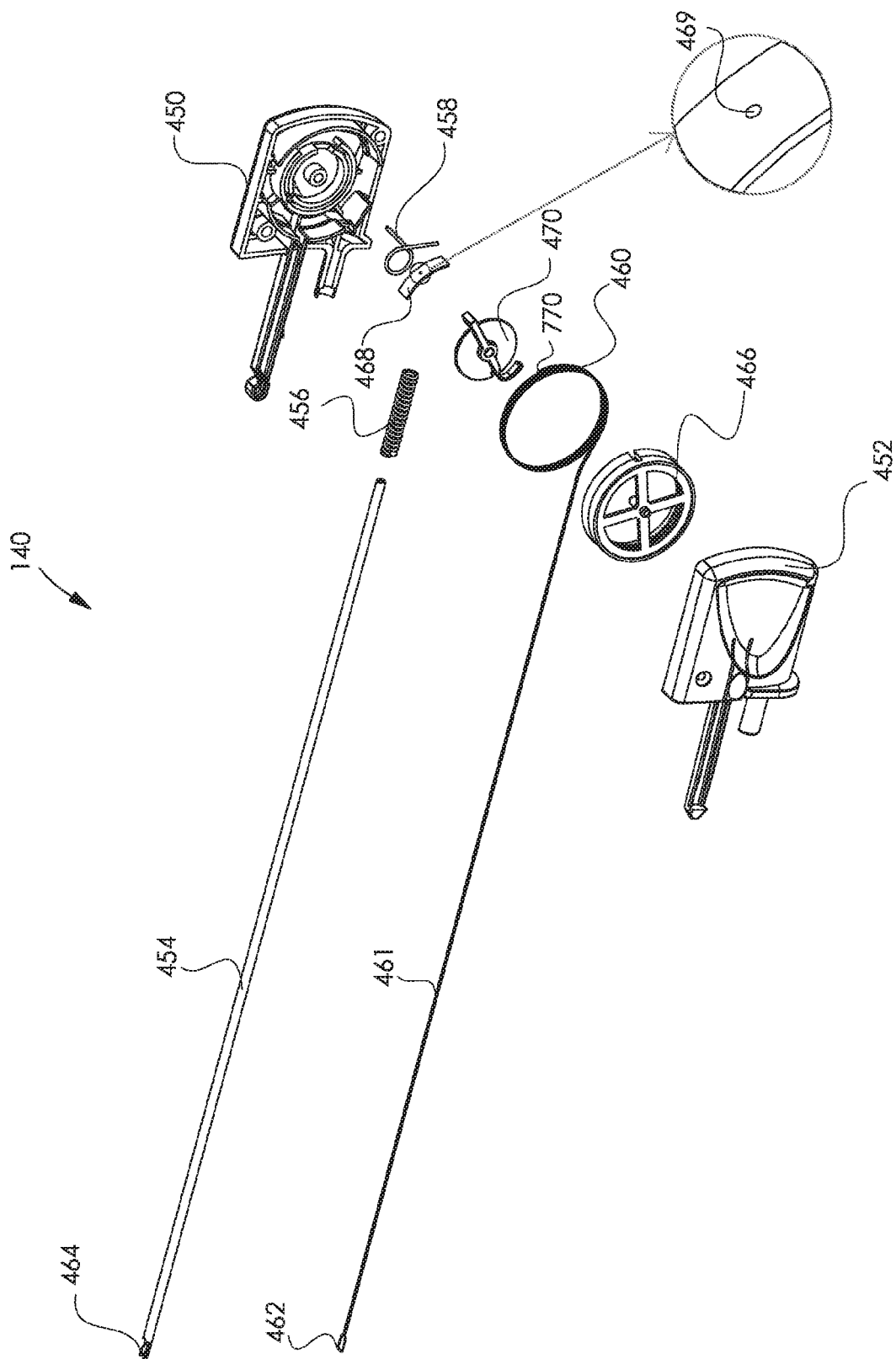
Figure 6O:
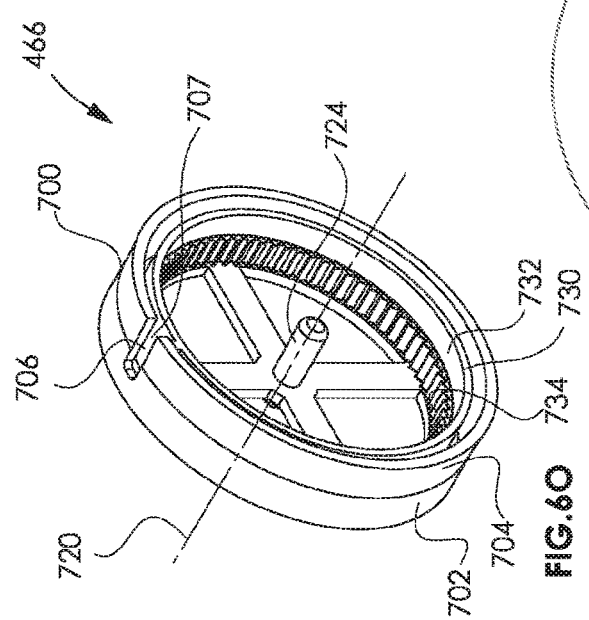
FIGS. 6M, 6N, 6O & 6P are simplified respective plan view, first and second pictorial view and edge view illustrations of a snare wire winding drum forming part of the snare wire cartridge assembly.
Figure 6P:
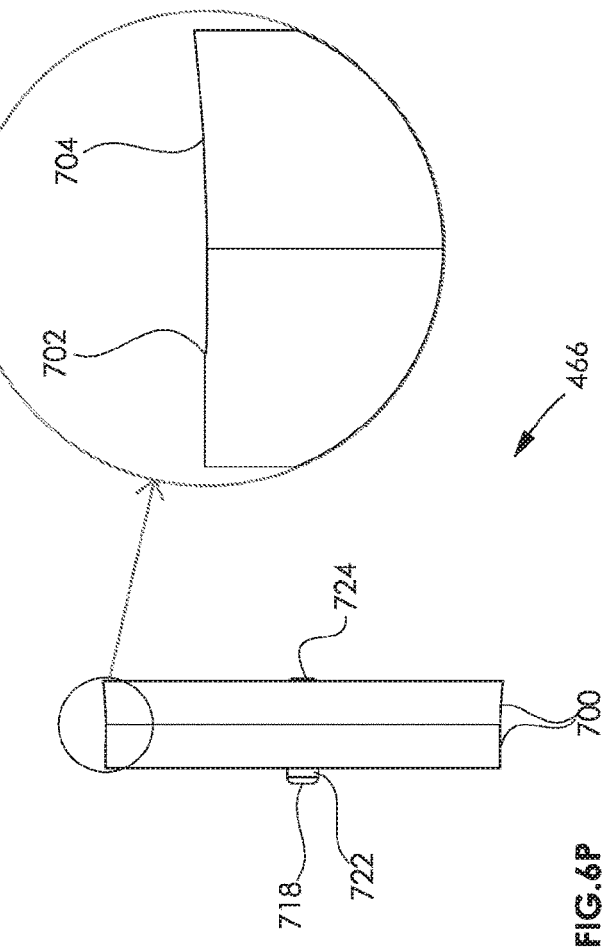
Figure 6N:
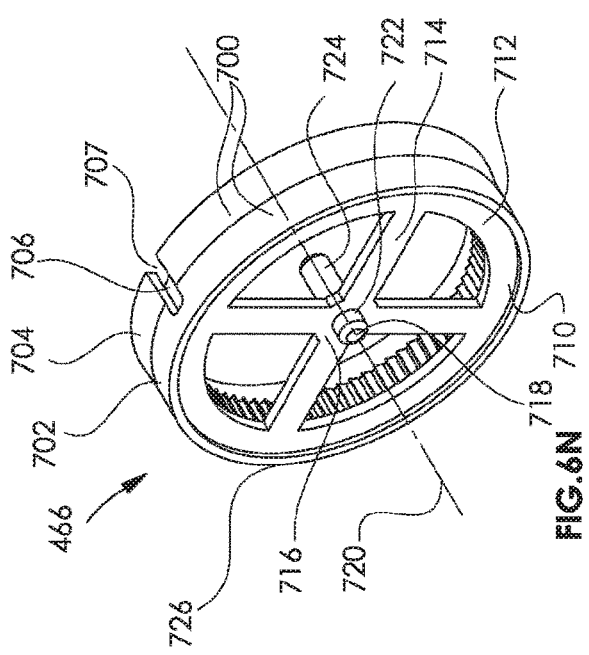
Figure 6M:
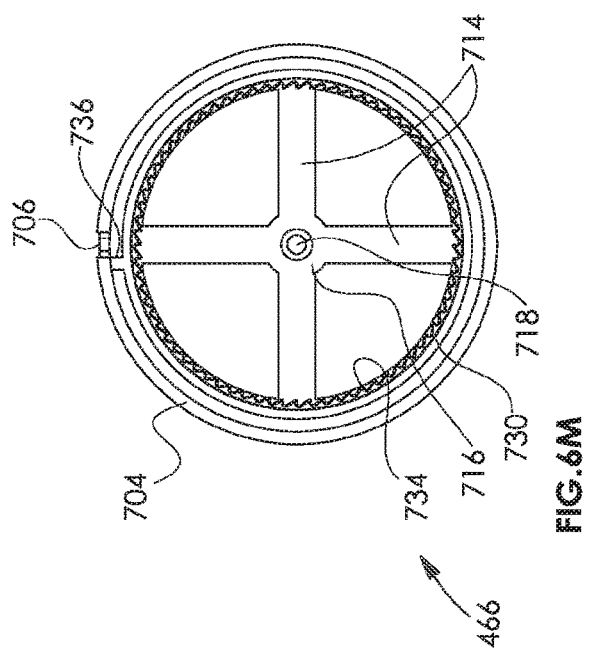
Figure 7A:
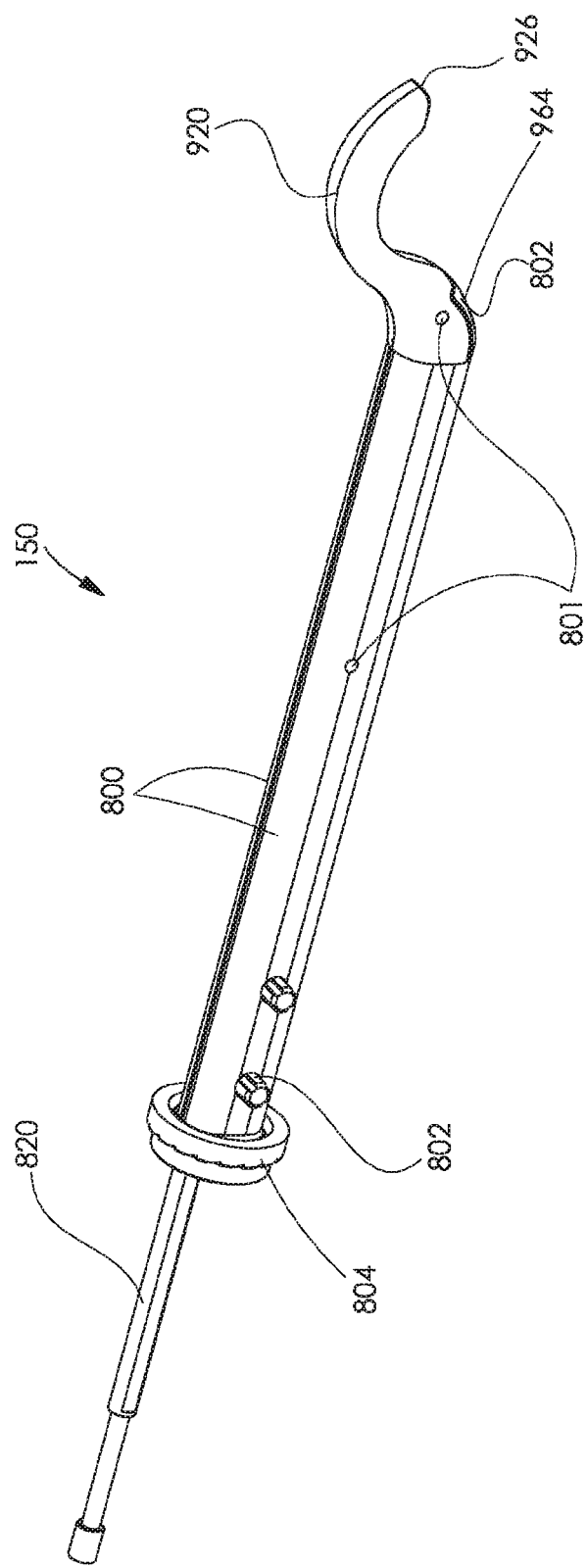
Figure 8A:
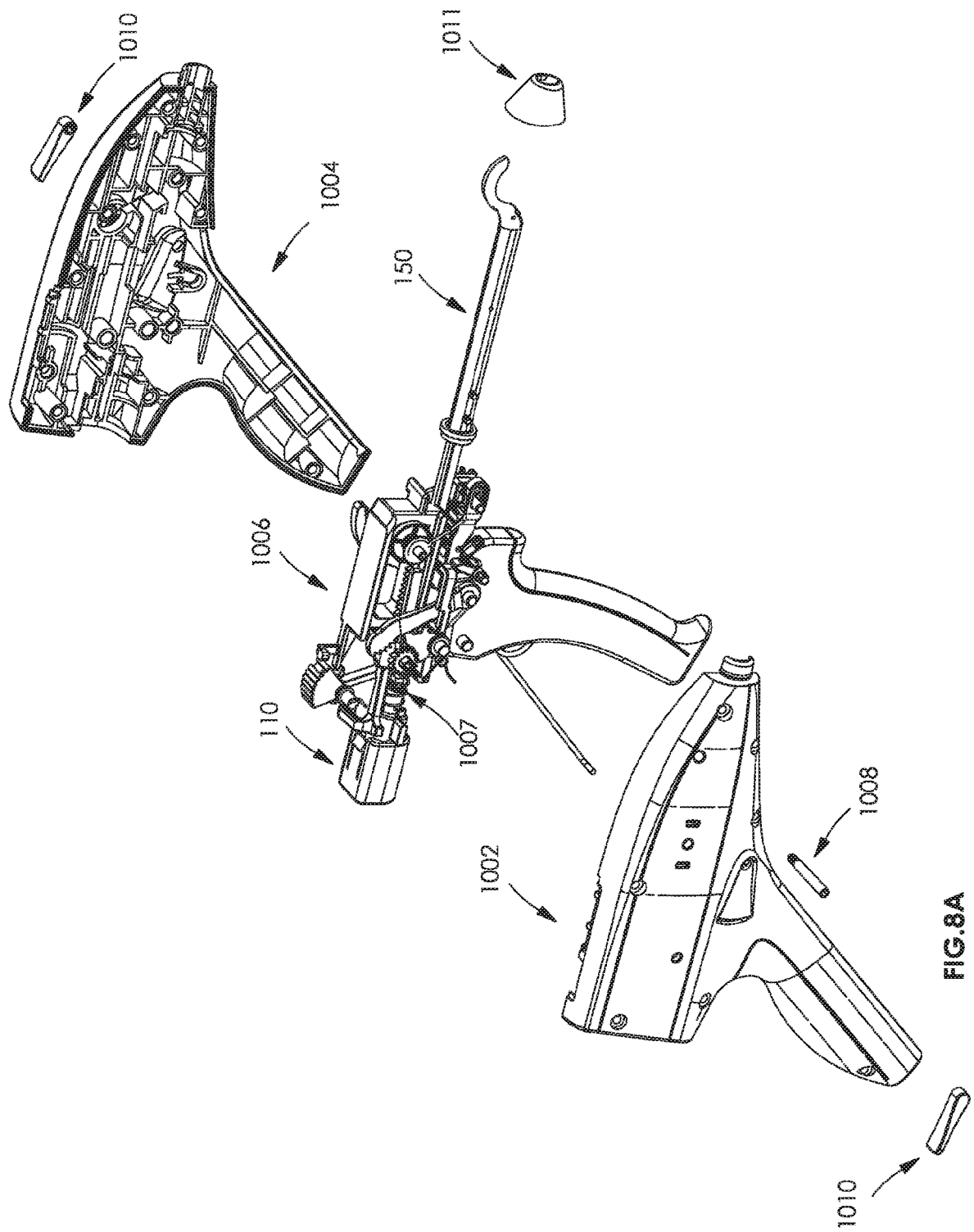
Figure 8B:
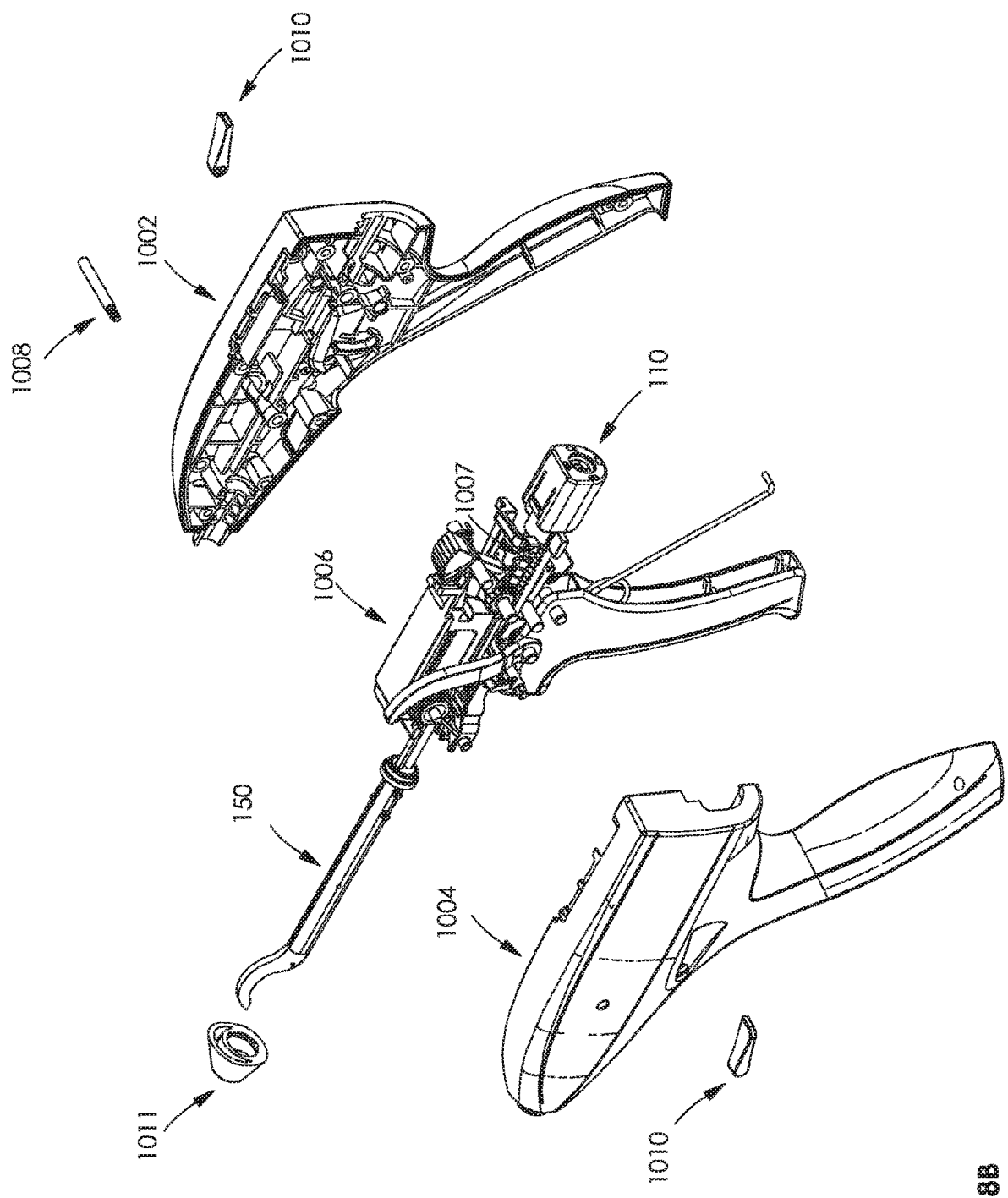

As seen in FIGS. 1A & 1B, the arthroscopic surgical assembly of FIGS. 1A & 1B includes a bone punch assembly 100, shown in FIGS. 2A & 2B; a work channel assembly 110, shown in FIGS. 3A & 3B; a quick connect element 120, shown in FIGS. 4A, 4B, 4C & 4D; a drill bit assembly 130, shown in FIGS. 5A & 5B; a snare wire cartridge assembly 140, shown in FIGS. 6A & 6B; a curved shaft assembly 150, shown in FIGS. 7A & 7B; an arthroscopic surgical device 160, shown in FIGS. 8A & 8B and manual override elements 170, shown in FIGS. 9A, 9B, 9C, 9D, 9E & 9F and comprising a manual override gear shifter 171 and a 2.5 mm hexagonal wrench 172.

Referring now additionally to FIGS. 2A & 2B, there is seen bone punch assembly 100, which preferably includes a handle portion 202, which is typically formed of plastic and is preferably 130 mm long, an intermediate portion 204, which is typically formed of steel and is preferably 85 mm long, and a forward portion 206, also typically foraged of steel and preferably 20 mm long, having a pointed tip 208. A circumferential marking 210 is preferably formed on forward portion 206 to indicate a desired extent of bone penetration to a surgeon using the punch. In the illustrated embodiment, indicia "8" indicates that the circumferential marking is 8 mm from the point of pointed tip 208. A generally convex impact surface 212 is preferably formed on a rearward end of punch 100, for impact thereon by a surgical hammer.

Figure 3P:
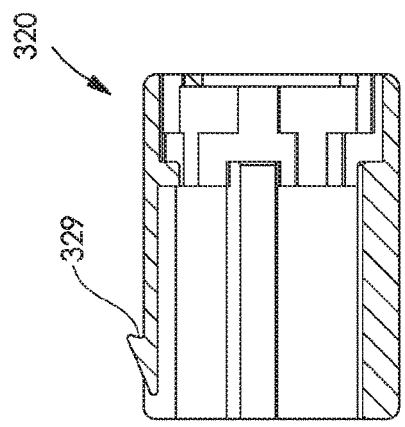
Figure 3M:
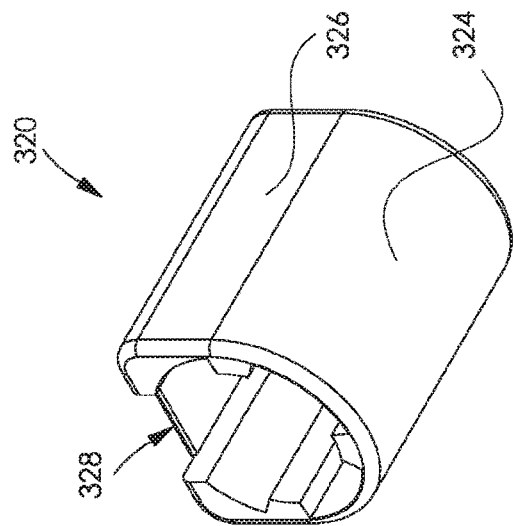
Figure 3O:
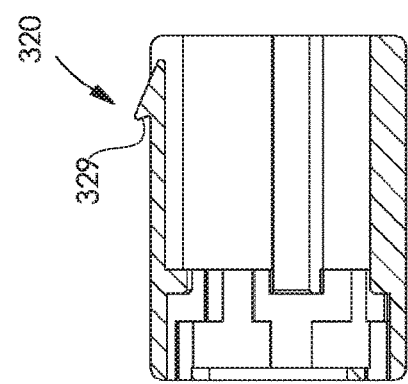
Figure 3N:
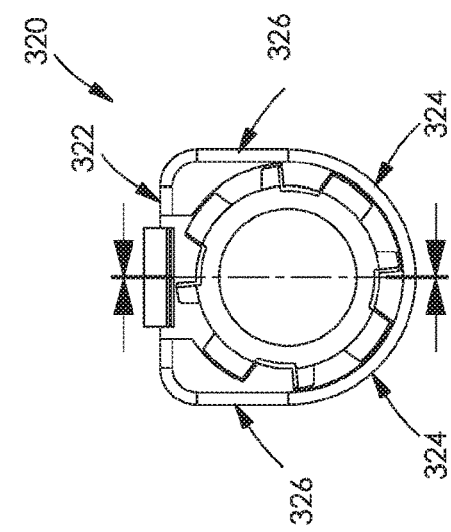

Reference is now made to FIGS. 3A, 3B, 3C, 3D, 3E, 3F, 3G, 3H, 3I, 3J, 3K, 3L, 3M, 3N, 3O & 3P which are simplified illustrations of work channel assembly 110 forming part of the arthroscopic surgical assembly of FIGS. 1A & 1B. As seen in FIGS. 3A-3P, the work channel assembly 110 preferably includes a hollow elongate tube 220, typically formed of stainless steel and preferably having an outer diameter of 3.2 mm and an inner diameter of 2.7 min and a total length of approximately 231 mm extending along a longitudinal axis 222. Preferably a front edge 224 of elongate tube 220 is inclined with respect to axis 222 by 100 degrees.

A rearward end 226 of elongate tube 220 is fixedly mounted within a socket 228 formed in a work channel hub 230. Work channel hub 230 is shown in FIGS. 3C, 3D, 3E & 3F, which are respectively a forwardly-facing pictorial illustration; a rearwardly-facing pictorial illustration, a side view illustration and a forwardly-facing rear end view illustration of work channel hub, forming part of the work channel assembly of FIGS. 3A & 3B.

As seen in FIGS. 3C-3F, work channel hub 230 is a generally circularly cylindrical integrally formed element having a forward socket-defining portion 232, having a transverse bore 233. Rearwardly of forward socket-defining portion 232 is a main cylindrical portion 234 having a forward annular surface 235 and preferably having formed at a forward end thereof a plurality, preferably four, azimuthally-distributed cut outs 236. Main cylindrical portion 234 is preferably formed with an axial central bore 238 having a flower-like cross-sectional configuration and preferably having a hexagonal chamfered intermediate entry portion 240 and a circularly chamfered rearward entry portion 242 adjacent a rear end 244 of hub 230. A flange 245 is provided at rear end 244 of hub 230 and defines a forward facing circumferential flange surface 246.

Main cylindrical portion 234 is preferably formed adjacent rear end 244 thereof with a partially circumferential slot 247 which removably accepts a retaining clip element 248

(FIG. 3B). Slot 247 communicates with axial central bore 238 such that clip element 248, when inserted, traverses axial central bore 238 at two azimuthal locations therein.

Work channel hub 230 is partially seated within a rack-defining intermediate element 260. Rack-defining intermediate element 260 is illustrated in FIGS. 3G, 3H, 3I & 3J, which are respectively a forwardly-facing pictorial illustration; a rearwardly-facing pictorial illustration, a side view illustration and a forwardly-facing rear end view illustration of a rack-defining intermediate element 260, forming part of the work channel assembly 110 of FIGS. 3A & 3B.

As seen in FIGS. 3G-3J, rack-defining intermediate element 260 includes a main cylindrical portion 262 having a rear surface 264 having four azimuthally distributed radially extending protrusions 266, each having a chamfered forwardly facing surface 268. Extending radially outward in opposite directions from main cylindrical portion 262 are a pair of wing-like protrusions 270 each having an upper surface 272 and a lower surface 274 joined by a forward-facing surface 276.

Main cylindrical portion 262 is formed with an axial bore 280, which extends along an axis 282 and has a somewhat narrowed forward bore aperture 284, having a chamfered rearward facing edge 286. At a forward end 290 of main cylindrical portion 262 there is provided a transverse angled flat portion 292, rearwardly of which is formed a transverse undercut 294 having a rearward facing surface 296 and a transverse surface 298 which joins surface 296 generally at a right angle.

Extending forwardly of forward end 290 of main cylindrical portion 262 is a shaft 300 of generally rectangular cross section and which is formed with a row of ratchet teeth 302 defining a linear ratchet gear rack 304.

Reference is now made to FIGS. 3K, 3L, 3M, 3N, 3O & 3P, which are respectively a forwardly-facing pictorial illustration; a top rearwardly-facing pictorial illustration, a bottom rearwardly-facing pictorial illustration, a rearwardly-facing front end view illustration and first and second interior side view illustrations of a retaining cap element 320, forming part of the work channel assembly of FIGS. 3A & 3B.

As seen in FIGS. 3K-3P, retaining cap element 320 is a generally cylindrical element having a generally flat top surface 322, a curved combined bottom and lower side surface 324 and generally flat side surfaces 326. An undercut hooked engagement finger 328, having a rearward-facing retaining surface 329, is provided on top surface 322. A rear surface 330 is formed with a plurality of apertures 332 which are configured to lockably receive protrusions 266 of rack-defining intermediate element 260.

Reference is now made to FIGS. 4A-4D, which are, respectively, a simplified forwardly-facing pictorial illustration, a rearwardly-facing pictorial illustration, a side view illustration and a forwardly-facing rear end view illustration, of a quick connect element 120, typically formed of plastic and preferably 56 mm long, forming part of the arthroscopic surgical assembly of FIGS. 1A & 1B, respectively.

As seen in FIGS. 4A-4D, the quick connect element 120 comprises a forward generally circularly cylindrical portion 340, preferably 35 mm long, and a rearward hexagonally cylindrical extension 342, preferably 21 mm long with a 6 mm diameter, having six elongate flat surfaces 343. To the rear of the circularly cylindrical section 340 is a tapered section 344, which tapers down to a rearwardly-facing flat surface 346. Extending from the rearwardly-facing flat surface 346 are a plurality of tapered hexagonal portions 348 which join flat surfaces 343 of hexagonal extension 342.

At the rear of the hexagonal extension 342 is a hexagonally-shaped rearward-facing flat surface 350 which is joined to elongate flat surfaces 343 by tapered surfaces 352.

The interior of cylindrical portion 340 is preferably formed with an axial central bore 354 having a flower-like cross-sectional configuration and preferably having a hexagonal chamfered intermediate entry portion 356 adjacent a rear end 358 of quick connect element 120. This bore serves as a socket for engaging the shaft portion 420 of drill bit assembly 130, as shown in FIGS. 5A & 5B and described hereinbelow.

Reference is now made to FIGS. 5A & 5B, which are simplified illustrations of drill bit assembly 130, forming part of the arthroscopic surgical assembly of FIGS. 1A & 1B. As seen in FIGS. 5A & 5B, the drill bit assembly 130 includes an elongate shaft portion 400, typically formed of steel and preferably having a total length of approximately 289 mm, having a sharpened helical drill tip 402 formed at a forward end thereof, typically 12 mm long. Preferably, overmolded over a rearward portion 404 of shaft portion 400 is an engagement portion 406, preferably formed of plastic and 32.1 mm long.

Engagement portion 406 preferably includes a flat rear-facing annular surface 408. Forward of flat rear-facing annular surface 408 is a tapered ribbed grasping portion 410. Forward of tapered ribbed grasping portion 410 is a preferably elongate work channel driving shaft portion 412 having a hexagonal outer cross-section, which is configured for driving engagement with axial central bore 238 of work channel hub 230. A shallow circumferential recess 414 is formed in work channel driving shaft portion 412 for receiving clip element 248 (FIG. 3B), which retains work channel driving shaft portion 412 in axial central bore 238 of work channel huh 230 against relative longitudinal displacement therebetween. Elongate work channel driving shaft portion 412 terminates forwardly in a tapered forward face 416, which engages circularly chamfered rearward entry portion 242 of hexagonal chamfered intermediate entry portion 240 adjacent rear end 244 of hub 230.

Rearwardly of flat rear-facing annular surface 408 is a shaft portion 420, having a hexagonal outer cross section and a chamfered end face 422. Shaft portion 420 engages bore 354 of quick connect element 120 for being driven thereby.

Figure 6S:
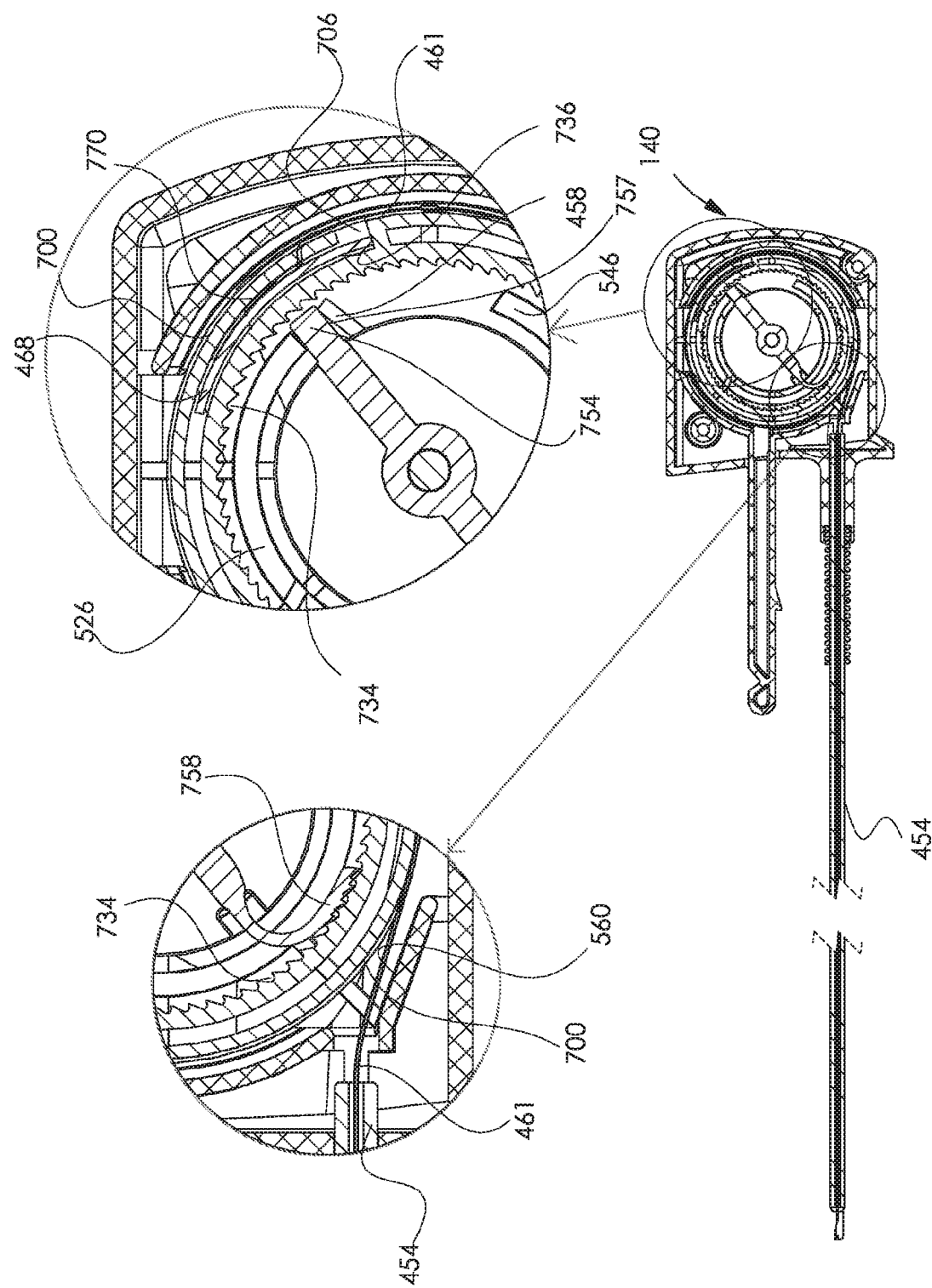
FIG. 6S is a simplified side view illustration of the snare wire cartridge assembly.

Reference is now made to FIGS. 6A, 6B, 6C & 6D, which are simplified respective rearward-facing and forward-facing pictorial illustrations and rearward-facing and forward-facing exploded view illustrations of snare wire cartridge assembly 140, forming part of the arthroscopic surgical assembly of FIGS. 1A & 1B; to FIGS. 6E, 6F, 6G & 6H, which are simplified respective interior plan view, first and second interior pictorial view and rearward facing end view illustrations of a main housing portion of the snare wire cartridge assembly; to FIGS. 6I, 6J, 6K & 6L, which are simplified respective interior plan view, first and second interior pictorial view and rearward facing end view illustrations of a secondary housing portion of the snare wire cartridge assembly; to FIGS. 6M, 6N, 6O & 6P, which are simplified respective plan view, first and second pictorial view and edge view illustrations of a snare wire winding drum forming part of the snare wire cartridge assembly; to FIGS. 6Q & 6R, which are simplified first and second interior pictorial view illustrations of a tensioning element cooperating with the snare wire winding drum; and to FIG. 6S, which is a simplified sectional illustration, taken along lines S-S in FIG. 6B.

Turning now to FIGS. 6A, 6B, 6C & 6D, which are simplified respective rearward-facing and forward-facing pictorial illustrations and rearward-facing and forward-facing exploded view illustrations of snare wire cartridge assembly 140, which preferably has a total length of 313.5 mm, it is seen that the snare wire cartridge assembly 140 preferably comprises a main housing portion 450 and a secondary housing portion 452 and an elongate hollow shaft 454, having an aperture 455 and preferably formed of stainless steel and extending 255.8 mm outside main and secondary housing portions 450 and 452, which is mounted onto the main and secondary housing portions 450 and 452.

Main housing portion 450 is described in detail hereinbelow with reference to FIGS. 6E, 6F, 6G & 6H and secondary housing portion 452 is described in detail hereinbelow with reference to FIGS. 6I, 6J, 6K & 6L.

A compression spring 456 is mounted over shaft 454 adjacent a rearward end thereof and a tension spring 458 is mounted within main housing portion 450 as described hereinbelow.

A folded over length 460 of snare wire 461 which also defines a pre-formed loop 462, is partially located within hollow shaft 454, with loop 462 mounted at a forward end 464 of elongate hollow shaft 454 thereof and partially wound about a snare wire winding drum 466 located within main housing portion 450 and retained thereon by means of a resilient retaining element 468 having a wire traversing aperture 469. Drum 466 is described hereinbelow in detail with reference to FIGS. 6M-6P. Desired tensioning of the snare wire 461 is provided by a tensioning element 470, cooperating with the snare wire winding drum 466. Tensioning element 470 is described hereinbelow in detail with reference to FIGS. 6Q & 6R.

Reference is now made additionally to FIGS. 6E, 6F, 6G & 6H, which illustrate main housing portion 450. As seen in FIGS. 6A-6D and 6E-6G, the main housing portion 450 comprises a generally rectangular outer surface 480 having a finger engagement detent 482, a curved rearward-facing edge 484, respective top and bottom edges 486 and 488 and a forward-facing edge 490.

The interior of main housing portion 450 is delimited by a circumferential wall surface 492 which includes a rearward wall surface 504 corresponding to curved rearward-facing edge 484, respective top and bottom wall surfaces 506 and 508 corresponding to respective top and bottom edges 486 and 488 and a forward wall surface 510 corresponding to forward-facing edge 490.

A generally circular rearward interior wall 520 is located adjacent rearward wall surface 504 and a generally circular forward interior wall 522 is located adjacent forward wall surface 510. Inner and outer generally circular mutually nested walls 524 and 526 defining respective openings 534 and 536 surround a central boss 538. Mutually aligned angled slits 540 and 542 are formed in respective walls 524 and 526. Opening 536 in wall 526 defines abutments 544 and 546.

Extending forwardly of forward-facing edge 490 is a shaft mounting socket defining hollow protrusion 550 having a bore 554 for receiving a rearward end of shaft 454 and a widened forward-facing recess 556 defining a rearward spring seat for compression spring 456. Located rearwardly and below protrusion 550 is a wall 560.

Also extending forwardly of forward-facing edge 490 at an opening 570 formed in generally circular forward interior wall 522 is cartridge assembly retaining shaft portion 572. Shaft 572 has a top-facing notch 574 having an inclined forward facing surface 575 and an inclined rearward facing surface 576. Notch 574 is formed adjacent a rounded forward end 577 thereof and a bottom-facing tooth 578, defining a retaining surface 579, formed rearwardly of notch 574 on a bottom-facing surface of shaft 572.

Reference is now made additionally to FIGS. 6I, 6J, 6K & 6L, which illustrate secondary housing portion 452. As seen in FIGS. 6A-6D and 6I-6L, the secondary housing portion 452 comprises a generally rectangular outer surface 580 having a finger engagement detent 582, a curved rearward-facing edge 584, respective top and bottom edges 586 and 588 and a forward-facing edge 590.

The interior of secondary housing portion 452 is delimited by a circumferential wall surface 592 which includes a rearward wall surface 604 corresponding to curved rearward-facing edge 584, respective top and bottom wall surfaces 606 and 608 corresponding to respective top and bottom edges 586 and 588 and a forward wall surface 610 corresponding to forward-facing edge 590.

Three radially extending protrusions 618 join a generally circular interior wall 620 to a central boss 628.

Extending forwardly of forward-facing edge 590 is a shaft mounting socket defining hollow protrusion 650 having a bore 654 for receiving a rearward end of shaft 454 and a widened forward-facing recess 656 defining a rearward spring seat for compression spring 456, having spring retaining protrusions 658. Located rearwardly and below protrusion 650 is a wall 660.

Also extending forwardly and rearwardly of forward-facing edge 590 through an opening 670 formed in generally circular interior wall 620 is a cartridge assembly retaining shaft portion 672. Shaft portion 672 has a doubly tapered front end 674 defining adjacent inclined surfaces 676 and 678. Surface 676 is preferably coplanar with surface 575 of shaft 572, which has a top-facing notch 574. As seen particularly in FIGS. 6B and 6L, shaft portion 672 is preferably formed with a dimple-like protrusion 680 for manual engagement thereof. It is appreciated that shaft portion 672 is cantilevered relative to secondary housing portion 452, such that when dimple-like protrusion 680 is pressed by a user, shaft portion 672 is brought closer to cartridge assembly retaining shaft portion 572, thus releasing the cartridge assembly 140 from snap-fit engagement with arthroscopic surgical device 160.

Reference is now additionally made to FIGS. 6M, 6N, 6O & 6P, which are simplified respective plan view, first and second pictorial view and edge view illustrations of snare wire winding drum 466, forming part of the snare wire cartridge assembly.

As seen in FIGS. 6M-6P, the snare wire winding drum 466 is a generally circularly symmetric element, which is preferably injection-molded of plastic and has a circumferential outer edge portion 700 defined by two mutually inclined edge portions 702 and 704, which are mutually inclined so as to define a ring of minimum radius therebetween. A transverse slot 706 has an opening 707 at an edge of edge portion 704 and extends thereacross and partially into edge portion 702.

Circumferential outer edge portion 700 is integrally formed with a generally planar base portion 710, having an annular ring portion 712 and a pair of cross pieces 714 which are joined at a central region 716. A hollow axle 718 extends perpendicularly to generally planar base portion 710 along an axis 720. Hollow axle 718 includes a short portion 722 and a longer portion 724, coaxial therewith.

It is appreciated that axis 720 is an axis of symmetry and rotation of snare wire winding drum 466. It is also seen that an edge region 726 of inclined edge portion 702 extends beyond generally planar base portion 710.

Disposed interiorly of outer edge portion 700 and extending in a circularly symmetric arrangement about longer portion 724 of axle 718 is an inner ring portion 730 having an inner facing circular surface 732. A circularly symmetric portion of inner facing circular surface 732 adjacent generally planar base portion 710 is formed with a circularly symmetric array 734 of gear teeth. Extending generally radially outwardly from a radially outwardly facing surface of inner ring portion 730 and joining a radially inwardly facing surface of outer edge portion 700 is a rib 736.

Reference is now made additionally to FIGS. 6Q & 6R, which are simplified first and second interior pictorial view illustrations of tensioning element 470 cooperating with the snare wire winding drum 466. Tensioning element 470 preferably comprises a disc portion 750 having a central aperture 752 and a spring engaging protrusion 754 which extends radially outwardly from and to one side of disc portion 750. Spring engaging protrusion 754 defines an inclined spring engaging surface 756 and an abutment engaging surface 757.

Extending radially outwardly from disc portion 750 generally in a direction opposite to spring engaging protrusion 754 is a flexible ratchet gear engaging portion 758 which extends radially outwardly and then circumferentially from a recess 759 formed in disc portion 750. Flexible ratchet gear engaging portion 758 includes at a top circumferentially outward portion thereof a curved linear array 760 of gear teeth that are configured for ratchet-like engagement with circularly symmetric array 734 of gear teeth of snare wire winding drum 466.

Reference is now made additionally to FIG. 6S which is a simplified side view illustration of the snare wire cartridge assembly 140. As seen in FIG. 6S, an end portion 770 of snare wire 461 is inserted through aperture 469 in pad 468, which in turn is located between a radially outer-facing surface of an inner ring portion 730 and a radially inner facing surface of circumferential outer edge portion 700 adjacent rib 736.

Snare wire 461 extends from end portion 770 through slot 706 and is wound about an outer surface of circumferential outer edge portion 700 of snare wire winding drum 466 and extends through elongate hollow shaft 454.

It is seen that curved linear array 760 of gear teeth of flexible ratchet gear engaging portion 758 engages curved linear array 734 of gear teeth on snare wire winding drum 466 such that counterclockwise rotation of tensioning element 470 produces corresponding counterclockwise rotation of snare wire winding drum 466 in the sense of FIG. 6S. Thus it is appreciated that the engagement of spring 458 with abutment engaging surface 757 of spring engaging protrusion 754 urges both tensioning element 470 and snare wire winding drum 466 into counterclockwise rotation in the sense of FIG. 6S, thereby tensioning the snare wire 461.

As will be described hereinbelow, pulling of the snare wire 461 which is wound under tension on snare wire winding drum 466 rotates the drum 466 in a clockwise direction in the sense of FIG. 6S, against the urging of spring 458. This clockwise rotation continues until the drum can no longer rotate clockwise due to the engagement of abutment engaging surface 757 of spring engaging protrusion 754 with abutment 546 of main housing portion 450. At this stage, continued pulling on the snare wire 461 causes the wire to disengage from resilient retaining element 468 and can then be freely unwound from drum 466 and drawn forwardly through elongate hollow shaft 454.

Reference is now made to FIGS. 7A, 7B, 7C, 7D, 7E, 7F, 7G, 7H, 7I, 7J, 7K, 7L, 7M, 7N, 7O & 7P, which are simplified illustrations of curved shaft assembly 150 forming part of the arthroscopic surgical assembly of FIGS. 1A & 1B.

Figure 7C:
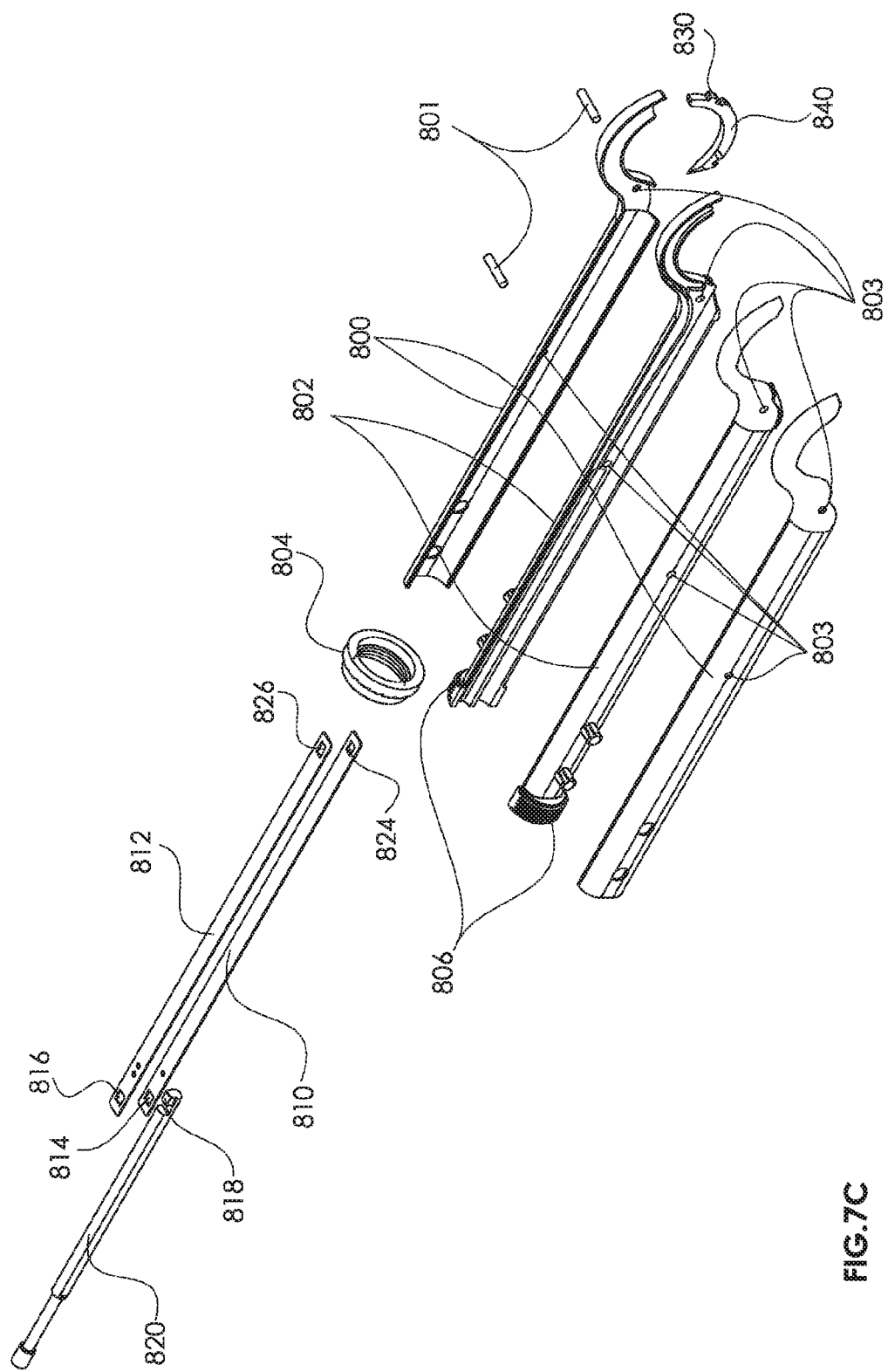
Figure 7D:
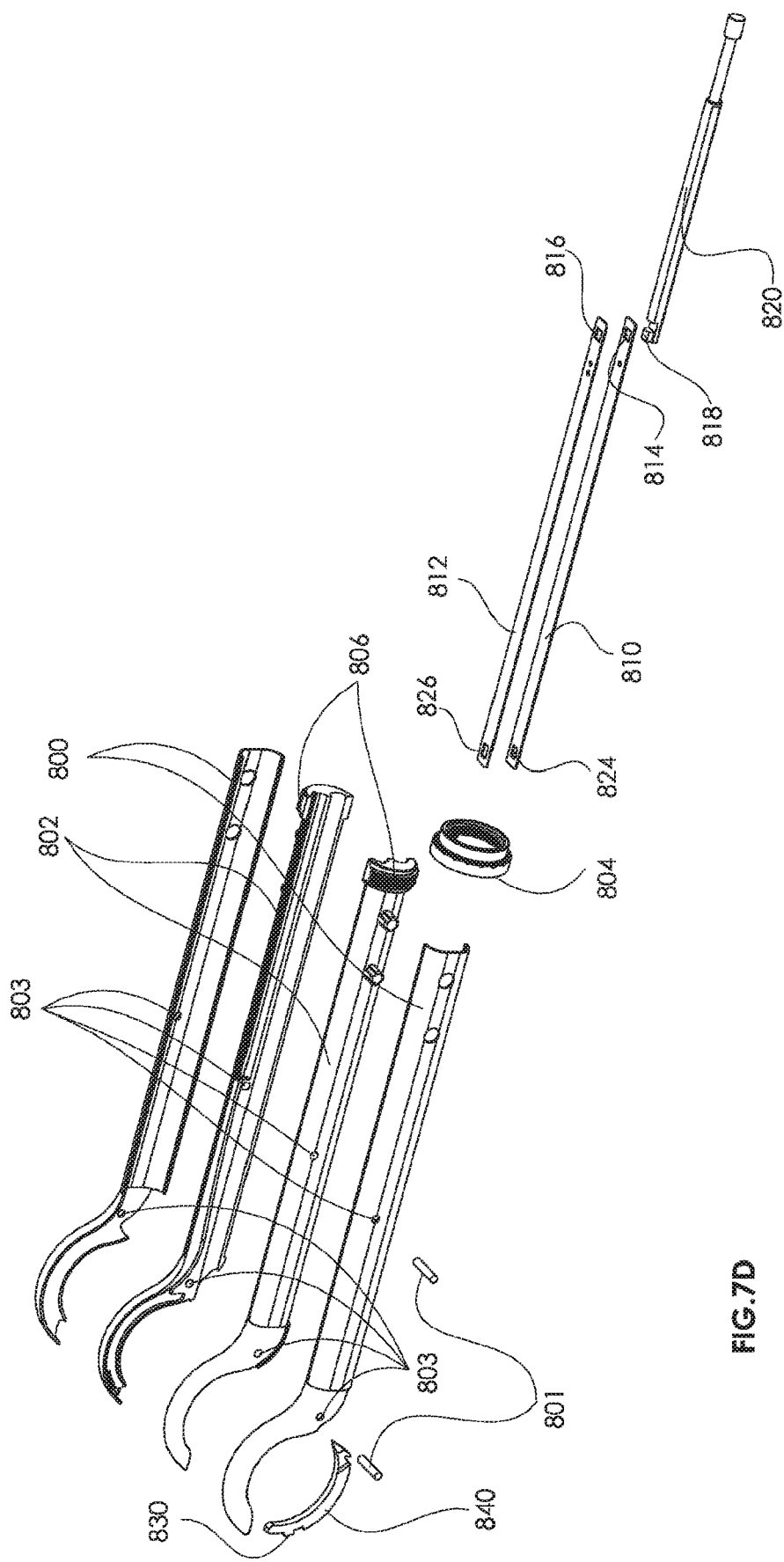

FIGS. 7A & 7B are simplified respective rearward-facing and forward-facing pictorial illustrations of the curved shaft assembly 150 and FIGS. 7C & 7D are respective rearward-facing and forward-facing exploded view illustrations of the curved shaft assembly 150. As seen in FIGS. 7A-7D, the curved shaft assembly 150 preferably comprises a pair of curved shaft assembly outer elements 800, which are preferably mirror images of each other, are formed of metal and are joined by alignment pins 801 and preferably also by laser welding. Disposed interiorly of outer structural elements 800 are a pair of curved shaft assembly inner elements 802, which are preferably mirror images of each other, and are formed of plastic. Alignment pins 801 extend through corresponding aligned apertures 803 formed in elements 800 and 802.

An internally threaded curved shaft assembly location ring 804 threadably engages corresponding threaded ends 806 of inner elements 802 and is retained at a fixed axial location within a housing of arthroscopic surgical device 160. It is appreciated that the threaded engagement between ring 804 and inner elements 802 provides axial adjustability of the position of the curved shaft assembly 150 relative to the remainder of arthroscopic surgical device 160 during manufacture.

Figure 7O:
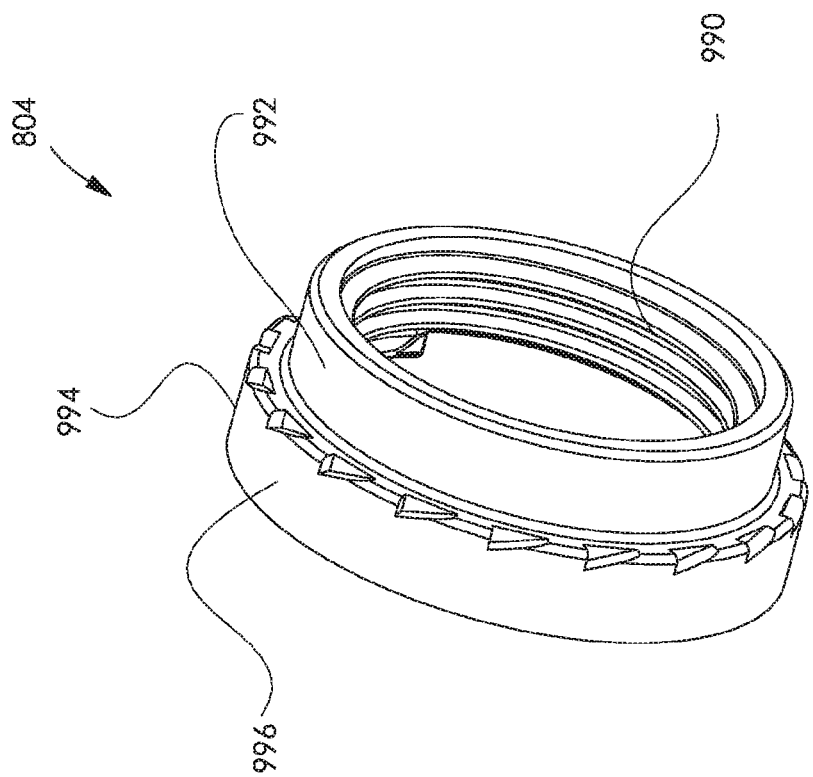
Figure 7N:
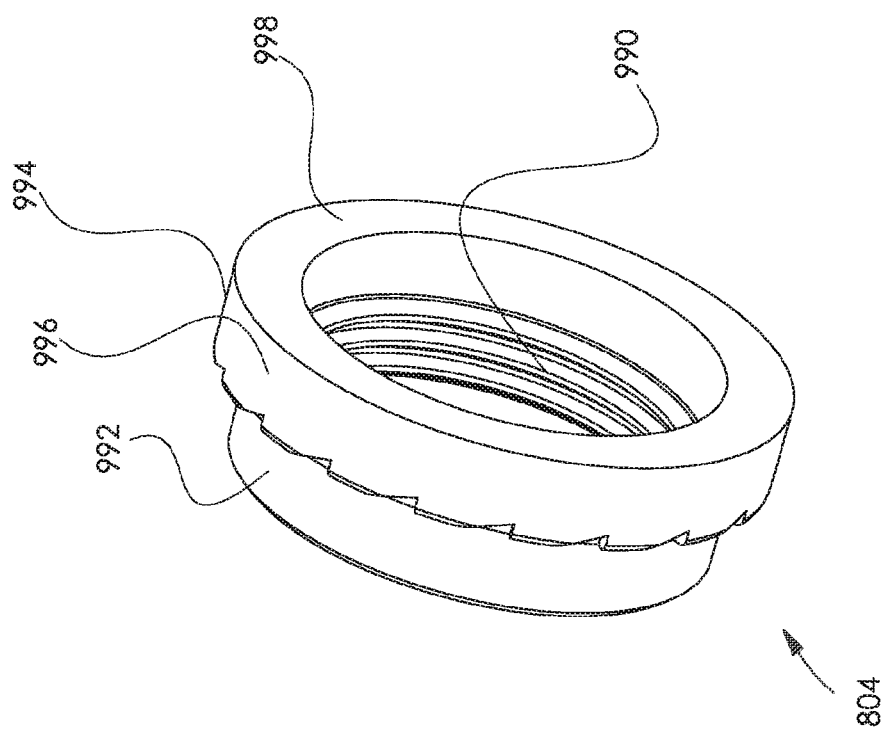
Figure 7P:
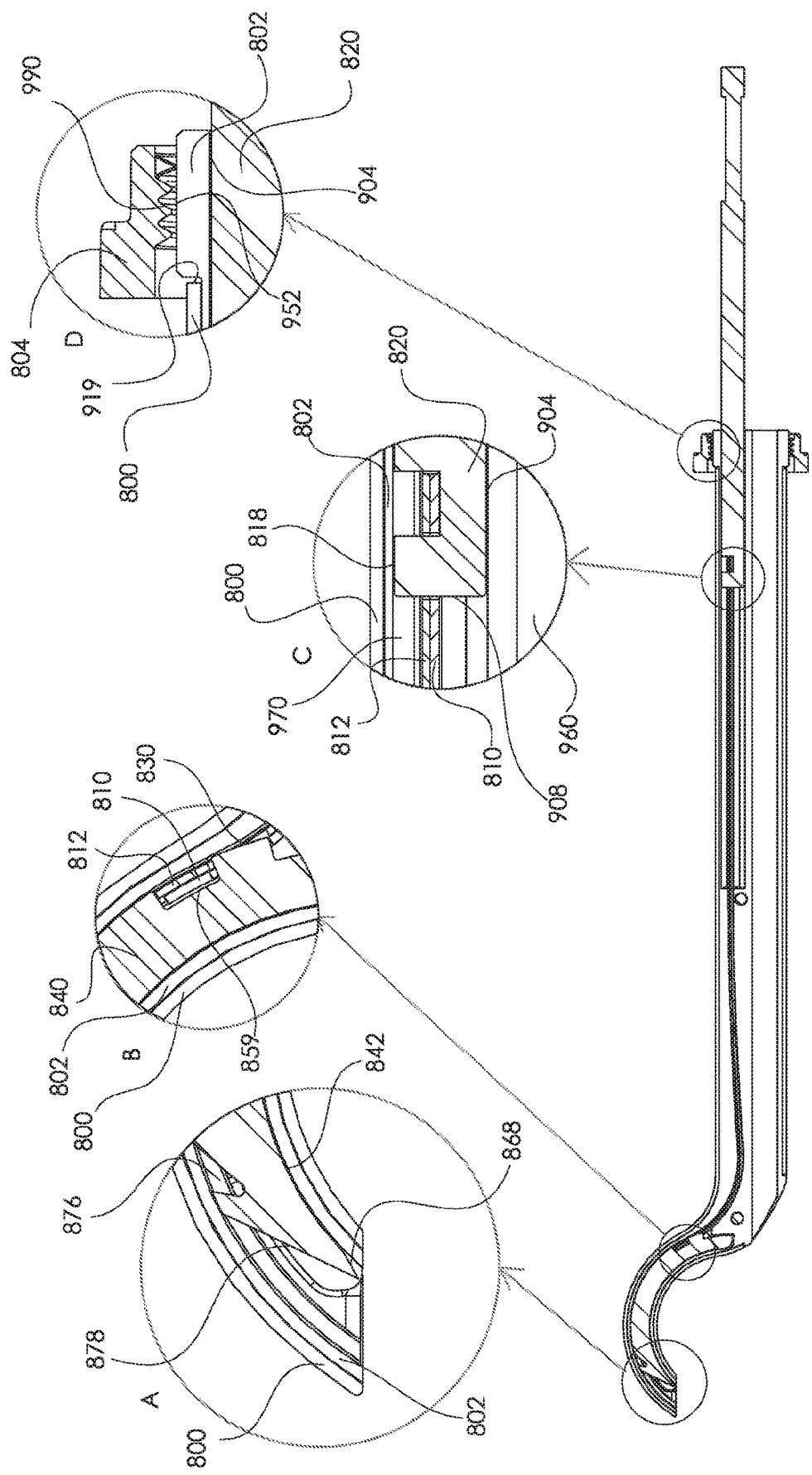

A pair of bendable pusher strips 810 and 812 extends through inner elements 802 and are preferably formed with push rod engagement apertures 814 and 816 for driven engagement with a top protrusion 818 of an elongate push rod 820, as seen particularly in enlargement C in FIG. 7P. Pusher strips 810 and 812 are also formed with bone puncture needle engagement apertures 824 and 826 for driving engagement with a top protrusion 830 of a bone puncture needle 840, as seen particularly in enlargement B in FIG. 7P.

Reference is now also made to FIGS. 7E, 7F & 7G, which illustrate bone puncture needle 840, which is preferably formed of stainless steel. It is seen that bone puncture needle 840 is a generally curved needle with a generally rectangular cross section. Bone puncture needle 840 is preferably formed with a radially inward-facing generally curved edge surface 842 which extends from a slightly rounded back end surface 844 to a tapered tip 866 at which it has a somewhat flattened surface 868, as seen particularly in enlargement A in FIG. 7P. Bone puncture needle 840 is formed with a rearward radially outward-facing generally curved surface portion 869 which extends from a generally non-rounded corner 870 at back end surface 844 to a top protrusion 830 (FIGS. 7C & 7D) and therebeyond to a shoulder 872 from which extends a forward radially outward-facing generally curved surface portion 874, as seen particularly in enlargement B in FIG. 7P. Top protrusion 830 engages push rod engagement apertures 824 and 826 of respective bendable pusher strips 810 & 812 for being driven by respective bendable push strips 810 and 812.

Forward radially outward-facing generally curved surface portion 874 extends to a forwardly and radially inwardly inclined notch 876, which defines a hook, and therebeyond to a forward, generally planar tapered top tip surface 878, as seen particularly in enlargement A in FIG. 7P.

Bone puncture needle 840 includes a pair of curved side surfaces 890, which are mirror images of each other and preferably comprise a marking 892, which can readily be seen by an operator using a suitably positioned camera. Curved side surfaces 890 each include a tapered tip side surface 894.

Reference is now made to FIGS. 7H & 7I, which illustrate elongate push rod 820. Elongate push rod 820 is preferably formed of stainless steel and includes a cylindrical rear portion 900 having a first radius, an intermediate rear portion 902 having a second radius smaller than the first radius and a main portion 904 having an overall radius equal to the first radius and having flattened side surfaces 906 on opposite sides thereof, as seen particularly in enlargements C & D in FIG. 7P. At a forward end 908 of elongate push rod 820 is formed top protrusion 818 (FIGS. 7C & 7D), which drivingly engages push rod engagement apertures 814 and 816 of respective bendable pusher strips 810 & 812, as seen particularly in enlargement C in FIG. 7P.

Reference is now made to FIGS. 7J & 7K, which illustrate one of curved shaft assembly outer elements 800. As seen in FIGS. 7J & 7K, each of curved shaft assembly outer elements 800 includes an elongate main portion 910 having top and bottom curved elongate portions 912 and 914 respectively and a flat elongate portion 916 extending therebetween. A pair of apertures 918 are formed on flat elongate portion adjacent a rearward end 919 thereof, as seen particularly in enlargement D in FIG. 7P.

Forwardly of main portion 910 is disposed a hook portion 920 having a curved outer surface 922 having a generally convex cross section and a curved inner surface 924 having a generally concave cross section, both of which terminate at a forward edge 926.

Reference is now made to FIGS. 7L & 7M, which illustrate one of curved shaft assembly inner elements 802. As seen in FIGS. 7L, & 7M, each of curved shaft assembly inner elements 802 includes an elongate main portion 930 having top and bottom curved elongate portions 932 and 934 respectively and a flat elongate portion 936 extending therebetween. A pair of alignment protrusions 938 are formed on flat elongate portion adjacent a rearward end thereof and are arranged to extend through corresponding apertures 918 on corresponding curved shaft assembly outer elements 800.

Forwardly of main portion 930 is disposed a hook portion 940 having a curved outer surface 942 having a generally convex cross section and an inner surface 944, both of which terminate at a forward edge 946. Rearwardly of main portion 930 is an end portion 950 having a threaded semicylindrical outer surface 952, which together with a similar surface on the other curved shaft assembly inner element 802 defines threaded end 806 (FIGS. 7C & 7D), as seen particularly in enlargement D in FIG. 7P.

As seen in FIG. 7L, a semicylindrical surface 960 extends from end portion 950 through main portion 930 to an inclined forward opening 962 and, together with a similar surface on the other curved shaft assembly inner element 802, defines a bore which receives work channel assembly 110 (FIGS. 3A-4D) having a forward opening 964.

Disposed above semicylindrical surface 960 is a generally semicylindrical surface 970 having an elongate recess 972. Semicylindrical surface 970 extends forwardly to a shoulder 974 and elongate recess 972 extends forwardly therebeyond entirely through main portion 930 and hook portion 940 to forward edge 946. Elongate recess 972 accommodates bendable pusher strips 810 and 812.

Inner surface 944 of hook portion 940 preferably defines three bearing surfaces, respectively designated 976, 978 and 980 for slidable engagement relative thereto of respective surfaces 874, 890 and 842 of bone puncture needle 840. Inner surface 944 of hook portion 940 also defines a receiving recess 982 for preformed loop 462, which recess has a flared opening 984 at forward edge 946.

Reference is now made additionally to FIGS. 7N & 7O, which illustrate curved shaft assembly location ring 804. Curved shaft assembly location ring 804 preferably is a generally cylindrical ring having a threaded inner bore 990, which is selectably threadably axially positionable over threaded semi-cylindrical outer surfaces 952 of curved shaft assembly inner elements 802, as seen particularly in enlargement D in FIG. 7P. Ring 804 defines an outwardly-facing cylindrical surface 992 and a flange 994 having an outwardly-facing cylindrical flange surface 996 and a forwardly-facing annular flange surface 998.

Reference is now made FIGS. 8A, 8B, 8C, 8D, 8E, 8F, 8G, 8H, 8I, 8J, 8K, 8L, 8M, 8N, 8O, 8P, 8Q, 8R, 8S, 8T, 8U, 8V, 8W, 8X, 8Y, 8Z, 8AA, 8AB, 8AC, 8AD, 8AE, 8AF, 8AG, 8AH, 8AI, 8AJ, 8AK, 8AL, 8AM, 8AN, 8AO, 8AP, 8AQ, 8AR, 8AS, 8AT, 8AU, 8AV, 8AW, 8AX, 8AY, 8AZ, 8BA, 8BB, 8BC, 8BD, 8BE, 8BF, 8BG, 8BH, 8BI, 8BJ, 8BK, 8BL, 8BM, 8BN, 8BO, 8BP, 8BQ, 8BR, 8BS, 8BT, & 8BU, which are simplified illustrations of arthroscopic surgical device 160, forming part of the arthroscopic surgical assembly of FIGS. 1A & 1B.

FIGS. 8A & 8B are respectively a rearward-facing exploded view illustration and a forward-facing partially exploded view illustration of arthroscopic surgical device 160. As seen in FIGS. 8A & 8B, arthroscopic surgical device 160 includes first and second housing portions 1002 and 1004, which enclose an arthroscopic surgical mechanism 1006, which is shown including work channel assembly 110 (FIGS. 3A-3N) and the curved shaft assembly 150 (FIGS. 7A-7P) and a spring 1007 associated with work channel assembly 110. Also seen in FIGS. 8A & 8B are a stopper pin 1008, a driving direction selector lever 1010 and a retaining cone 1011, which is operative for retaining first and second housing portions 1002 and 1004 together over and in engagement with the curved shaft assembly 150.

FIG. 8C shows a partially exploded view of arthroscopic surgical mechanism 1006 in which elements 1012, 1014, 1016 and 1018, which are operative for retraction of the work channel assembly 110, are shown separately. As seen particularly in FIG. 8D, element 1012 is a ratchet gear having a non-circular aperture 1022 and defining driving surfaces 1024 on each of a multiplicity of gear teeth 1026, which, in turn, engage linear ratchet gear track 304 (FIGS. 3H-3J).

Element 1014 is shown in FIGS. 8E & 8F and is an axle-mounted gear, which is preferably integrally formed and includes a cylindrical axle 1030 having a ratchet gear portion 1032 located intermediate therealong and defining driving surfaces 1034 on each of a multiplicity of gear teeth 1036 thereof. At a first end 1038 of cylindrical axle 1030 a recess 1040, preferably having an hexagonal cross-section and a pair of oppositely facing flat side surface portions 1042 are provided. Ratchet gear 1012 is preferably mounted onto the first end 1038 of cylindrical axle 1030.

Element 1016, shown in FIG. 8O, is a rotation urging spring having a coil 1044 arranged about an axis 1045 and a pair of spring end arms 1046 and 1048 which extend radially with respect to axis 1045.

Element 1018 is seen in FIGS. 8H & 8I from opposite directions and is a work channel assembly retaining hook element, which selectably locks and releases work channel assembly 110 with respect to arthroscopic surgical device 160. Work channel assembly retaining hook element 1016 is preferably integrally formed of plastic and includes a cylindrical axle portion 1050 from a side of which extends an arm 1052 having an undercut hook 1054 at an extreme end thereof. Hook 1054 includes an inclined outer surface 1056 and an inclined inner surface 1058. A transverse bore 1060 extends through hook 1054 under surface 1056 and receives spring end arm 1046.

Arm 1052 includes a curved cam surface 1062 which is separated from hook 1054 by an intermediate arm portion 1064.

It is appreciated that hook 1054 is urged by spring 1016 into engagement with transverse undercut 294 of main cylindrical portion 234 of the work channel assembly 110, thereby locking the work channel assembly 110 with respect to arthroscopic surgical device 160.

Figure 8J:
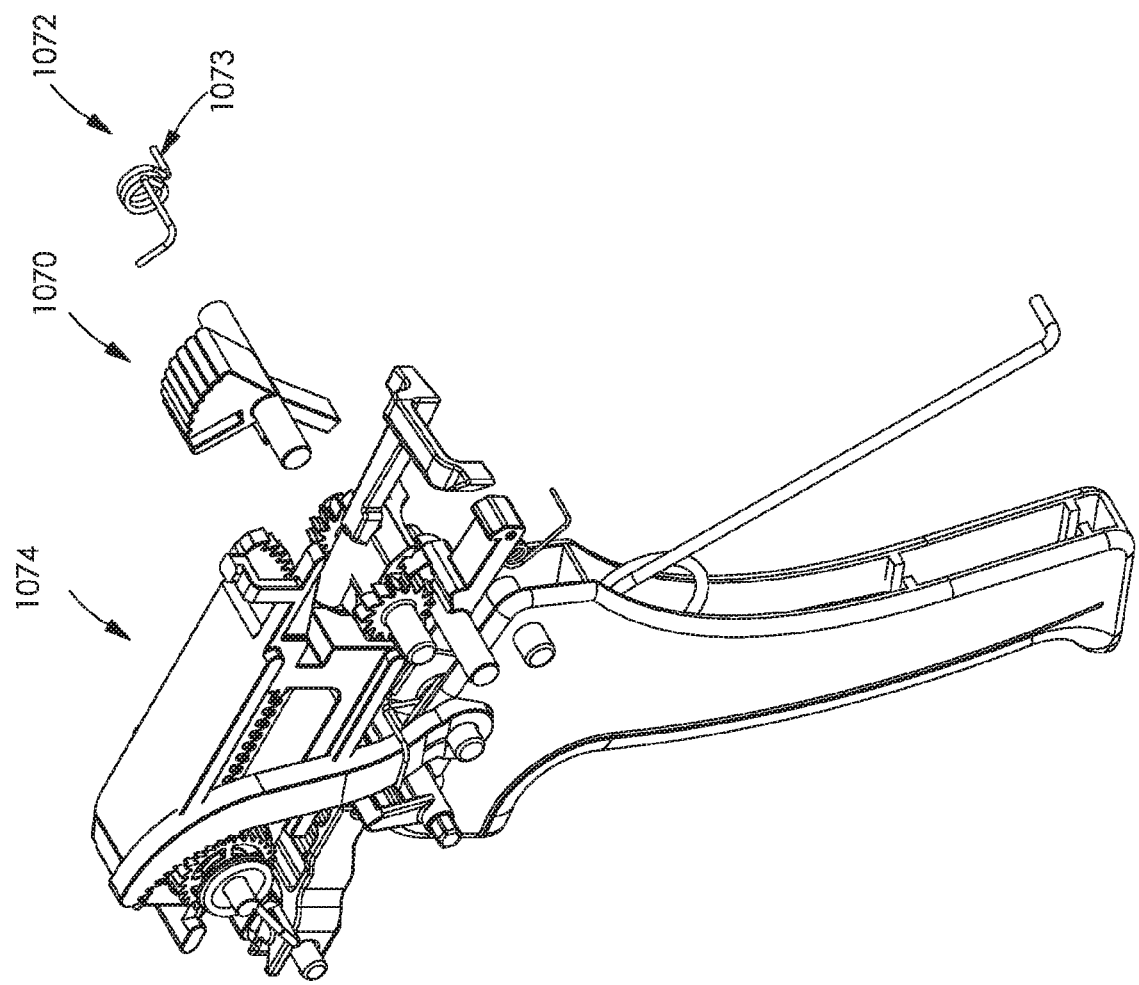
Figure 8M:
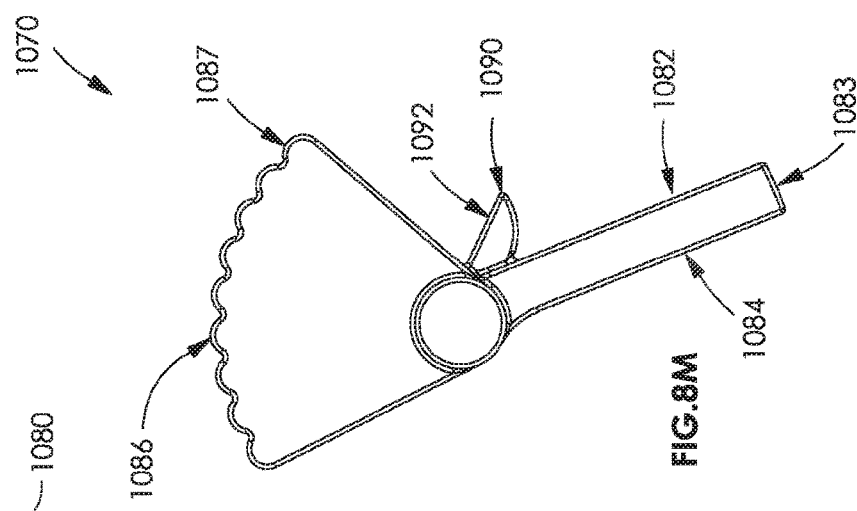
Figure 8L:
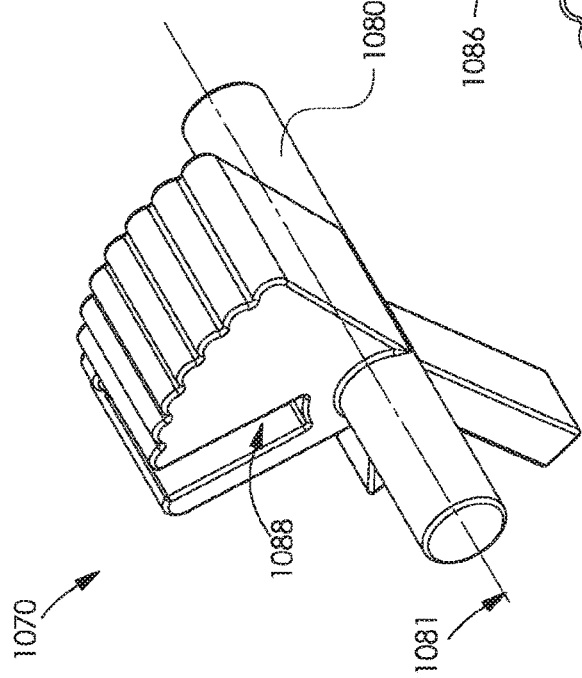
Figure 8K:
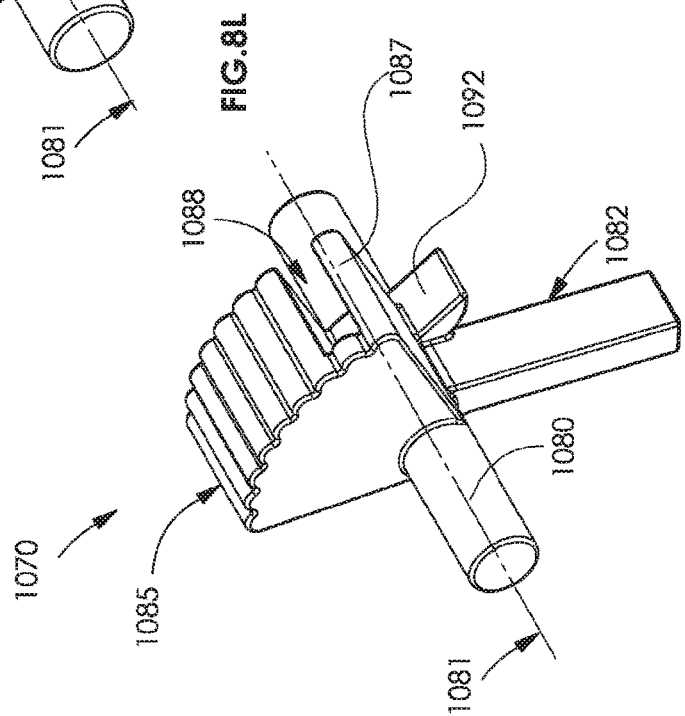
Figure 8N:
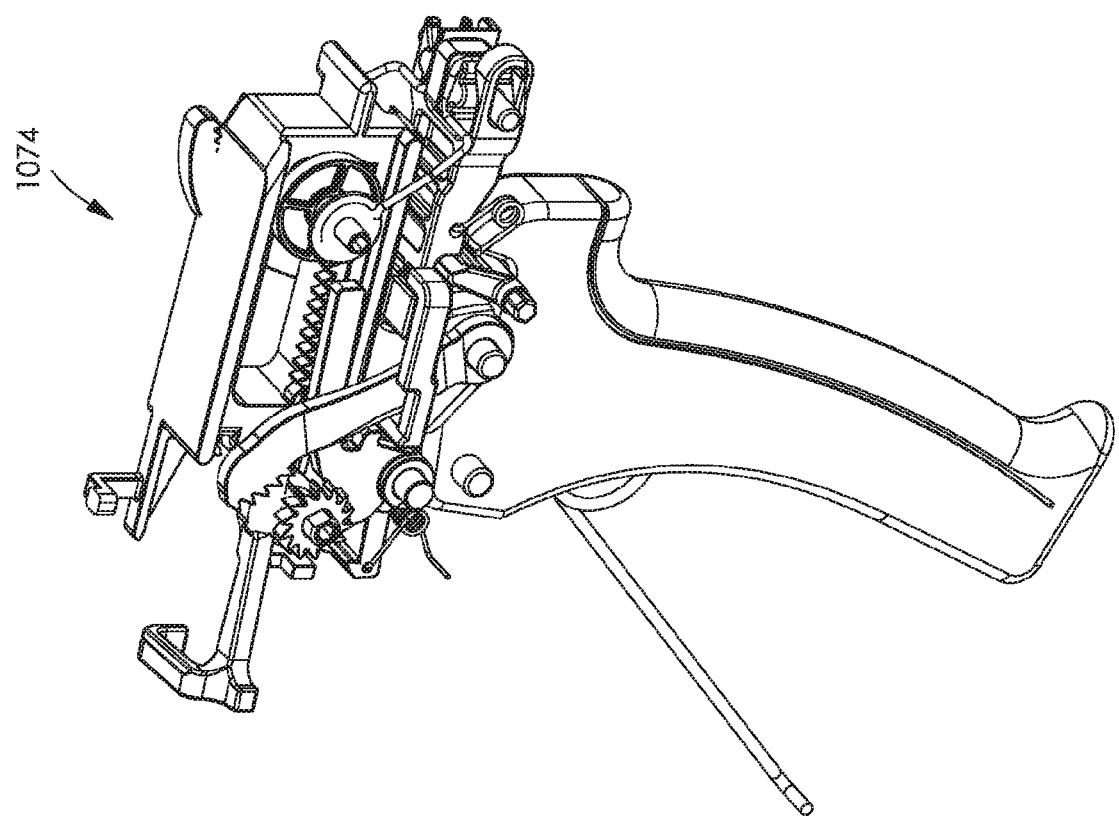
Figure 80:
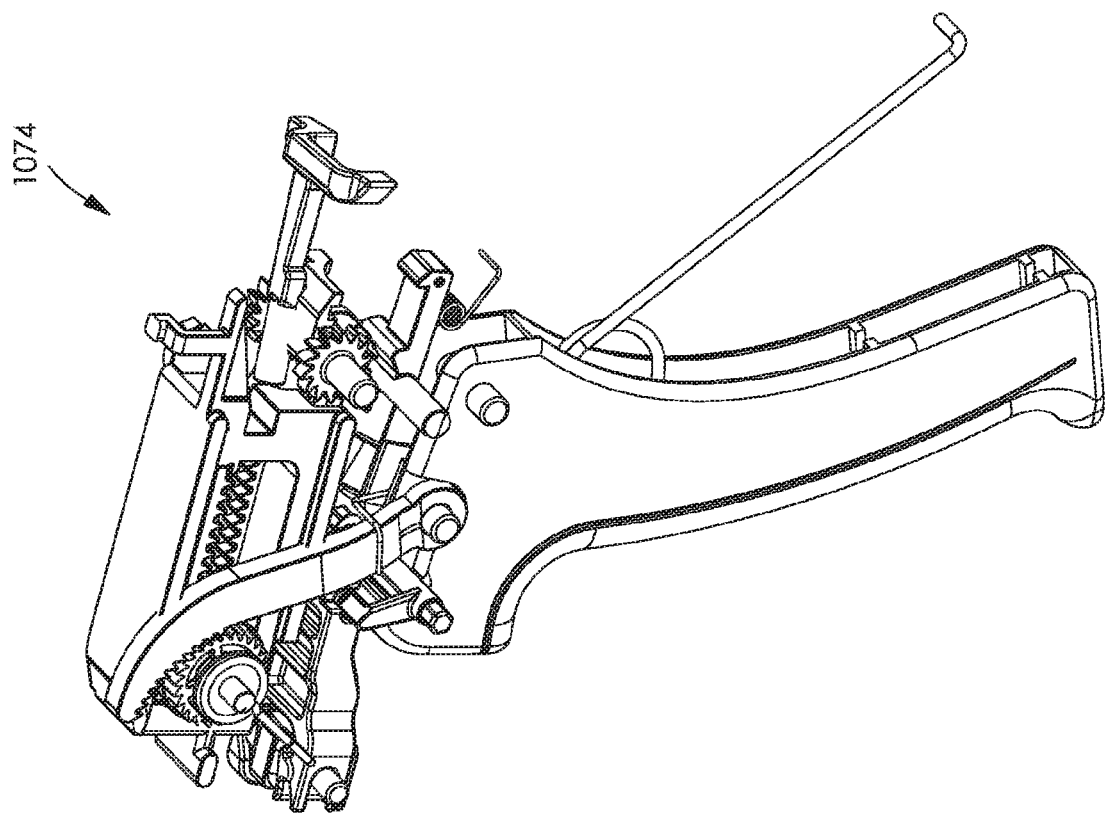
Figure 8P:
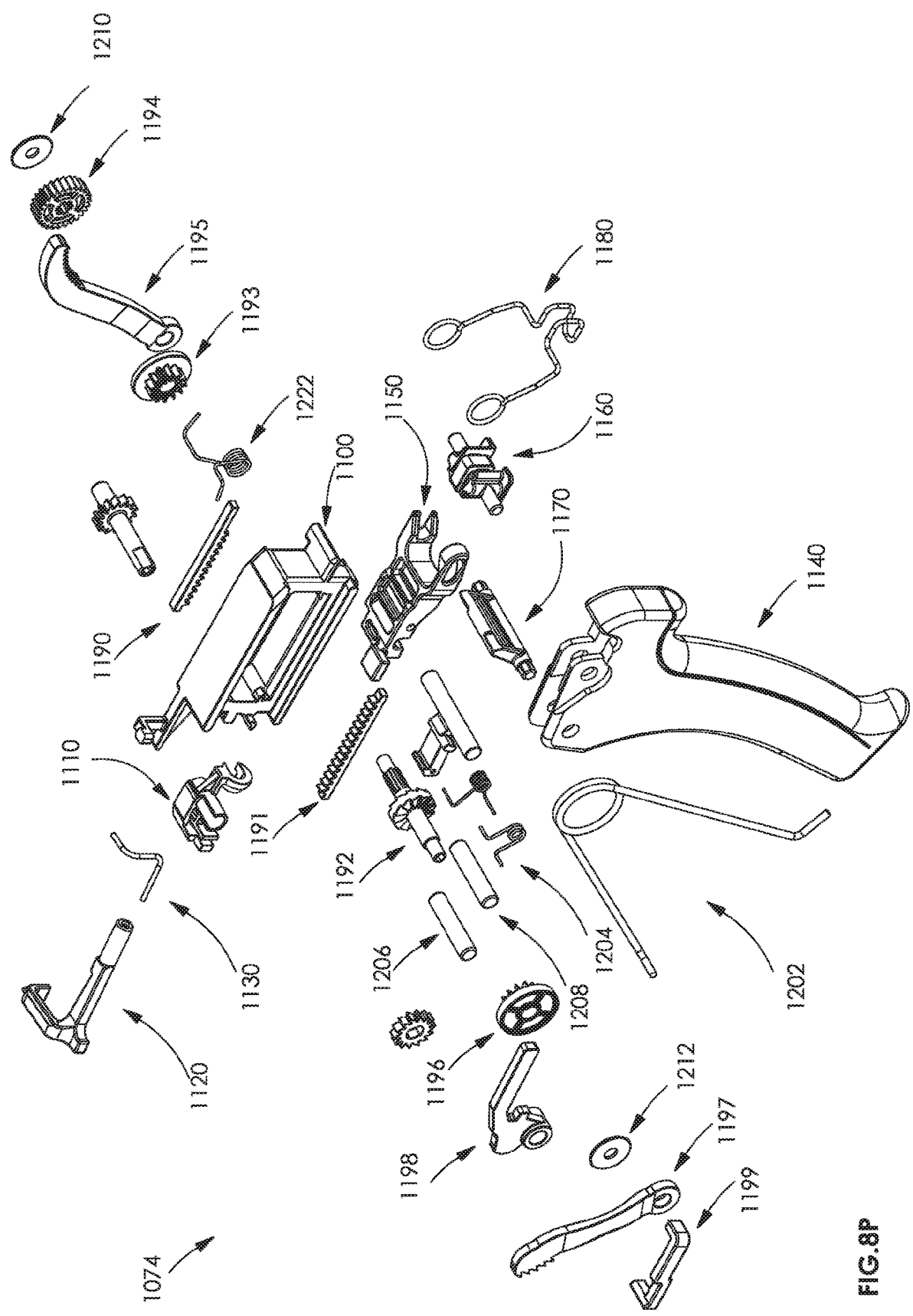
Figure 8Q:
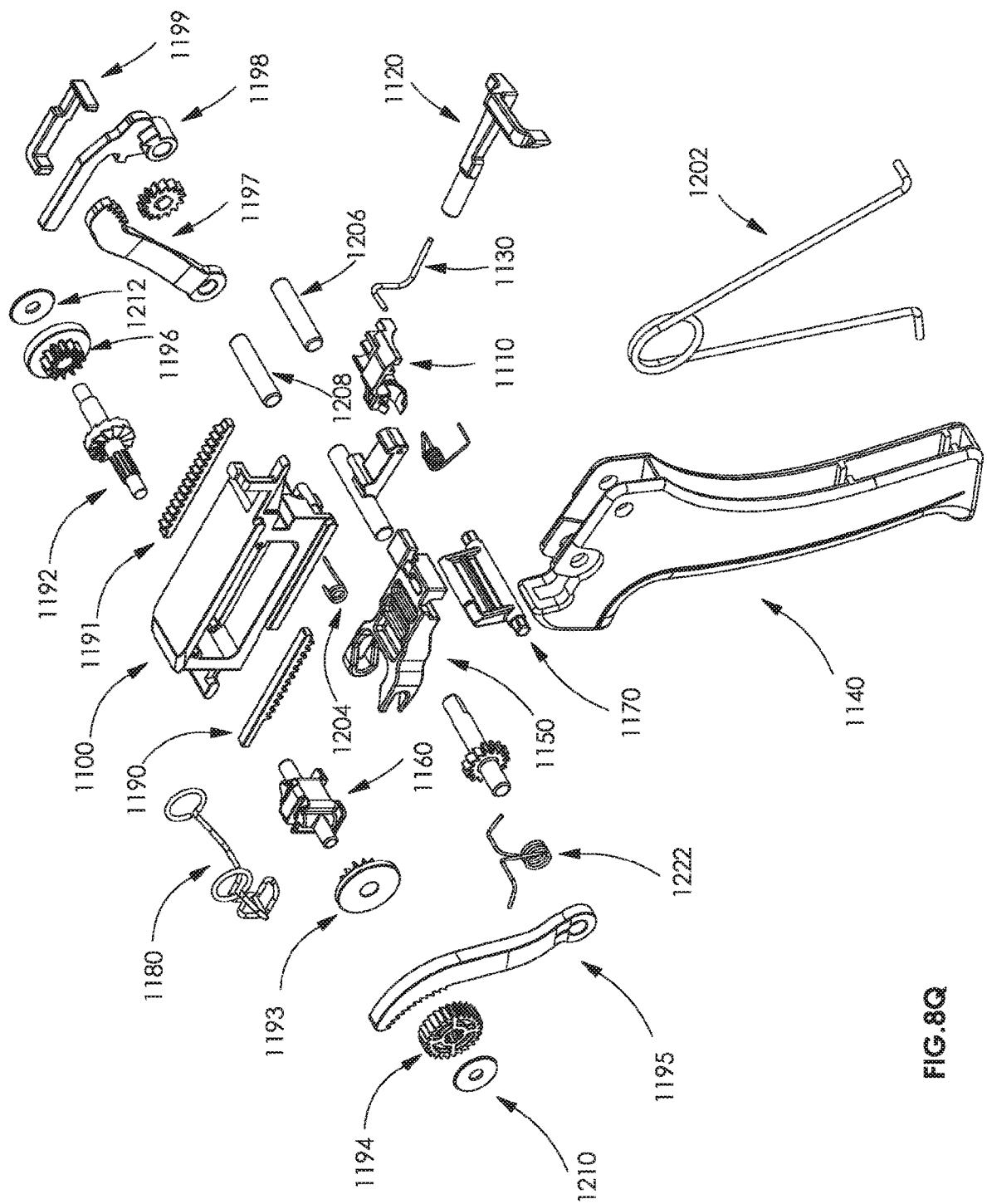
Figure 8A:
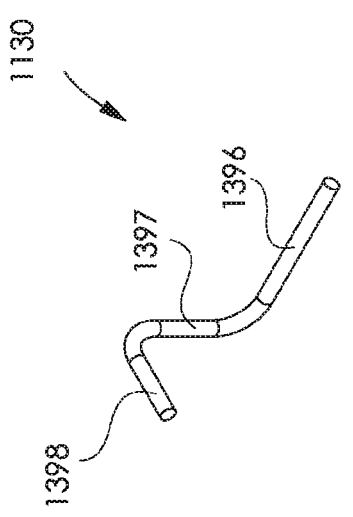
Figure 8A:
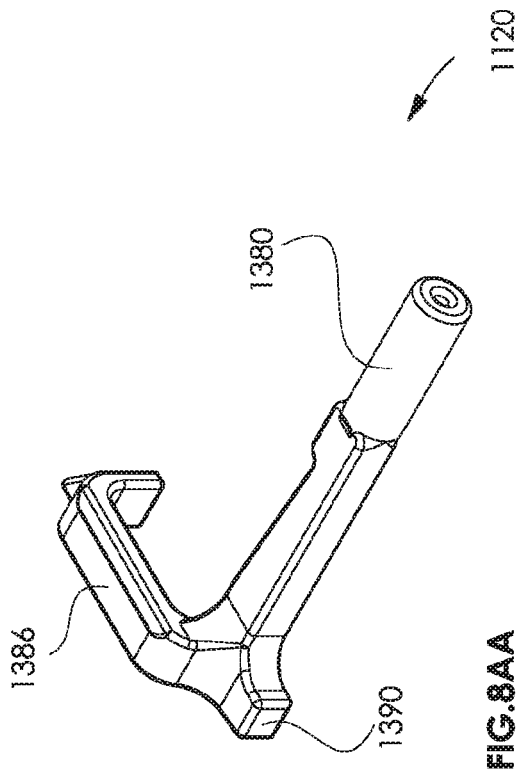
Figure 8A:
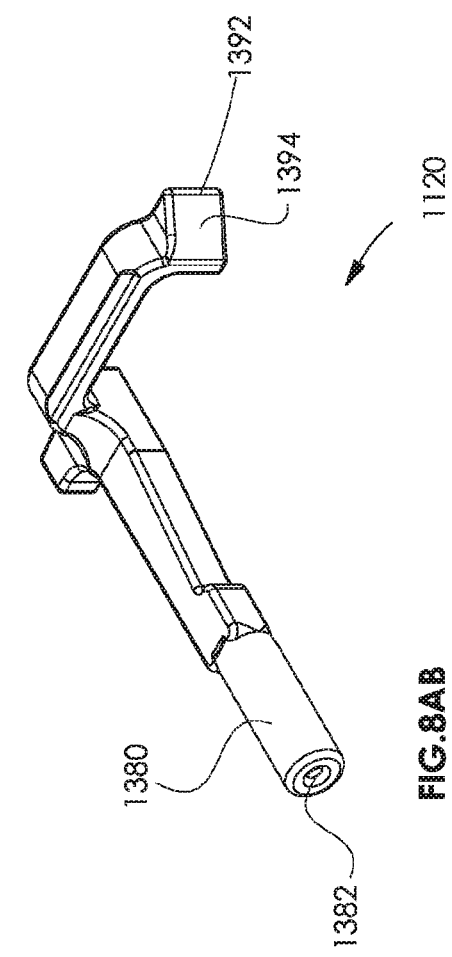

Reference is now made additionally to FIG. 8J, which shows an additional partially exploded view of arthroscopic surgical mechanism 1006 in which a cartridge assembly retaining element 1070, a cartridge assembly retaining spring 1072 which defines a retaining arm 1073 and a manually actuable driving engine assembly 1074 are isolated. Cartridge assembly retaining element 1070 is illustrated in FIGS. 8K, 8L & 8M and is preferably an integrally formed element made of plastic. Cartridge retaining element 1070 preferably includes an axle 1080, extending along an axis 1081 and having a cartridge retaining arm 1082 extending from a side thereof. Arm 1082 defines an end surface 1083 and a side surface 1084.

Extending to a side of axle 1080 generally in a direction opposite to that of arm 1082 is a manually engageable rotator surface defining portion 1085, which defines a splined thumb engagement surface 1086 comprising forward-most convex surface 1087 and, rearward of convex surface 1087, a notch 1088 for engagement therewith by a lever (not shown) for providing rotation of cartridge retaining element 1070 about axis 1081, when manual engagement with surface 1086 is not sufficient.

Also extending from a side of axle 1080 adjacent portion 1085 is a cartridge release cam portion 1090, which defines a cam surface 1092.

Reference is now made to FIGS. 8N & 8O, and FIGS. 8P & 8Q, which are respectively pairs of assembled and exploded view illustrations of manually actuable driving engine assembly 1074, each pair being taken from an opposite direction.

As seen in FIGS. 8N-8Q, the manually actuable driving engine assembly 1074 includes a main chassis 1100, which is described in detail hereinbelow with reference to FIGS. 8R-8U, an auxiliary chassis 1110, which is described in detail hereinbelow with reference to FIGS. 8V-8Y, a cartridge pusher 1120, which is described in detail hereinbelow with reference to FIGS. 8Z-8AB; a cartridge pusher connector 1130, which is described in detail hereinbelow with reference to FIG. 8AC; a hand-engageable driving handle 1140, which is described in detail hereinbelow with reference to FIGS. 8AD-8AG; a main driving direction shifting element 1150, which is described in detail hereinbelow with reference to FIGS. 8AH-8AK; a shiftable element 1160, which is described in detail hereinbelow with reference to FIGS. 8AL-8AO; a driving direction selector lever responsive toggle element 1170, which is described in detail hereinbelow with reference to FIGS. 8AP-8AR; a direction-shifting spring 1180, which is described in detail hereinbelow with reference to FIG. 8AS; a rearward driving gear rack 1190, which is described in detail hereinbelow with reference to FIGS. 8AT & 8AU, a forward driving gear rack 1191, which is described in detail hereinbelow with reference to FIGS. 8AV & 8AW; a clutch 1192, which is described in detail hereinbelow with reference to FIGS. 8AX & 8AY; a rearward driving gear 1193, which is described in detail hereinbelow with reference to FIG. 8AZ; a main driving gear 1194, which is described in detail hereinbelow with reference to FIG. 8BA; a needle driving ratchet arm 1195, which is described in detail hereinbelow with reference to FIGS. 8BB & 8BC; a forward driving gear 1196, which is described in detail hereinbelow with reference to FIG. 8BD; a work channel retracting ratchet arm 1197, which is described in detail hereinbelow with reference to FIGS. 8BE & 8BF; a pivotable arm 1198, which is described in detail hereinbelow with reference to FIGS. 8BG & 8BH and a shiftable link 1199, which is described in detail hereinbelow with reference to FIGS. 8BI & 8BJ.

Manually actuable driving engine assembly 1074 also includes a driving handle spring 1201 having ends 1202 and 1203; main driving direction shifting element spring 1204, a handle pivot axle 1206, a driving pin 1208; first and second washers 1210 and 1212; and a ratchet arm urging spring 1222.

Reference is now made to FIGS. 8R-8U, which show main chassis 1100. As seen in FIGS. 8R-8U, main chassis 1100 is a generally rectangular element having a, top portion 1250, a bottom portion 1252, a forward side portion 1254, a rearward side portion 1256, a forwardly-directed protrusion 1258, extending from forward side portion 1254 and having an edge surface 1259 and a rearwardly extending protrusion 1260, extending rearwardly from top portion 1250.

Disposed below top portion 1250 between forward side portion 1254 and rearward side portion 1256 is a socket 1262 which accommodates rearward driving gear rack 1190.

Disposed above bottom portion 1252 between forward side portion 1254 and rearward side portion 1256 is a socket 1270 which accommodates forward driving gear rack 1191.

As seen in FIG. 8R, disposed along one side of bottom portion 1252 is an elongate protrusion 1272, having an elongate top surface 1274 and an elongate edge surface 1276. Opposite rearward side portion 1256 on rear side of main chassis 1100, as seen in balloon of FIG. 8R, is an aperture 1277, a recessed surface 1278 and a semicircular elongate protrusion 1279 which together work to engage cartridge pusher connector 1130. The transverse portion 1398 of the cartridge pusher connector 1130 is seated in aperture 1277, the curved intermediate portion 1397 of cartridge pusher connector 1130 resides against the recessed surface 1278 and is further supported by the semicircular elongate protrusion 1279. As seen in FIG. 8S, disposed along an opposite side of bottom portion 1252 is an elongate protrusion 1282, having an elongate top surface 1284 and an elongate edge surface 1286.

As seen in FIG. 8T, disposed along one side of top portion 1250 is an elongate protrusion 1292, having an elongate top surface 1294 and an elongate edge surface 1296. As seen in FIG. 8R, disposed along an opposite side of top portion 1250 is an elongate protrusion 1302, having an elongate top surface 1304 and an elongate edge surface 1306. Extending rearwardly from forward side portion 1254 is a elongate push rod retaining socket 1310 which engages portion 902 of push rod 820. Rearwardly of socket 1310 is a recess 1312, which accommodates portion 900 of push rod 820.

Extending rearwardly and transversely from rearward side portion 1256 is a cam protrusion 1320, which defines a curved forwardly and downwardly directed cam surface 1322. Rearwardly extending protrusion 1260 includes a curved rearwardly and downwardly extending cam surface 1328 and also defines an upwardly and transversely extending portion 1330 having an upwardly facing indicator surface 1332.

Reference is now made to FIGS. 8V-8Y, which illustrate auxiliary chassis 1110. Auxiliary chassis 1110 includes a top, generally planar surface 1350 which extends forwardly in the sense of FIG. 8P to an inclined planar surface 1352. Underlying planar surface 1350 and extending transversely is a generally cylindrical socket 1354, which rotatably accommodates cylindrical axle 1030 of axle mounted gear element 1014. Rearwardly of socket 1354, auxiliary chassis 1110 defines generally cylindrical axial socket 1356, whose outer surfaces 1358 and 1360 together define a spring seat for spring 1007 (FIGS. 8A-8C). Auxiliary chassis 1110 also defines a mounting socket 1370, which is defined by surfaces 1372, 1374 and 1376.

Figure 8Z:
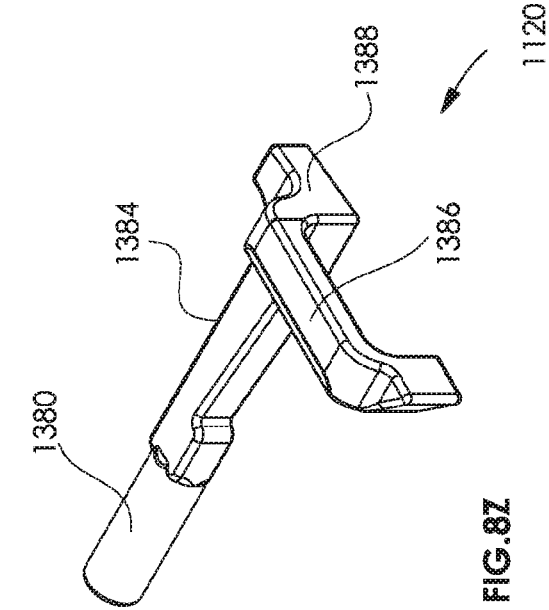
Figure 8A:
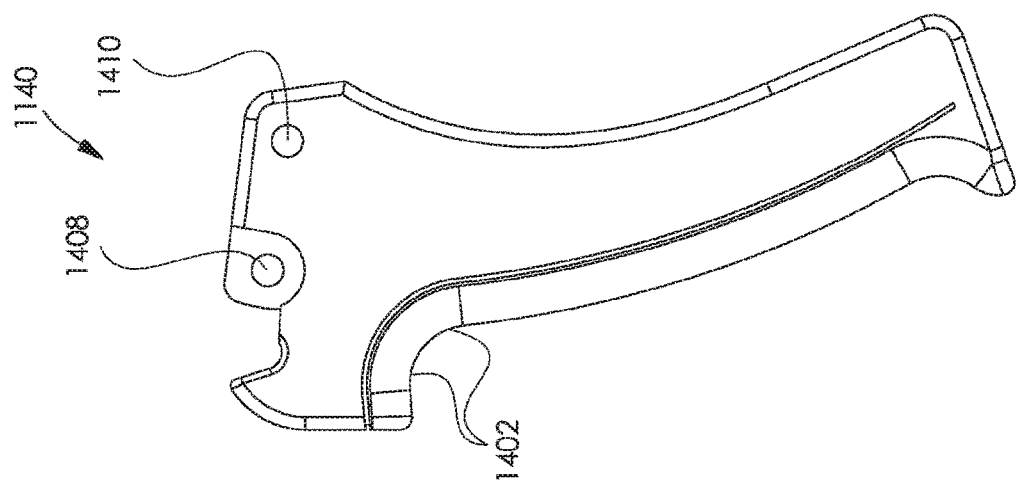
Figure 8A:
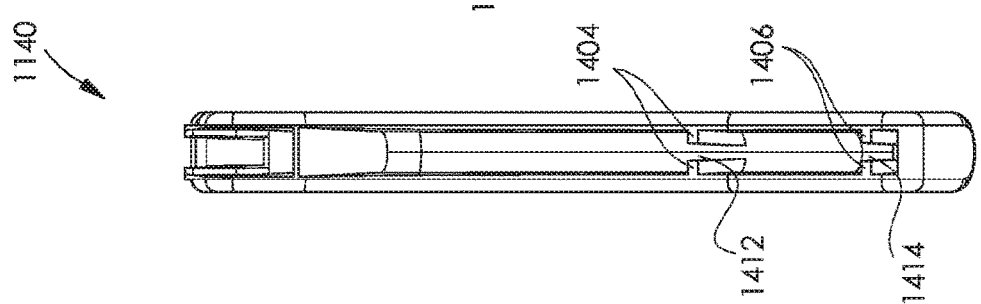
Figure 8A:
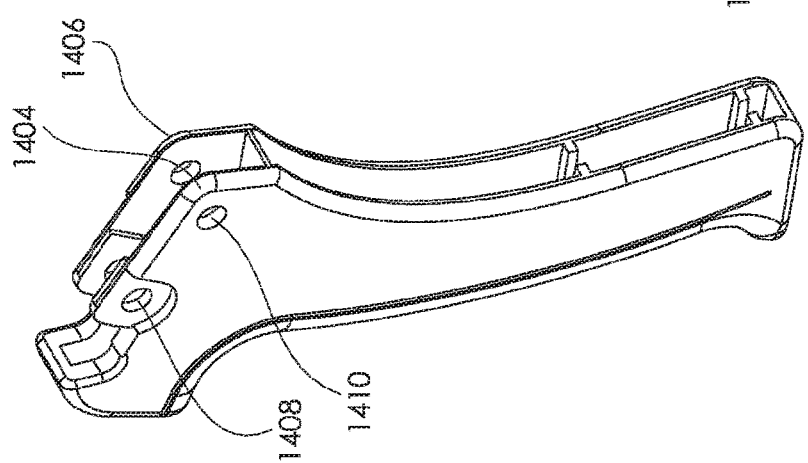
Figure 8A:
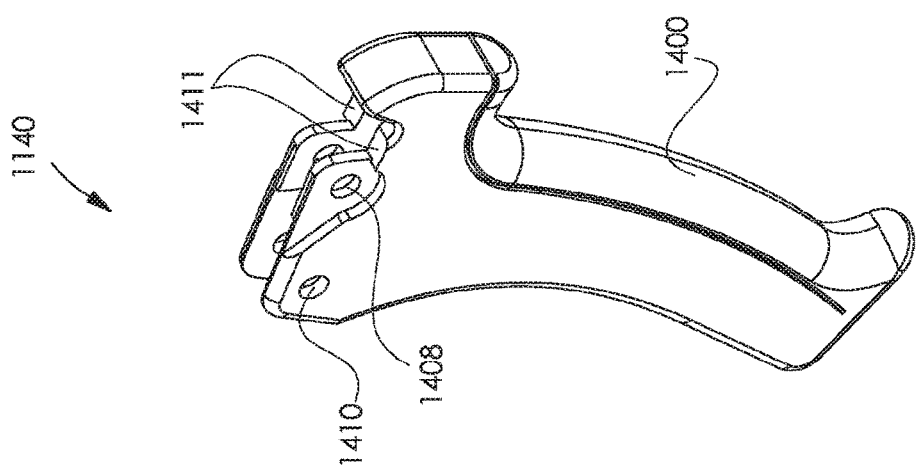
Figure 8A:
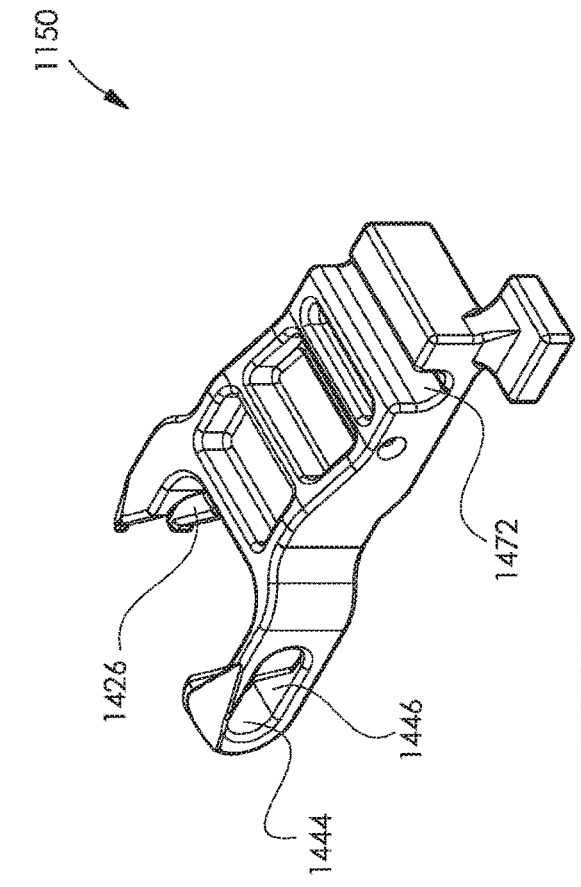
Figure 8A:
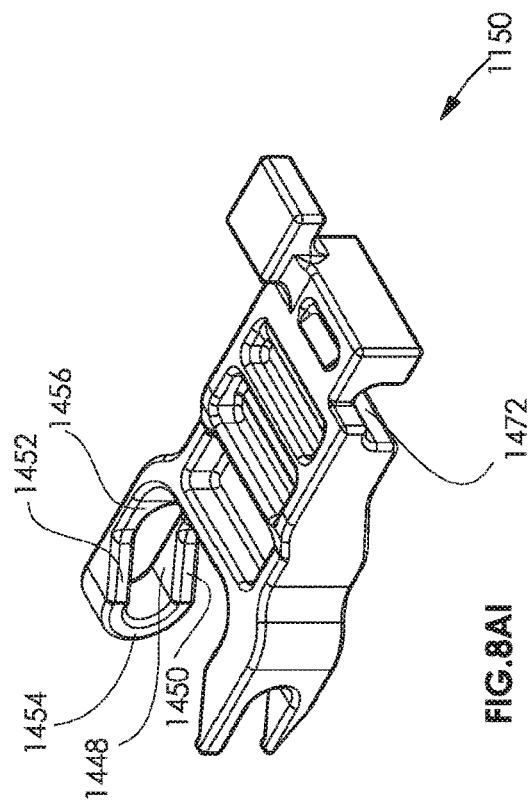
Figure 8A:
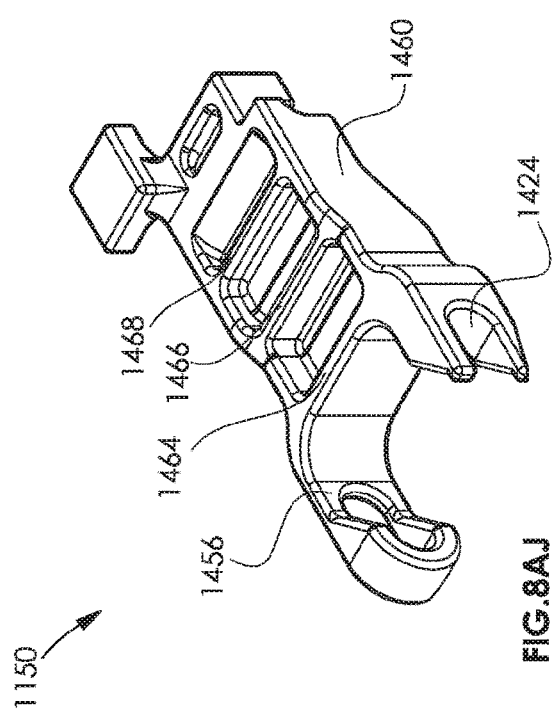
Figure 8A:
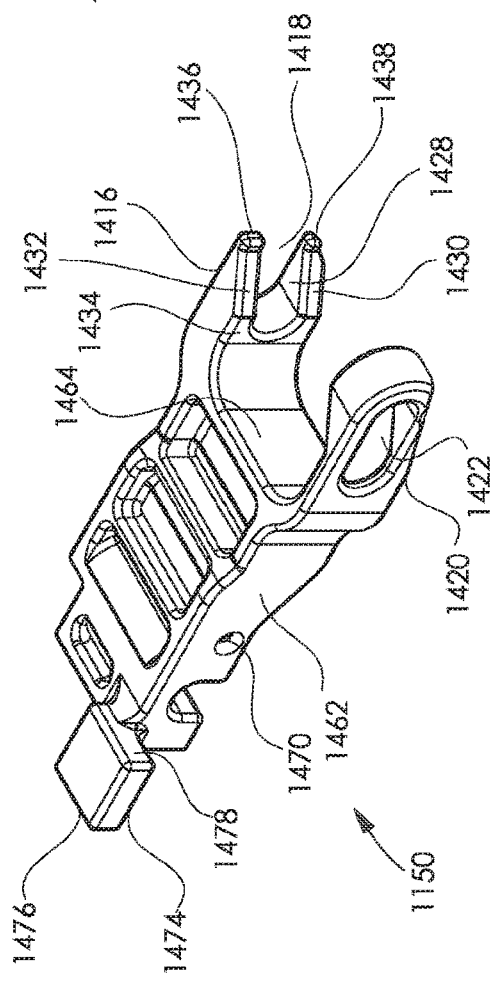
Figure 8B:
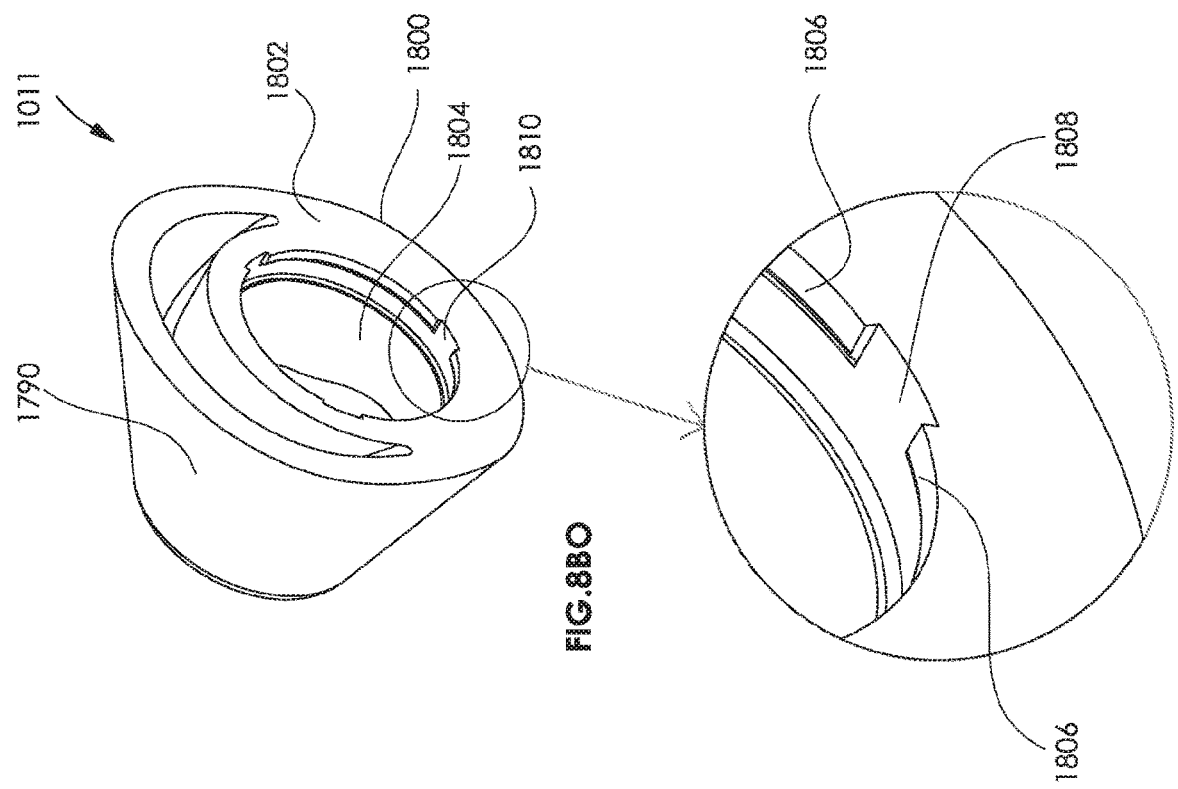
Figure 8B:
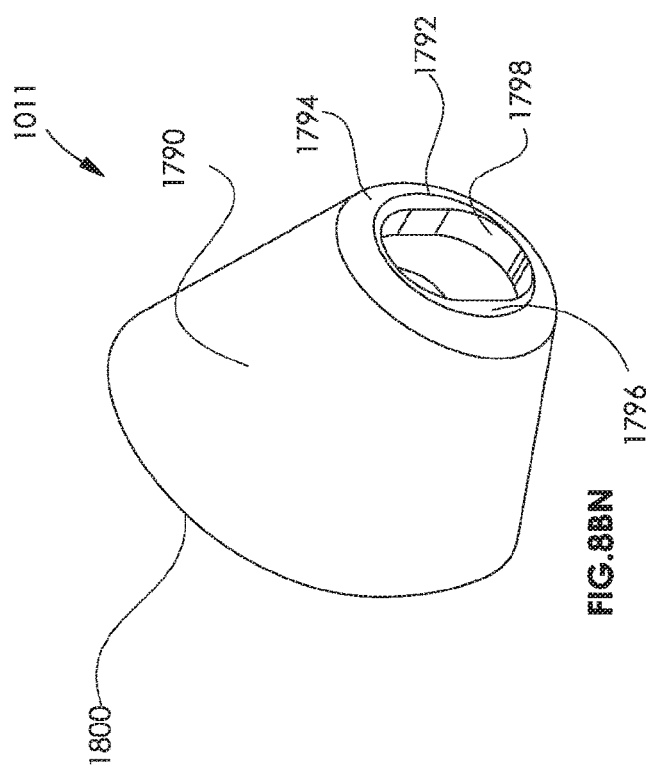
Figure 8B:
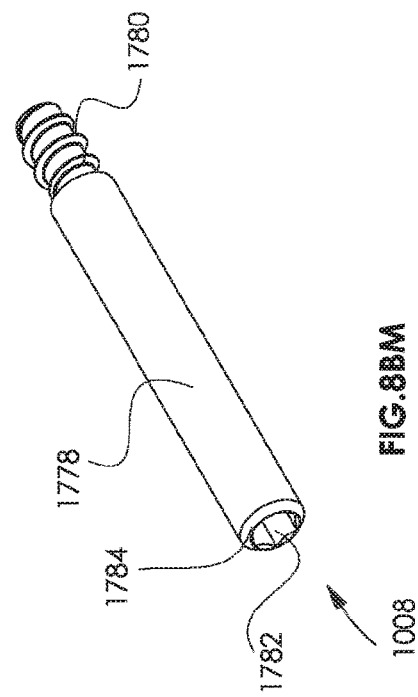
Figure 8B:
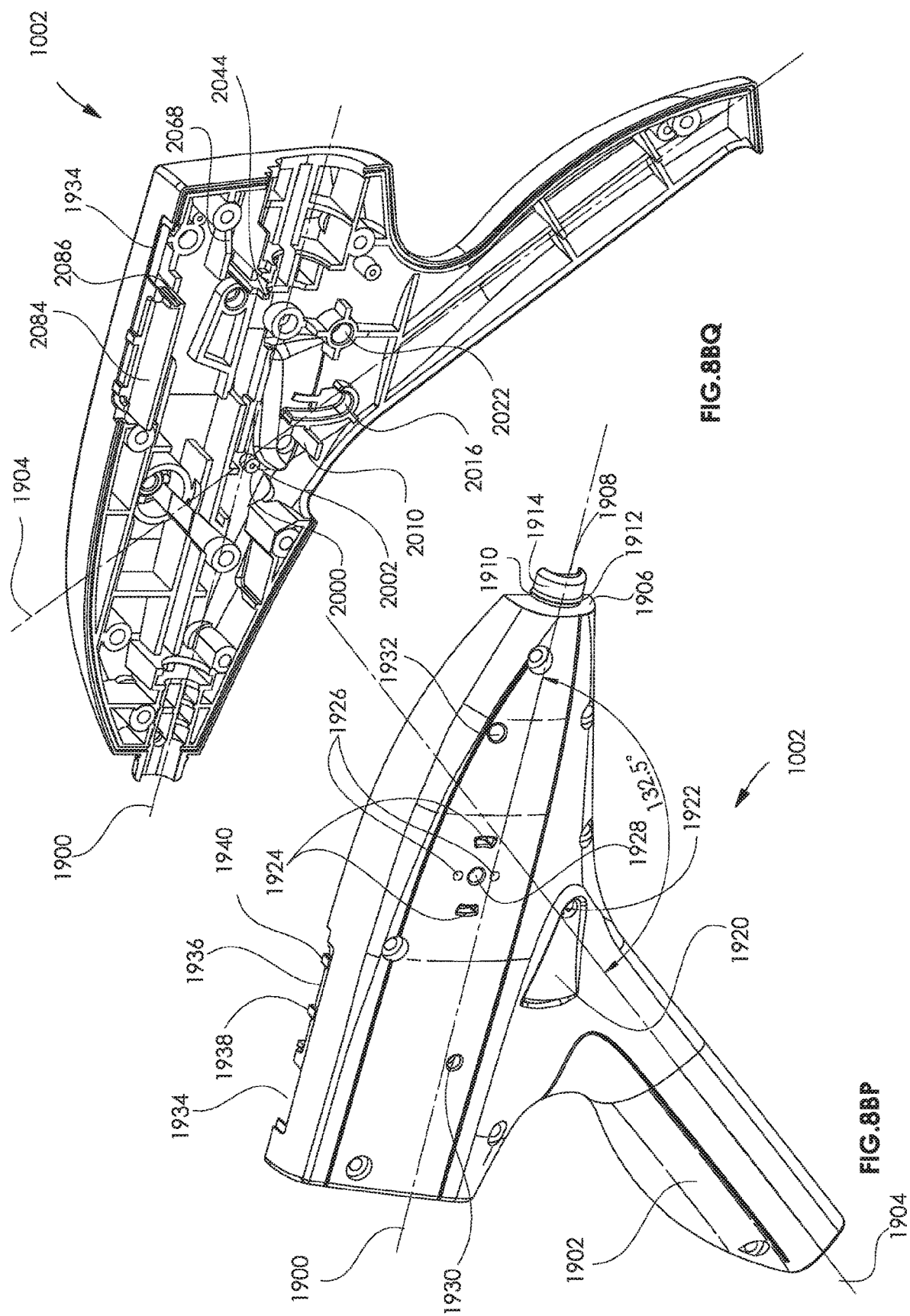
Figure 8B:
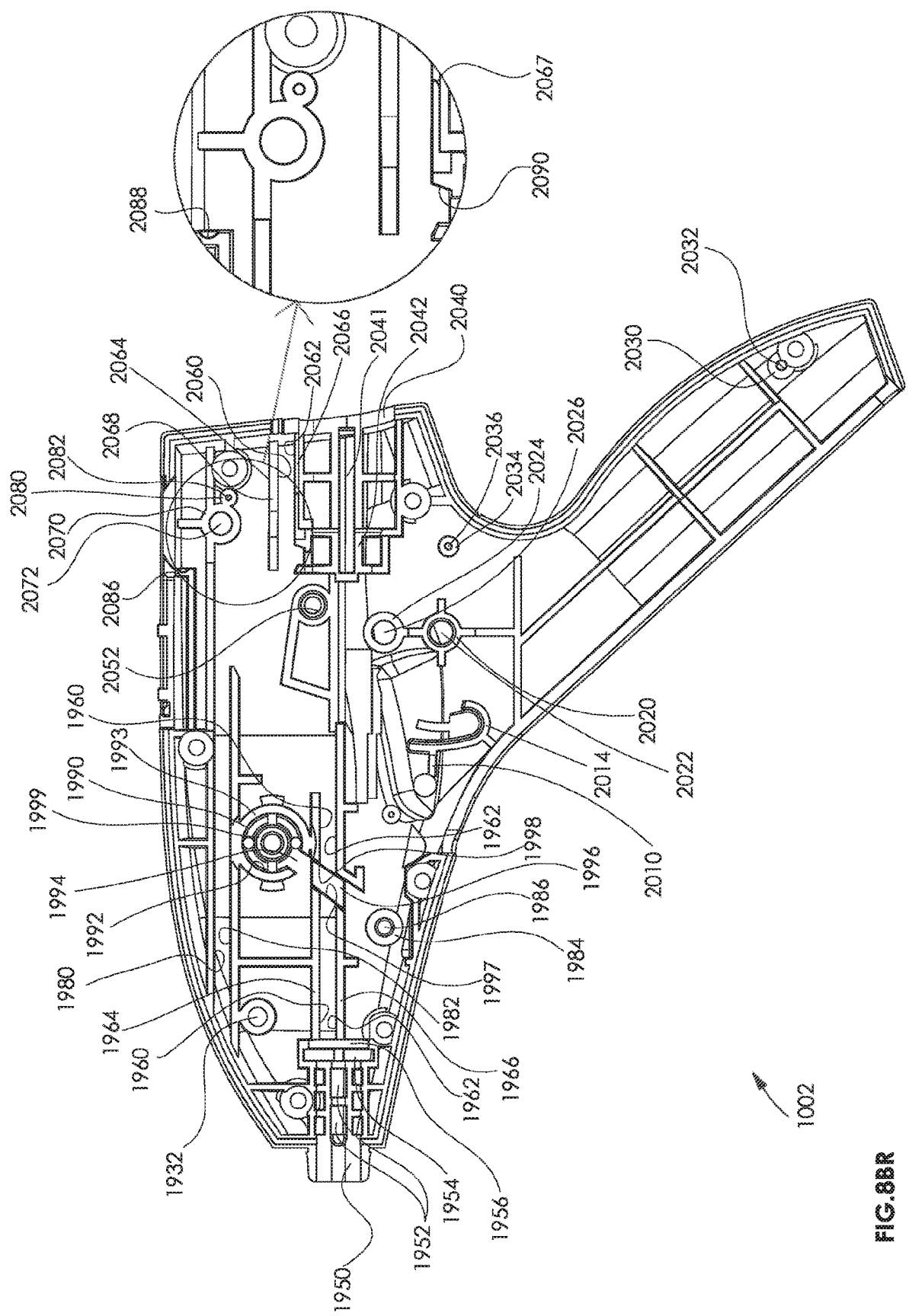
Figure 8B:
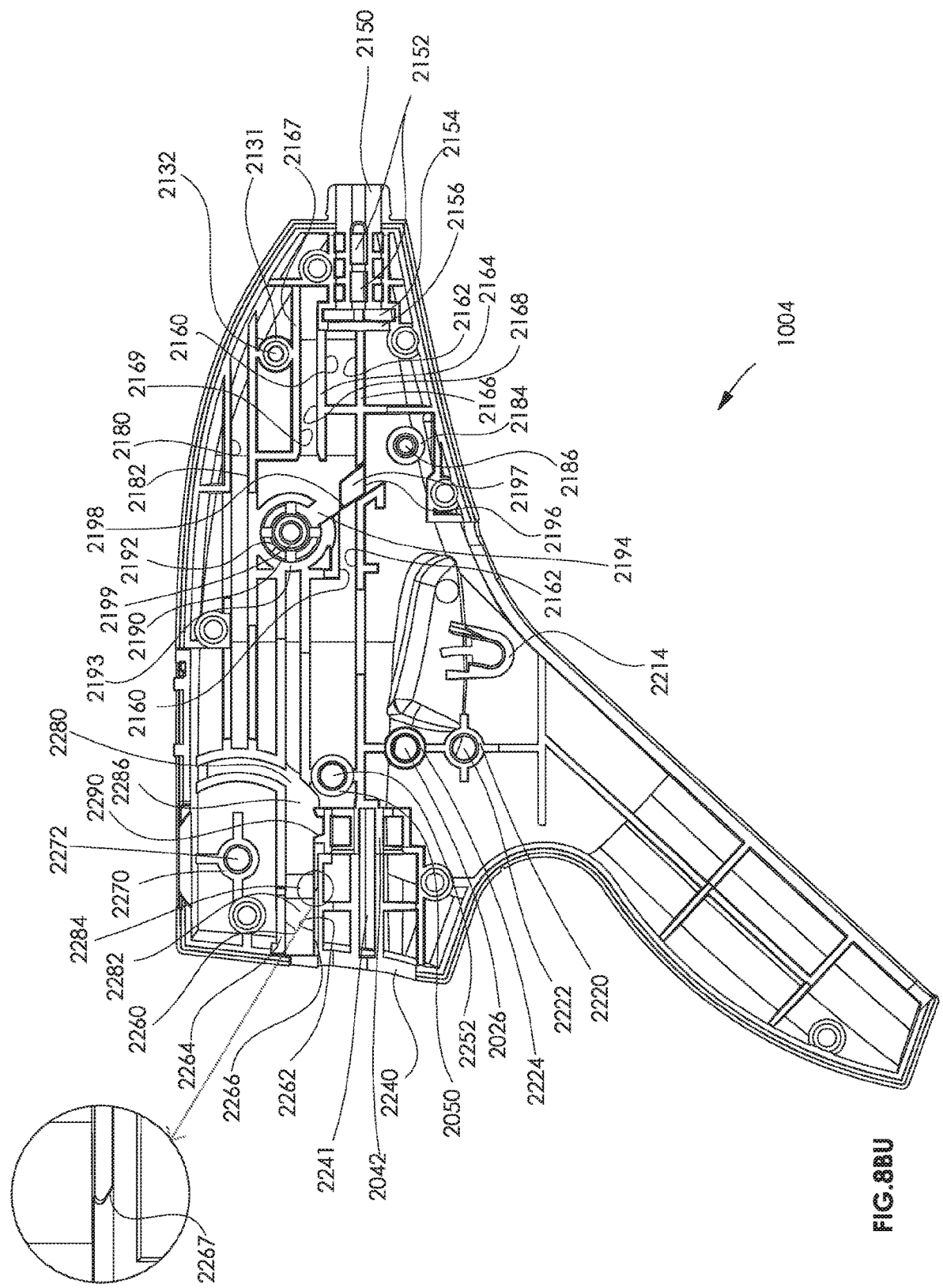

Reference is now made to FIGS. 8Z-8AB, which illustrate cartridge pusher 1120. Cartridge pusher 1120 preferably includes a generally cylindrical portion 1380 having an elongate bore 1382, which accommodates an end of cartridge pusher connector 1130. Rearwardly of cylindrical portion 1380 is an intermediate arm portion 1384 which extends to a transversely extending rearward portion 1386, having a rearward-facing surface 1388 and having a first end portion 1390 and a second end portion 1392 having an inclined planar surface 1394.

Reference is now made to FIG. 8C, which illustrates cartridge pusher connector 1130 and includes an axial portion 1396, which is seated in elongate bore 1382 of cartridge pusher 1120, a curved intermediate portion 1397 and a transverse portion 1398, which is seated in aperture 1277 formed in main chassis portion 1100.

Reference is now made to FIGS. 8AD-8AG, which illustrate hand engageable driving handle 1140. Hand engageable driving handle 1140 is preferably molded from plastic as one piece and includes a grip portion 1400 and a rest portion 1402. Hand engageable driving handle 1140 preferably includes a pair of generally parallel upstanding portions 1404 and 1406, each of which is formed with a forward aperture 1408 and a rearward aperture 1410. Forward apertures 1408 of upstanding portions 1404 and 1406 are mutually aligned in a transverse direction and accommodate driving pin 1208. Rearward apertures 1410 of upstanding portions 1404 and 1406 are mutually aligned in a transverse direction and accommodate handle pivot axle 1206.

Upstanding portions 1404 and 1406 each define a stop engaging surface 1411.

As seen particularly in FIG. 8AF, the pair of generally parallel upstanding portions 1404 and 1406 together define upper and lower spring retaining slots 1412 and 1414.

Reference is now made to FIGS. 8AH-8AK, which illustrate main driving direction shifting element 1150. As seen in FIGS. 8AH-8AK, main driving direction shifting element 1150 includes at a forward portion thereof a first arm 1416 defining an open socket 1418 and a second arm 1420, spaced from the first arm 1416 and defining a closed socket 1422. Open socket 1418 and closed socket 1422 together slidably accommodate main driving direction shifting element 1150.

Open socket 1418 is defined, inter alia, by a semi-cylindrical surface 1424 and respective top and bottom forward tapered surface 1426 and 1428. First arm 1416 also is defined by an inward facing angled bottom edge surface 1430, an inward facing angled top edge surface 1432, an arch-shaped inward facing surface 1434. Respective top and bottom forward protrusions 1436 and 1438 extend forwardly of respective edge surfaces 1430 and 1432. Closed socket 1422 is defined, inter glia, by a semi-cylindrical surface 1444 and respective top and bottom rearward tapered surface 1446 and 1448. Second arm 1420 also is defined by an inward facing angled bottom edge surface 1450, an inward facing angled top edge surface 1452, and respective outer and inner arch-shaped inward facing surfaces 1454 and 1456.

Extending rearwardly of first and second arms 1416 and 1420 is a central portion including side walls 1460 and 1462 and transverse walls 1464, 1466 and 1468. Side wall 1462 is formed with a spring end engagement aperture 1470 for accommodating spring 1204. Rearwardly of the central portion is an end portion that includes a transverse semi-cylindrical downwardly-facing transverse socket 1472 which pivotably accommodates driving direction selector lever responsive toggle element 1170.

Rearwardly of socket 1472 there is provided an end portion 1474 which defines an upwardly directed table 1476 having a forward edge surface 1478.

Reference is now made to FIGS. 8AL-8AO, which illustrate shiftable element 1160, which is slidably retained by the respective open and closed sockets 1416 and 1420 of main driving direction shifting element 1150. Shiftable element 1160 is preferably injection molded of plastic and includes a central portion 1500 and identical first and second side portions 1502 and 1504, having respective axles 1506 and 1508, which respectively engage open socket 1416 and closed socket 1420.

First and second side portions 1502 and 1504 define respective generally convex cam engagement surfaces 1512 and 1514 and each define respective downwardly-facing planar surfaces 1516 and 1518. Central portion 1500 preferably defines a nearly circumferential spring engagement surface 1520 and a nearly circumferential edge surface 1522 for engagement with direction-shifting spring 1180. Surfaces 1520 and 1522 cooperate with corresponding facing edge surfaces 1524 and 1526 of first and second side portions to define a spring seat 1530 for direction-shifting spring 1180.

Reference is now made to FIGS. 8AP-8AR, which illustrate driving direction selector lever responsive toggle element 1170. Driving direction selector lever responsive toggle element 1170 is preferably a unitary element, injection molded of plastic and includes a main axial portion 1550 and a transverse portion 1552, including a pair of side directed arms 1554 and 1556 and a pair of elongate portions 1558 and 1560 extending therebetween.

Main axial portion 1550 preferably includes a pair of axial end protrusions 1562 and 1564, preferably having a hexagonal cross section. Elongate portion 1560 preferably includes a pair of planar cam surfaces 1568 and 1570 and is engaged with semi-cylindrical downwardly-facing transverse socket 1472 of main driving direction shifting element 1150.

Reference is now made to FIG. 8AS, which illustrates direction shifting spring 1180. As seen in FIG. 8AS, the direction shifting spring 1180 includes a central, generally planar, loop portion 1580, which is bent by approximately 90 degrees to define a first generally planar intermediate portion 1582 and further bent by approximately 90 degrees to define a second generally planar intermediate portion 1584. Portions 1580, 1582 and 1584 preferably engage spring seat 1530 of shiftable element 1160.

A pair of closed loop rings 1586 and 1588 define respective ends of spring arms 1590 and 1592, which are, in turn extensions of respective ends of second generally planar intermediate portion 1584.

Reference is now made to FIGS. 8AT & 8AU, which illustrate forward driving gear rack 1191. It is seen that forward driving gear rack 1191 includes a multiplicity of linearly arranged gear teeth 1594, each having a rearwardly facing engagement surface 1596.

Reference is now made to FIGS. 8AV & 8AW, which illustrate rearward driving gear rack 1190. It is seen that rearward driving gear rack 1190 includes a multiplicity of linearly arranged gear teeth 1597, each having a forwardly facing engagement surface 1598.

Reference is now made to FIGS. 8AX & 8AY, which illustrate clutch 1192. As seen in FIGS. 8AX & 8AY, clutch 1192 includes an elongate axle 1600 having a first generally circularly cylindrical end portion 1602 having a hexagonal recess 1604 formed therein and having a first diameter. First end portion 1602 defines a shoulder 1606 with a second circularly cylindrical portion 1608 having a second diameter, greater than the first diameter.

Second portion 1608 terminates in a first annular surface 1610 of a gear disk portion 1612, which is also formed with a second annular surface 1614. First annular surface 1610 is formed with a circular array of gear teeth 1616, each having a tooth engagement surface 1618 arranged on a counterclockwise-facing edge thereof, in the sense of FIG. 8AX. Second annular surface 1614 is formed with a circular array of gear teeth 1620, each having a tooth engagement surface 1622 arranged on a counterclockwise-facing edge thereof, in the sense of FIG. 8AX and on a clockwise-facing edge thereof, in the sense of FIG. 8AY.

Extending beyond second annular surface 1614 is a third circularly cylindrical portion 1628 having a third diameter, equal to the second diameter and therebeyond, in the sense of FIG. 8AX is a outer-facing linearly splined portion 1630, followed by a fourth circularly cylindrical portion 1632, having a diameter identical to that of first circularly cylindrical portion 1602.

Reference is now made to FIG. 8AZ, which illustrates a rearward driving gear 1193. As seen in FIG. 8AZ, rearward driving gear 1193 includes a disk-like portion 1650 from one planar surface of which extends a circular array 1652 of complex gear teeth 1654. It is seen that each tooth 1654 is provided with a pair of convex, oppositely-facing driving surfaces 1656. In addition, each tooth is provided with a planar, clockwise-facing, in the sense of FIG. 8AZ, driven surface 1658. It is also seen that rearward driving gear 1193 is provided with a central bore 1660, which accommodates third circularly cylindrical portion 1628 of clutch 1192.

Reference is now made to FIG. 8BA, which illustrates main driving gear 1194. As seen in FIG. 8BA, main driving gear 1194 is of generally disk-like configuration and is formed with a central splined bore 1670, which accommodates outer-facing linearly splined portion 1630 for driving of clutch 1192. Main driving gear includes a circular array 1672 of gear teeth 1674, each having clockwise-facing generally planar driven surface 1676.

Reference is now made to FIGS. 8BB & 8BC which illustrate needle-driving ratchet arm 1195. As seen in FIGS. 8BB & 8BC, needle-driving ratchet arm includes a pivot portion 1680 including a pivot axle accommodating aperture 1682 for pivotably receiving driving pin 1208. Ratchet arm 1195 includes a generally straight intermediate portion 1684 from which extends a curved gear engagement portion 1686 having on an inner curved surface thereof a curved elongate array 1688 of gear teeth 1690, each having a generally planar driving surface 1692.

Reference is now made to FIG. 8BD, which illustrates a forward driving gear 1196. As seen in FIG. 8BD, forward driving gear 1196 includes a disk-like portion 1693 from one planar surface of which extends a circular array 1694 of complex gear teeth 1695. It is seen that each tooth 1695 is provided with a pair of convex, oppositely-facing driving surfaces 1696. In addition, each tooth is provided with a planar, counterclockwise-facing, in the sense of FIG. 8BD driven surface 1698. It is also seen that forward driving gear 1196 is provided with a central bore 1699, which accommodates second circularly cylindrical portion 1608 of clutch 1192.

Reference is now made to FIGS. 8BE & 8BF which illustrate work channel retracting ratchet arm 1197. As seen in FIGS. 8BE and 8BC, work channel retracting ratchet arm 1197 includes a pivot portion 1700 including a pivot axle accommodating aperture 1702 for pivotably receiving driving pin 1208. Ratchet arm 1197 includes a generally straight intermediate portion 1704 from which extends a curved gear engagement portion 1706 having on an outer curved surface thereof a curved elongate array 1708 of gear teeth 1710, each having a generally planar driving surface 1712.

Reference is now made to FIGS. 8BG & 8BH which illustrate pivotable arm 1198. As seen in FIGS. 8BG & 8BH, pivotable arm 1198 includes a pivot portion 1720 including a pivot axle accommodating aperture 1722 for pivotably receiving work channel assembly retaining hook element 1018. Pivotable arm 1198 includes an intermediate portion 1723, having a protrusion 1724 defining a concave surface 1725 and a convex surface 1726, which engages intermediate arm portion 1064 of work channel assembly retaining hook element 1018. An elongate portion 1727 extends outwardly from intermediate portion 1723 and has a top surface 1728, a bottom surface 1729 and an end surface 1730.

Reference is now made to FIGS. 8BI & 8BJ, which illustrate shiftable link 1199. As seen in FIGS. 8BI & 8BJ, shiftable link 1199 includes a first arm portion 1750 including a forward and top facing curved elongate portion 1752 and a generally planar forward facing elongate portion 1754. Extending perpendicularly to first arm portion 1750 is a first elongate portion 1756, which extends to a second elongate portion 1758, which is upwardly offset with respect to first elongate portion 1756. A second arm portion 1760 extends from and generally perpendicularly to second elongate portion 1758 and defines a rearwardly facing generally planar surface 1762.

Reference is now made to FIGS. 8BK & 8BL, which illustrate driving direction selector lever 1010, As seen in FIGS. 8BK & 8BL, driving direction selector lever 1010 includes upper and lower finger contact surfaces 1770 and 1772 respectively, an inner surface 1773 and a pivot portion 1774 having a hexagonal recess 1776 for receiving one of axial end protrusions 1562 and 1564.

Reference is now made to FIG. 8BM, which illustrates stopper pin 1008. Stopper pin 1008 is a generally cylindrical element having a main portion 1778, a threaded end 1780 and a hexagonal socket 1782 at an end 1784 opposite to threaded end 1780.

Reference is now made to FIGS. 8BN & 8BO, which illustrate a generally hollow retaining cone 1011. Retaining cone 1011 preferably has an outer generally truncated conical shaped surface 1790. At a narrow end 1792 thereof, retaining cone 1011 defines an inclined annular surface 1794. Interior of inclined annular surface is formed a generally flat surface 1796 having a rounded rectangular aperture 1798 formed therein.

At a wide end 1800 thereof, retaining cone 1011 defines a flat surface 1802 including a circular aperture 1804 having an interior circumferential aperture wall 1806 including three, generally evenly azimuthally distributed recesses 1808, which extend interiorly of flat surface 1802 to a circumferential interior recessed wall 1810.

Reference is now made to FIGS. 8BP, 8BQ & 8BR, which are respectively simplified pictorial illustrations of inside and outside surfaces of first housing portion 1002 and a plan view illustration of the inside housing surface of the first housing portion.

As seen in FIGS. 8BP-8BR, it is seen that the first housing portion 1002 defines a main driving axis 1900 and a hand engageable driving handle portion 1902, having an axis 1904 which is preferably angled with respect to main driving axis 1900 by 132.5 degrees. At a forward end of first housing portion 1002 there is defined a cone engagement surface 1906, which preferably engages wide end 1800 of retaining cone 1011. Forwardly of cone engagement surface 1906 is a semi-cylindrical cone engageable portion 1908 having a circumferential recess 1910 adjacent cone engagement surface 1906. Forward of circumferential recess 1910 is a circumferential protrusion 1912 and forward of circumferential protrusion 1912 is another circumferential recess 1914. Recesses 1910 and 1912 and protrusion 1914 are arranged for snap-fit engagement with circumferential aperture wall 1806 of retaining cone 1011.

An outer surface of first housing portion 1002 defines a recess 1920 for receiving driving direction selector lever 1010 and including an aperture 1922. As seen particularly in FIGS. 8BP and 8BR, the first housing portion 1002 is formed with a pair of curved apertures 1924 and a pair of round apertures 1926, all of which surround a central aperture 1928.

An aperture 1930 and an aperture 1932 are also formed in the first housing portion, as are a first top edge cut out 1934 and a second top edge cut out 1936, which includes a pair of protrusions 1938 and 1940.

Turning now particularly to FIGS. 8BQ & 8BR, it is seen that an inner surface of first housing portion 1002 includes a forward generally concave surface 1950, which accommodates curved shaft assembly 150. Concave surface 1950 defines a pair of recesses 1952, which accommodate pins 938 of curved shaft assembly 150. A recess 1954 is defined rearwardly of surface 1950 and accommodates curved shaft assembly location ring 804. A rear wall of recess 1954 defines a concave surface 1956, which also accommodates curved shaft assembly location ring 804.

A pair of elongate mutually spaced facing surfaces 1960 and 1962 on respective protrusions 1964 and 1966 together define a slidable pathway for respective, surfaces 1274 and 1276 of elongate protrusion 1272 of bottom portion 1252 of main chassis 1100.

A pair of elongate mutually spaced facing surfaces 1980 and 1982 together define a slidable pathway for respective surfaces 1304 and 1306 of elongate protrusion 1302 of top portion 1250 of main chassis 1100.

A boss 1984 defines a socket 1986, which slidably receives second side axle 1508 of main driving direction shifting element 1150.

A partially cylindrical protrusion 1990 defines an inner cylindrical surface 1992 and a partially annular surface 1993 and has an inclined cut 1994 formed therein. Aligned diagonally with inclined cut 1994 is a pathway 1996, having mutually spaced walls 1997 and 1998, which extends through respective protrusions 1964 and 1966 Disposed inwardly of and coaxially with partially cylindrical protrusion 1990 and surrounding aperture 1928 is a protruding socket 1999, which accommodates first end portion 1602 of clutch 1192. Inner cylindrical surface 1992 of cylindrical protrusion 1990 accommodates closed loop ring 1586 as well as second washer 1212. Pathway 1996 accommodates end 1590 of central generally planar loop portion 1580 of direction shifting spring 1180. Surface 1993 is rotatably engaged by forward driving gear 1196.

A boss 2000 defines a socket 2002, which defines a spring seat for main driving direction shifting element spring 1204.

A stop defining protrusion 2010 is provided for providing a travel limiting stop for rearward motion of hand engageable driving handle 1140 and engaging stop engaging surfaces 1411 thereof.

A hook shaped protrusion 2012 defines an edge surface 2014 and an inner surface 2016 which define a slidable travel path for work channel retracting ratchet arm 1197 and driving pin 1208.

A boss 2020 defines a socket 2022, which rotatably receives handle pivot axle 1206. A boss 2024 defines a socket 2026, which rotatably receives cylindrical axle portion 1050 of work channel assembly retaining hook element 1018.

A boss 2030 defines a socket 2032, which, in turn, defines a spring seat for engaging end 1202 of driving handle spring 1201.

A boss 2034 defines a socket 2036, which, in turn, defines a spring seat for engaging lower spring end arm 1048 of rotation urging spring element 1016.

A concave surface 2040 is defined at a rearward end of first housing portion 1002 and slidably receives retaining cap element 320 of the work channel 110. Generally centrally located within concave surface 2040 is an elongate recess 2041. Recess 2041 engages wing-like protrusion 270 of rack defining intermediate element 260. Inwardly of concave surface 2040 is a narrower concave surface 2042, which slidably receives rack defining intermediate element 260 of the work channel 110.

A protrusion 2044 is provided for engagement with mounting socket opening 1370 of auxiliary chassis 1110.

A boss 2050 defines a socket 2052, which surrounds aperture 1930 and rotatably receives cylindrical axle 1030 of axle mounted gear element 1014.

Rearward of boss 2050 are a pair of mutually spaced mutually facing planar surfaces 2060 and 2062 of respective protrusions 2064 and 2066 which slidably receive first end portion 1390 of cartridge pusher 1120. Protrusion 2066 also defines a chamfered edge surface 2067 which engages undercut hooked engagement finger 328 of retaining cap element 320. Protrusion 2064 also defines an inclined edge surface 2068, Boss 2070 is defined near rearward upper corner of first housing portion 1002, as seen in FIG. 8BR, and comprises socket 2072 which accepts axle 1080 of cartridge retaining element 1070. Adjacent and rearward of boss 2070 is defined boss 2080 which has a smaller diameter than boss 2070 and comprises socket 2082, which accepts retaining arm 1073 of cartridge assembly retaining spring 1072. Recessed relative to top surface of first housing portion 1002 is an elongated flat back surface 2084. Rearward of and perpendicular to back surface 2084 is stop portion 2086. Stop portion 2086 comprises a forward-facing flat side 2087 and a rearward-facing flat side 2088 with a concave recess 2089. Concave recess acts a stop for forward-most convex surface 1087 of splined thumb engagement surface 1086. Protrusion 2066 further defines a stop 2090. Stop 2090 acts as a stop for cartridge retaining arm 1082 of cartridge assembly retaining element 1070.

Reference is now made to FIGS. 8BS, 8BT & 8BU, which are respectively simplified pictorial illustrations of inside and outside surfaces of second housing portion 1002 and a plan view illustration of the inside housing surface of the second housing portion.

As seen in FIGS. 8BS-8BU, it is seen that the second housing portion 1002 defines a main driving axis 2100 and a hand engageable driving handle portion 2102, having an axis 2104 which is preferably angled with respect to main driving axis 2100 by 132.5 degrees. At a forward end of second housing portion 1002 there is defined a cone engagement surface 2106, which preferably engages wide end 1800 of retaining cone 1011. Forwardly of cone engagement surface 2106 is a semi-cylindrical cone engageable portion 2108 having a circumferential recess 2110 adjacent cone engagement surface 2106. Forward of circumferential recess 2110 is a circumferential protrusion 2112 and forward of circumferential protrusion 2112 is another circumferential recess 2114. Recesses 2110 and 2112 and protrusion 2114 are arranged for snap-fit engagement with circumferential aperture wall 1806 of retaining cone 1011.

An outer surface of second housing portion 1002 defines a recess 2120 for receiving driving direction selector lever 1010 and including an aperture 2122. As seen particularly in FIGS. 8BS and 8BU, the second housing portion 1002 is formed with a central aperture 2128.

A boss 2131 comprising a socket 2132 is also formed in the second housing portion, as are a first top edge cut out 2134 and a second top edge cut out 2136, which includes a pair of protrusions 2138 and 2140.

Turning now particularly to FIGS. 8BT & 8BU, it is seen that an inner surface of second housing portion 1002 includes a forward generally concave surface 2150, which accommodates curved shaft assembly 150. Concave surface 2150 defines a pair of recesses 2152, which accommodate pins 938 of curved shaft assembly 150. A recess 2154 is defined rearwardly of surface 2150 and accommodates curved shaft assembly location ring 804. A rear wall of recess 2154 defines a concave surface 2156, which also accommodates curved shaft assembly location ring 804.

A pair of elongate mutually spaced facing surfaces 2160 and 2162 on respective protrusions 2164 and 2166 together define a slidable pathway for respective surfaces 1274 and 1276 of elongate protrusion 1272 of bottom portion 1252 of main chassis 1100. Protrusion 2167 is situated above, in the sense of FIG. 8BU, and parallel to protrusion 2164. Another pair of elongate mutually spaced facing surfaces, 2168 and 2169, on respective protrusions 2164 and 2167 together define a slidable pathway for edge surface 1259 of forwardly-directed protrusion 1258 of main chassis 1100.

A pair of elongate mutually spaced facing surfaces 2180 and 2182 together define a slidable pathway for respective surfaces 1304 and 1306 of elongate protrusion 1302 of top portion 1250 of main chassis 1100.

A boss 2184 defines a socket 2186, which slid ably receives first side axle 1506 of main driving direction shifting element 1150.

A partially cylindrical protrusion 2190 defines an inner cylindrical surface 2192 and a partially annular surface 2193 and has an inclined cut 2194 formed therein. Aligned diagonally with inclined cut 2194 is a pathway 2196, having mutually spaced walls 2197 and 2198, which extends through respective protrusions 2164 and 2166 Disposed inwardly of and coaxially with partially cylindrical protrusion 2190 and surrounding aperture 2128 is a protruding socket 2199, which accommodates first end portion 1602 of clutch 1192. Inner cylindrical surface 2192 of cylindrical protrusion 2190 accommodates closed loop ring 1586 as well as second washer 1212. Pathway 2196 accommodates end 1590 of central generally planar loop portion 1580 of direction shifting spring 1180. Surface 2193 is rotatably engaged by forward driving gear 1196.

A boss 2200 defines a socket 2202, which defines a spring seat for main driving direction shifting element spring 1204.

A stop defining protrusion 2210 is provided for providing a travel limiting stop for rearward motion of hand engageable driving handle 1140 and engaging stop engaging surfaces 1411 thereof.

A hook shaped protrusion 2212 defines an edge surface 2214 and an inner surface 2216 which define a slidable travel path for work channel retracting ratchet arm 1197 and driving pin 1208.

A boss 2220 defines a socket 2222, which rotatably receives handle pivot axle 1206. A boss 2224 defines a socket 2226, which rotatably receives cylindrical axle portion 1050 of work channel assembly retaining hook element 1018.

A boss 2230 defines a socket 2232, which, in turn, defines a spring seat for engaging end 1202 of driving handle spring 1201.

A boss 2234 defines a socket 2236, which, in turn, defines a spring seat for engaging lower spring end arm 1048 of rotation urging spring element 1016.

A concave surface 2240 is defined at a rearward end of second housing portion 1002 and slidably receives retaining cap element 320 of the work channel 110. Inwardly of concave surface 2240 is a narrower concave surface 2242, which slidably receives rack defining intermediate element 260 of the work channel 110.

A protrusion 2244 is provided for engagement with mounting socket opening 1370 of auxiliary chassis 1110.

A boss 2250 defines a socket 2252, which surrounds aperture 2130 and rotatably receives cylindrical axle 1030 of axle mounted gear element 1014.

Rearward of boss 2250 are a pair of mutually spaced mutually facing planar surfaces 2260 and 2262 of respective protrusions 2264 and 2266 which slidably receive first end portion 1390 of cartridge pusher 1120. Protrusion 2266 also defines a chamfered edge surface 2267 which engages undercut hooked engagement finger 328 of retaining cap element 320. Protrusion 2264 also defines an inclined edge surface 2268. Boss 2270 is defined near rearward upper corner of second housing portion 1004, as seen in FIG. 8BU, and comprises socket 2272 which accepts axle 1080 of cartridge retaining element 1070.

Cam surfaces 2280 comprise an upper cam surface 2282, a cam surface ramp 2284 and a lower cam surface 2286. Cam surfaces 2280 engage inclined planar surface 1394 of cartridge pusher 1120.

Reference is now made to FIGS. 9A, 9B & 9C, which are simplified respective top view, side view and bottom view illustrations of a manual override element useful in the operation of the arthroscopic surgical assembly of FIGS. 1A & 1B. It is seen that manual override gear shifter 171 has two elongate protrusions 2352 on the inner surface 2353 thereof, each protrusion having a gear engagement surface 2354. Also located on the inner surface 2353 of manual override gear shifter 171 are two snap-fit arms 2356 which comprise angled engaging surfaces 2358 and locking engagement surfaces 2360. On the outer surface 2361 of the manual override gear shifter 171 are two thumb engagement surfaces 2362 and a central aperture 2364. Manual override gear shifter 171 is used specifically in the first of the three manual override applications, as described below in reference to FIG. 6D.

Figure 9D:
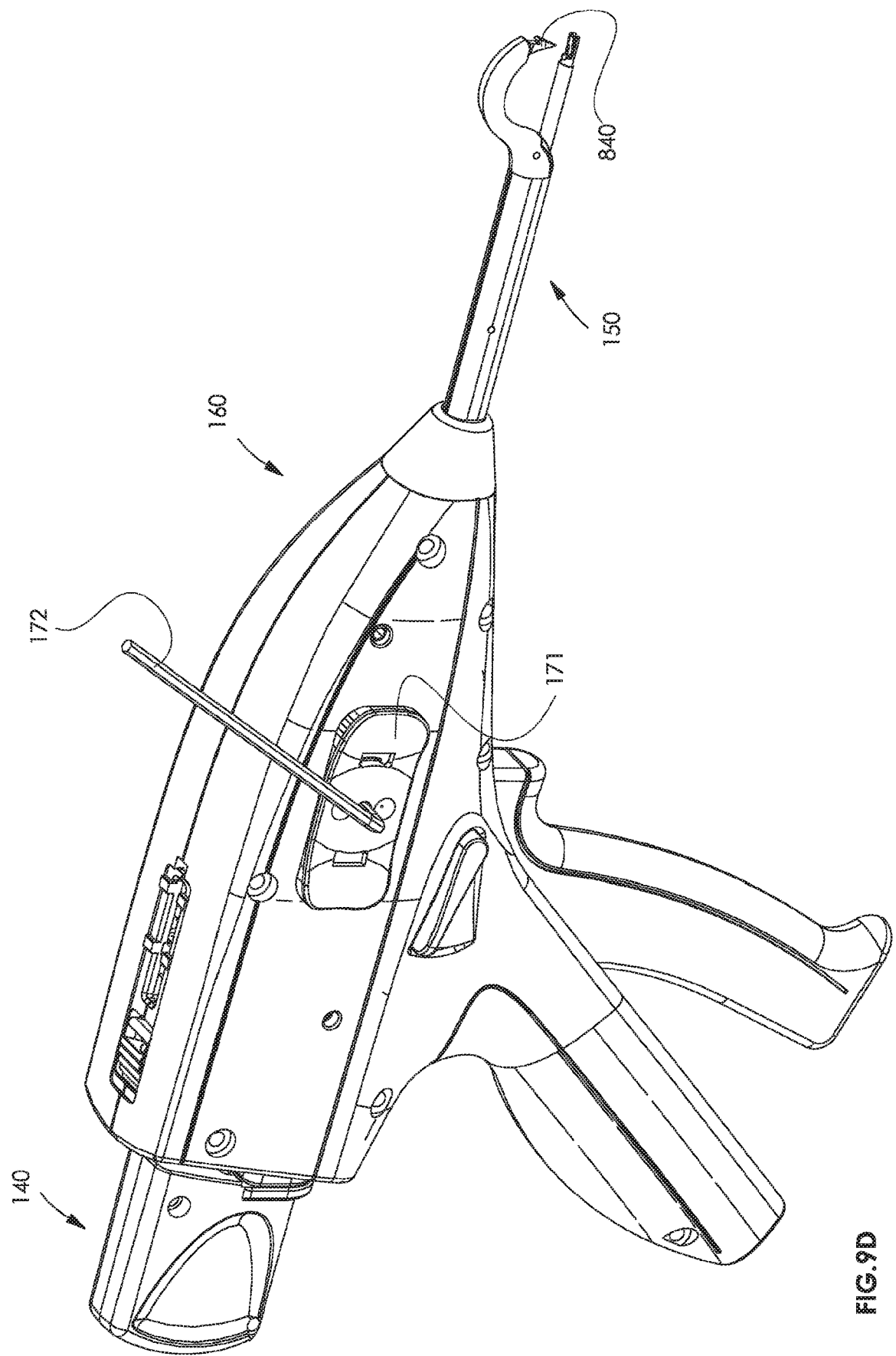
FIGS. 9D, 9E & 9F are simplified illustrations of respective applications of manual override in the operation of the arthroscopic surgical assembly of FIGS. 1A & 1B.
Figure 9E:
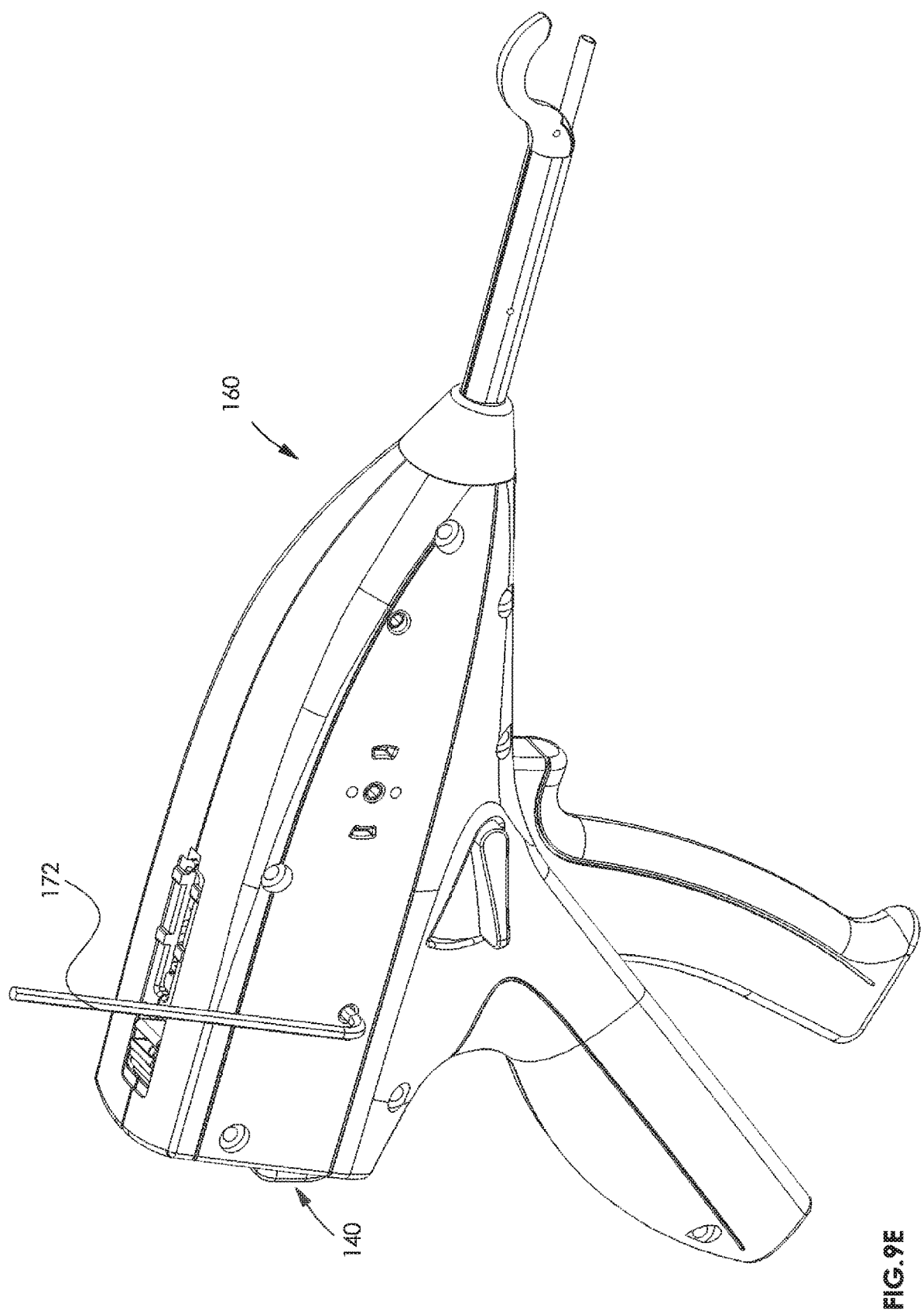
Figure 9F:
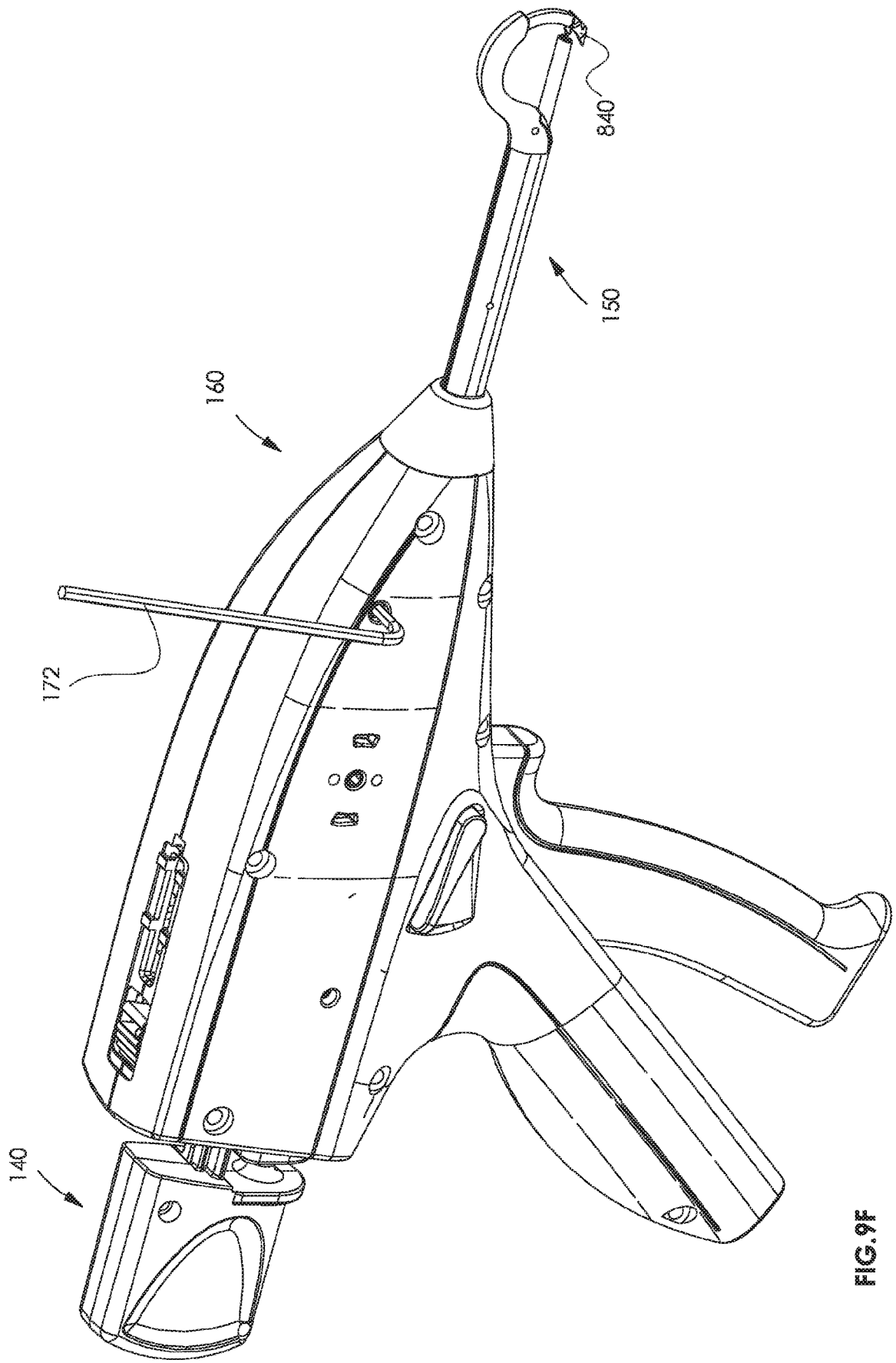

Reference is now made to FIGS. 9D, 9E & 9F, which are simplified illustrations of respective applications of manual override in the operation of the arthroscopic surgical assembly of FIGS. 1A & 1B.

Reference is now made particularly to FIG. 9D, which is a simplified illustration of a first manual override orientation. In cases where the user wishes to effect a manual override of the device once bone puncture needle 840 has been partially or fully extended, the manual override gear shifter 171 is attached to the outside of first housing 1002 by inserting two snap-fit arms 2356 into the pair of curved apertures 1924 until they become engaged. At the same time, the two elongate protrusions 2352 are inserted into the pair of round apertures 1926 also on the outside of first housing portion 1002, as seen for example in FIG. 8BP. When manual override gear shifter 171 is thus engaged on the first housing portion 1002, the gear engagement surfaces 2354 of the two elongate protrusions 2352 press against closed loop ring 1586 of direction shifting spring 1180 which in turn urges second washer 1212 pushing clutch 1192 to rearward position.

As seen in FIG. 9D, the manual override gear shifter 171 has been engaged on the first housing portion 1002 of the arthroscopic surgical device 160. Once manual override gear shifter 171 is thus engaged on the first housing portion 1002, a 2.5 mm hexagonal wrench 172 can be inserted into central aperture 1928 (as shown) thus causing it to enter into hexagonal recess 1604 of clutch 1192, within the arthroscopic surgical device 160. Once hexagonal wrench 172 has been thus inserted, clutch 1192 can be rotated by turning the hexagonal wrench 172 counterclockwise. This causes the bone puncture needle 840 to be withdrawn into the curved shaft assembly 150.

Reference is now made particularly to FIG. 9E, which is a simplified illustration of a second manual override orientation. As seen in FIG. 9E, the work channel assembly 110 is engaged within the arthroscopic surgical device 160. In this orientation, a 2.5 mm hexagonal wrench 172 has been inserted through aperture 1930 of first housing portion 1002. Hexagonal wrench 172 extends into recess 1040 of the axle mounted gear element 1014, within the arthroscopic surgical device 160. Hexagonal wrench 172 can now be rotated clockwise to cause the work channel assembly 110 to be withdrawn from the arthroscopic surgical device 160.

Reference is now made particularly to FIG. 9F, which is a simplified illustration of a third manual override orientation. As seen in FIG. 9F, the bone puncture needle 840 extends through curved shaft assembly 150. It is understood that bone puncture needle 840 may be either partially or fully extended. In this orientation, a 2.5 mm hexagonal wrench 172 has been inserted through aperture 1932 of first housing portion 1002. Hexagonal wrench 172 extends into hexagonal socket 1782 of stopper pin 1008, within the arthroscopic surgical device 160, Hexagonal wrench 172 can now be rotated counterclockwise to cause the stopper pin 1008 to be unscrewed and released from within the arthroscopic surgical device 160. Removal of the stopper pin 1008 allows the main chassis 1100 to move forward and in turn causes the bone puncture needle 840 to be released from within the curved shaft assembly 150.

Figure 10A:
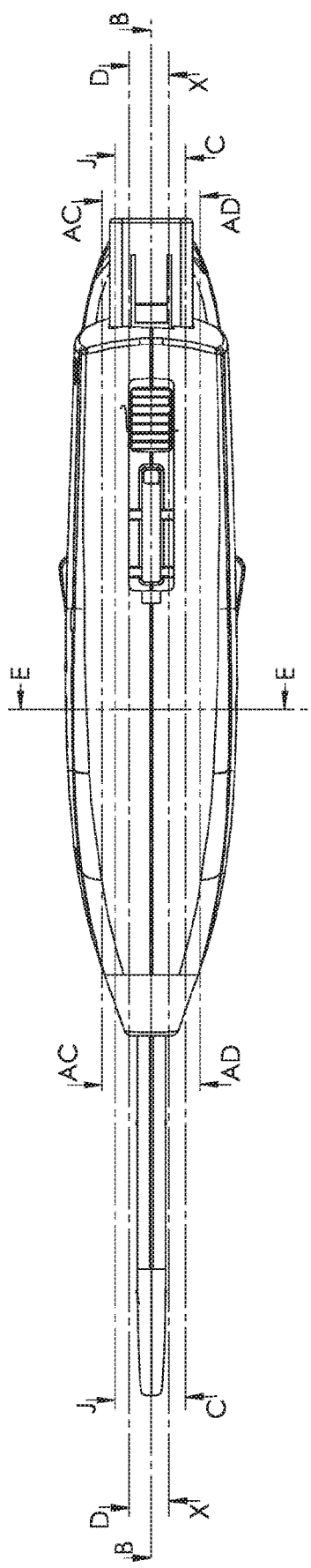

Reference is now made to FIGS. 10A-10AN, which are simplified illustrations of details of the operation of the arthroscopic surgical assembly of FIGS. 1A-9C. FIG. 10A is a simplified top view illustration of the arthroscopic surgical device 160, showing the location of various section lines referenced in FIGS. 10B-10AN.

Figure 10B:
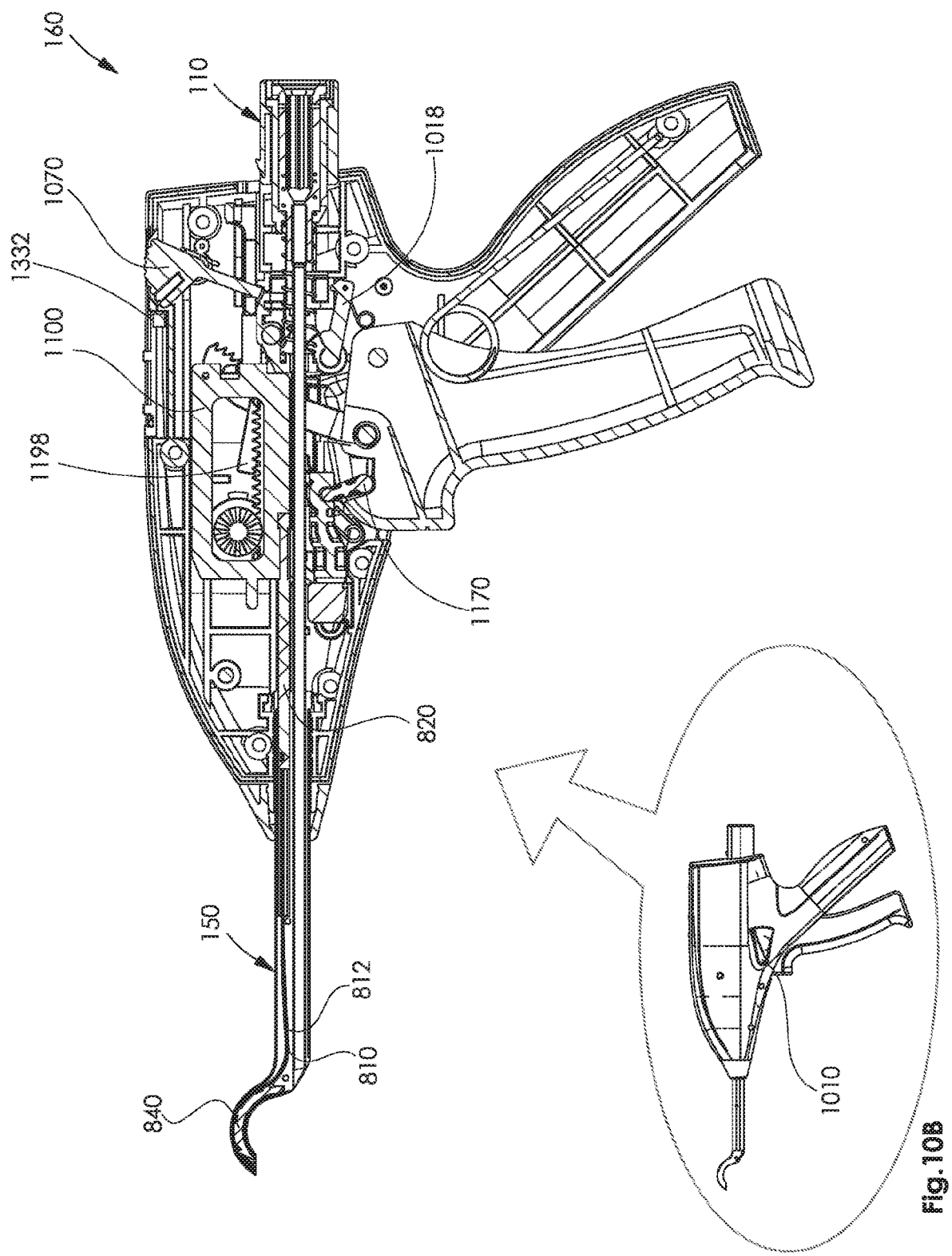
Figure 10C:
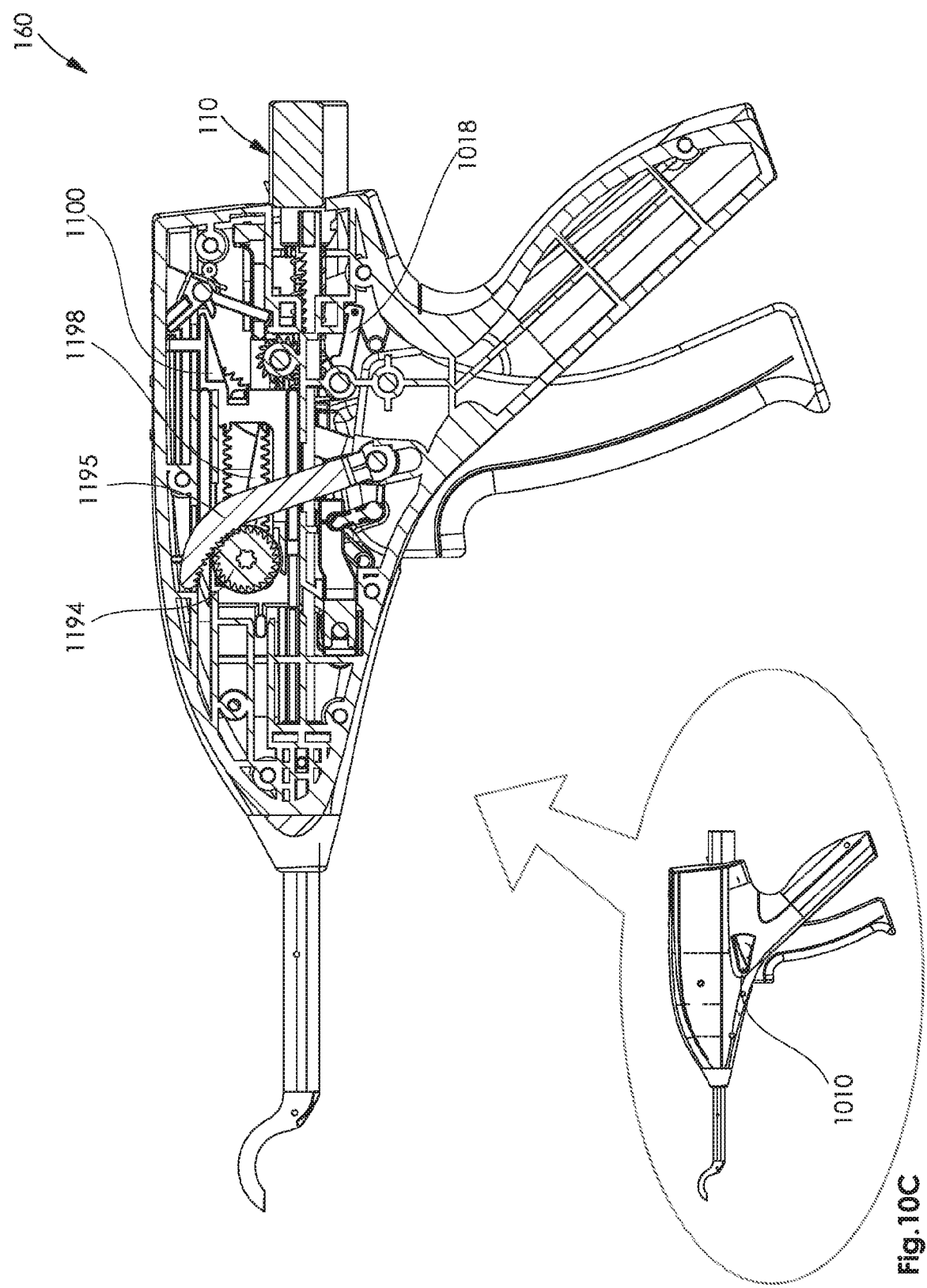
Figure 10D:
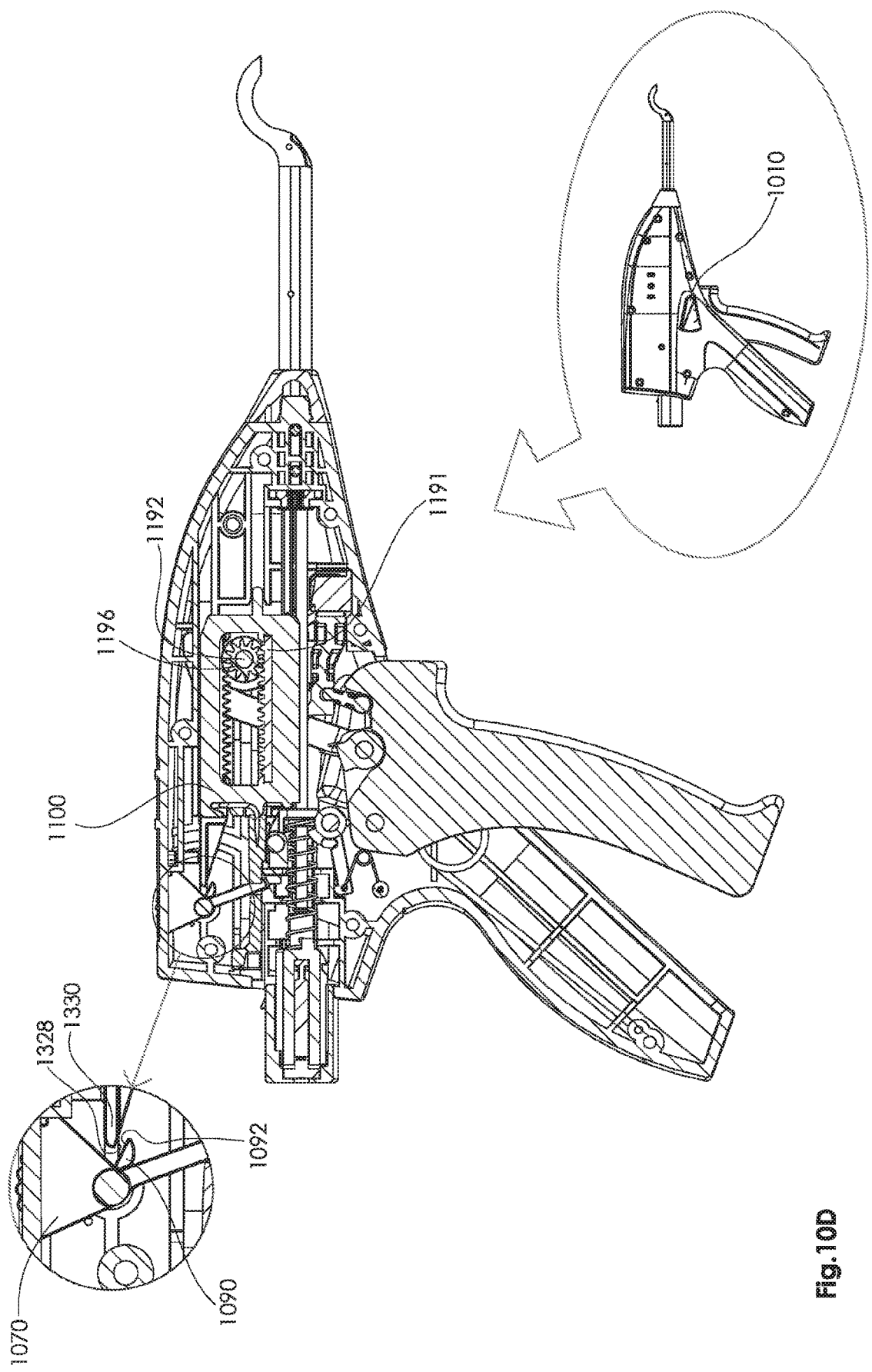
Figure 10E:
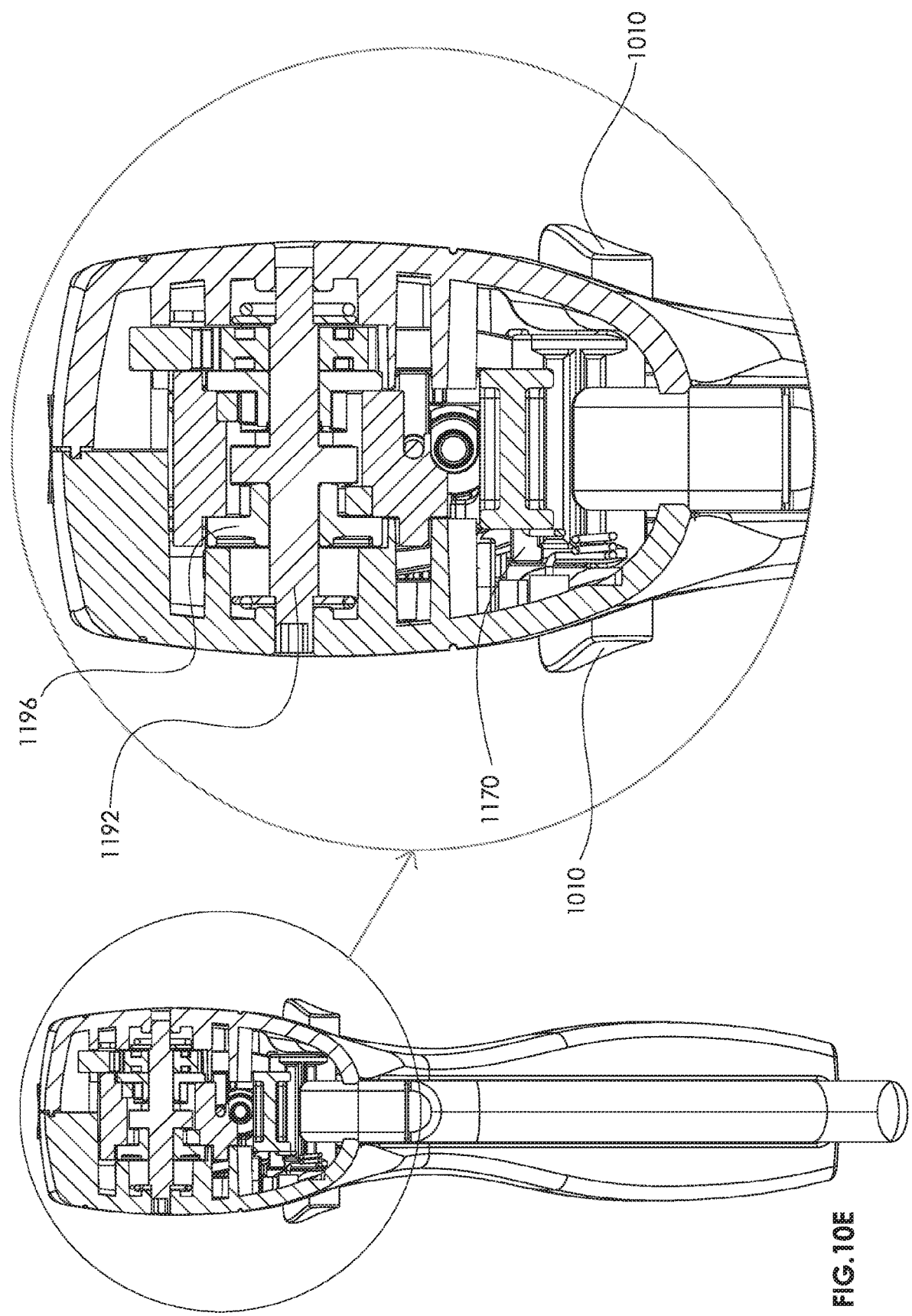

Reference is now made to FIGS. 10B 10E, which include enlargements taken along respective section lines B-B, C-C, D-D and E-E in FIG. 10A and which illustrate a first operative orientation of the arthroscopic surgical device 160, which is set for forward motion, as indicated by a raised rotated orientation of driving direction selector lever 1010.

As seen in FIGS. 10B-10E, bone puncture needle 840 is in a fully retracted operative orientation at a forward end of curved shaft assembly 150 responsive to the fact that main chassis 1100 is in a rearwardmost operative orientation, as indicated by the position of upwardly-facing indicator surface 1332. The retracted orientation of bone puncture needle 840 results from retraction of bendable pusher strips 810 and 812, which are in turn retracted by retraction of elongate push rod 820, which is fixedly connected to main chassis 1100.

As seen in FIGS. 10B & 10C, driving direction selector lever responsive toggle element 1170 is seen to be in a forwardly-tilted operative orientation responsive to the orientation of driving direction selector lever 1010. Work channel assembly 110 is seen to be in a retracted operative orientation. As seen particularly in FIG. 10B, work channel assembly retaining hook element 1018 is in the downward oriented position. As also seen in FIG. 10B, pivotable arm 1198 is in the upward oriented position. As a result of work channel assembly retaining hook element 1018 being in the downward position, work channel assembly 110 is unengageable by the arthroscopic surgical device 160.

Reference is now made to FIGS. 10C & 10D. As particularly seen in FIG. 10C, needle driving ratchet arm 1195 is operatively engaged with the gear teeth 1674 of main driving gear 1194 under the urging of ratchet arm urging spring 1222 (FIG. 8A). As further shown in FIGS. 10C & 10D, downwardly extending cam surface 1328 of transversely extending portion 1330 of main chassis 1100 faces cam surface 1092 on cartridge release cam portion 1090 of the cartridge assembly retaining element 1070, thus limiting cartridge assembly retaining element 1070 upward counterclockwise rotation with respect to arthroscopic surgical device 160. The limitation provided by downwardly extending cam surface 1328 of transversely extending portion 1330 of main chassis 1100 prevents snare wire cartridge assembly from being engaged by cartridge assembly retaining element 1070. FIG. 10D illustrates the engagement of forward driving gear 1196 with forward driving gear rack 1191, which is mounted in main chassis 1100.

As seen particularly in FIG. 10E, the operative orientation of driving direction selector lever responsive toggle element 1170 causes clutch 1192 to engage forward driving gear 1196.

Figure 10F:
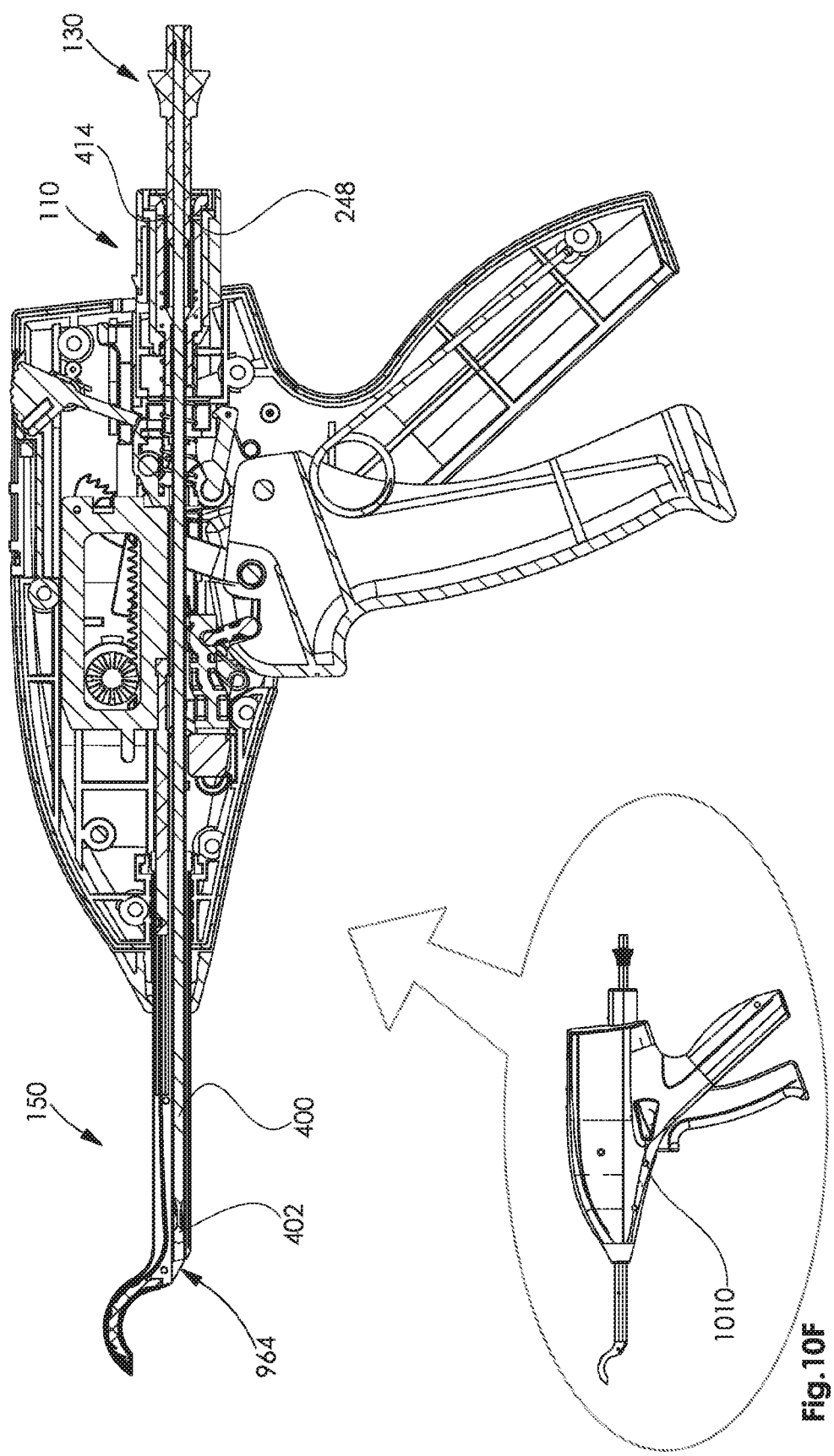

Reference is now made to FIG. 10F, taken along section lines B-B in FIG. 10A, which shows a second operative orientation of the arthroscopic surgical assembly of FIGS. 1A-9C. It is seen that drill bit assembly 130 is partially inserted into work channel assembly 110. Clip element 248 of work channel assembly 110 engages shallow circumferential recess 414 of drill bit assembly 130. It is seen that sharpened helical drill tip 402 of elongate shaft portion 400 of drill bit assembly 130 does not protrude from opening 964 of curved shaft assembly 150.

Figure 10H:
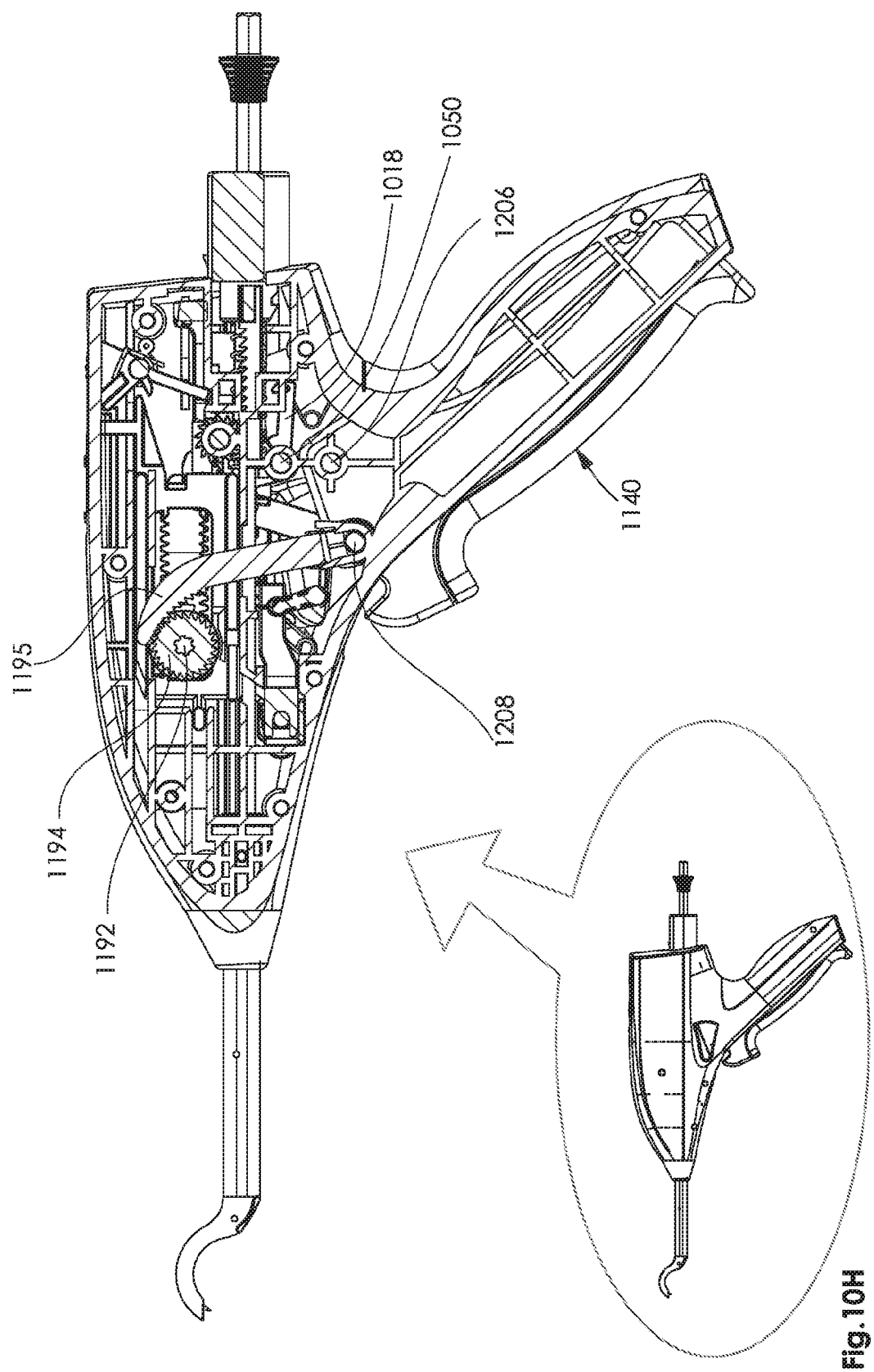
Figure 101:
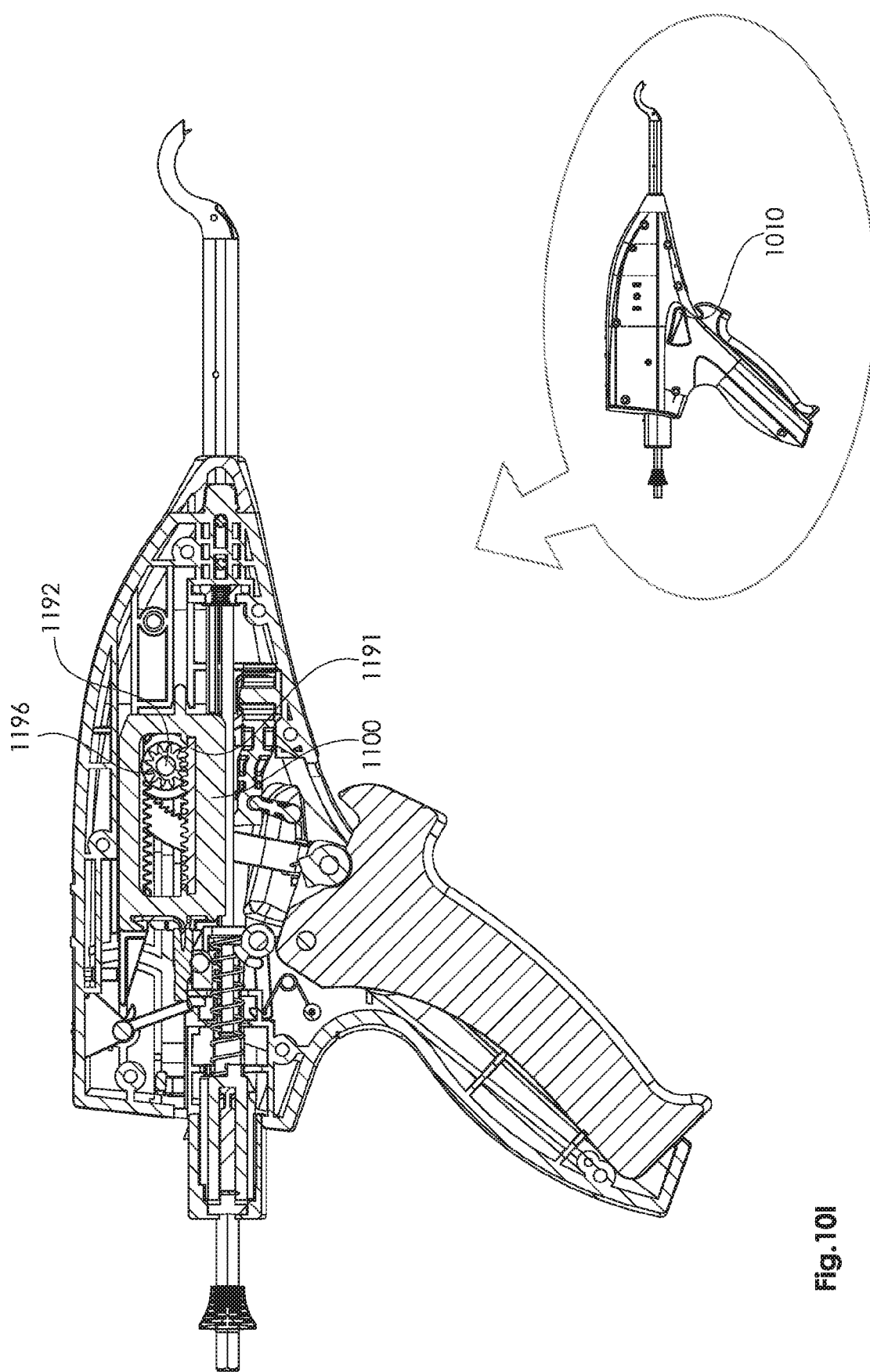
Figure 10J:
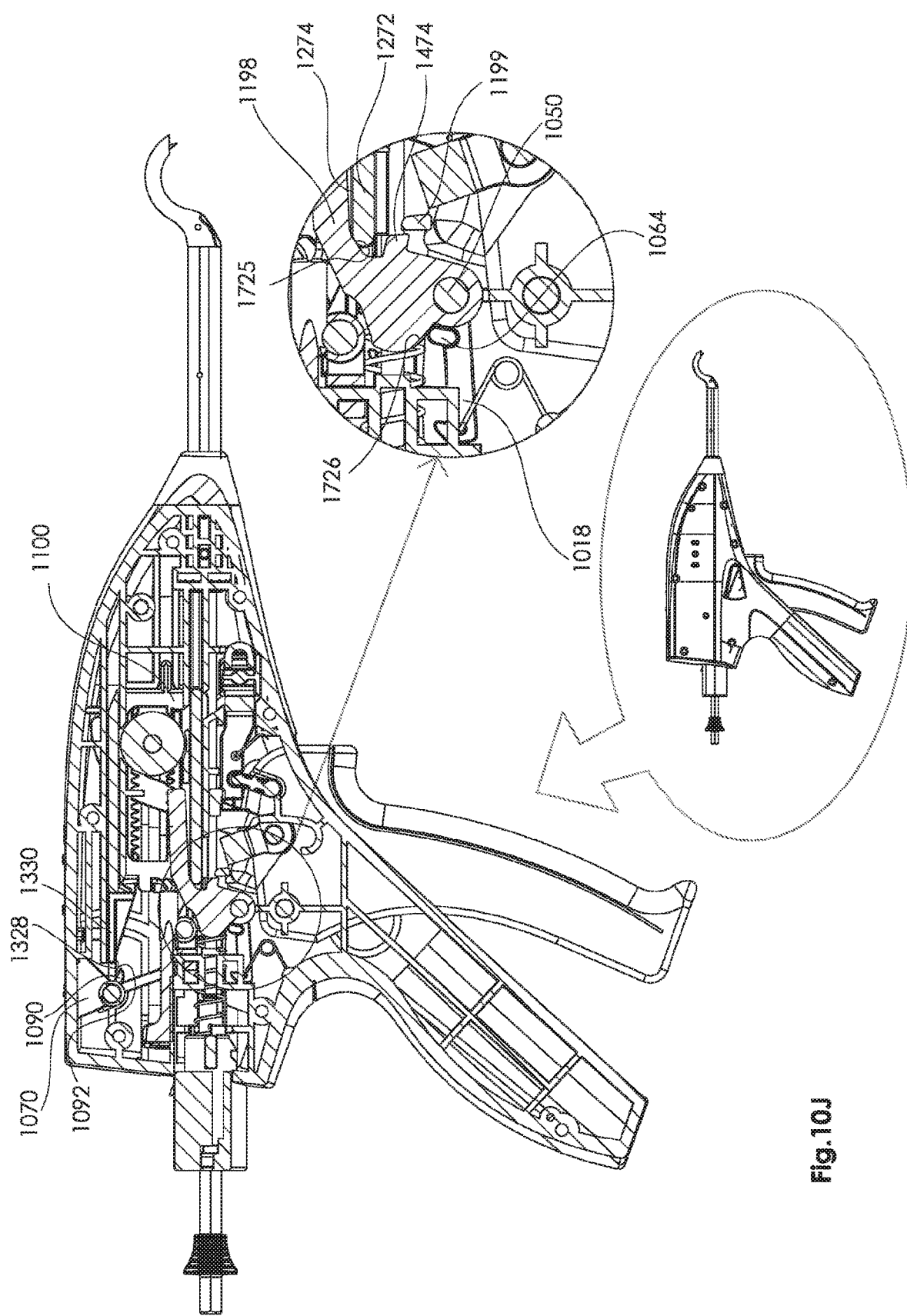

Reference is now made to FIG. 10G, taken along section lines B-B in FIG. 10A, 10H, taken along section lines C-C in FIG. 10A, 10I, taken along section lines D-D in FIGS. 10A, and 10J, taken along section lines J-J in FIG. 10A, which show a third operative orientation of the arthroscopic surgical assembly of FIGS. 1A-9C. In this operative orientation, hand engageable driving handle 1140 is rotated rearwardly about handle pivot axis 1206. This causes main chassis 1100 to move forwardly, thereby forwardly displacing elongate push rod 820, and thereby forwardly displacing bendable pusher strips 810 and 812, causing bone puncture needle 840 to emerge from forward end 926 of hook portion 920, as seen by the position of upwardly facing indicator surface 1332.

As seen particularly in FIG. 10H, rearward rotation of hand engageable driving handle 1140 causes needle driving ratchet arm 1195, which is pivotably mounted thereon by driving pin 1208, to be downwardly displaced while in engagement with main driving gear 1194, thereby producing clockwise rotation of main driving gear 1194 in the sense of FIG. 10H. Clockwise rotation of main driving gear 1194 produces corresponding rotation of clutch 1192.

As also seen particularly in FIGS. 10H & 10I, rotation of clutch 1192 rotates forward driving gear 1196 in a clockwise direction in the sense of FIG. 10H. As seen particularly in FIG. 10I, counterclockwise rotation of forward driving gear 1196, in the sense of FIG. 10I, in engagement with forward driving gear rack 1191, located within main chassis 1100, thereby produces forward displacement of main chassis 1100.

As also seen particularly in 10H & 10I, downwardly extending cam surface 1328 of transversely extending portion 1330 of main chassis 1100 disengages cam surface 1092 on cartridge release cam portion 1090 of the cartridge assembly retaining element 1070, thus releasing cartridge assembly retaining element 1070 to a lowered position in respect to arthroscopic surgical device 160.

As seen particularly in FIGS. 10G, 10H, 10I & 10J, work channel assembly retaining hook element 1018 is in the upward oriented position. Also seen particularly in FIG. 10J, pivotable arm 1198 is in the downward oriented position. As a result of the work channel assembly retaining hook element 1018 being in the upward position, work channel assembly 110 is now engageable by the arthroscopic surgical device 160.

As further shown in FIG. 10J, downwardly extending cam surface 1328 of transversely extending portion 1330 of main chassis 1100, no longer faces cam surface 1092 on cartridge release cam portion 1090 of the cartridge assembly retaining element 1070, thus no longer limiting cartridge assembly retaining element's 1070 upward counterclockwise rotation with respect to arthroscopic surgical device 160. As a result of the cartridge assembly retaining element 1070 no longer limiting cartridge assembly retaining element's 1070 upward counterclockwise rotation, the snare wire cartridge assembly 140 can now be engaged by the cartridge assembly retaining element 1070.

Figure 10K:
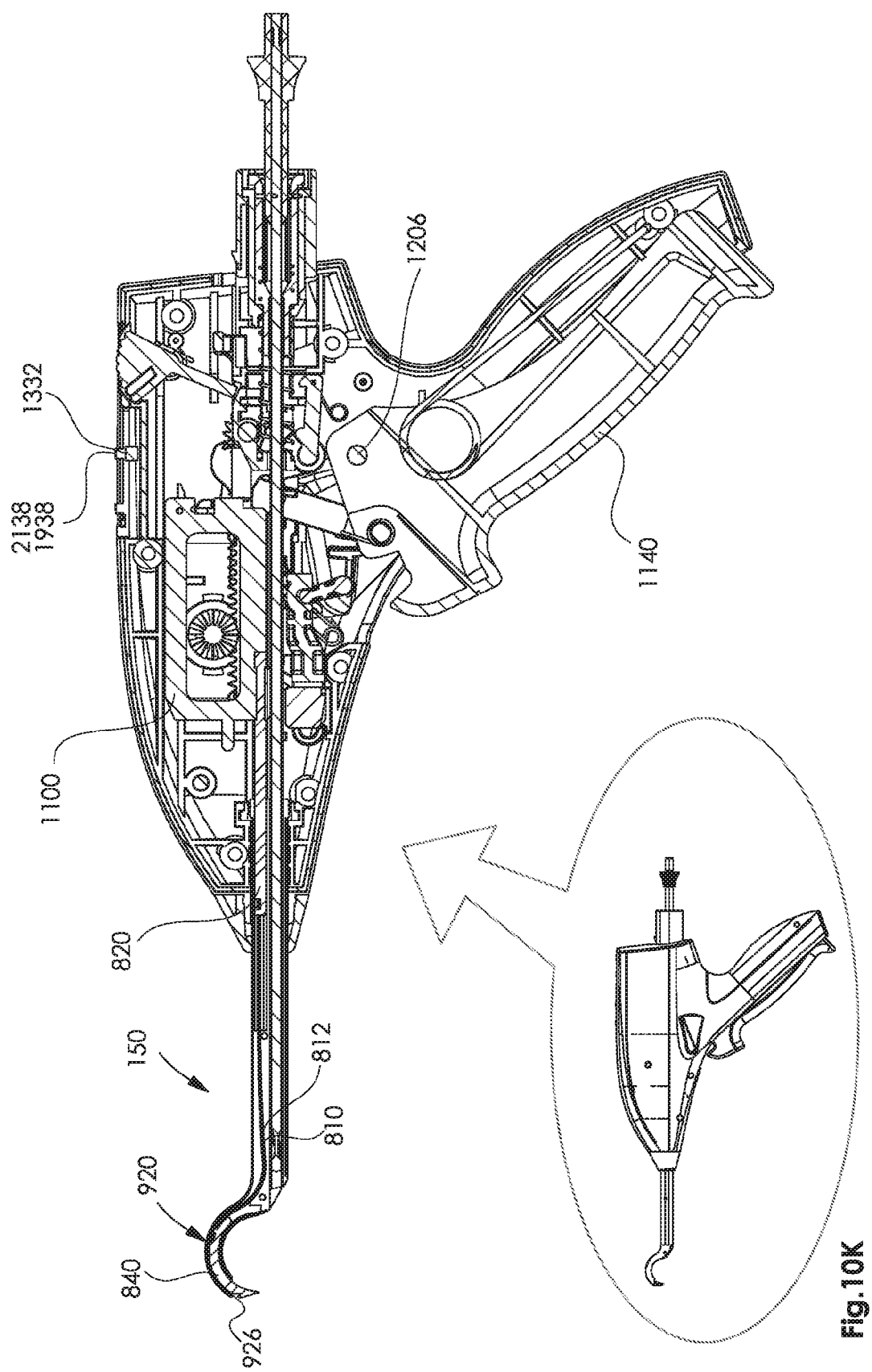
Figure 10M:
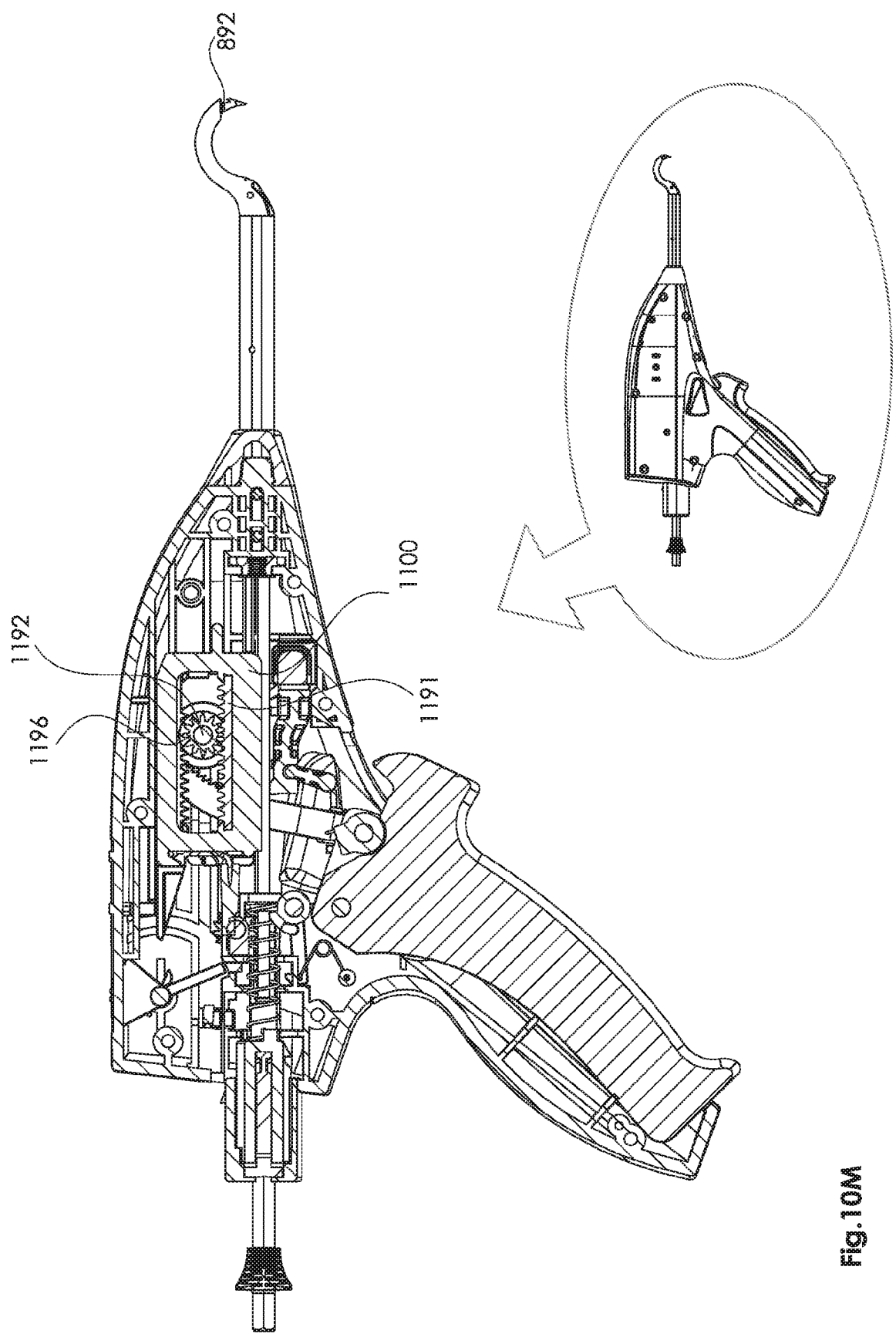

Reference is now made to FIG. 10K, taken along section lines B-B in FIG. 10A, 10L, taken along section lines C-C in FIGS. 10A, and 10M, taken along section lines D-D in FIG. 10A, which show a fourth operative orientation of the arthroscopic surgical assembly of FIGS. 1A-9C. In this operative orientation, hand engageable driving handle 1140 is again rotated rearwardly about handle pivot axis 1206. This causes main chassis 1100 to move further forwardly, thereby further forwardly displacing elongate push rod 820, and thereby further forwardly displacing bendable pusher strips 810 and 812, causing bone puncture needle 840 to emerge further from forward end 926 of hook portion 920, as seen by the position of upwardly facing indicator surface 1332. It is seen that indicator surface 1332 is aligned with protrusions 1938 and 2138 which indicate that 8 mm of the bone puncture needle 840 protrudes from the forward end 926 of hook portion 920, as can also be seen in FIGS. 10L and 10M relative to marking 892.

As seen particularly in FIG. 10L, this further rearward rotation of hand engageable driving handle 1140 causes needle driving ratchet arm 1195, which is pivotably mounted thereon by driving pin 1208, to be further downwardly displaced while in engagement with main driving gear 1194 thereby producing further clockwise rotation of main driving gear 1194 in the sense of FIG. 10L. This further clockwise rotation of main driving gear 1194 produces corresponding further rotation of clutch 1192.

As seen particularly in FIG. 10M, rotation of clutch 1192 further rotates forward driving gear 1196 in a counterclockwise direction in the sense of FIG. 10I, in engagement with forward driving gear rack 1191, located within main chassis 1100, thereby producing further forward displacement of main chassis 1100.

Figure 10N:
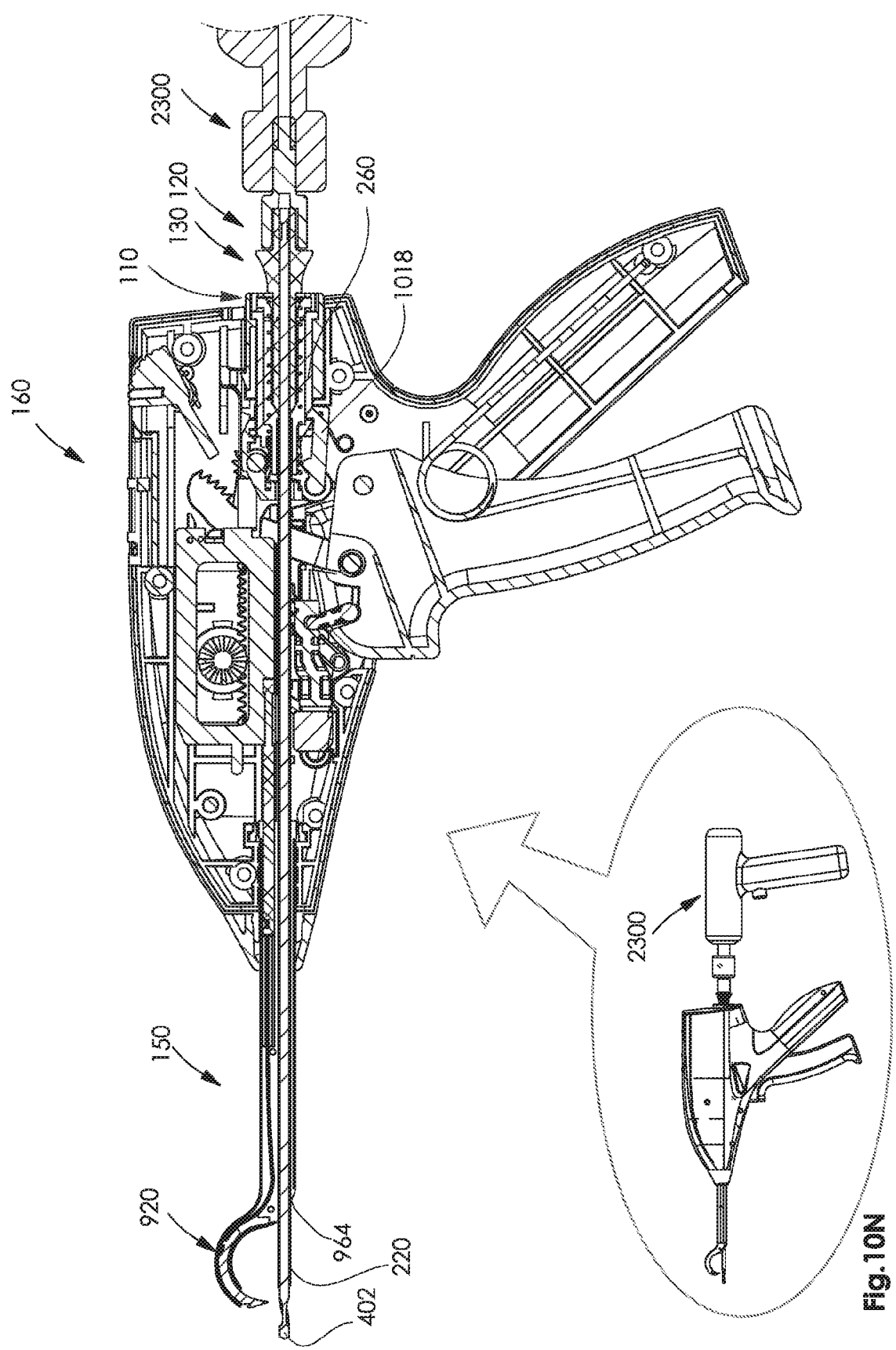
Figure 100:
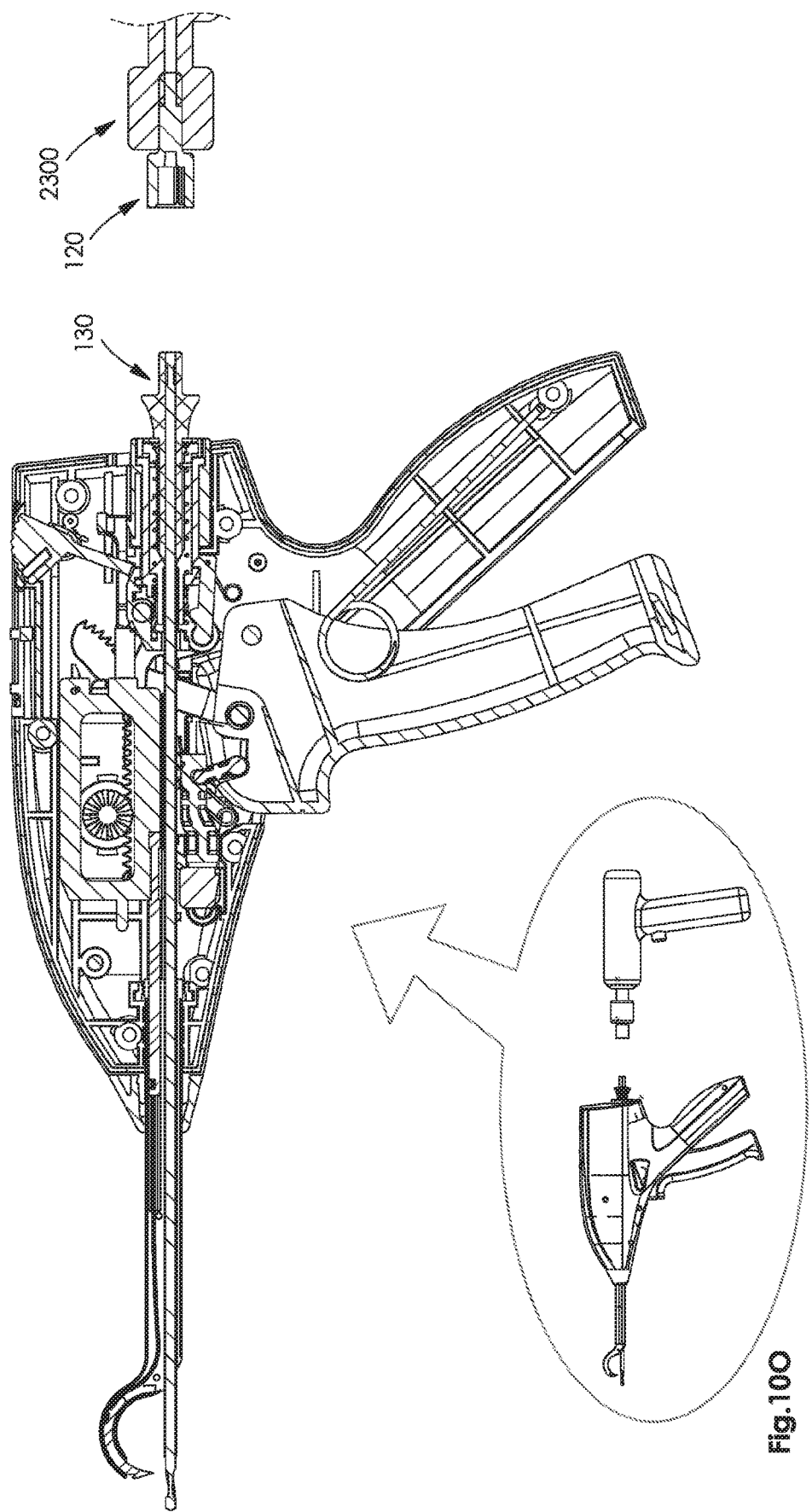

Reference is now made to FIG. 10N, taken along section lines B-B in FIG. 10A, which illustrates a fifth operative orientation of the arthroscopic surgical assembly of FIGS. 1A-9C. As seen in FIG. 10N, a conventional surgical drill 2300 is seen driving quick connect element 120, which in turn drives drill bit assembly 130 rotationally and linearly forwardly. As a result hollow elongate tube 220 of work channel assembly 110 extends forwardly from opening 964 beyond hook portion 920.

Work channel assembly retaining hook element 1018 engages rack defining intermediate element 260 of work channel assembly 110 and locks the work channel assembly 110 against linear motion relative to the arthroscopic surgical device 160. Thus work channel assembly 110 and drill bit assembly 130 become fully engaged within the arthroscopic surgical device 160, as seen in FIG. 10N.

Reference is now made to FIG. 10O, taken along section lines B-B in FIG. 10A, which illustrates a sixth operative orientation of the arthroscopic surgical assembly of FIGS. 1A-9C. As seen in FIG. 10O, the surgical drill 2300 and the driving quick connect element 120 are decoupled from the drill hit assembly 130.

Figure 10P:
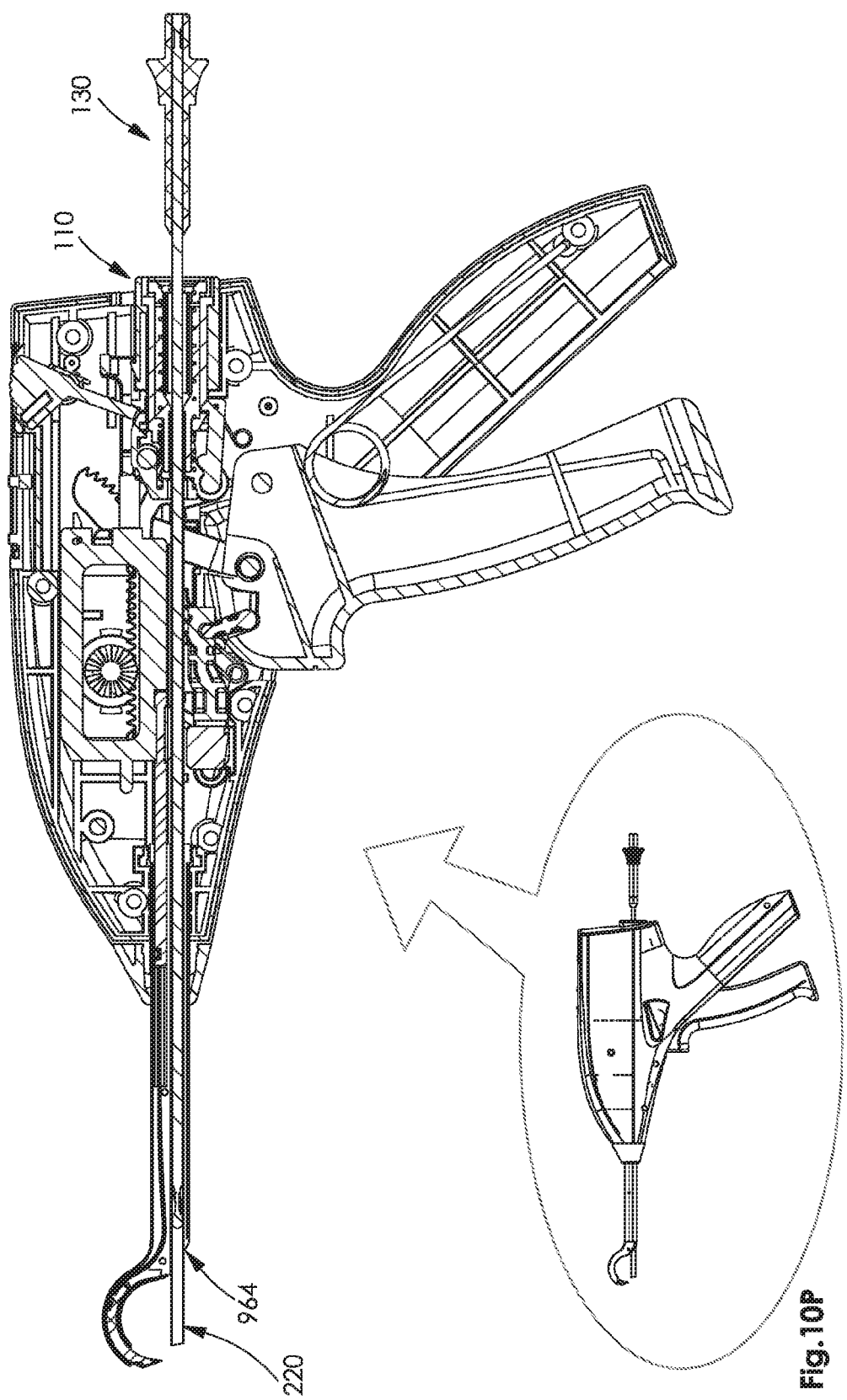

Reference is now made to FIG. 10P, taken along section lines B-B in FIG. 10A, which illustrates a seventh operative orientation of the arthroscopic surgical assembly of FIGS. 1A-9C. As seen in FIG. 10P, the drill bit assembly 130 is partially withdrawn from the arthroscopic surgical device 160, leaving the work channel assembly 110 and the hollow elongate tube 220 in place, protruding from opening 964.

Figure 10Q:
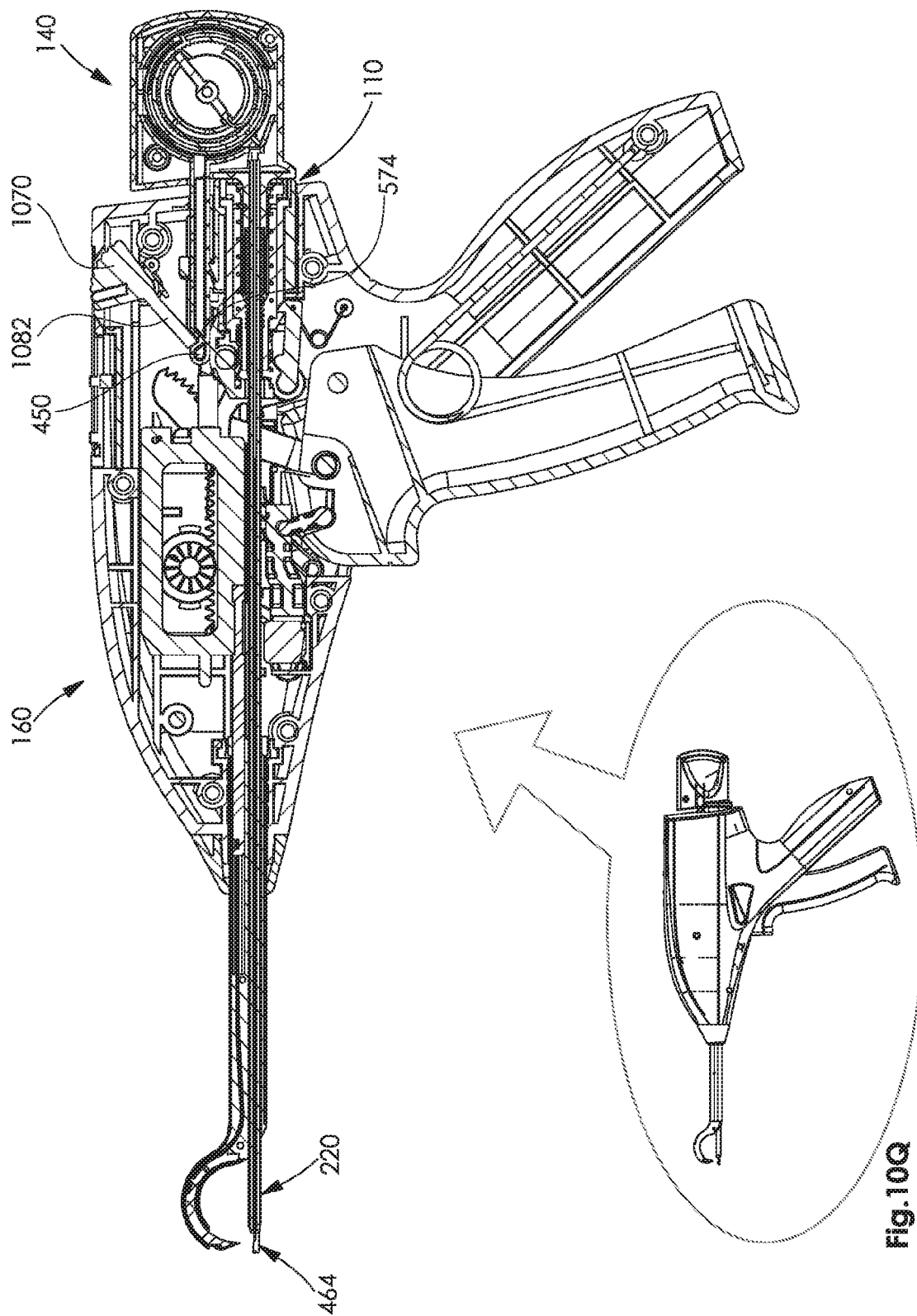

Reference is now made to FIG. 10Q, taken along section lines B-B in FIG. 10A, which illustrates an eighth operative orientation of the arthroscopic surgical assembly of FIGS. 1A-9C. As seen in FIG. 10Q, snare wire cartridge assembly 140 is seen to be fully inserted into operative engagement with the work channel assembly 110. It is seen that forward end 464 of elongate hollow shaft 454 extends forwardly of a forward end of hollow elongate tube 220. Top facing notch 574 of main housing portion 450 engages cartridge retaining arm 1082 cartridge assembly retaining element 1070.

Figure 10R:
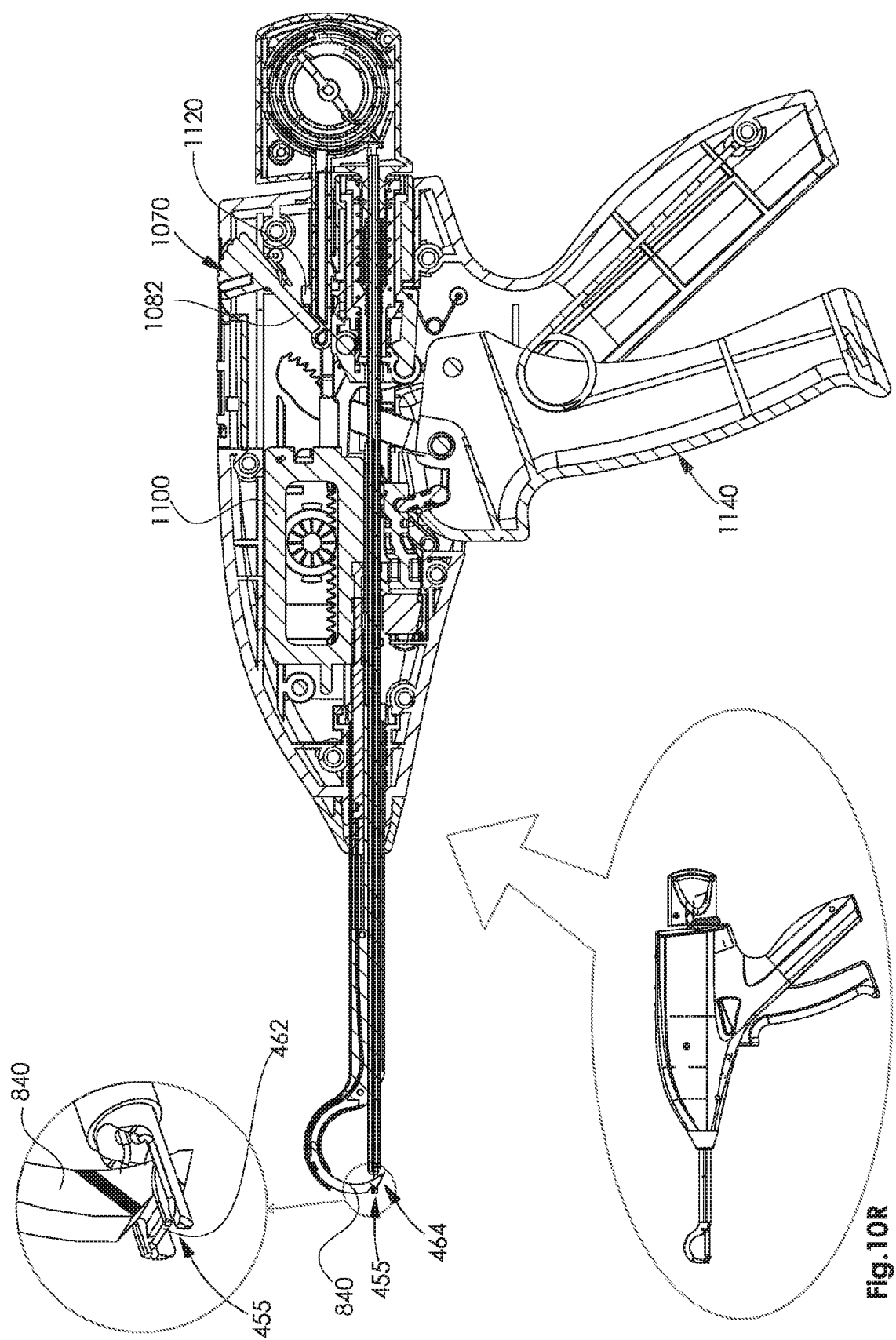

Reference is now made to FIG. 10R, taken along section lines B-B in FIG. 10A, which illustrates a ninth operative orientation of the arthroscopic surgical assembly of FIGS. 1A-9C, which occurs at an instantaneous moment in time following multiple rearward rotations of hand engageable driving handle 1140. As seen in FIG. 10R, cartridge pusher 1120, which is connected to main chassis 1100 by a cartridge pusher connector 1130 (FIGS. 8P & 8AC) is touching cartridge retaining arm 1082 of cartridge assembly retaining element 1070. At this instant, aperture 455 of forward end 464 of elongate hollow shaft 454 is penetrated by bone puncture needle 840.

Figure 10S:
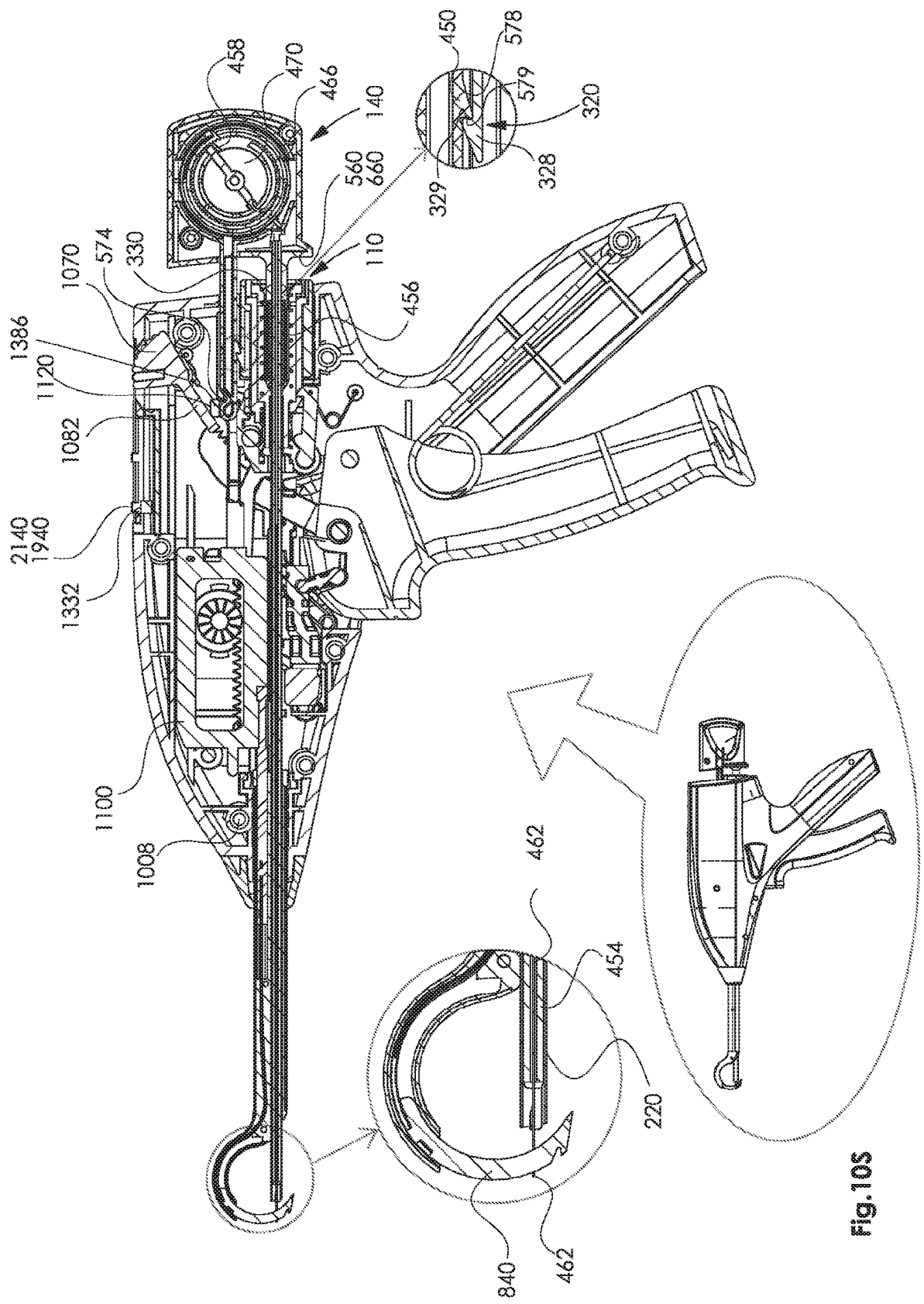

Reference is now made to FIG. 10S, taken along section lines B-B in FIG. 10A, which illustrates a tenth operative orientation of the arthroscopic surgical assembly of FIGS. 1A-9C, which occurs immediately after the instantaneous moment in time depicted in FIG. 10R. Transversely extending rearward portion 1386 of cartridge pusher 1120 engages cartridge retaining arm 1082 of cartridge assembly retaining element 1070, thus causing it to disengage from top facing notch 574 of cartridge assembly retaining shaft 572, producing immediate partial axial retraction of snare wire cartridge assembly 140 from work channel assembly 110, preferably defining a gap of at least 8 mm between rear surface 330 of retaining cap element 320 and forward facing walls 550 and 660 of main and secondary housing portions 450 and 452 of snare wire cartridge assembly 140.

At this stage, it is seen that preformed loop 462 of the snare wire 461 is looped over bone puncture needle 840 and elongate hollow shaft 454 is retracted into hollow elongate tube 220 of work channel assembly 110. It is also seen that main chassis 1100 is at the forwardmost position in engagement with stopper pin 1008 of arthroscopic surgical device 160.

It is additionally seen at this stage that upwardly-facing indicator surface 1332 is located at protrusions 1940 and 2140, which represent the forward limit of travel of bone puncture needle 840.

It is further seen that, at this stage compression spring 456 and cartridge pusher 1120 have retracted the snare wire cartridge assembly 140 such that rearward facing retaining surface 329 of undercut hooked engagement finger 328 of retaining cap element 320 have come into snap fit engagement with retaining surface 579 of bottom facing tooth 578 of main housing portion 450, thereby retaining the snare wire cartridge assembly 140 and stopping any linear forward displacement.

It is still further seen that at this stage, tensioning element 470 and snare wire winding drum 466 rotate clockwise, in the sense of FIG. 10S, against the urging of tension spring 458.

Figure 10T:
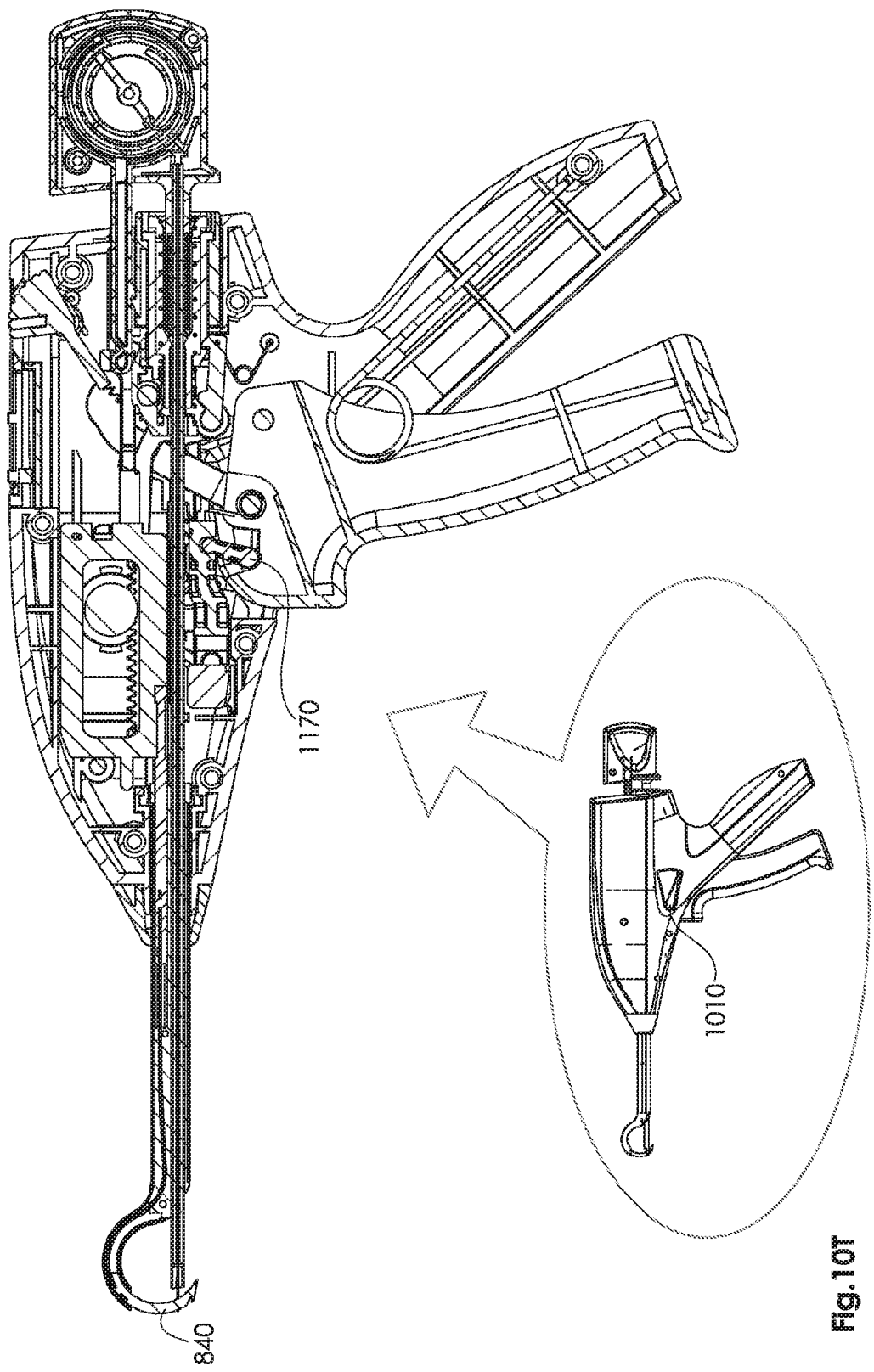
Figure 10U:
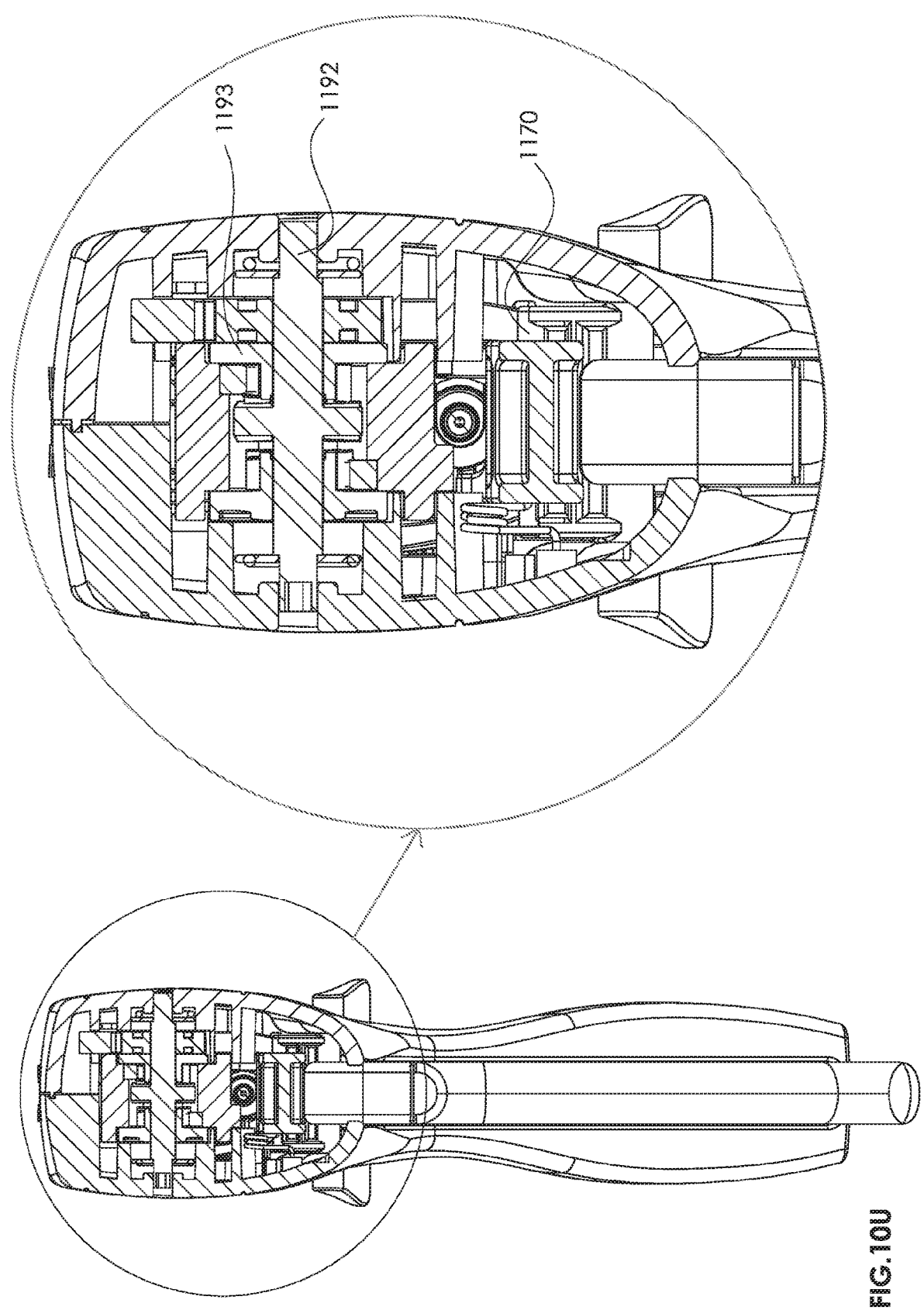

Reference is now made to FIG. 10T, taken along section lines B-B in FIGS. 10A, and 10U, taken along section lines E-E in FIG. 10A, which illustrate an eleventh operative orientation of the arthroscopic surgical assembly of FIGS. 1A-9C. As seen in FIGS. 10T & 10U, bone puncture needle 840 is fully extended.

Driving direction selector lever responsive toggle element 1170 is now seen to be in a rearwardly-lilted operative orientation responsive to a lowered orientation of driving direction selector lever 1010.

As seen particularly in FIG. 10U, the operative orientation of driving direction selector lever responsive toggle element 1170 now causes clutch 1192 to engage rearward driving gear 1193.

Figure 10V:
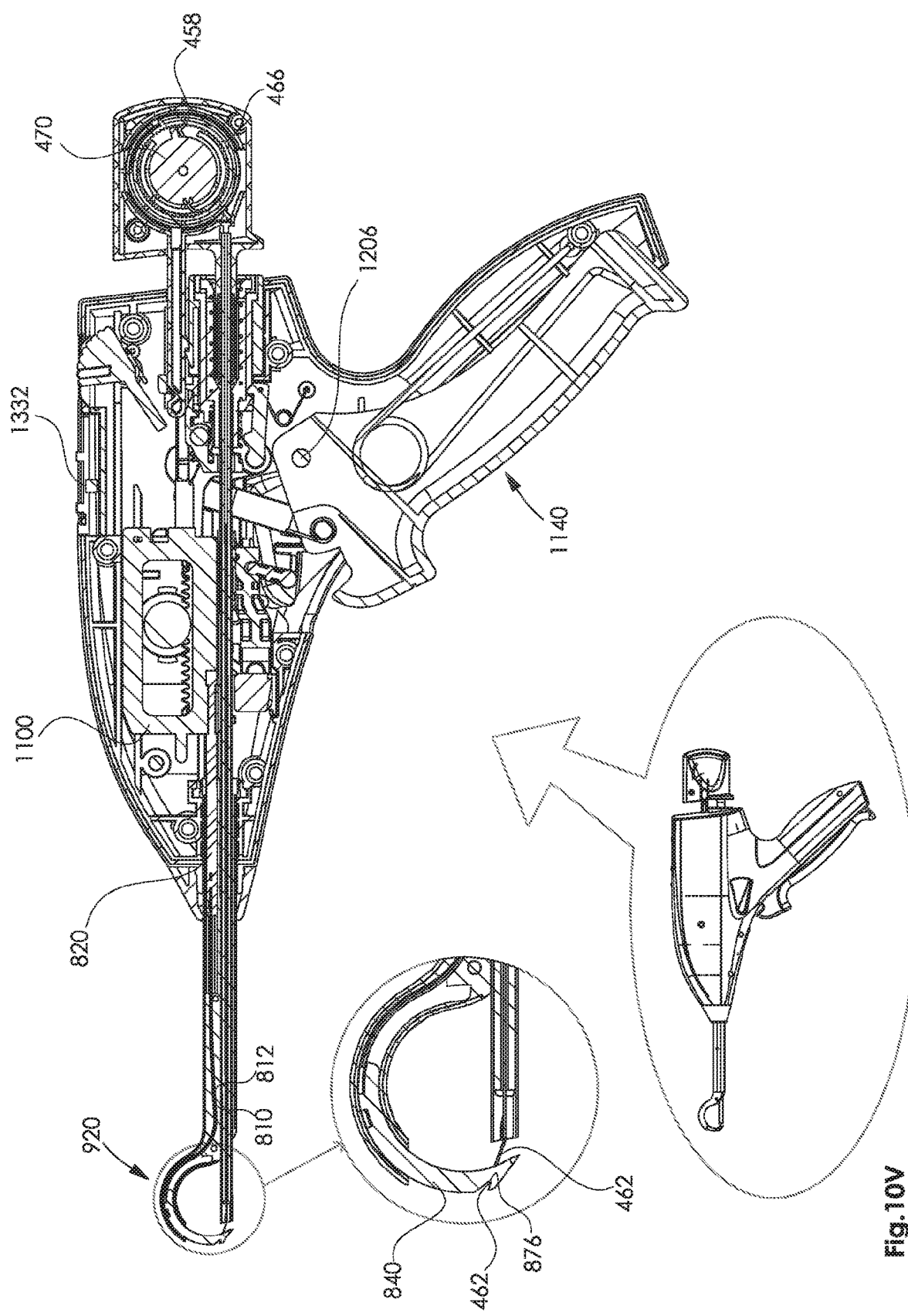
Figure 10W:
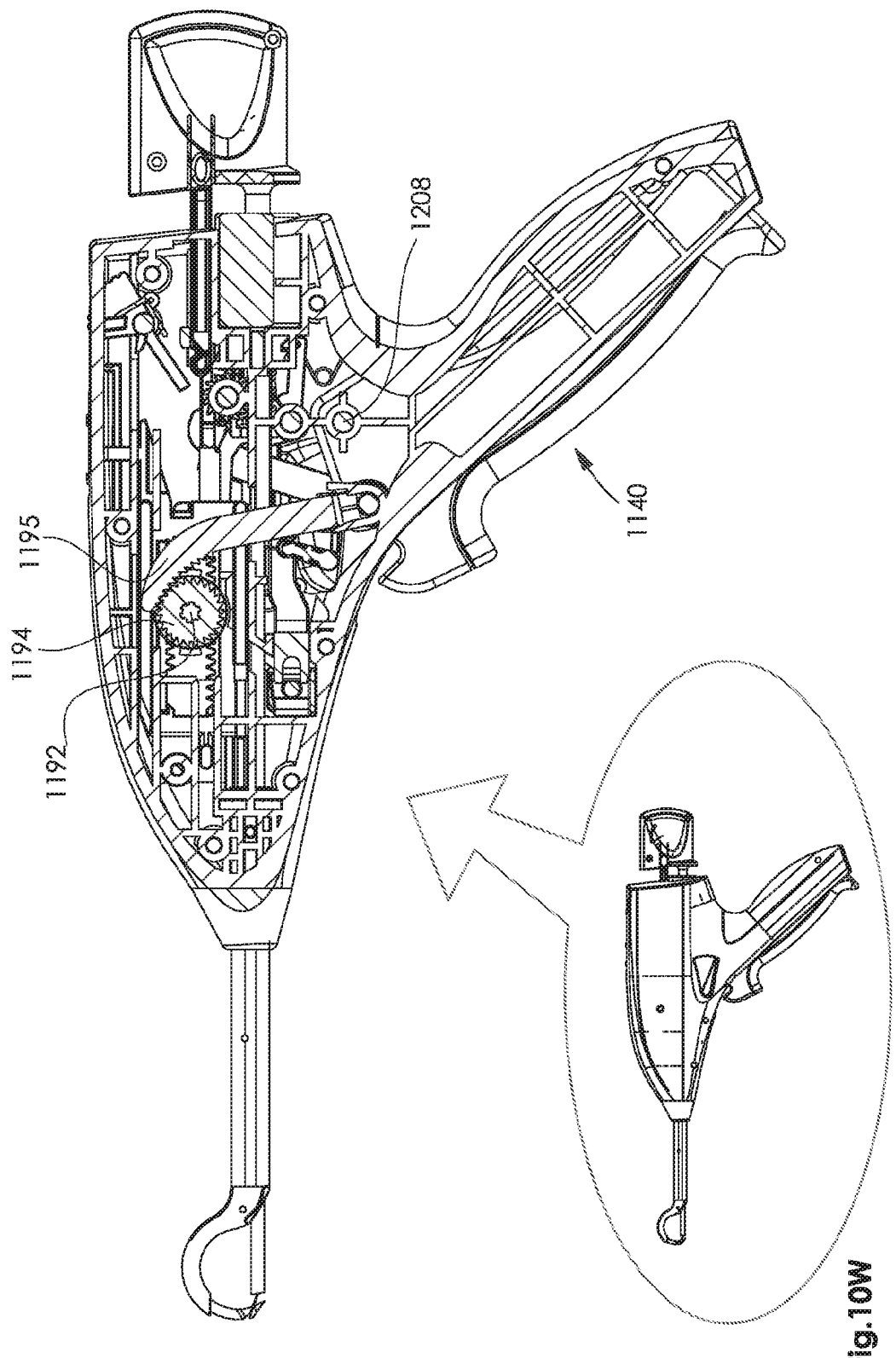
Figure 10X:
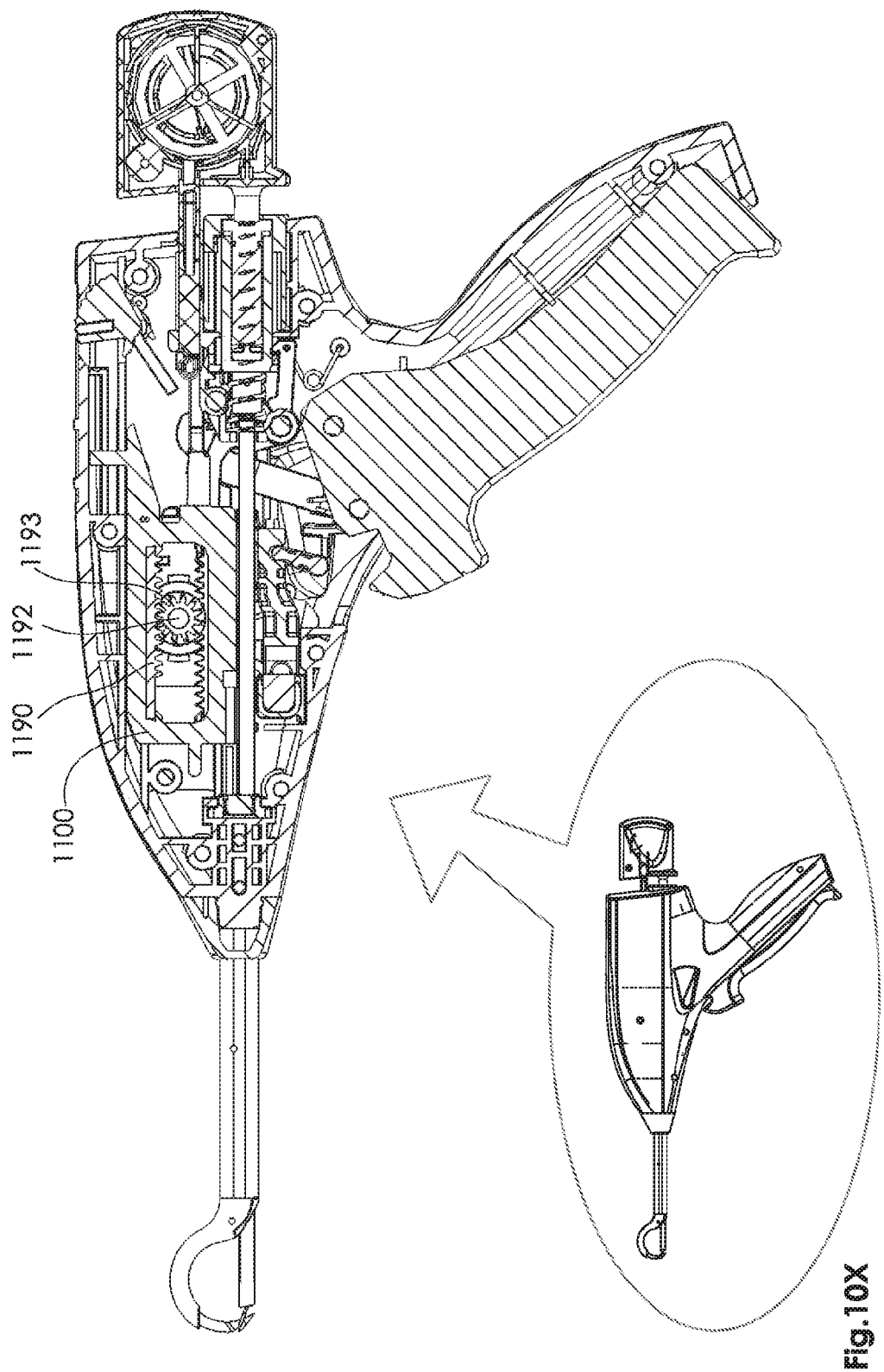

Reference is now made to FIG. 10V, taken along section lines B-B in FIG. 10A, 10W, taken along section lines C-C in FIGS. 10A, and 10X, taken along section lines X-X in FIG. 10A, which illustrate a twelfth operative orientation of the arthroscopic surgical assembly of FIGS. 1A-9C.

In this operative orientation, hand engageable driving handle 1140 is rotated rearwardly about handle pivot axis 1206. This causes main chassis 1100 to move rearwardly, thereby rearwardly displacing elongate push rod 820, and thereby rearwardly displacing bendable pusher strips 810 and 812, causing bone puncture needle 840 to partially retract, as seen by the position of upwardly facing indicator surface 1332.

This partial retraction of bone puncture needle 840 causes loop 462 to be engaged with forwardly and radially inwardly inclined notch 876 of bone puncture needle 840.

It is seen that at this stage tensioning element 470 and snare wire winding drum 466 further rotate clockwise, in the sense of FIG. 10V, against the urging of tension spring 458.

As seen particularly in FIG. 10W, rearward rotation of hand engageable driving handle 1140 causes needle driving ratchet arm 1195, which is pivotably mounted thereon by driving pin 1208, to be downwardly displaced while in engagement with main driving gear 1194 thereby producing clockwise rotation of main driving gear 1194 in the sense of FIG. 10W. Clockwise rotation of main driving gear 1194, in the sense of FIG. 10W, produces corresponding rotation of clutch 1192.

As seen particularly in FIGS. 10W & 10X, rotation of clutch 1192 rotates rearward driving gear 1193 in a clockwise direction in the sense of FIG. 10X. As seen particularly in FIG. 10X, clockwise rotation of rearward driving gear 1193, in the sense of FIG. 10X, in engagement with rearward driving gear rack 1190, located within main chassis 1100, thereby produces rearward displacement of main chassis 1100.

Figure 10Y:
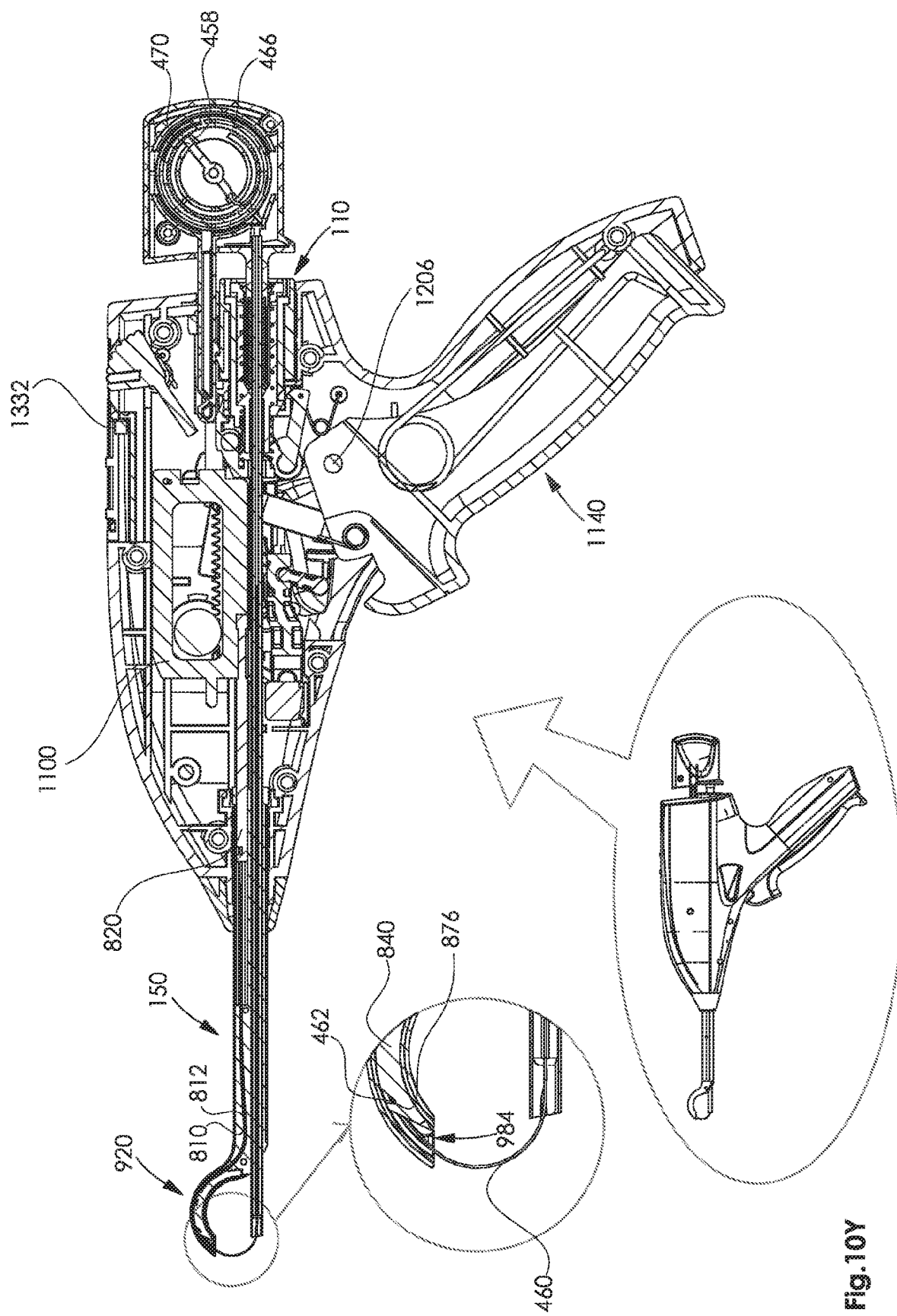
Figure 107:
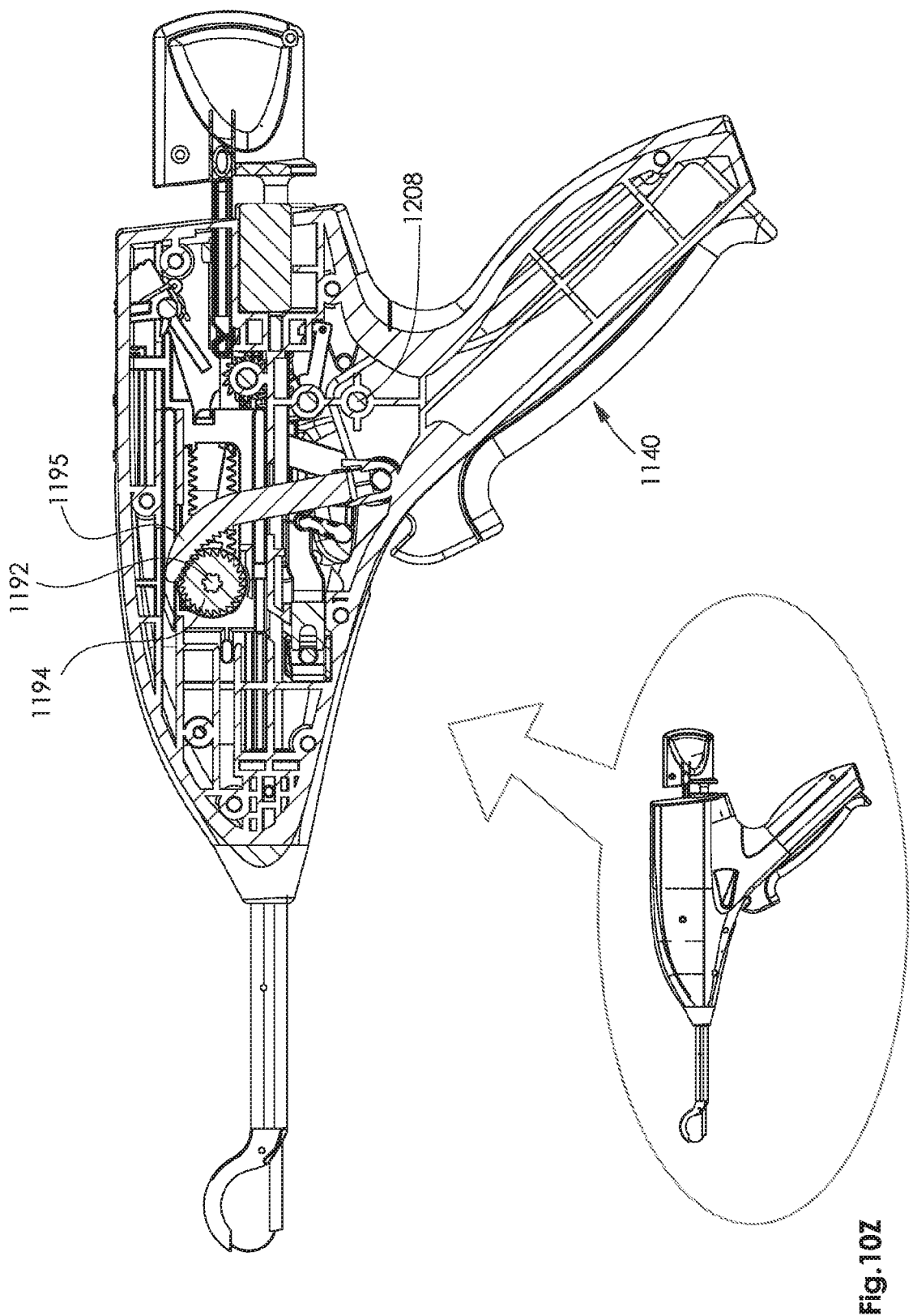
Figure 10A:
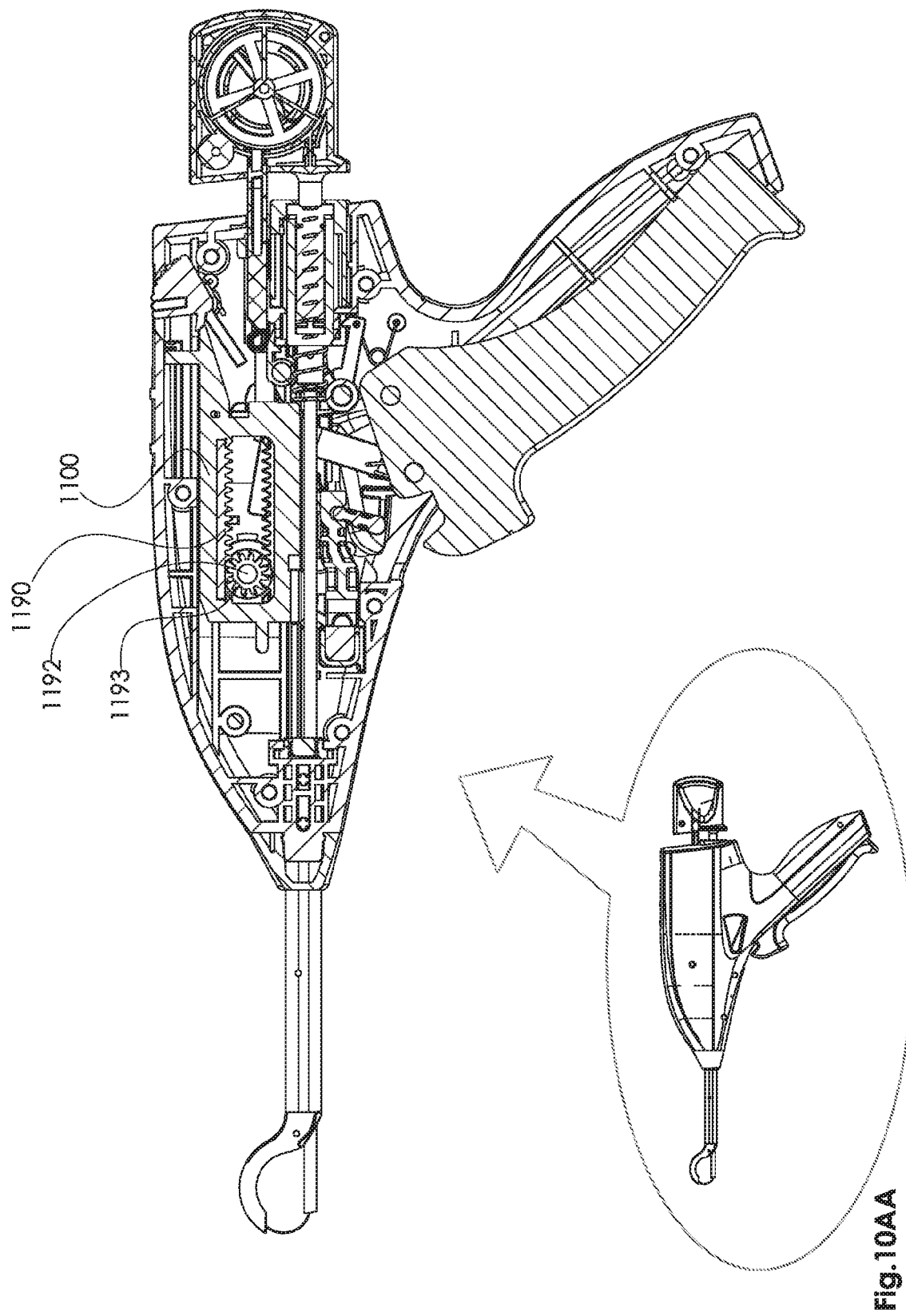
Figure 10A:
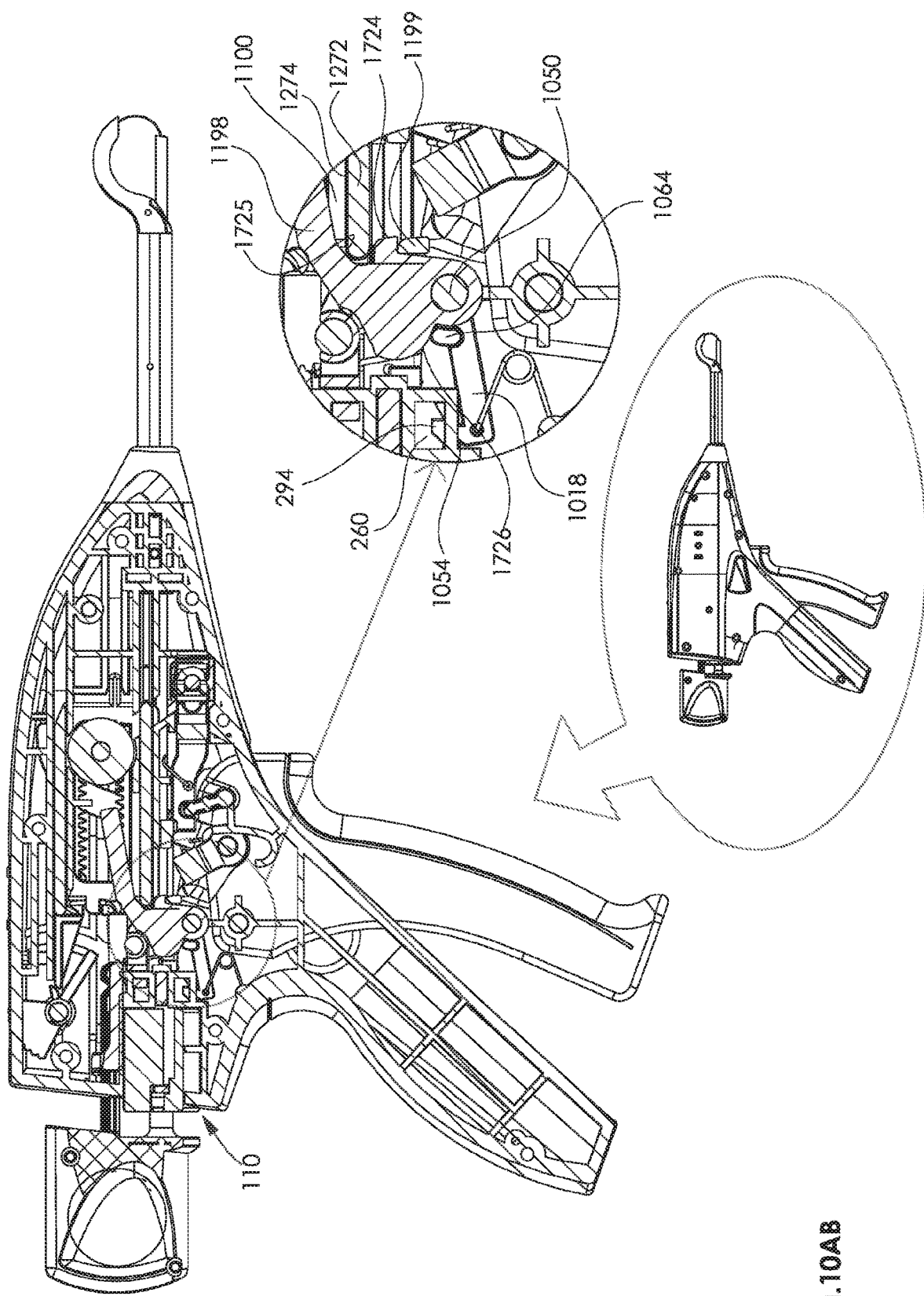
Figure 10A:
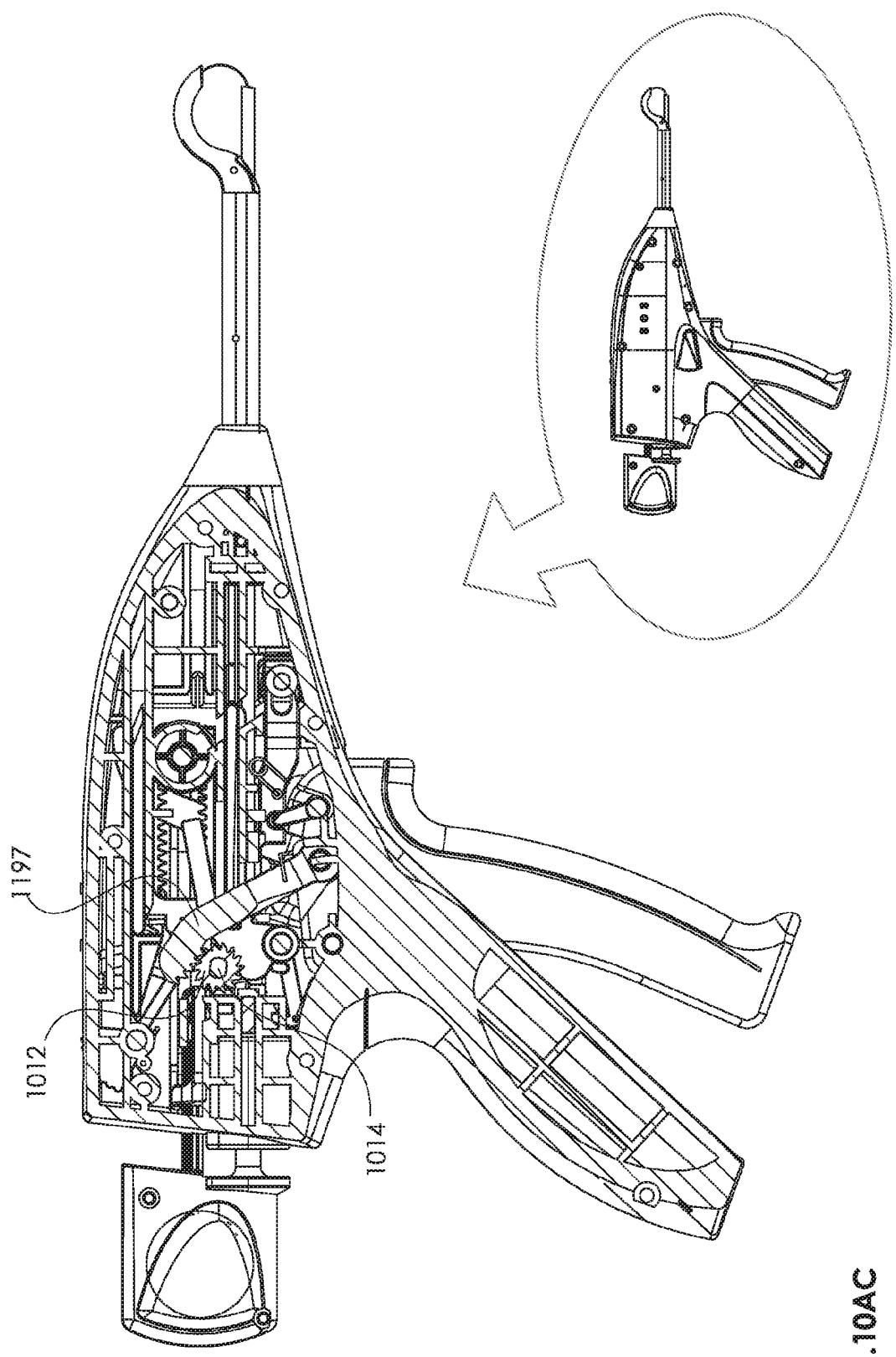
Figure 10A:
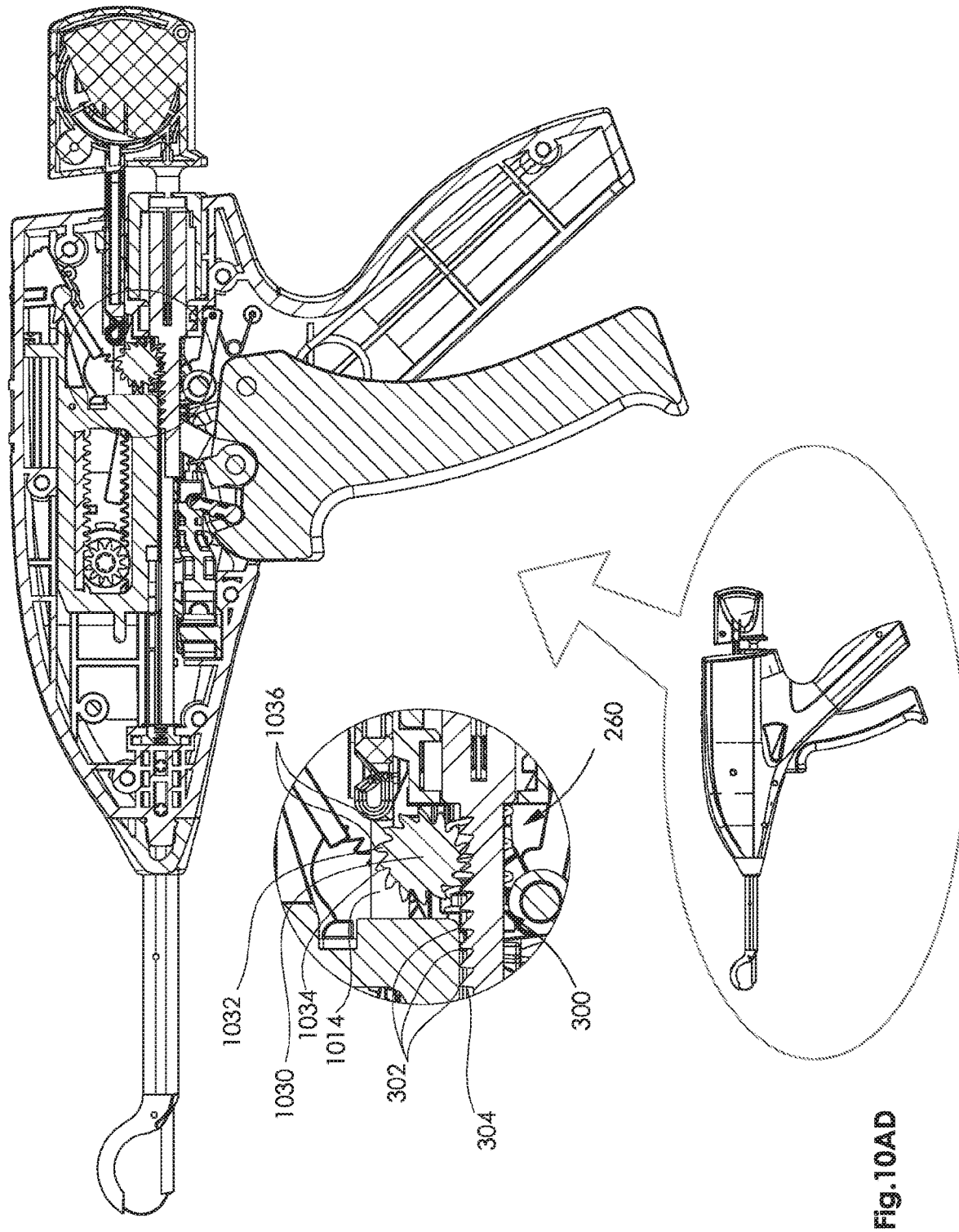
Figure 10A:
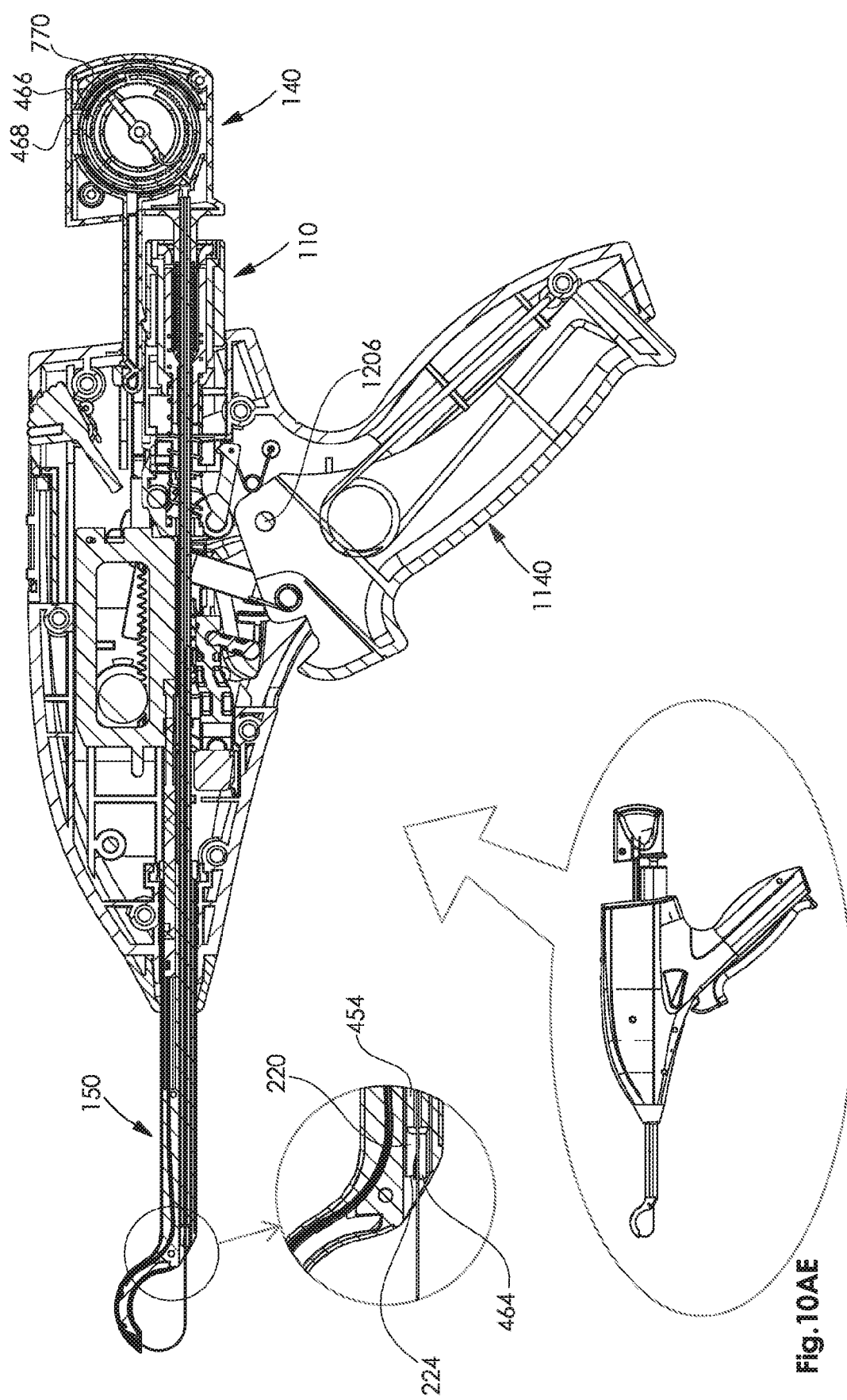
Figure 10A:
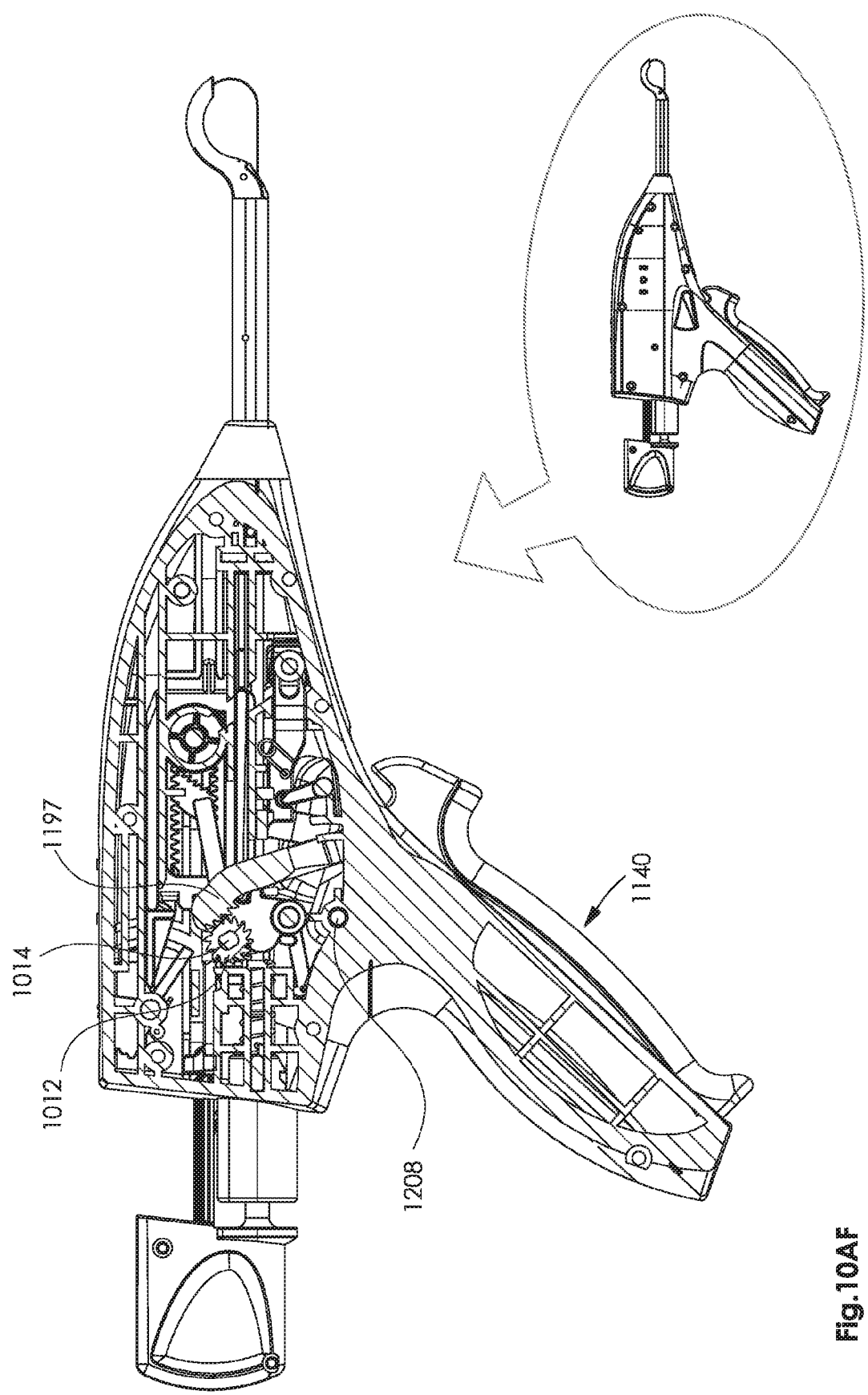
Figure 10A:
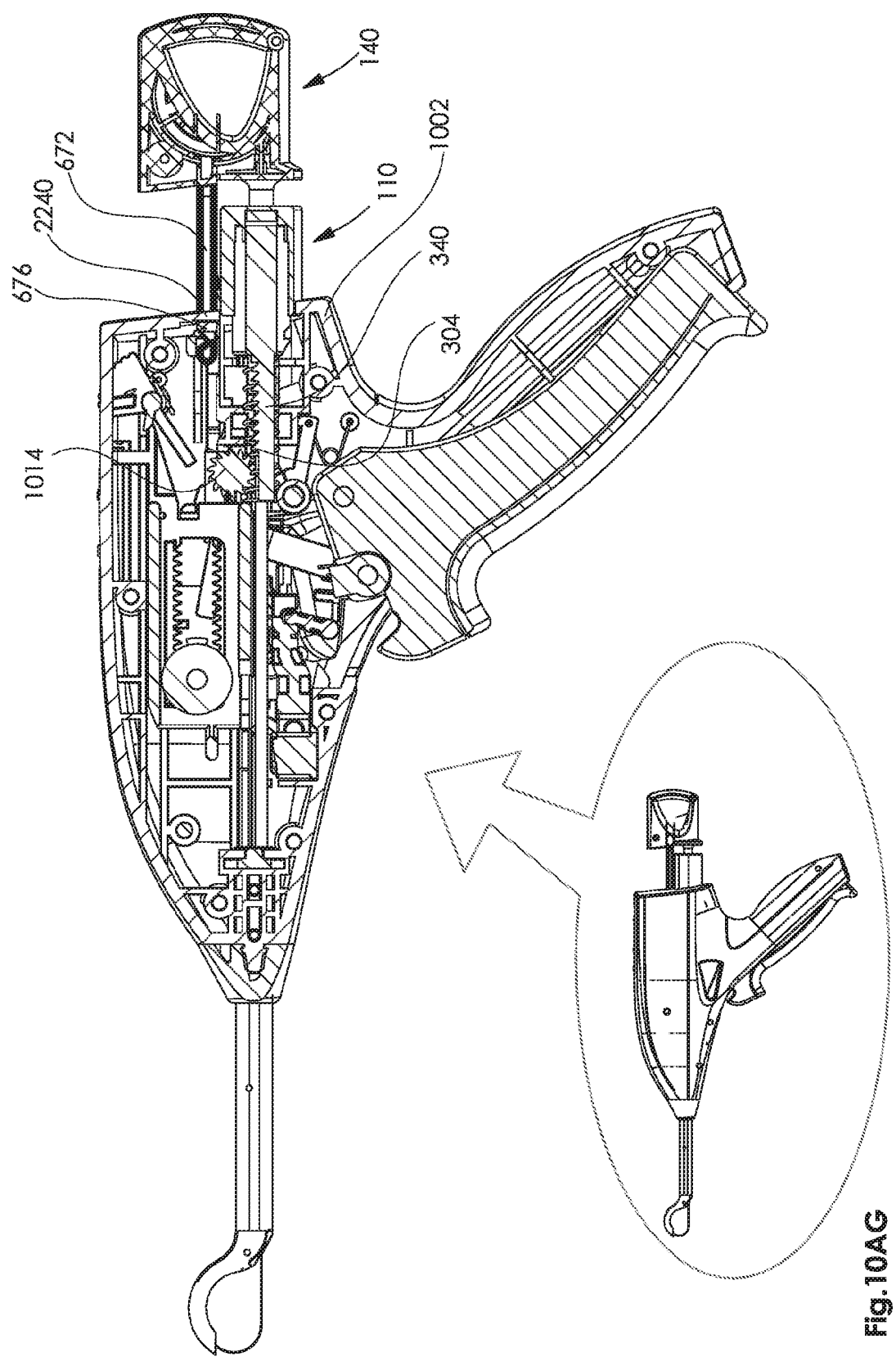
Figure 10A:
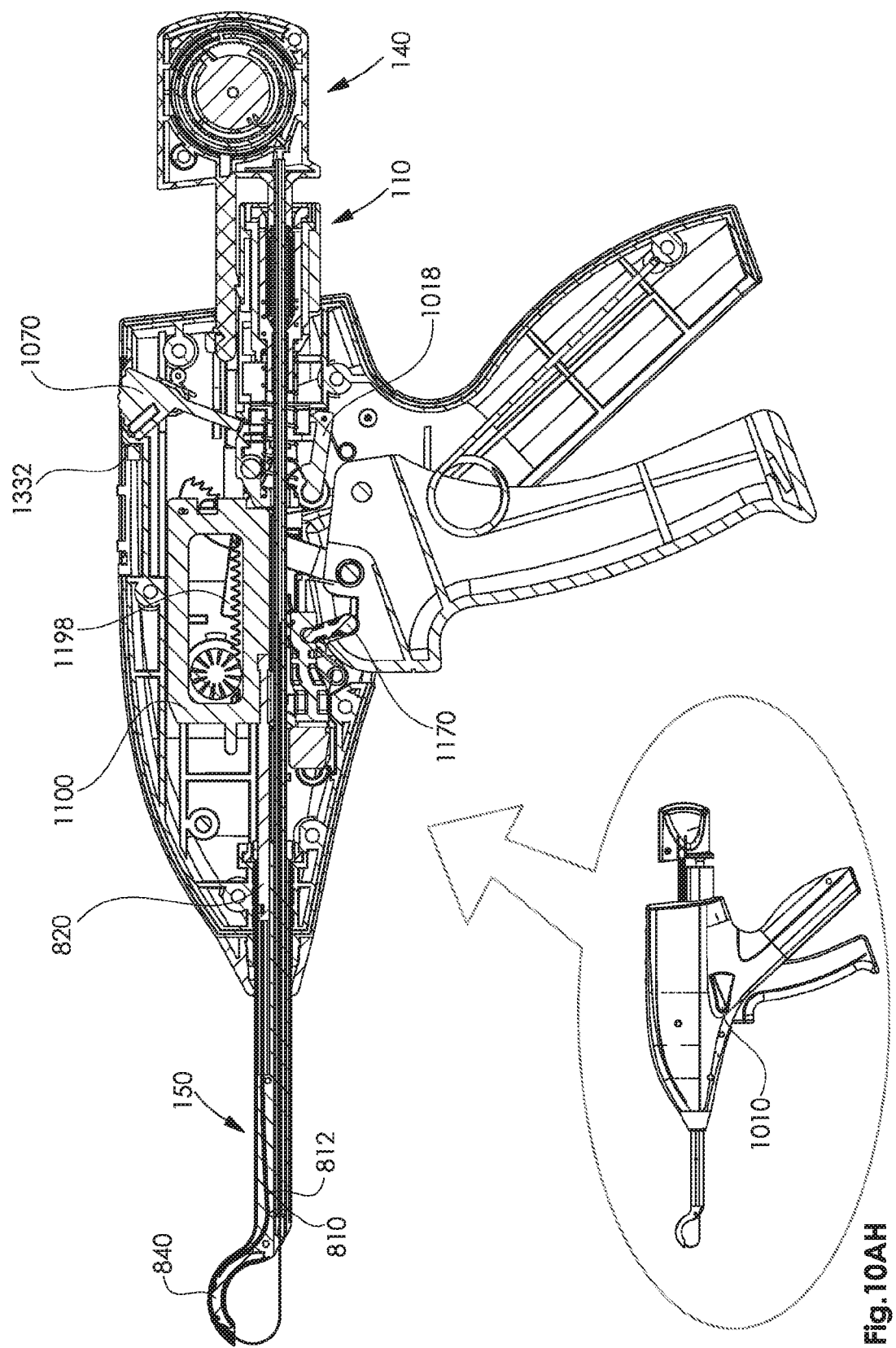
Figure 10A:
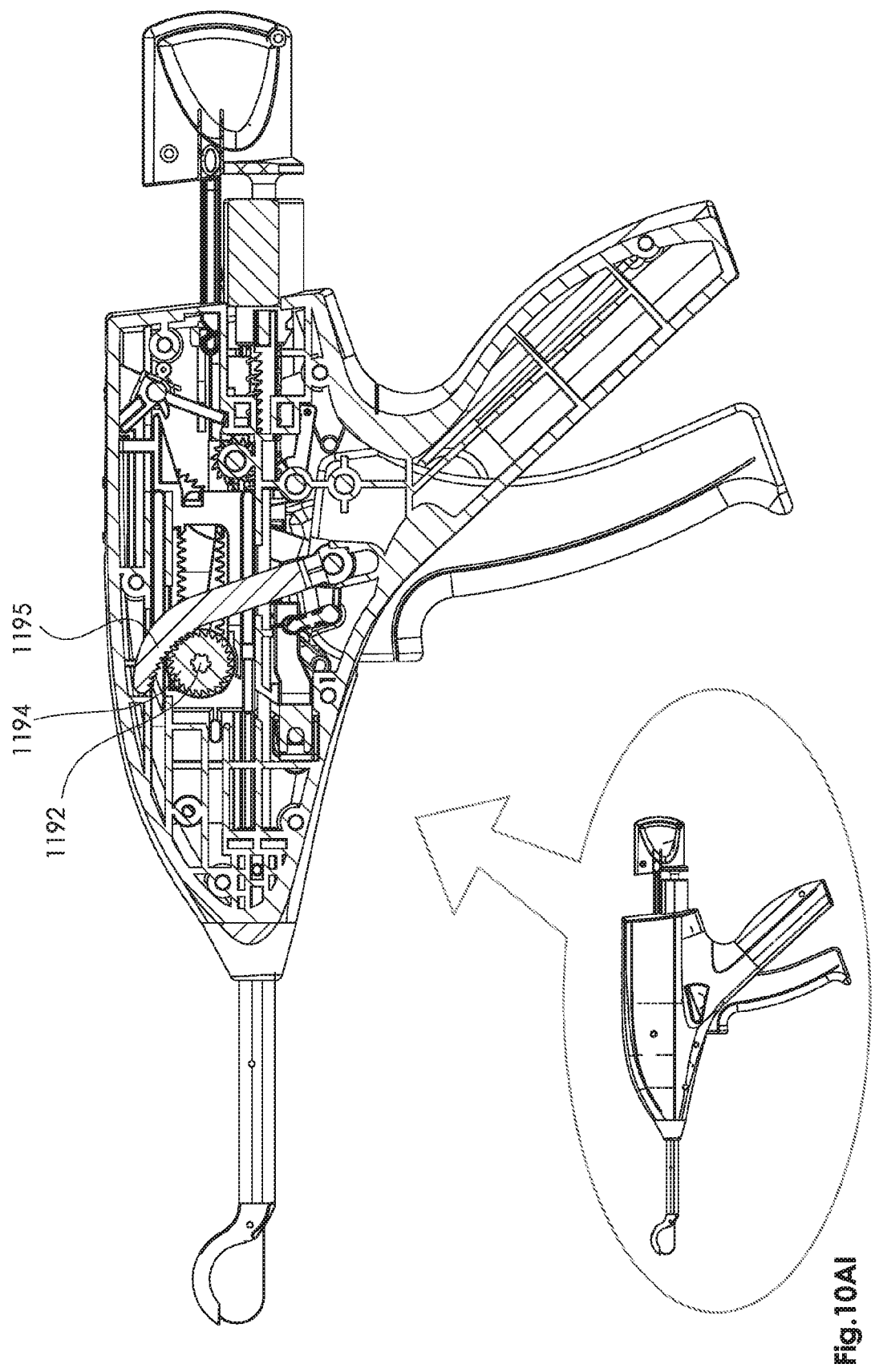
Figure 10A:
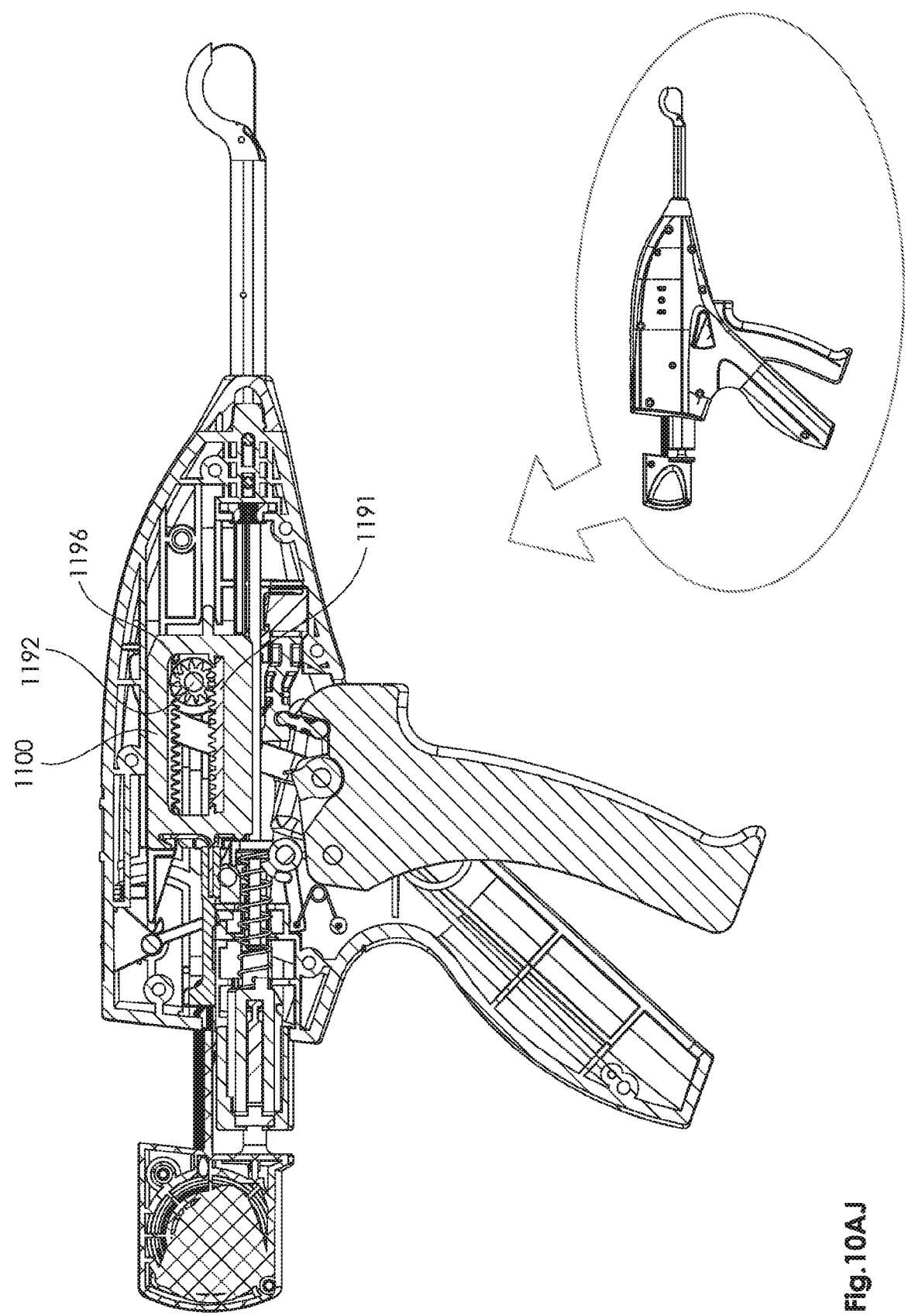
Figure 10A:
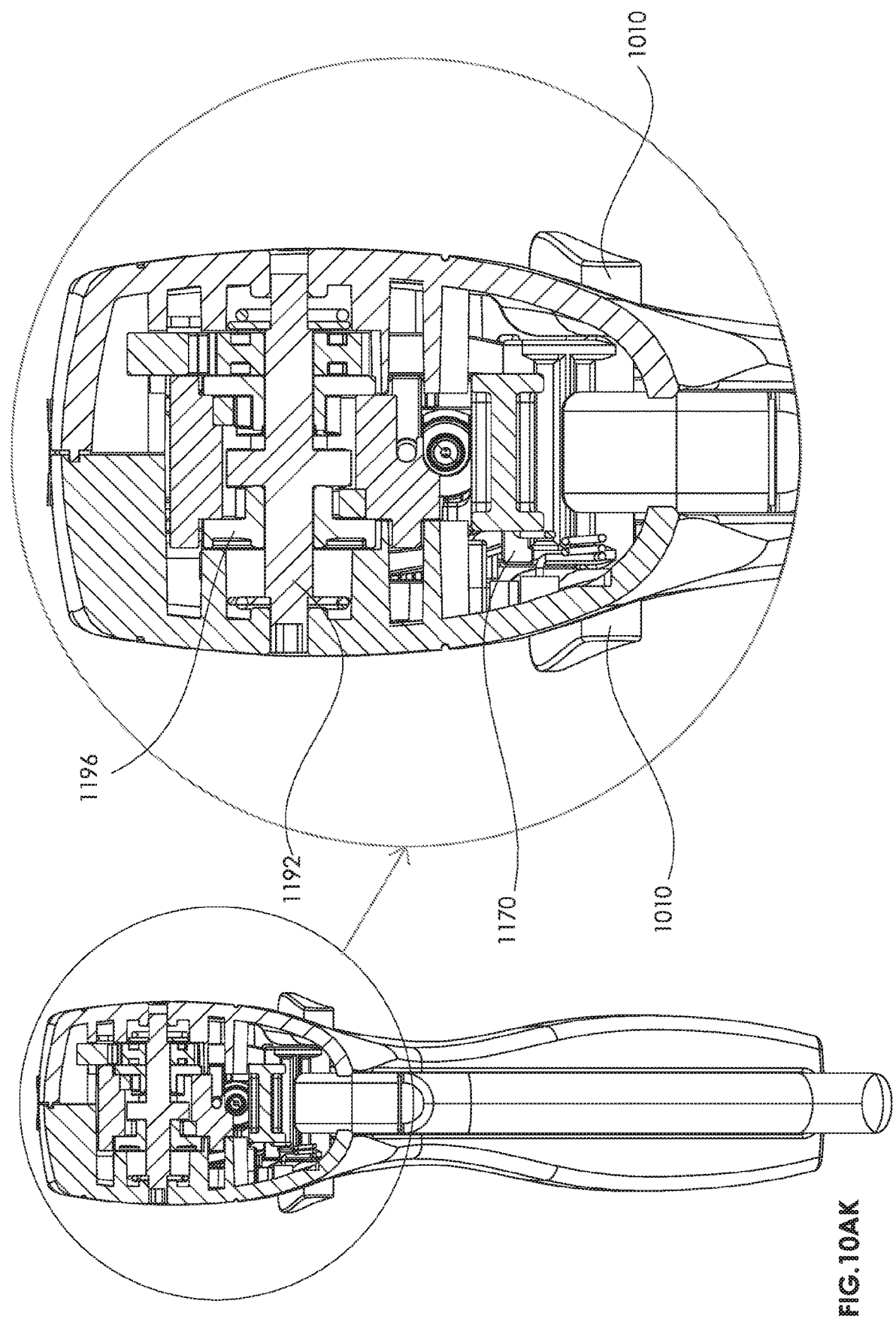
Figure 10A:
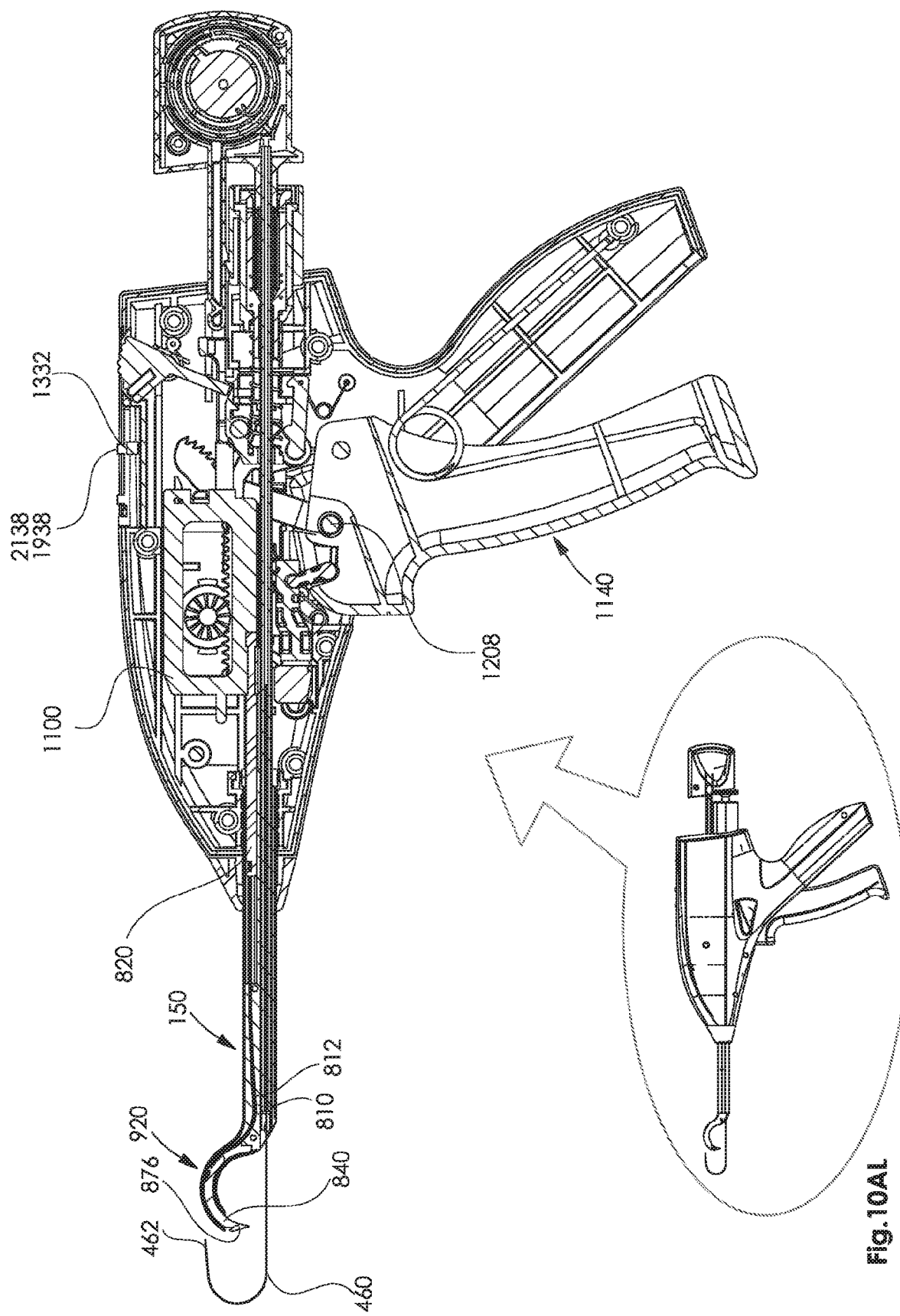
Figure 10A:
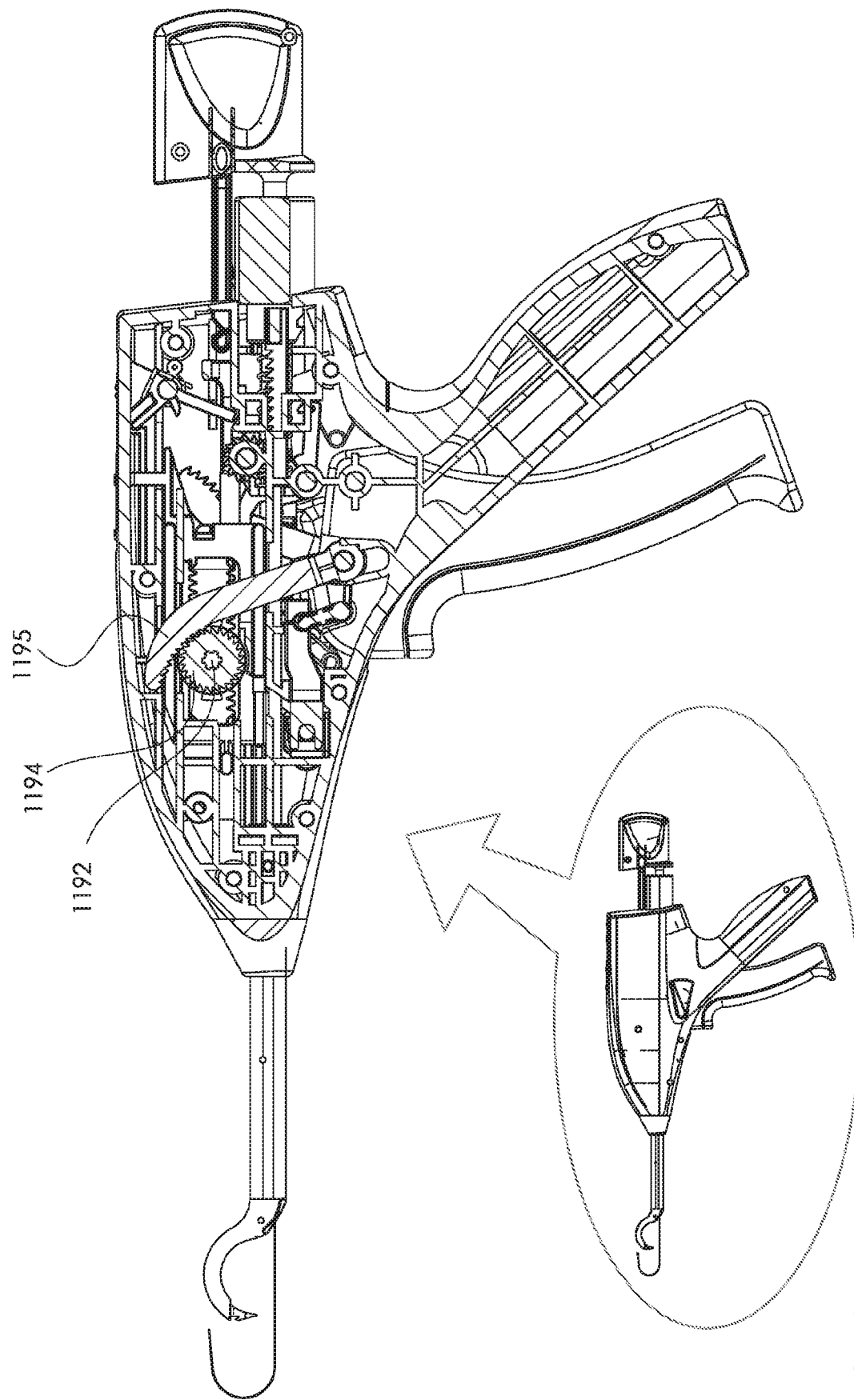
Figure 10A:
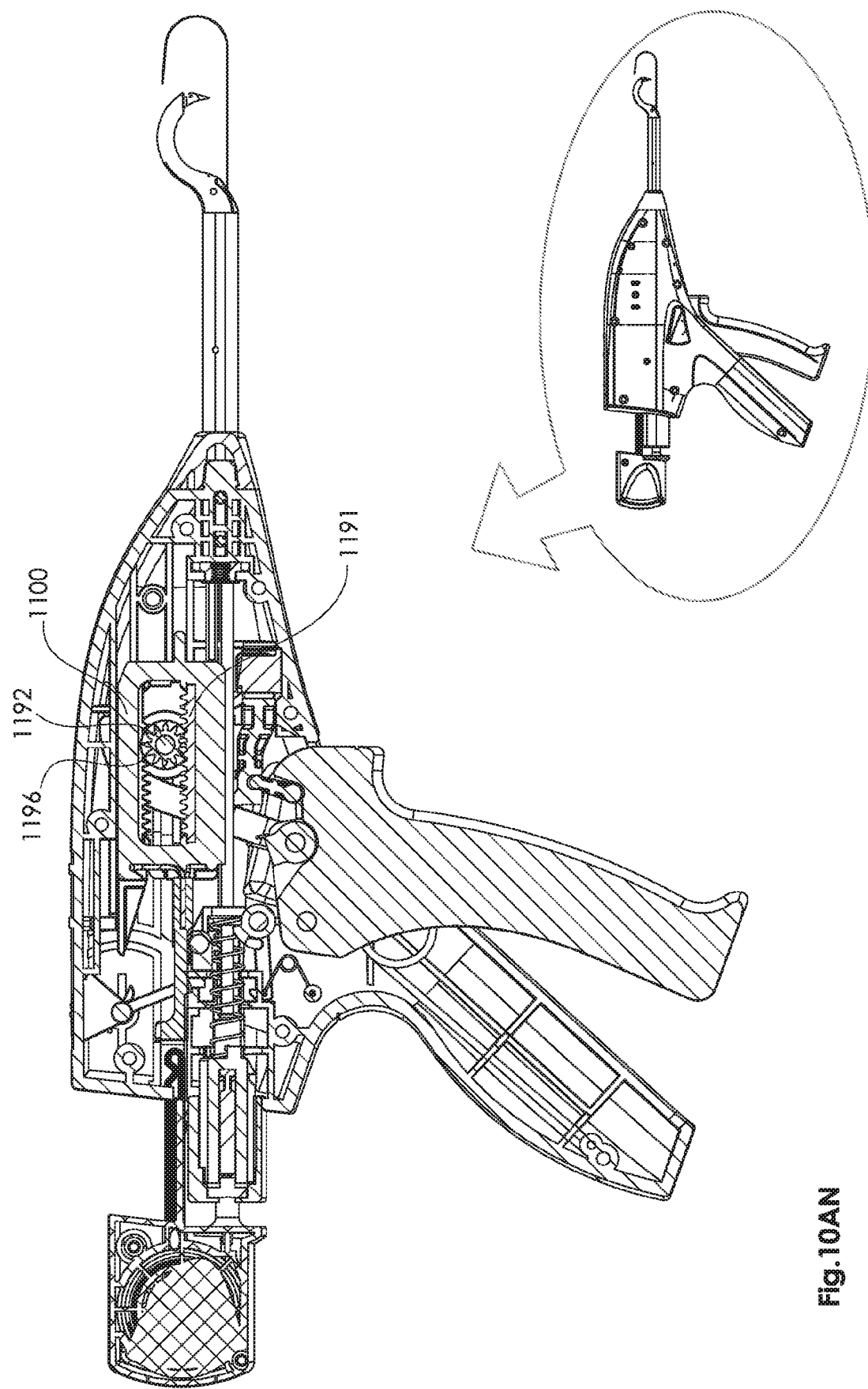

Reference is now made to FIG. 10Y, taken along section lines B-B in FIG. 10A, 10Z, taken along section lines C-C in FIGS. 10A, and 10AA, taken along section lines X-X in FIG. 10A, which illustrate a thirteenth operative orientation of the arthroscopic surgical assembly of FIGS. 1A-9C.

In this operative orientation, hand engageable driving handle 1140 is further rotated rearwardly about handle pivot axis 1206. This causes main chassis 1100 to move further rearwardly to the rearwardmost position. This rearward motion of main chassis 1100 rearwardly displaces elongate push rod 820, and thereby rearwardly displaces bendable pusher strips 810 and 812, causing bone puncture needle 840 to fully retract, as seen by the position of upwardly facing indicator surface 1332.

This full retraction of bone puncture needle 840 causes the pre: formed loop 462 of snare wire 461 to be drawn through flared opening 984 of receiving recess 982 in the hook portion 920 of curved shaft assembly 150, by virtue of pre-formed loop 462 engaging with forwardly and radially inwardly inclined notch 876 of bone puncture needle 840.

It is seen at this stage that tensioning element 470 and snare wire winding drum 466 rotate clockwise still further, in the sense of FIG. 10Y, against the urging of tension spring 458.

As seen particularly in FIG. 10Z, rearward rotation of hand engageable driving handle 1140 causes needle driving ratchet arm 1195, which is pivotably mounted thereon by driving pin 1208, to be downwardly displaced while in engagement with main driving gear 1194, thereby producing clockwise rotation of main driving gear 1194, in the sense of FIG. 10Z. Clockwise rotation of main driving gear 1194 produces corresponding rotation of clutch 1192.

As seen particularly in FIGS. 10Z & 10AA, rotation of clutch 1192 rotates rearward driving gear 1193 in a clockwise direction in the sense of FIG. 10AA. As seen particularly in FIG. 10AA, clockwise rotation of rearward driving gear 1193, in the sense of FIG. 10AA, produces no further rearward displacement of main chassis 1100 because rearward driving gear 1193 is no longer in driving engagement with rearward driving gear rack 1190 located within main chassis.

Reference is now made to FIG. 10AB, taken along section lines J-J in FIG. 10A; 10AC, taken along section lines A-AC in FIGS. 10A; and 10AD, taken along section lines AD-AD in FIG. 10A, which illustrate a fourteenth operative orientation of the arthroscopic surgical assembly of FIGS. 1A-9C.

In this operative orientation, elongate top surface 1274 of elongate protrusion 1272 of main chassis 1100, which is in the rearwardmost operative orientation, engages concave surface 1725 of pivotable arm 1198, causing pivotable arm 1198 to pivot counterclockwise, in the sense of FIG. 10AB, about cylindrical axle portion 1050 of work channel assembly retaining hook element 1018. This counterclockwise pivotal motion of pivotable arm 1198 pivots intermediate arm portion 1064 of work channel assembly retaining hook element 1018 about cylindrical axle portion 1050 of work channel assembly retaining hook element 1018, against the urging of rotation urging spring element 1016. This pivotal movement of work channel assembly retaining hook element 1018 causes disengagement of undercut hook 1054 from transverse undercut 294 of rack defining intermediate element 260 of work channel assembly 110.

Work channel retracting ratchet arm 1197, under the urging of ratchet arm urging spring 1222, pivots about driving pin 1208 and pushes first arm portion 1750 of shiftable link 1199 underneath and into locking engagement with a protrusion 1724 of pivotable, arm 1198, thereby locking pivotable arm 1198 in place in an upward position. This enables work channel retracting ratchet arm 1197 to drivingly engage ratchet gear element 1012.

As seen particularly in FIG. 10AC, work channel retracting ratchet arm 1197, under the urging of ratchet arm urging spring 1222, engages ratchet gear element 1012 which is coaxially connected with axle-mounted gear element 1014.

As seen particularly in FIG. 10AD, axle mounted gear element 1014 is engaged with rack-defining intermediate element 260 (refer back to FIG. 10N). The multiplicity of gear teeth 1036 on axle mounted gear 1014 engages the row of ratchet teeth 302 on linear ratchet gear rack 304 on the shaft 300 of the rack defining intermediate element 260.

Reference is now made to FIG. 10AE, taken along section lines B-B in FIG. 10A; 10AF, taken along section lines AC-AC in FIGS. 10A; and 10AG, taken along section lines AD-AD in FIG. 10A, which illustrate a fifteenth operative orientation of the arthroscopic surgical assembly of FIGS. 1A-9C.

In this operative orientation, hand engageable driving handle 1140 is further rotated rearwardly about handle pivot axis 1206. This causes work channel assembly 110 along with snare wire cartridge assembly 140 to move rearwardly to their rearwardmost positions. This rearward motion of work channel assembly 110 along with snare wire cartridge assembly 140 causes end portion 770 of snare wire 461 to become disengaged from wire traversing aperture 469 of resilient retaining element 468 which is mounted in snare wire winding drum 466.

This full retraction of work channel assembly 110 along with snare wire cartridge assembly 140 causes front edge 224 of hollow elongated tube 220 in the work channel assembly 110 and forward end 464 of elongated hollow shaft 454 in snare wire cartridge assembly 140 to fully retract into curved shaft assembly 150.

As seen particularly in FIG. 10AF, rearward rotation of hand engageable driving handle 1140 causes work channel retracting ratchet arm 1197 which is pivotably mounted thereon by driving pin 1208 to be downwardly displaced while in engagement with ratchet gear element 1012, thereby producing clockwise rotation of ratchet gear element 1012, in the sense of FIG. 10AF. Clockwise rotation of ratchet gear element 1012 produces corresponding clockwise rotation of axle mounted gear element 1014.

As seen particularly in FIG. 10AG, rotation of ratchet gear element 1012 rotates axle mounted gear element 1014 in a clockwise direction in the sense of FIG. 10AF. As further seen in FIG. 10AG, counterclockwise rotation of axle mounted gear element 1014 produces no further rearward displacement of work channel assembly 110 or snare wire cartridge assembly 140, because axle mounted gear element 1014 is no longer in driving engagement with the row of ratchet teeth 302 on linear ratchet gear rack 304 on the shaft 300 of the rack defining intermediate element 260. Following the disengagement of end portion 770 of snare wire 461 from wire traversing aperture 469 of resilient retaining element 468 which is mourned in snare wire winding drum 466, the snare wire cartridge assembly 140 is retained by the cartridge assembly retaining shaft portion 672 of the secondary housing portion 452. Upper adjacent inclined surface 676 of the cartridge assembly retaining shaft portion 672 on the secondary housing portion 452 engages concave surface 2240 in first housing portion 1002.

Reference is now made to FIGS. 10AH-10AK, which include enlargements taken along respective section lines B-B, C-C, D-D and E-E in FIG. 10A and which illustrate a sixteenth operative orientation of the arthroscopic surgical device 160, which is set for forward motion, as indicated by a raised rotated orientation of driving direction selector lever 1010.

As seen in FIGS. 10AH-10AK, bone puncture needle 840 is fully retracted in this operative orientation at a forward end of curved shaft assembly 150, responsive to the fact that main chassis 1100 is in a rearwardmost operative orientation as indicated by the position of upwardly-facing indicator surface 1332. The retracted orientation of bone puncture needle 840 results from retraction of bendable pusher strips 810 and 812, which are in turn retracted by retraction of elongate push rod 820, which is fixedly connected to main chassis 1100.

As seen in FIGS. 10AH & 10AI, driving direction selector lever responsive toggle element 1170 is seen to be in a forwardly-tilted operative orientation responsive to the orientation of driving direction selector lever 1010. Work channel assembly 110 is seen to be in a retracted operative orientation. As seen particularly in FIG. 10AH, work channel assembly retaining hook element 1018 is in the downward oriented position. Also seen in FIG. 10AH, pivotable arm 1198 is in the upward oriented position. As a result of work channel assembly retaining hook element 1018 being in the downward position, work channel assembly 110 is unengageable by the arthroscopic surgical device 160.

As particularly seen in FIG. 10AI, needle driving ratchet arm 1195 is operatively engaged with the gear teeth 1674 of main driving gear 1194 under the urging of ratchet arm urging spring 1222 (FIG. 8BA). As further shown in FIGS. 10AI & 10AJ, downwardly extending earn surface 1328 of transversely extending portion 1330 of main chassis 1100 faces cam surface 1092 on cartridge release cam portion 1090 of the cartridge assembly retaining element 1070, thus limiting cartridge assembly retaining element's 1070 upward counterclockwise rotation with respect to arthroscopic surgical device 160. The limitation provided by downwardly extending cam surface 1328 of transversely extending portion 1330 of main chassis 1100 prevents snare wire cartridge assembly from being engaged by cartridge assembly retaining element 1070. FIG. 10AJ, particularly, illustrates the engagement of forward driving gear 1196 with forward driving gear rack 1191, which is mounted in main chassis 1100.

As seen particularly in FIG. 10AK, the operative orientation of driving direction selector lever responsive toggle element 1170 causes clutch 1192 to engage forward driving gear 1196.

Reference is now made to FIG. 10AL, taken along section lines B-B in FIG. 10A, 10AM, taken along section lines C-C in FIGS. 10A, and 10AN, taken along section lines D-D in FIG. 10A, which show a seventeenth operative orientation of the arthroscopic surgical assembly of FIGS. 1A-9C. In this operative orientation, hand engageable driving handle 1140 is rotated rearwardly about handle pivot axis 1206. This causes main chassis 1100 to move forwardly, thereby forwardly displacing elongate push rod 820, and thereby forwardly displacing bendable pusher strips 810 and 812, causing bone puncture needle 840 to emerge from forward end 926 of hook portion 920, as seen by the position of upwardly facing indicator surface 1332. It is seen that indicator surface 1332 is aligned with protrusions 1938 and 2138 which indicate that 8 mm of the bone puncture needle 840 protrudes from the forward end 926 of hook portion 920, as can also be seen in FIGS. 10AM & 10AN relative to marking 892.

As seen in FIGS. 10AL-10AN, the emerging of the bone puncture needle 840 from forward end 962 of hook portion 920 of curved shaft assembly 150 releases the pre-formed loop 462 of the snare wire 461 from the forwardly and radially inwardly-inclined notch 876 of the bone puncture needle 840.

As seen particularly in FIG. 10AM, this further rearward rotation of hand engageable driving handle 1110 causes needle driving ratchet arm 1195, which is pivotably mounted thereon by driving pin 1208, to be further downwardly displaced while in engagement with main driving gear 1194, thereby producing further clockwise rotation of main driving gear 1194 in the sense of FIG. 10AM. This further clockwise rotation of main driving gear 1194 produces corresponding further rotation of clutch 1192.

As seen particularly in FIG. 10AN, rotation of clutch 1192 further rotates forward driving gear 1196 in a counterclockwise direction in the sense of FIG. 10AN, in engagement with forward driving gear rack 1191 located within main chassis 1100, thereby producing further forward displacement of main chassis 1100.

Reference is now made to 11A, 11B, 11C, 11D, 11E, 11F, 11G, 11H, 11I, 11J, 11K, 11L, 11M, 11N, 11O, 11P, 11Q, 11R, 11S & 11T, which are simplified illustrations of operation of the arthroscopic surgical device of FIGS. 1A-10AN in a clinical context.

Reference is initially made to FIG. 11A-11D, which show initial steps of using bone punch assembly 100 (FIGS. 1A & 1B) to form a socket in a bone, such as a humerus. Prior to using bone punch assembly 100, the surgeon preferably forms at least three incisions 2500, 2502 and 2504 in the upper shoulder of the patient. Bone bunch assembly 100 engages the bone via incision 2500. Incision 2504 is employed for insertion of a camera (not shown) and for introduction of fluid for separating flesh from the bone and thus creating a clear vision space at the bone which enables the bone to be viewed via the camera.

Figure 11B:
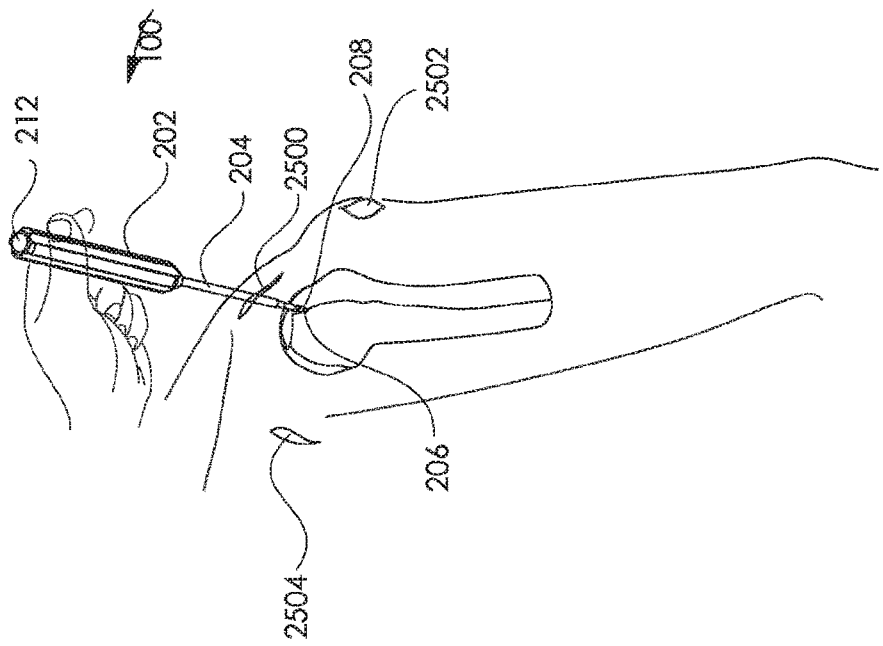
Figure 11A:
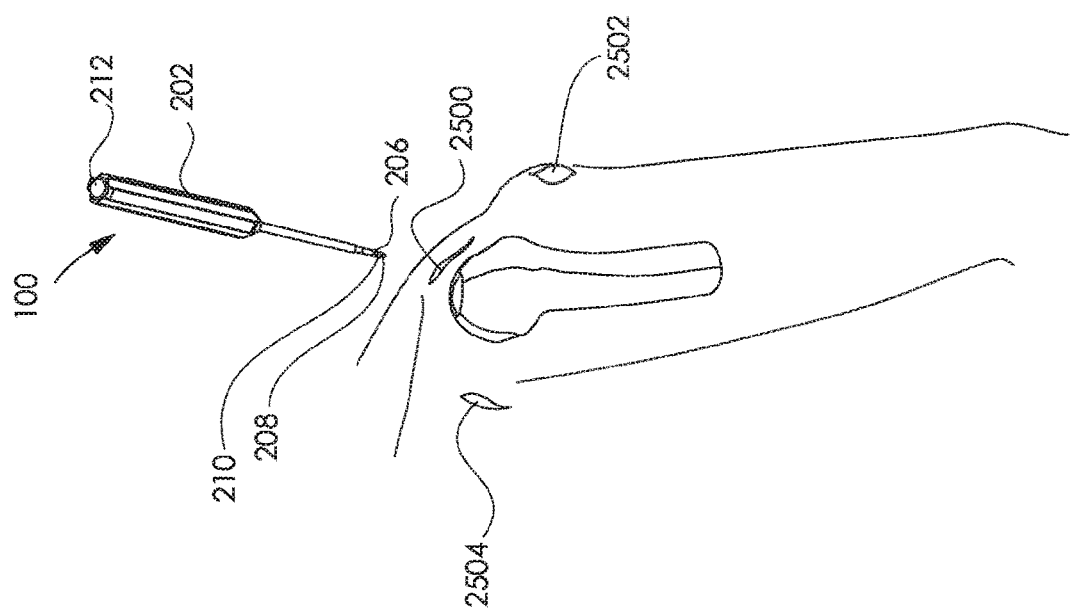
Figure 11C:
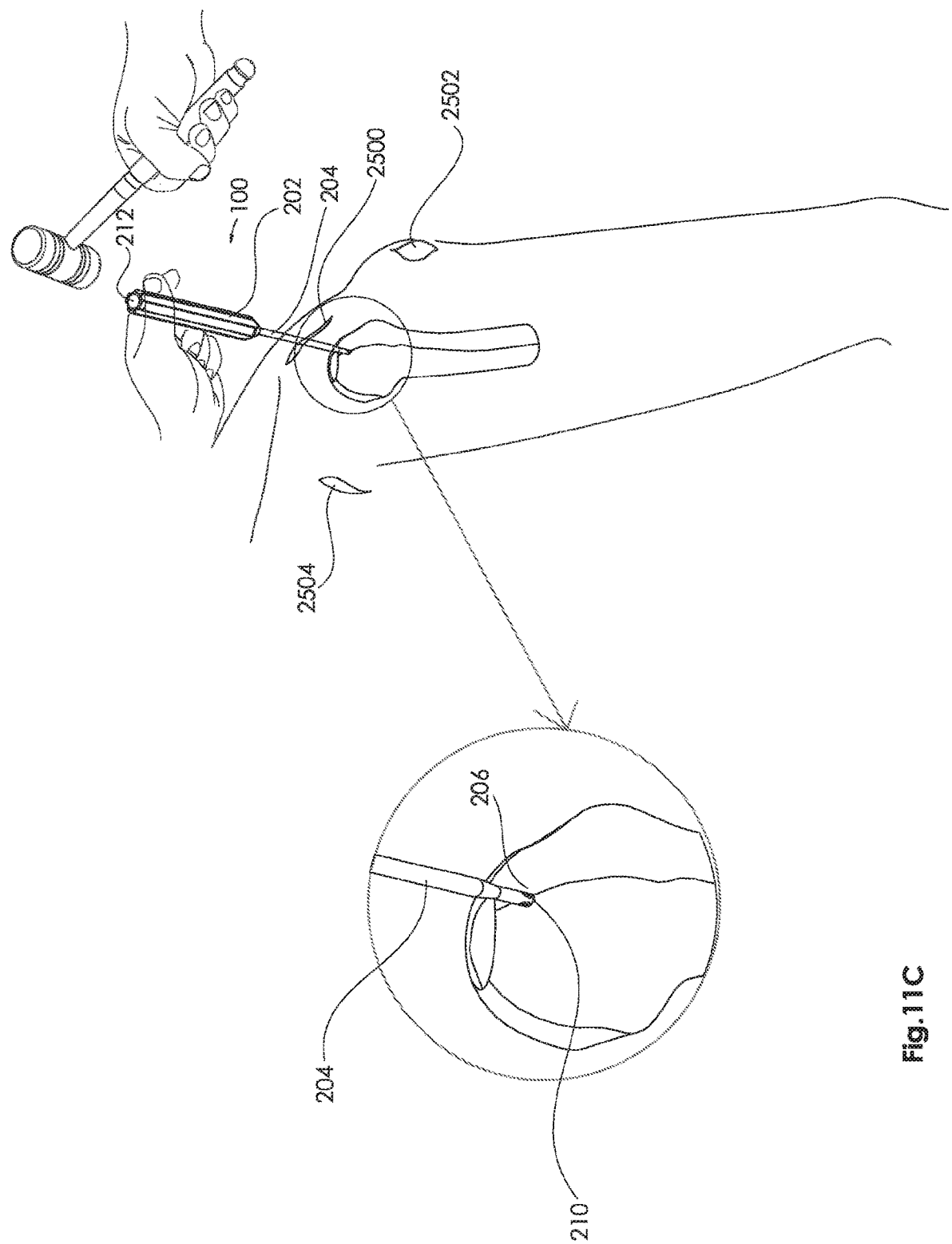

As seen in FIG. 11B, the surgeon initially positions the pointed tip 208 of the forward portion 206 of bone punch assembly 100 through incision 2500 precisely at a location desired for creating a tunnel. The surgeon views this location and the placement of the pointed tip 208 by using the camera. Once the surgeon is satisfied that the location and orientation of the pointed tip 208 is correct, he employs a surgical hammer which engages generally convex impact surface 212 to drive the pointed tip 208 into the bone, thereby creating a socket 2506, as seen in FIG. 11C. The desired depth of the socket 2506, preferably 8 mm, can be seen by the surgeon using the camera and using circumferential marking 210 on forward portion 206.

Figure 11D:
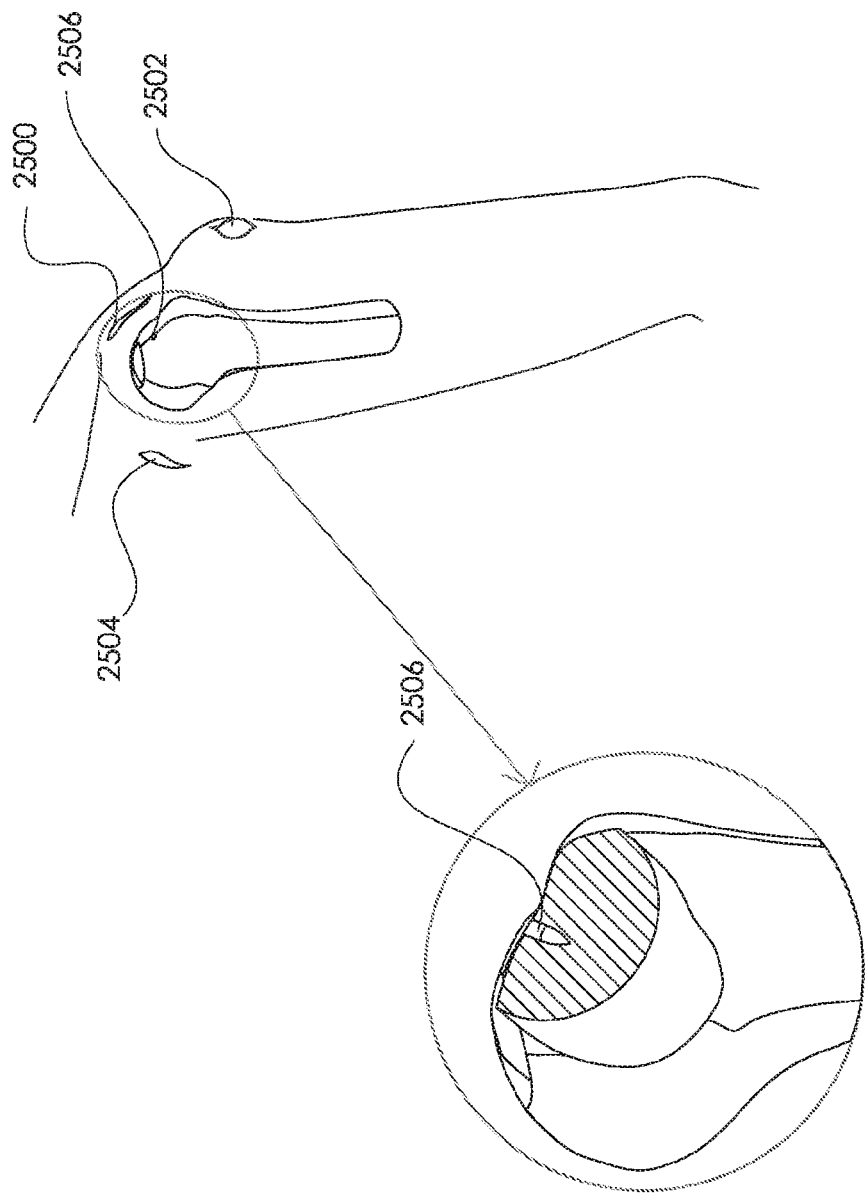
Figure 111:
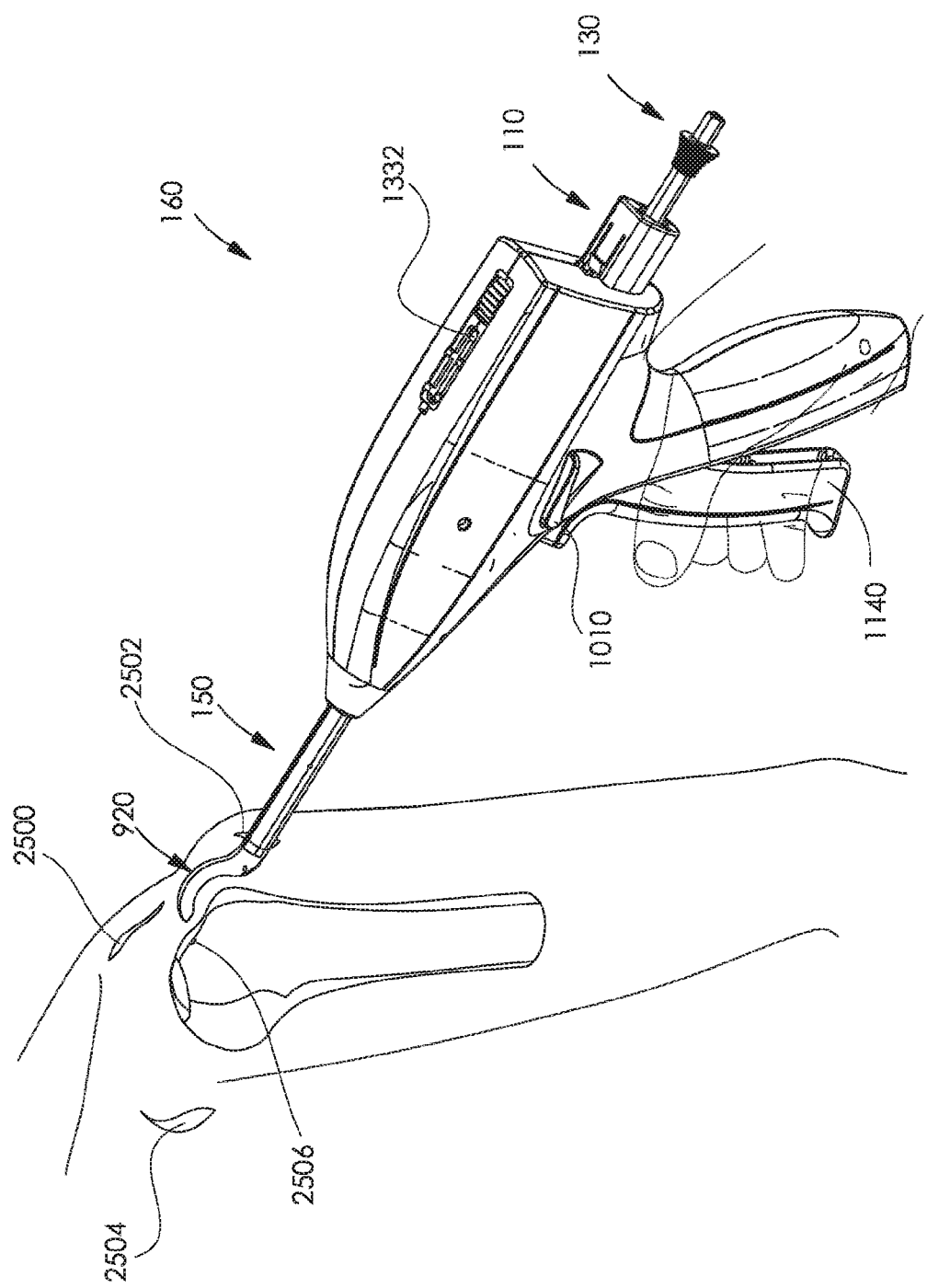

The surgeon then removes the bone punch assembly 100, via incision 2500, leaving the socket 2506 intact, as seen in FIG. 11D.

Figure 11F:
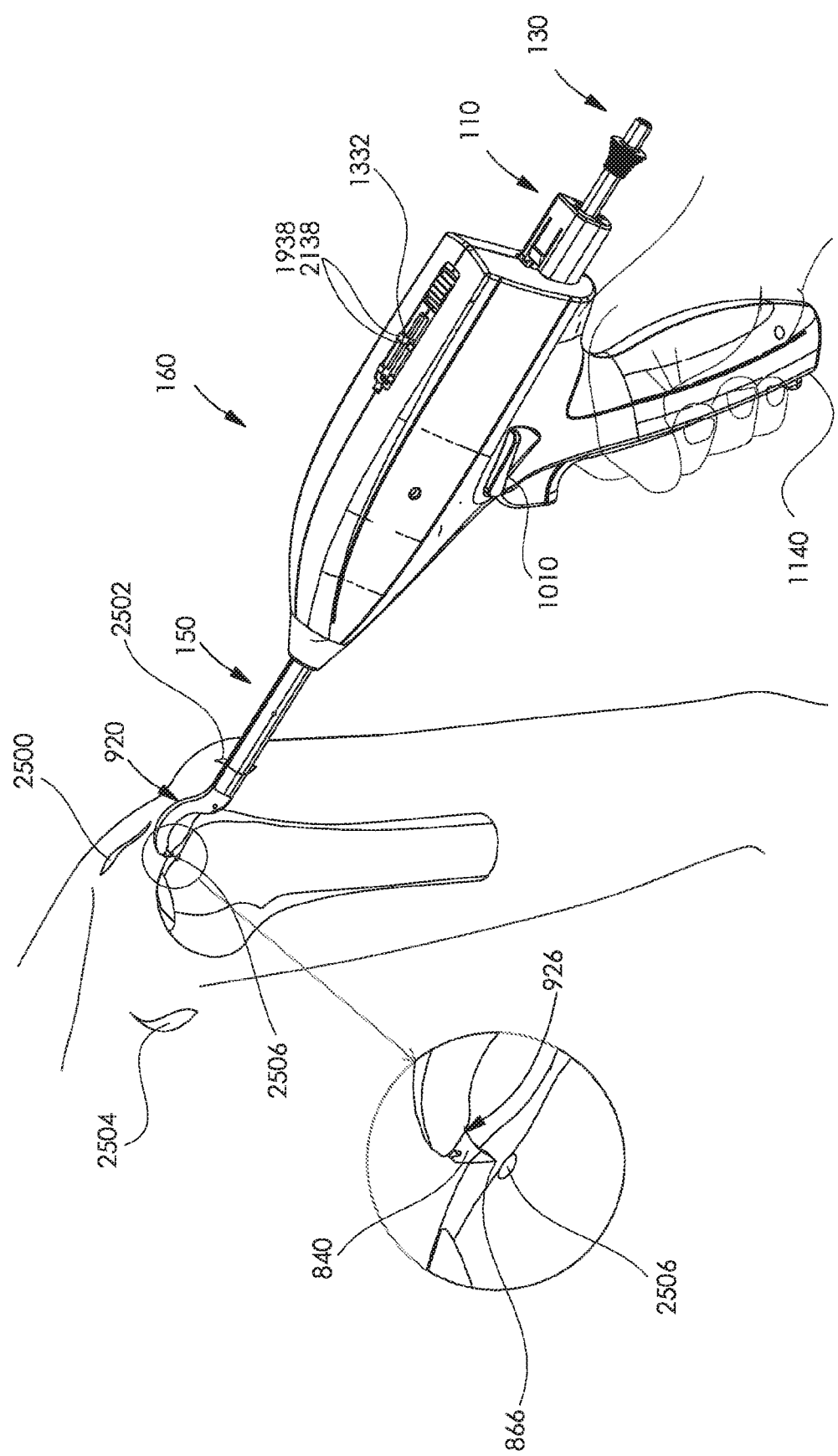
Figure 11G:
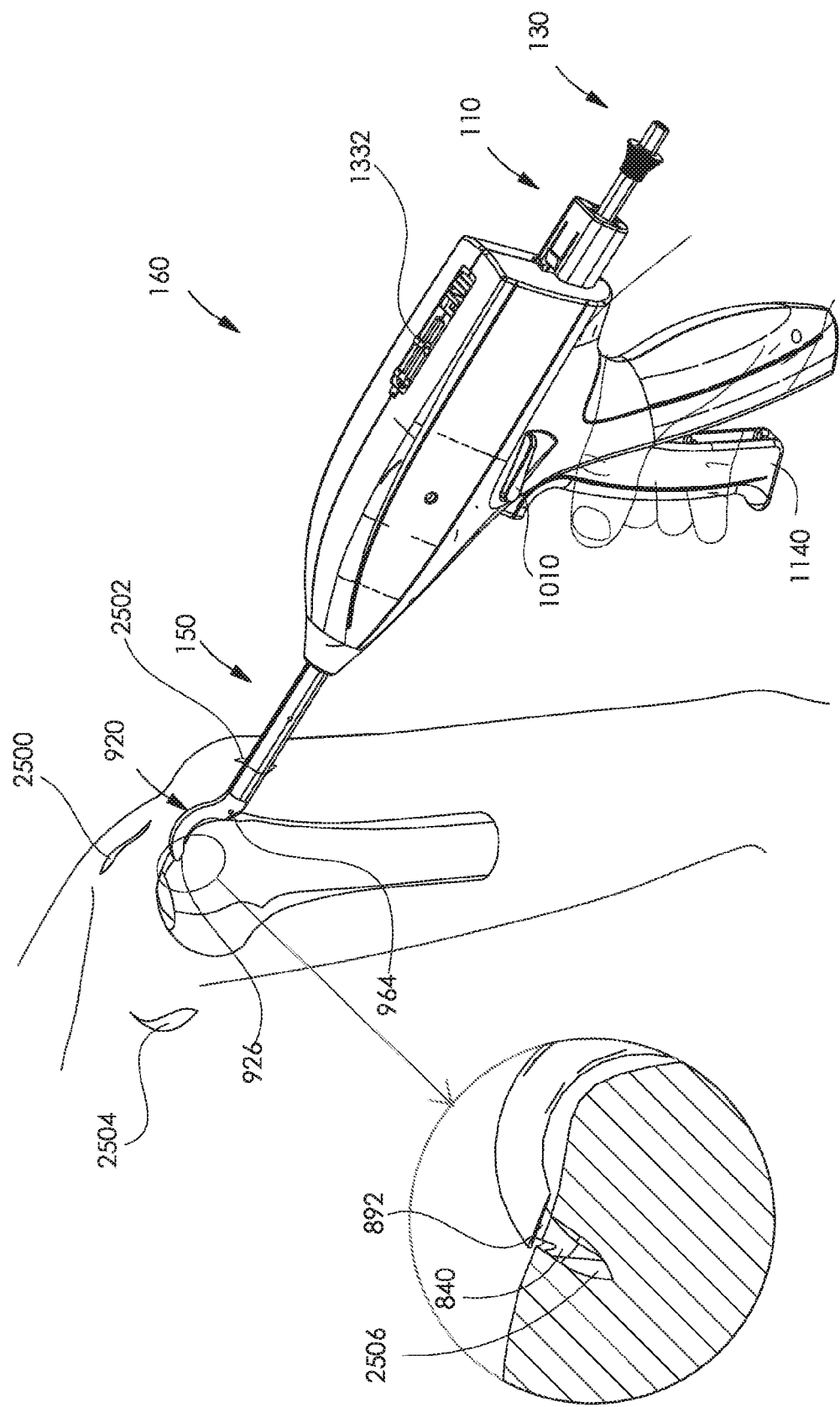
Figure 11H:
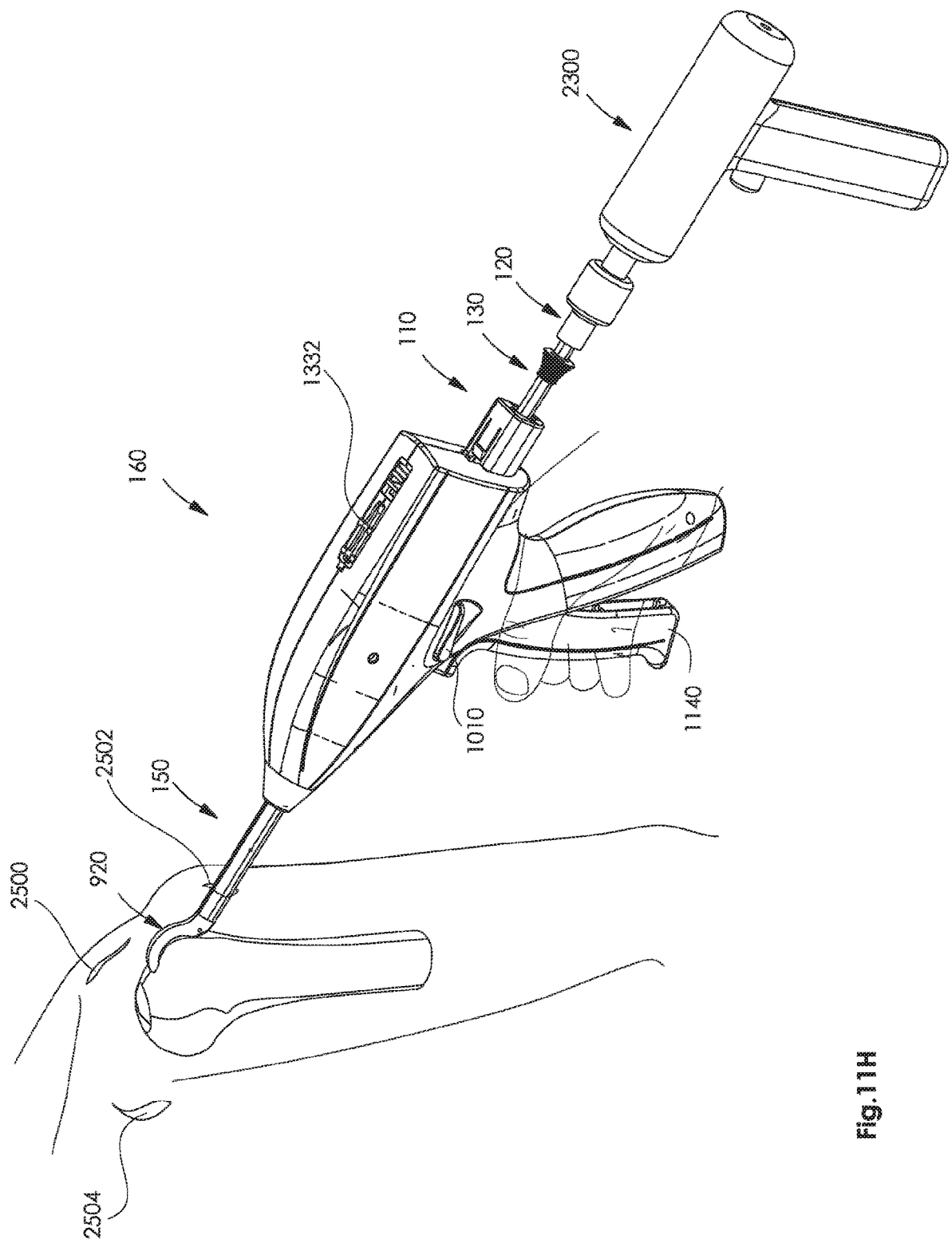
Figure 111:
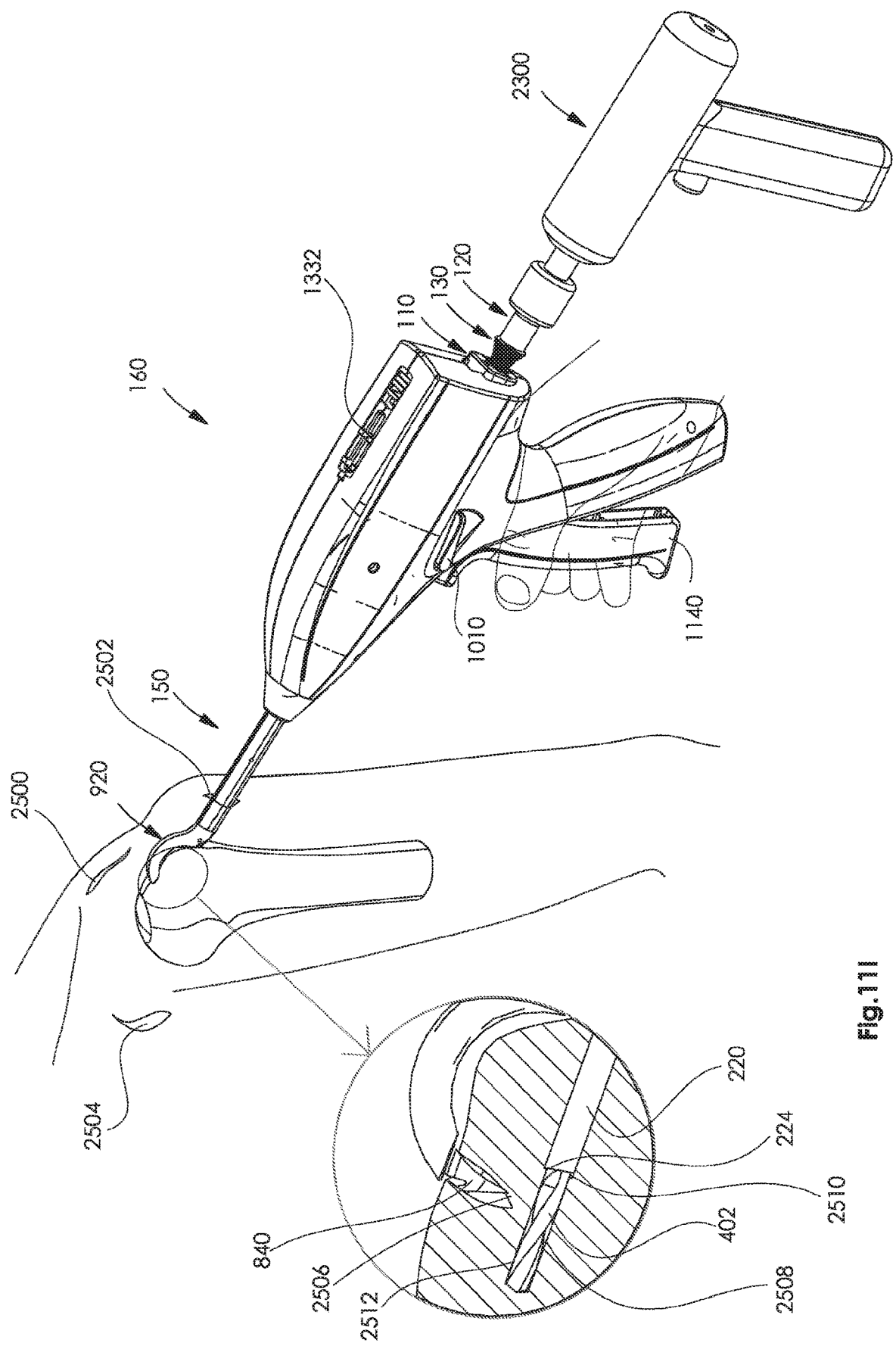
Figure 11J:
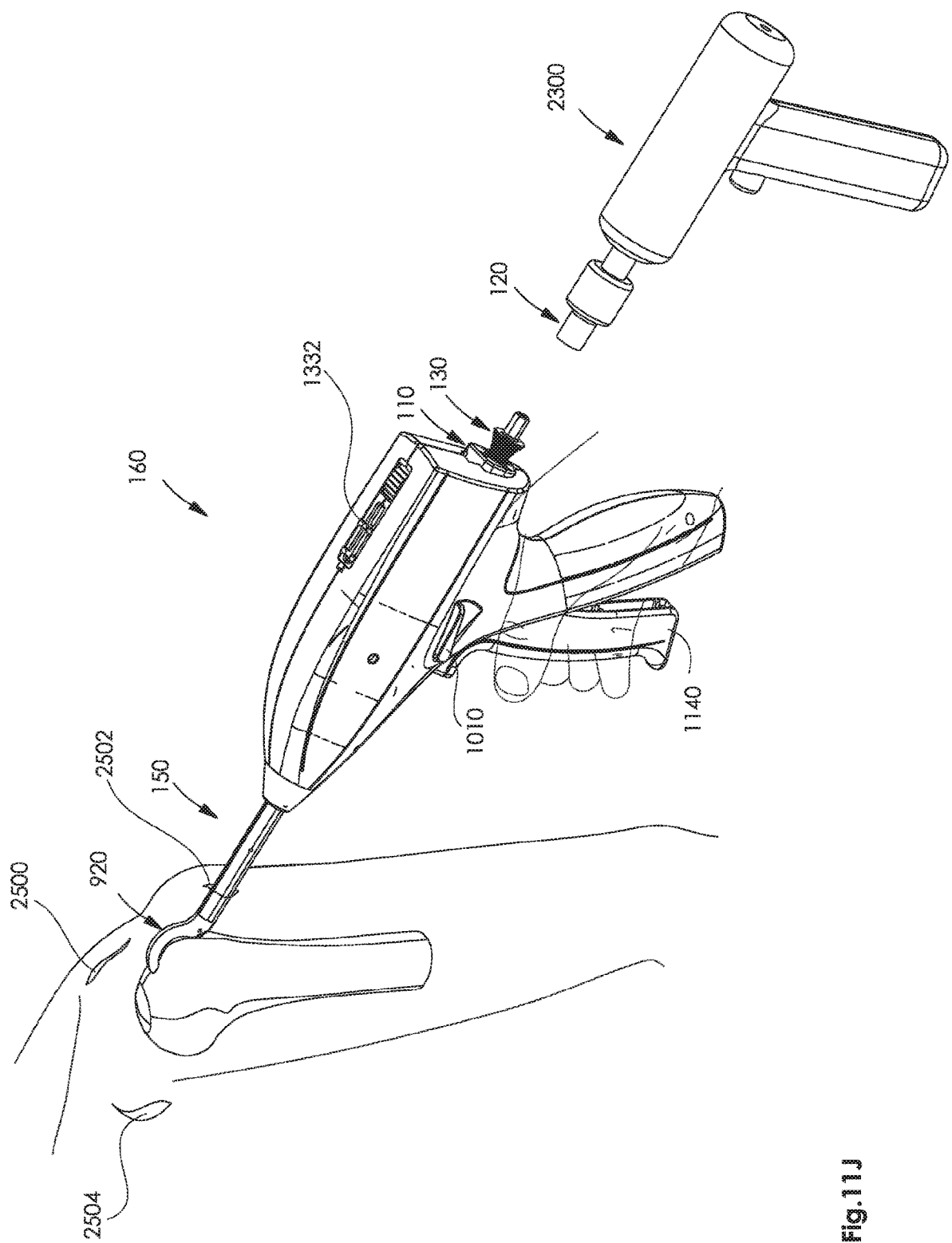
Figure 11E:
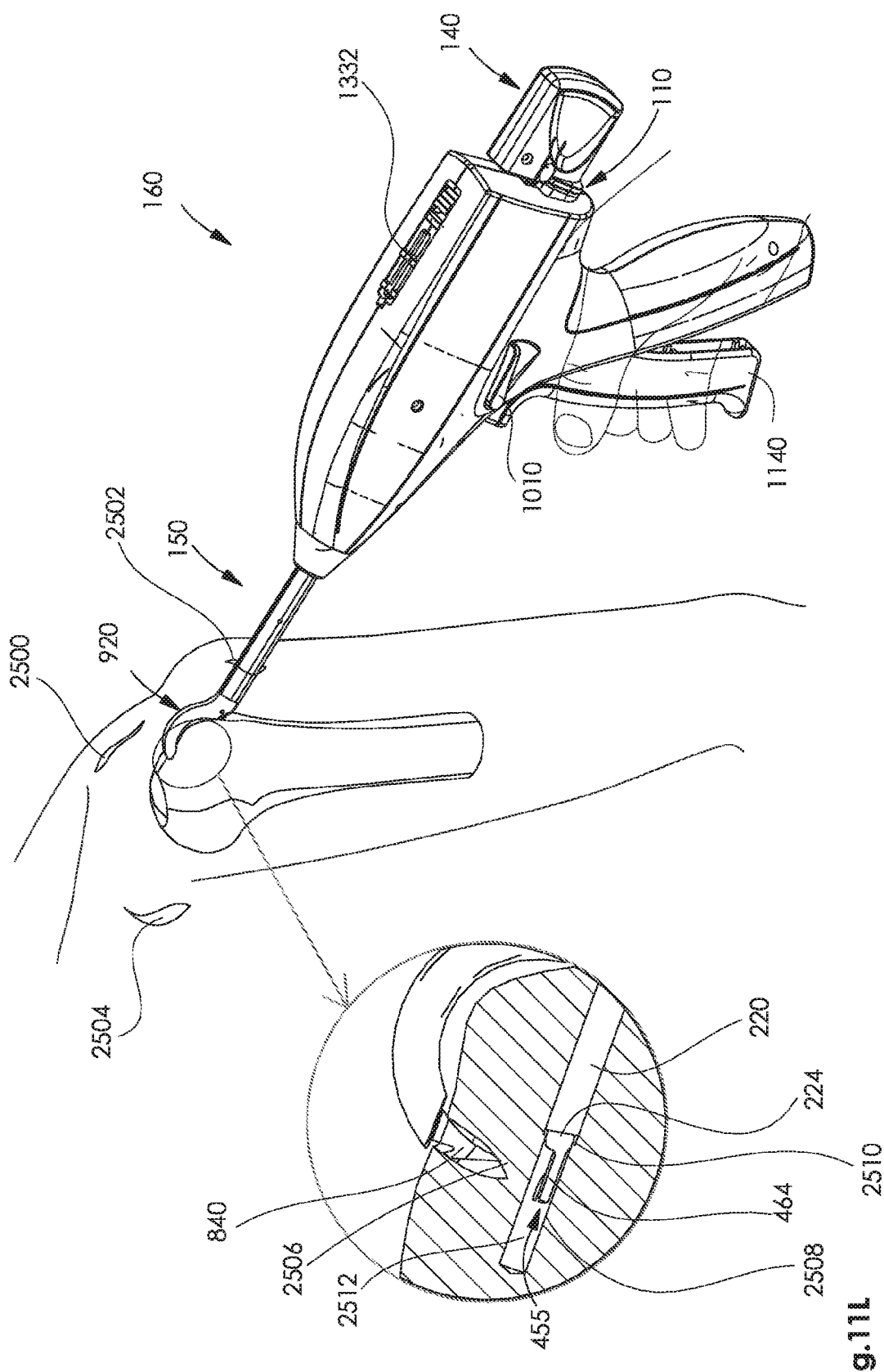

Reference is now made to FIG. 11E, which illustrates initial insertion of hook portion 920 of curved shaft assembly 150 of the arthroscopic surgical device 160 in the second operative orientation, as shown in FIG. 10F, through incision 2502 into the flesh of the patient. Thereafter, the arthroscopic surgical device 160 is caused to assume the third operative orientation shown in FIGS. 10G-10I, while it is oriented as shown in FIG. 11E.

As seen in FIGS. 11F-11H, the arthroscopic surgical device 160 is caused to assume the fourth operative orientation shown in FIGS. 10K-10M. While in this operative orientation, the arthroscopic surgical device 160 is maneuvered so that the tapered tip 866 of bone puncture needle 840 is positioned at least partially within the socket 2506 which has been formed in the bone by the bone punch 100.

Reference is now made to FIG. 11F, which shows further insertion of hook portion 920 of curved shaft assembly 150 of the arthroscopic surgical device 160 through incision 2502. It is seen that tapered tip 866 of bone puncture needle 840 extends forwardly of forward edge 926 of hook portion 920. It is also seen that tapered tip 866 lies opposite socket 2506.

Reference is now made to FIG. 11G, which shows still further insertion of hook portion 920 of curved shaft assembly 150 of the arthroscopic surgical device 160 through incision 2502, downward shifting and clockwise rotation of the hook portion 920 relative to socket 2506, such as tapered tip 866 of bone puncture needle 840 lies at least partially within socket 2506 and forward opening 964 of curved shaft assembly 150 lies against a surface of the bone.

Reference is now made to FIG. 11H, which shows hook portion 920 of curved shaft assembly 150 of the arthroscopic surgical device 160 in the same orientation relative to the bone as shown in FIG. 11G and attachment of surgical drill 2300 and quick connect element 120 to drill bit assembly 130.

Reference is now made to FIG. 11I, which shows hook portion 920 of curved shaft assembly 150 of the arthroscopic surgical device 160 in the fifth operative orientation shown in FIG. 10N in the same orientation relative to the bone as shown in FIGS. 11G and 11H. Use of surgical drill 2300 to rotate and advance sharpened helical drill tip of elongate shaft portion 400 of drill bit assembly 130 through the hollow elongate tube 220 causes the sharpened helical drill bit 402 to exit front edge 224 of hollow elongate tube 220 and create a bore 2508 in the bone. Bore 2508 has a wider diameter portion 2510 close to the outer bone surface and a narrower diameter portion 2512 inset deeper into the bone, as shown in FIG. 11I.

Reference is now made to FIG. 11J, which shows the arthroscopic surgical device 160 now in the sixth operative orientation as shown in FIG. 10O in the same orientation relative to the bone as shown in FIGS. 11G and 11H. FIG. 11J shows surgical drill 2300, attached to quick connect element 120, withdrawn from drill bit assembly 130 which is still fully engaged in work channel assembly 110.

Reference is now made to FIG. 11K, which shows the arthroscopic surgical device 160 now in the seventh operative orientation as shown in FIG. 10P in the same orientation relative to the bone as shown in FIGS. 11G and 11H. As seen in FIG. 11K, drill bit assembly 130 has been withdrawn from bore 2508, particularly the smaller diameter portion 2512 of the bore 2508, and completely disengaged from work channel assembly 110.

Reference is now made to FIG. 11L, which shows the arthroscopic surgical device 160 now in the eighth operative orientation as shown in FIG. 10Q in the same orientation relative to the bone as shown in FIGS. 11G and 11H. In this eighth operative orientation, the snare wire cartridge assembly 140 has been deployed and is fully engaged within the work channel assembly 110. Snare wire cartridge assembly 140 is seen to extend through hollow elongate, tube 220 of work channel assembly 110 and protrude from front edge 224 of hollow elongate tube 220 into bore 2508 and particularly to extend into the smaller diameter portion 2512 of the bore 2508. Thereafter, the arthroscopic surgical device 160 is caused to assume the ninth operative orientation shown in FIG. 10R, while it is oriented as shown in FIG. 11L.

Figure 11M:
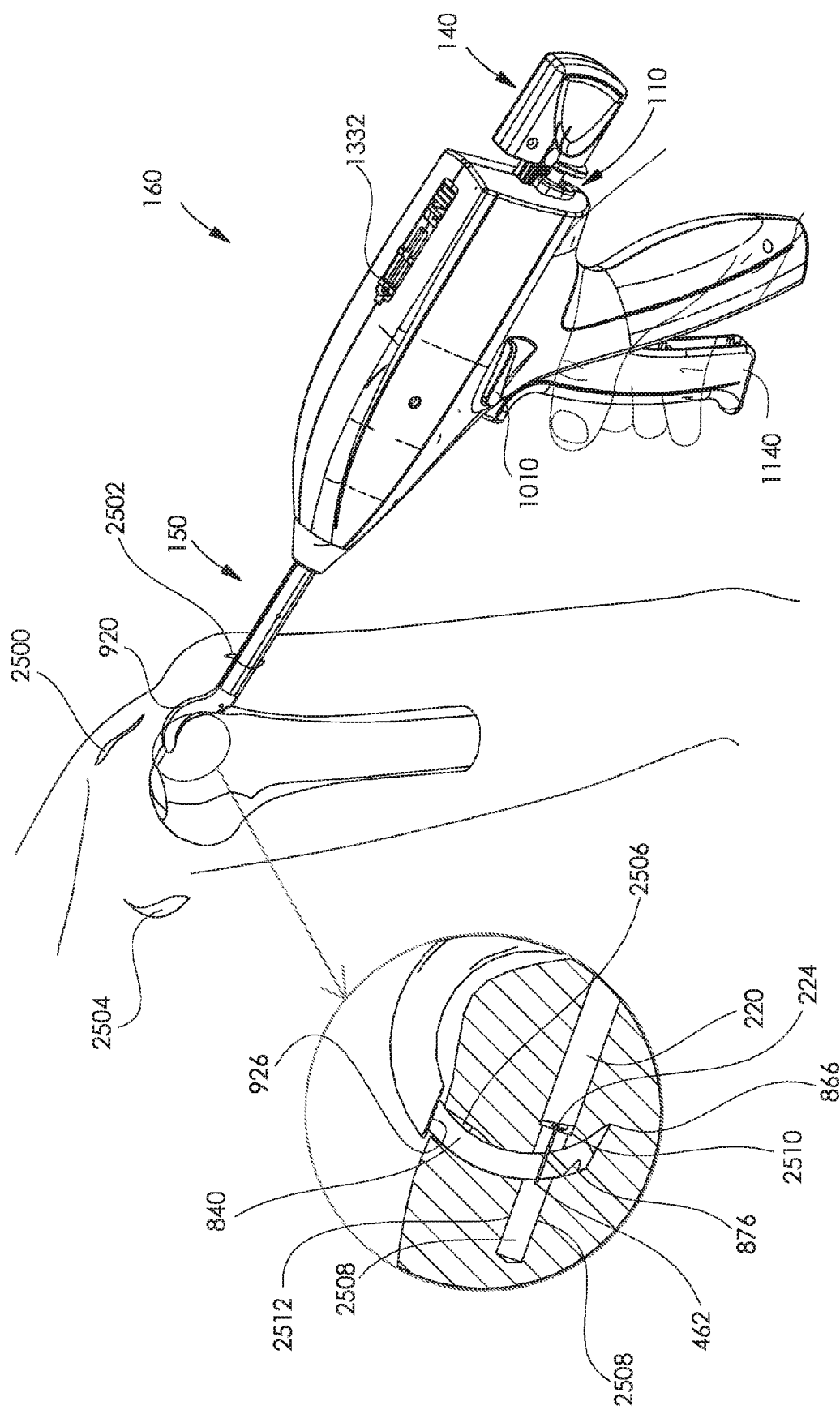
Figure 1N:
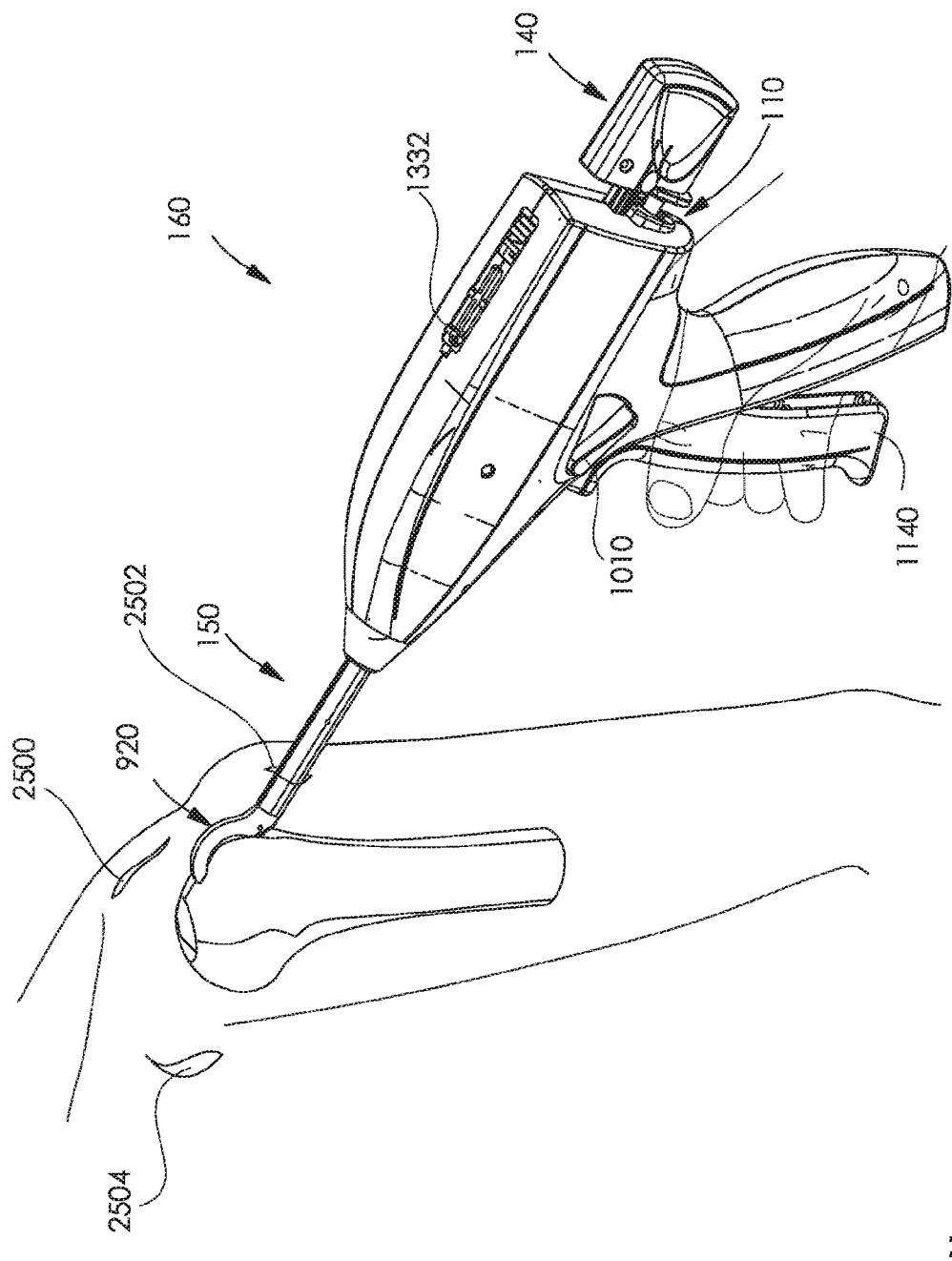
Figure 110:
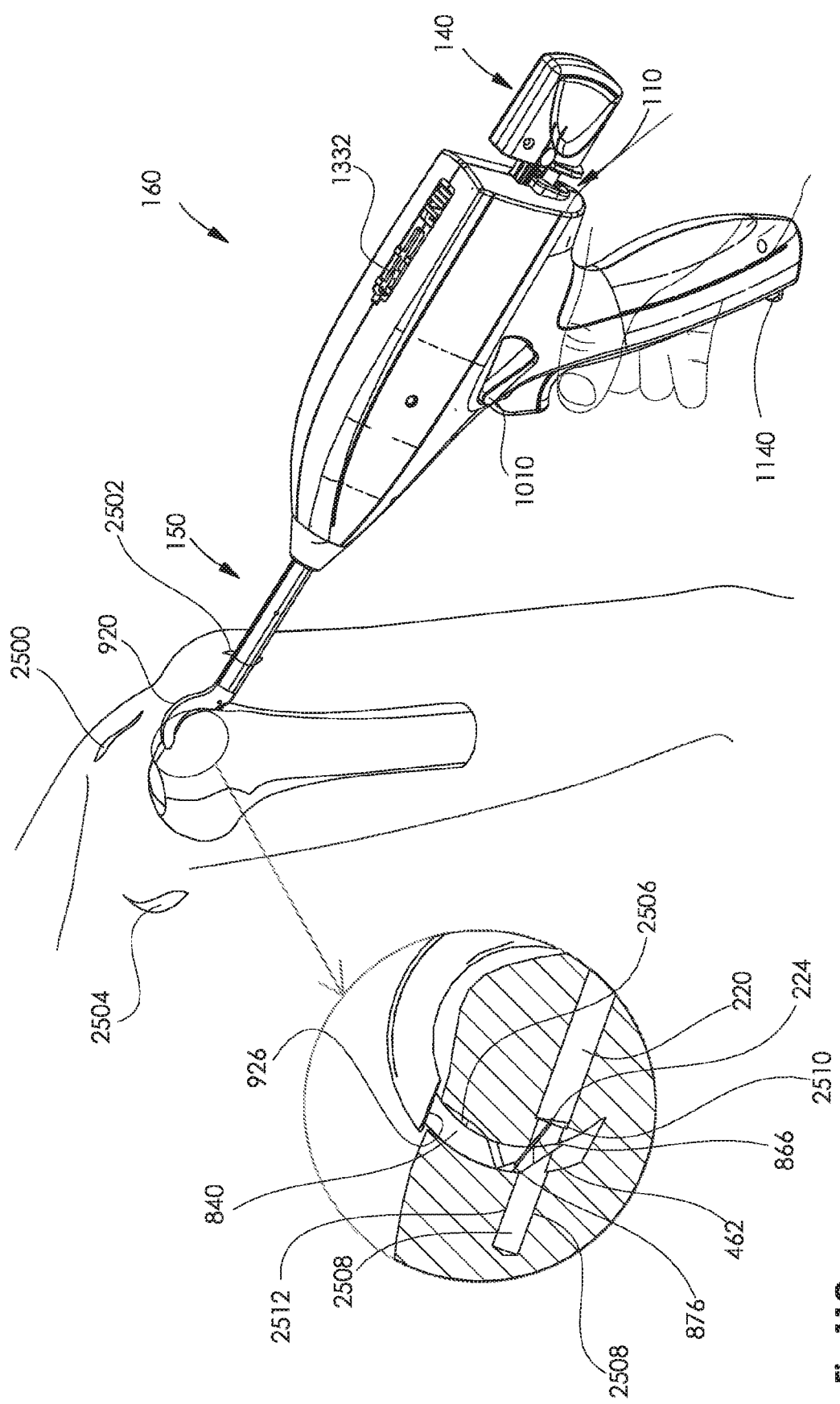

Reference is now made to FIG. 11M, which shows the arthroscopic surgical device 160 now in the tenth operative orientation as shown in FIG. 10S in the same orientation relative to the bone as shown in FIGS. 11G and 11H but with the tapered tip 866 of bone puncture needle 840 having further breeched the bone socket 2506 and extended into, and passing through, both sides of the smaller diameter portion 2512 of the bore 2508. It is seen that the tapered tip 866 of the bone puncture needle 840 also passes through the pre-formed loop 462 of the snare wire 461. Once the bone puncture needle 840 is fully extended, the snare wire assembly 140 is released and becomes disengaged from the cartridge assembly retaining element 1070, while the snare wire loop 462 is pulled taut against the bone puncture needle 840 as seen in FIG. 11M. It is additionally seen in FIG. 11M that forwardly and radially inwardly-inclined notch 876 has passed through snare wire loop 462.

Reference is now made to FIG. 11N, which shows the arthroscopic surgical device 160 now in the eleventh operative orientation as shown in FIGS. 10T 10U, in the same orientation relative to the bone as shown in FIGS. 11G and 11H. It is seen that the driving direction selector lever 1010 has been pressed downward in a clockwise direction.

Reference is now made to FIG. 11O, which shows the arthroscopic surgical device 160 now in the twelfth operative orientation as shown in FIGS. 10V, 10W & 10X, in the same orientation relative to the bone as shown in FIGS. 11G and 11H. In this operative orientation, as seen in FIG. 11O, forwardly and radially inwardly-inclined notch 876 of the bone puncture needle 840 has been partially withdrawn, in a clockwise direction, into forward edge 926 of the hook portion 920 of the curved shaft assembly 150 and, as a result, through snare wire loop 462 until snare wire loop 462 is engaged by the forwardly and radially inwardly-inclined notch 876 of the bone puncture needle 840.

Figure 11P:
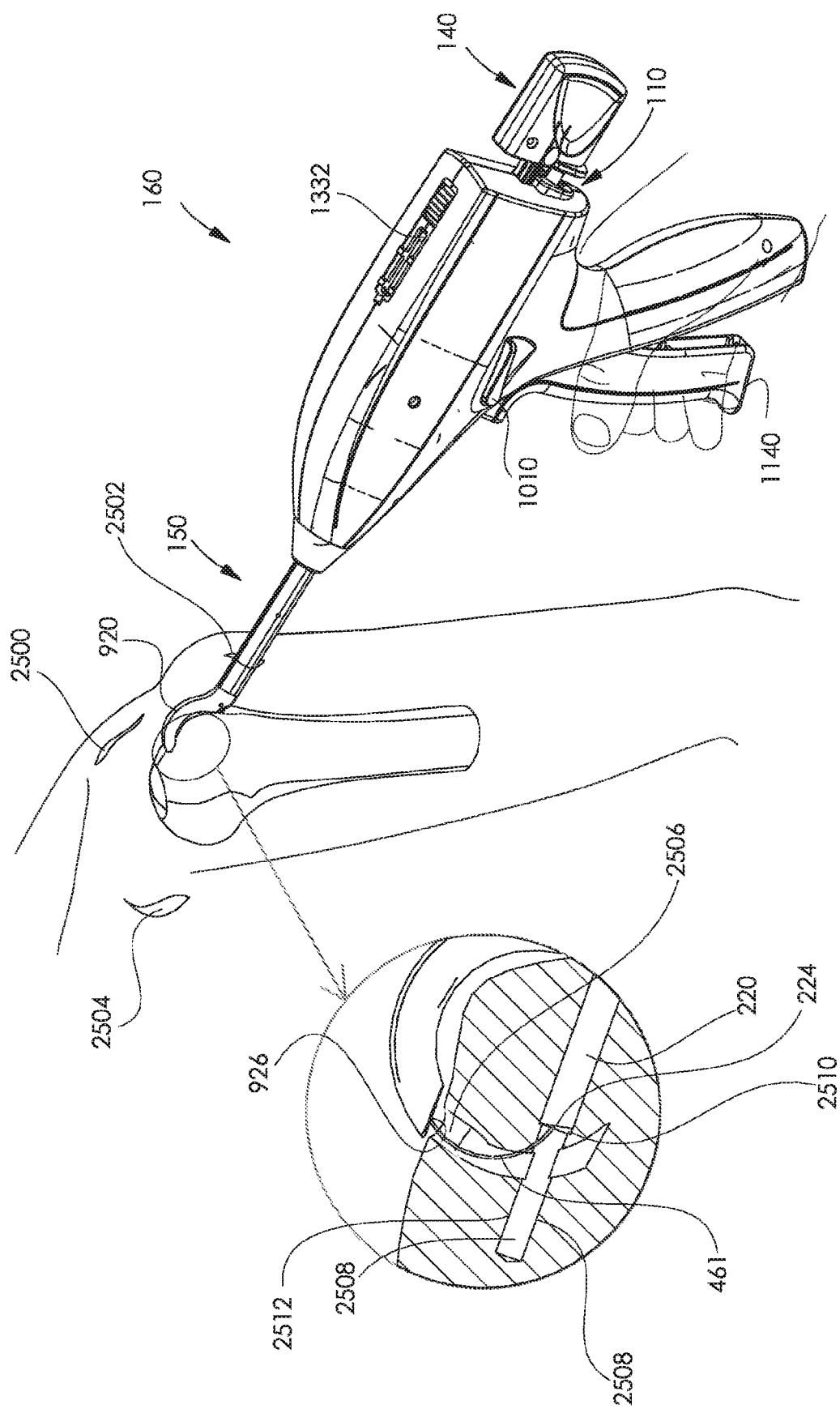

Reference is now made to FIG. 11P, which shows the arthroscopic surgical device 160 now in the thirteenth operative orientation as shown in FIGS. 10Y, 10Z & 10AA, in the same orientation relative to the bone as shown in FIGS. 11G and 11H. In this operative orientation, as seen in FIG. 11P, the bone puncture needle 840 has been fully withdrawn, in a clockwise direction, into the hook portion 920 of the curved shaft assembly 150 and, as a result, the snare wire 461 has been pulled into the hook portion 920 due to snare wire loop 462 being engaged by the forwardly and radially inwardly-inclined notch 876 of the bone puncture needle 840, as seen in FIG. 11O.

Figure 11Q:
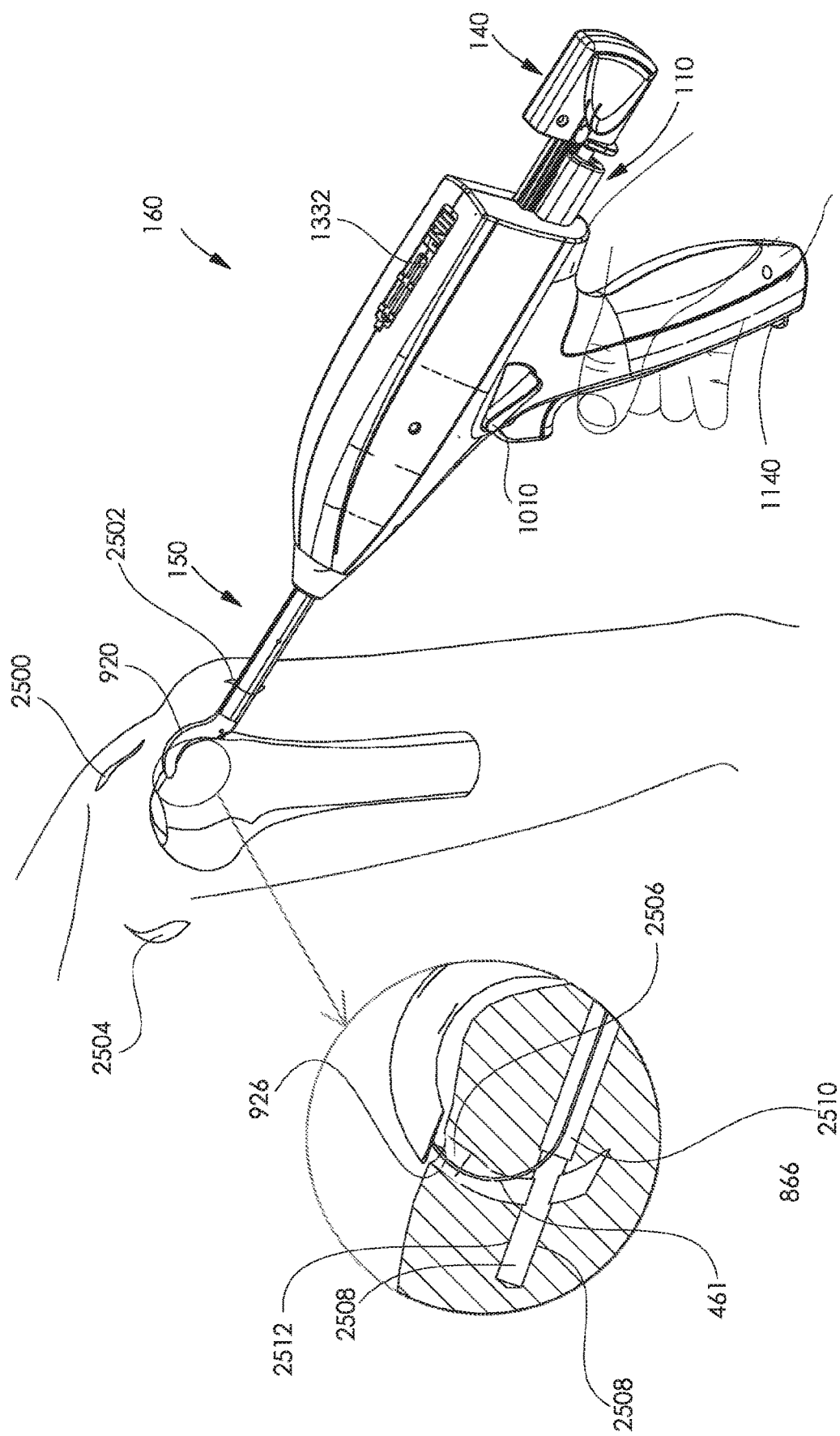

Reference is now made to FIG. 11Q, which shows the arthroscopic surgical device 160 now in the fourteenth operative orientation as shown in FIGS. 10AB, 10AC & 10AD, in the same orientation relative to the bone as shown in FIGS. 11G and 11H. In this operative orientation, as seen in FIG. 11Q, the snare wire assembly 140 and the work channel assembly 110 have been partially withdrawn rearwardly front the arthroscopic surgical device 160, but not disengaged.

Figure 11R:
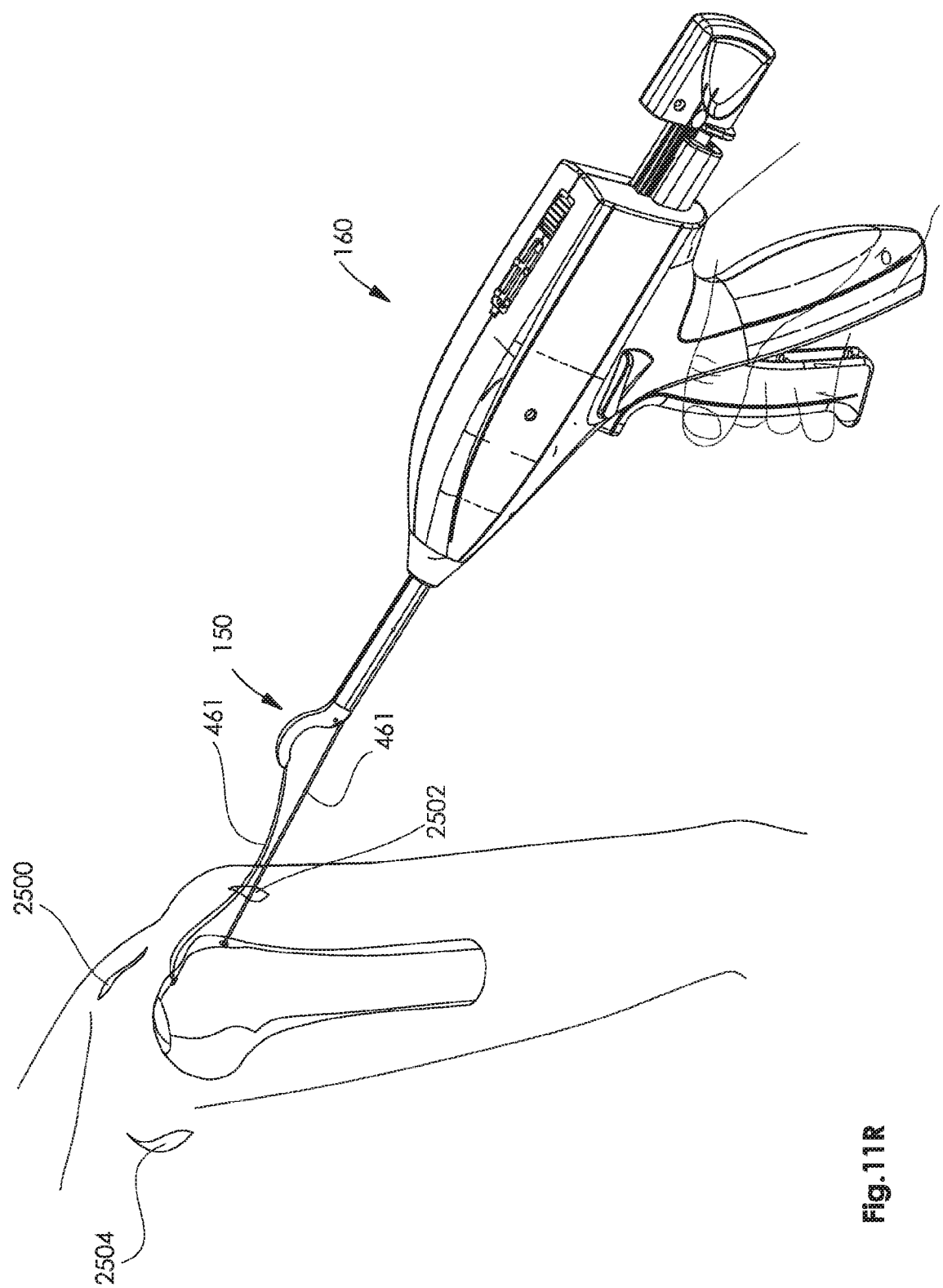

Reference is now made to FIG. 11R, which shows the arthroscopic surgical device 160 now in the fifteenth operative orientation as shown in FIGS. 10AE-10AG. In this operative orientation, as seen in FIG. 11R, the work channel assembly 110 and the snare wire cartridge assembly 140 have been fully withdrawn from the bone. The work channel assembly 110 and the snare wire cartridge assembly 140 have been pulled back into the curved shaft assembly 150, pulling the snare wire 461 with them. The snare wire 461, as shown in FIG. 11R, is the only portion of the arthroscopic surgical device 160 remaining in the bone, extending outside incision 2502.

Figure 11S:
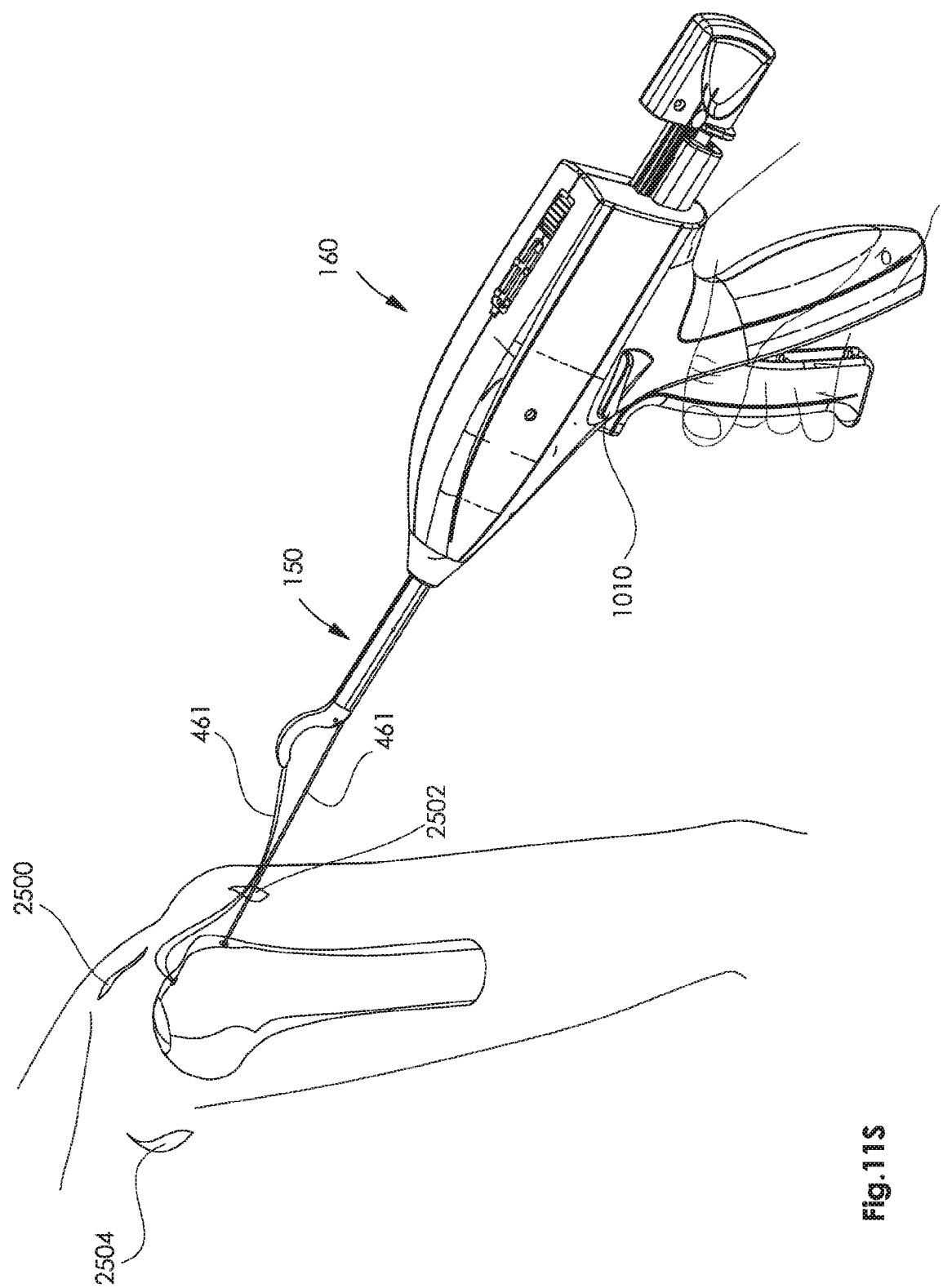

Reference is now made to FIG. 11S, which shows the arthroscopic surgical device 160 now in the sixteenth operative orientation as shown in FIGS. 10AH-10AK. In this operative orientation, the driving direction selector lever 1010 has been rotated counterclockwise into the forward position.

Figure 11T:
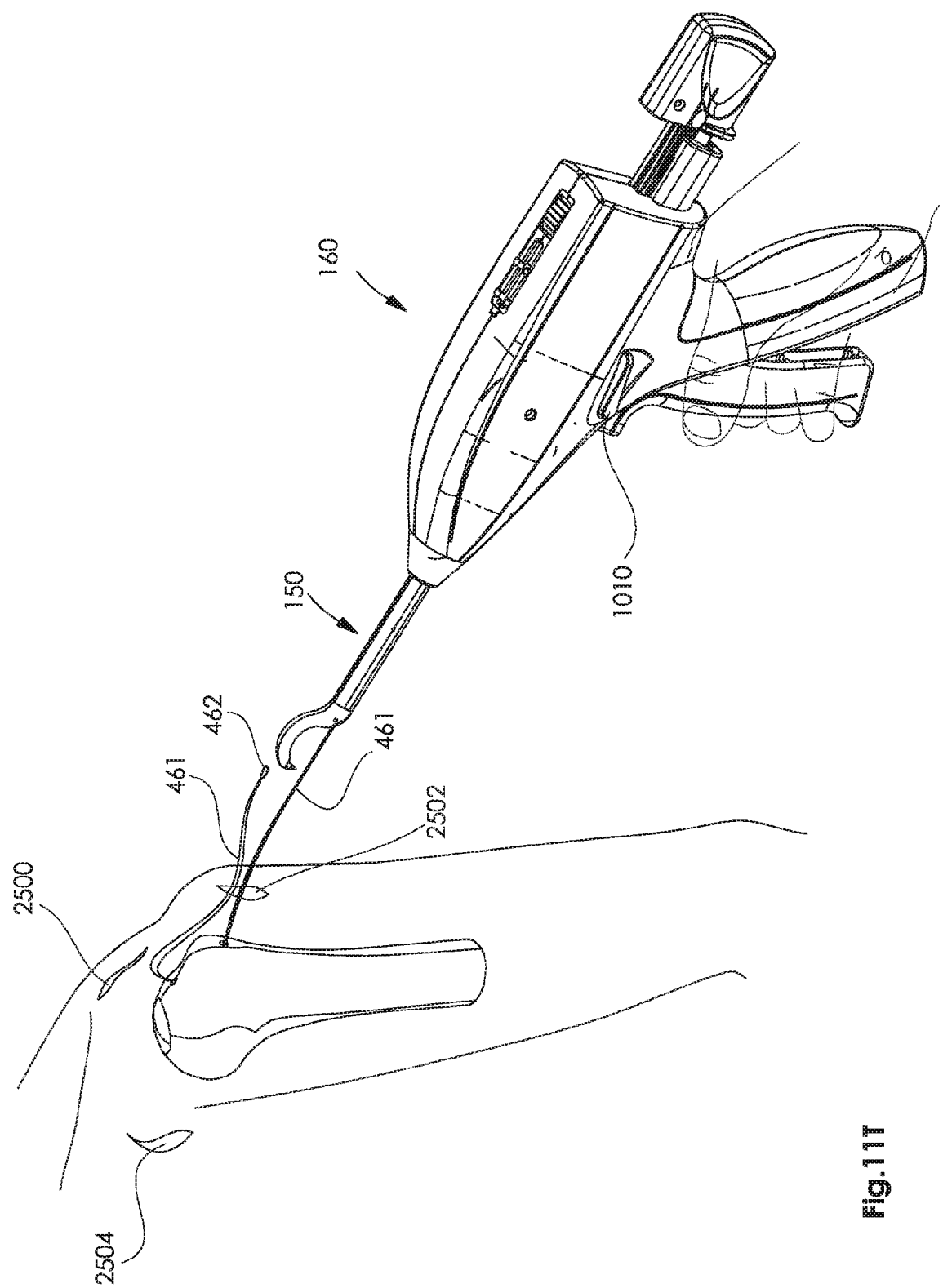

Reference is now made to FIG. 11T, which shows the arthroscopic surgical device 160 now in the seventeenth operative orientation as shown in FIGS. 10AL-10AN. It is seen that tapered tip 866 of bone puncture needle 840 extends forwardly of forward edge 926 of hook portion 920, releasing the pre-formed loop 462 of the snare wire 461 from the forwardly and radially inwardly-inclined notch 876 of the bone puncture needle 840.

Reference is now made to FIGS. 12A-31B, which describe an alternative embodiment of the present invention wherein the shaft assembly and the retaining cap element are removable from the remainder of the arthroscopic surgical device, which is normally reusable.

Figure 12A:
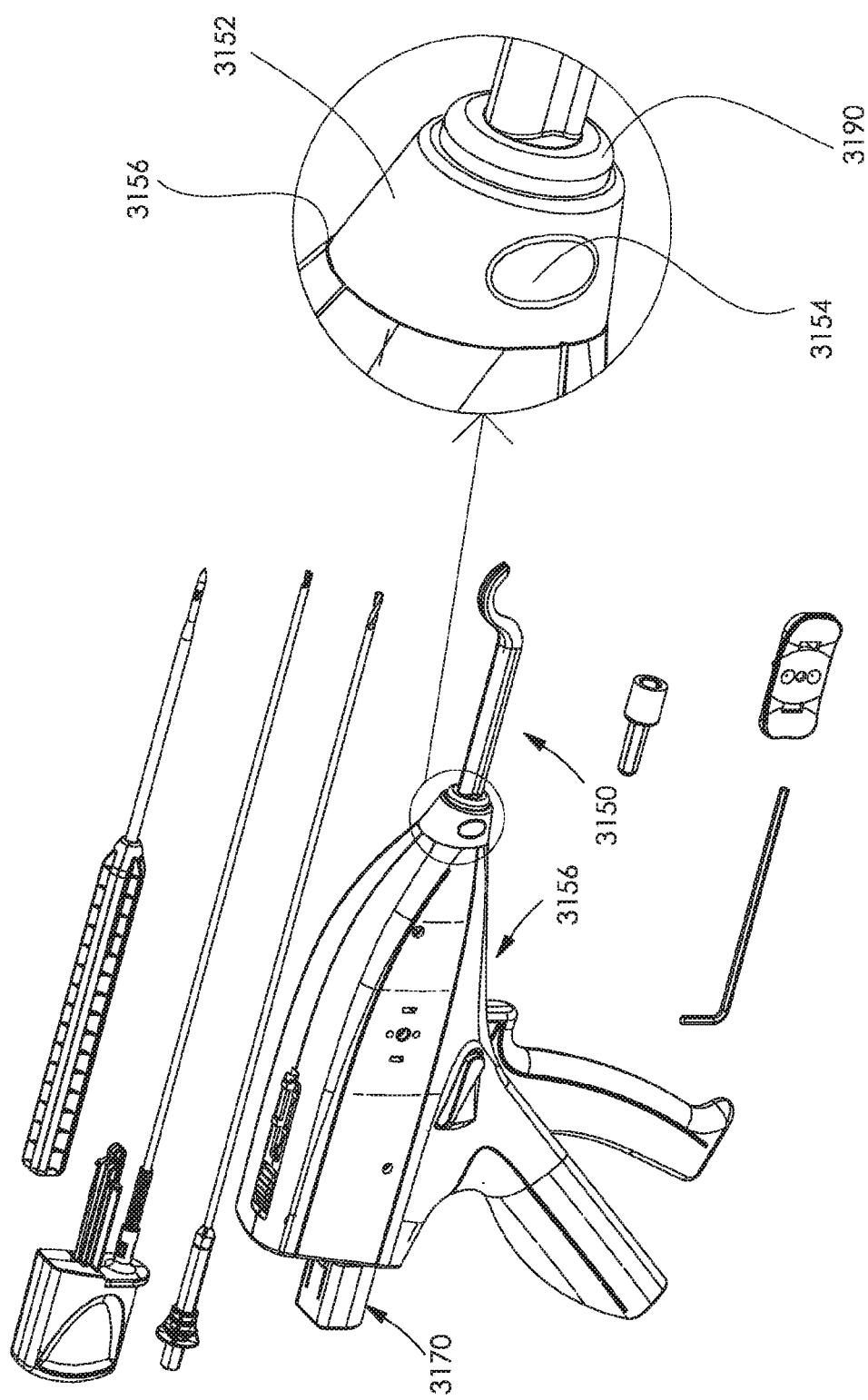
FIGS. 12A & 12B are simplified pictorial illustrations of an arthroscopic surgical assembly constructed and operative in accordance with another preferred embodiment of the present invention, showing opposite views and corresponding to FIGS. 1A & 1B.
Figure 12B:
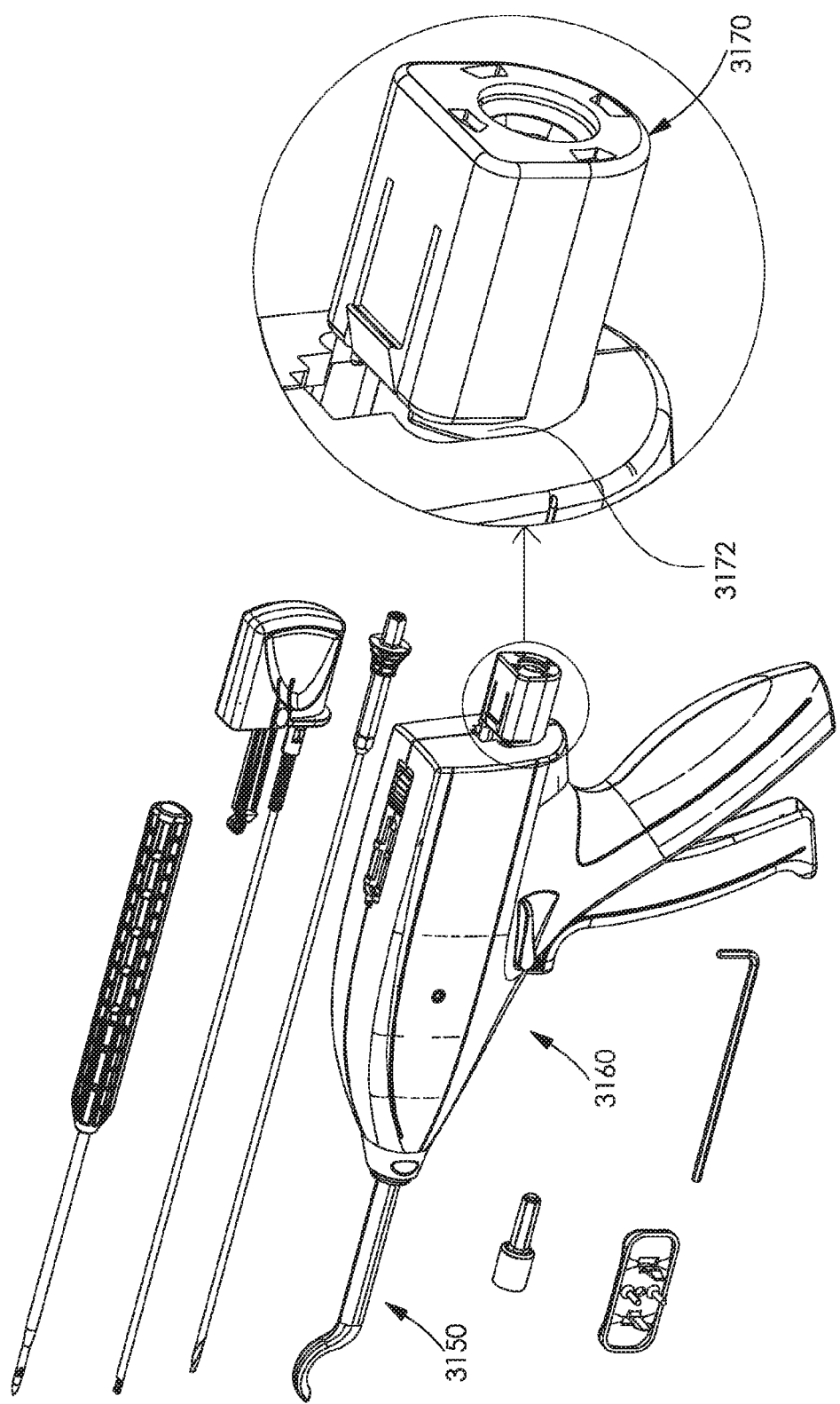
Figure 13A:
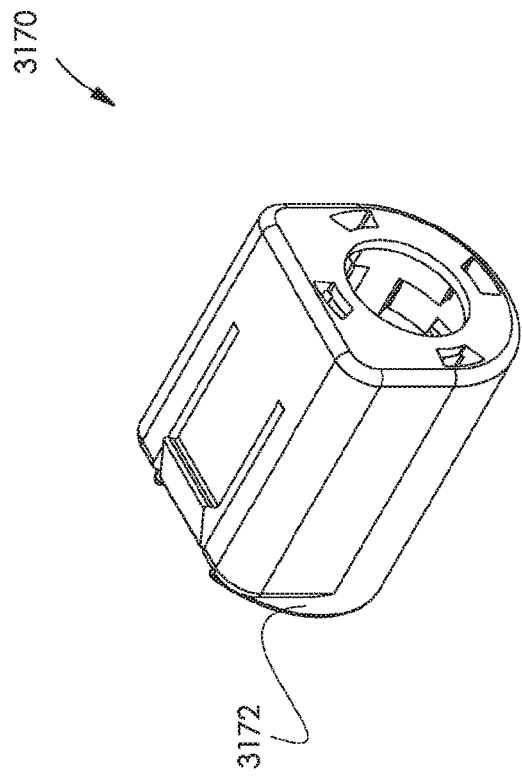
FIGS. 13A, 13B, 13C and 13D are respectively a forwardly-facing pictorial illustration; a top rearwardly-facing pictorial illustration, a bottom rearwardly-facing pictorial illustration, a rearwardly-facing front cud view illustration of a retaining cap element, forming part of the work channel assembly of FIGS. 3A & 3B and corresponding to FIGS. 3K, 3L, 3M and 3N.
Figure 13C:
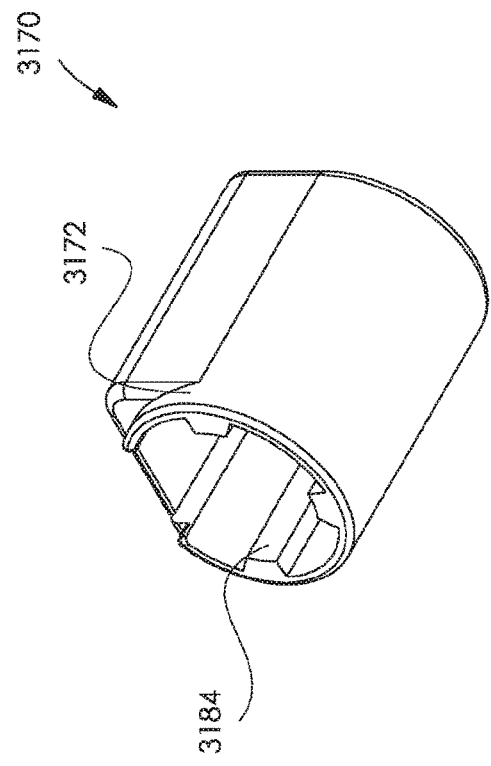
Figure 13B:
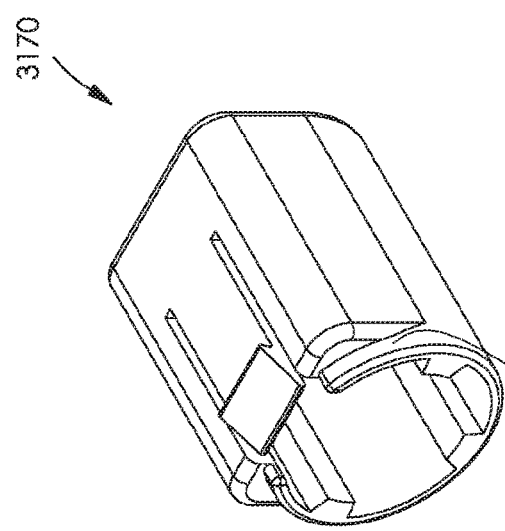
Figure 13D:
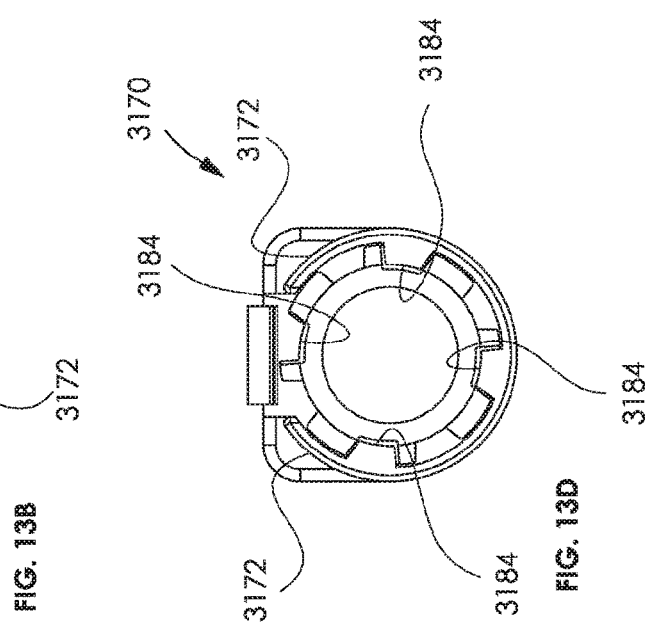

Reference is now made specifically to FIGS. 12A and 12B, which correspond generally to FIGS. 1A and 1B described hereinabove. The apparatus of FIGS. 12A and 12B differs from that shown and described hereinabove with reference to FIGS. 1A & 1B at least in the following respects:

In the embodiment of FIGS. 12A-31B, there is provided a readily detachable curved shaft assembly 3150, which corresponds generally to curved shaft assembly 150 (FIGS. 1A & 1B) and is provided with a generally conical mounting portion 3152. As see in FIGS. 12A & 12B, generally conical mounting portion 3152 is formed with a pair of oppositely located finger engagement recesses 3154 and is detachably mounted onto a front end portion 3156 of an arthroscopic surgical device 3160, which corresponds to arthroscopic surgical device 160 (FIGS. 1A & 1B)

In the embodiment of FIGS. 12A-31B, there is provided a readily detachable retaining cap element 3170, which corresponds to retaining cap element 120 (FIGS. 1A & 1B). The detachable retaining cap element 3170 includes a cylindrical surface 3172 which rotates relative to the arthroscopic surgical device 3160.

Reference is now made to FIGS. 13A-13D, which correspond generally to FIGS. 3K-3P described hereinabove. The detachable retaining cap element 3170 of FIGS. 13A-13D differs from that shown and described hereinabove with reference to FIGS. 3K-3P at least in that it includes cylindrical surface 3172.

Figure 14:
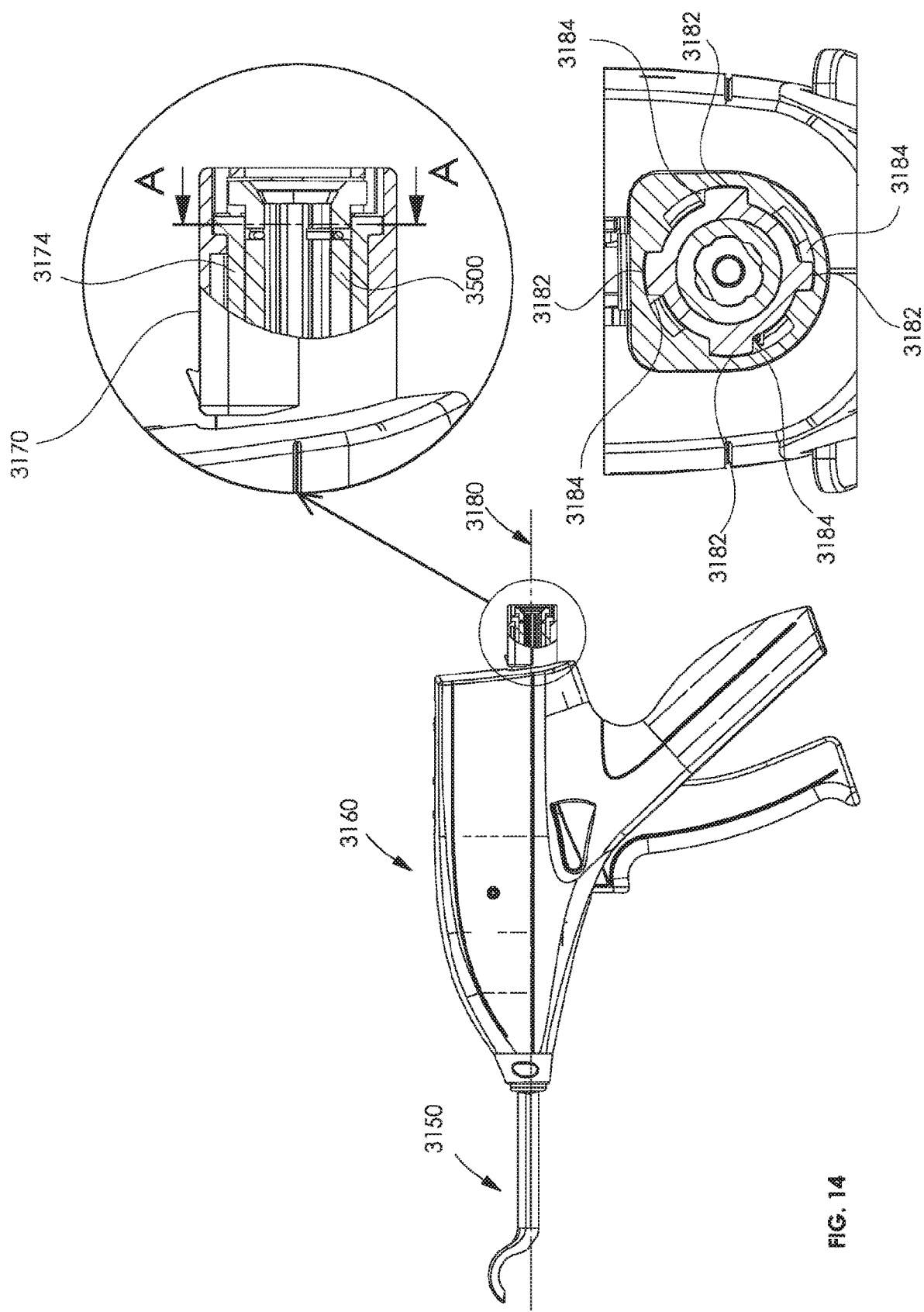
FIG. 14 is a simplified illustration of engagement of the retaining cap element of FIGS. 13A-13D with a rack-defining intermediate element shown in FIGS. 3G-3J.

Reference is now made to FIG. 14, which shows a bayonet-type detachable locking engagement between detachable retaining cap element 3170 and a rack-defining intermediate element 3174, which is identical to rack-defining intermediate element 260 described above. The bayonet-type detachable locking engagement is produced by rotation of the detachable retaining cap element 3170 about an axis 3180 relative to rack-defining intermediate element 3174, such that azimuthally distributed radially outwardly extending protrusions 3182 of rack-defining intermediate element 3174 interlock with azimuthally distributed radially inwardly extending protrusions 3184 of the detachable retaining cap element 3170.

Figure 15A:
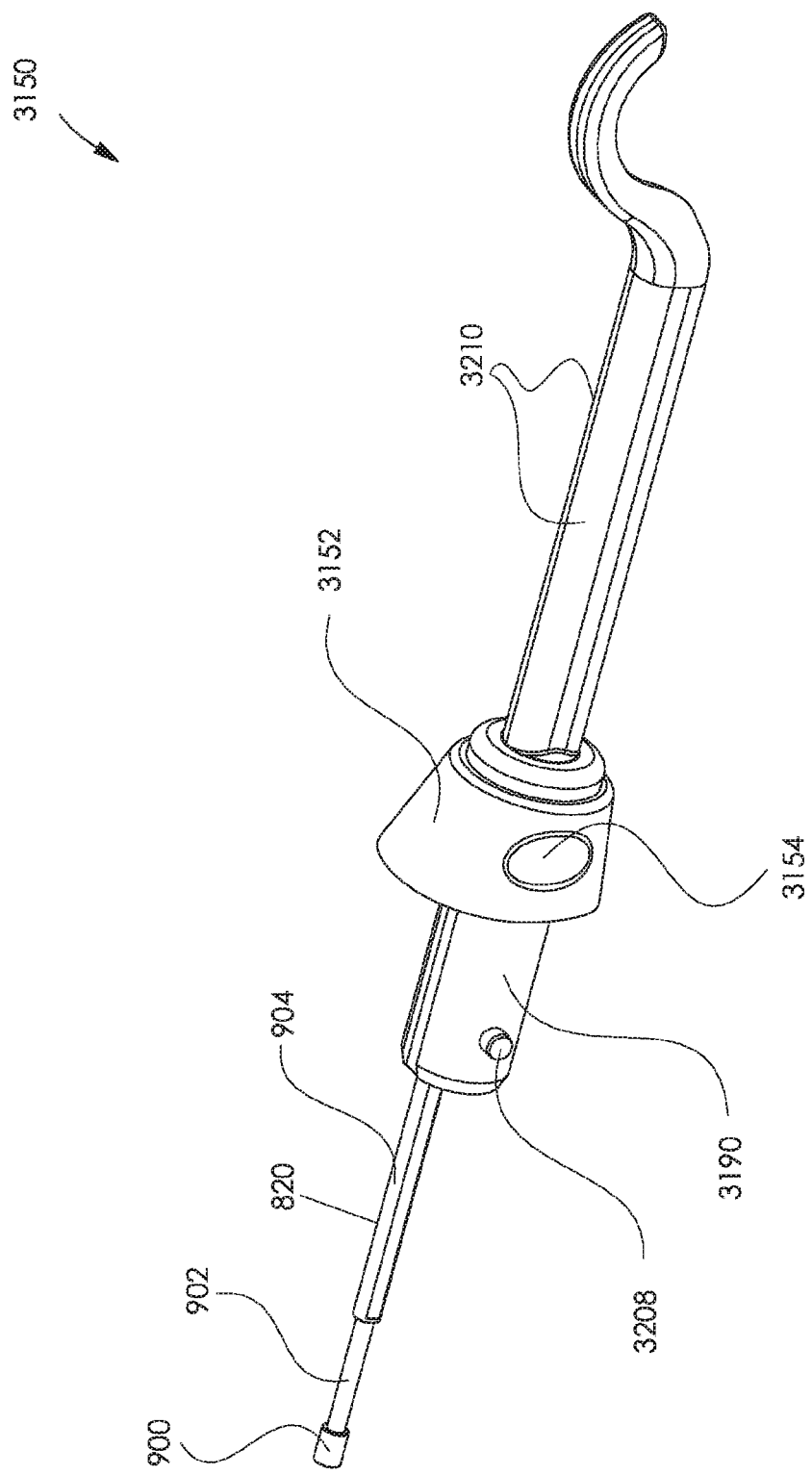
FIGS. 15A & 15B are simplified assembled view illustrations of a curved shaft assembly forming part of the arthroscopic surgical assembly of FIGS. 1A & 1B showing opposite views and corresponding to FIGS. 7A & 7B.
Figure 15B:
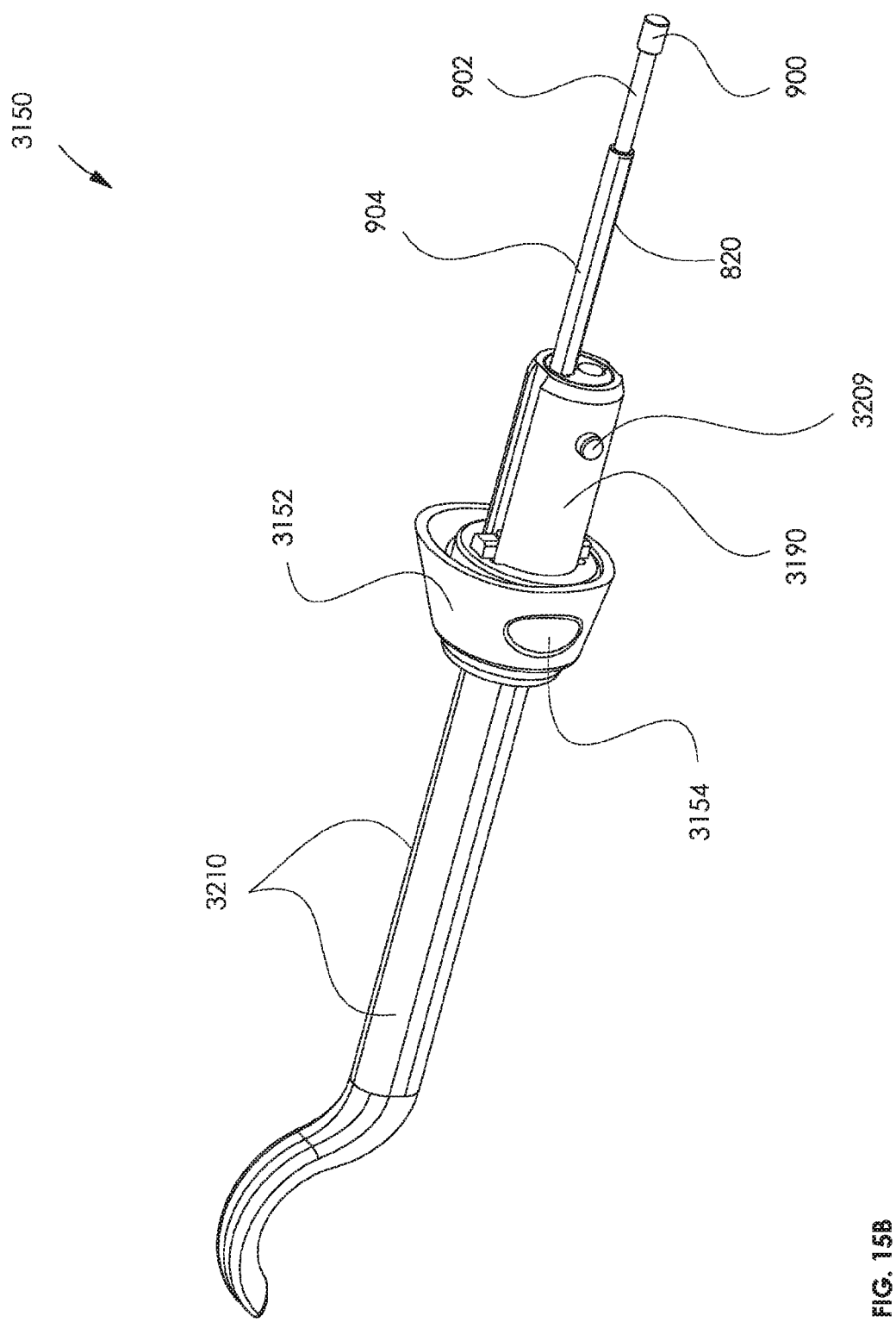
Figure 15C:
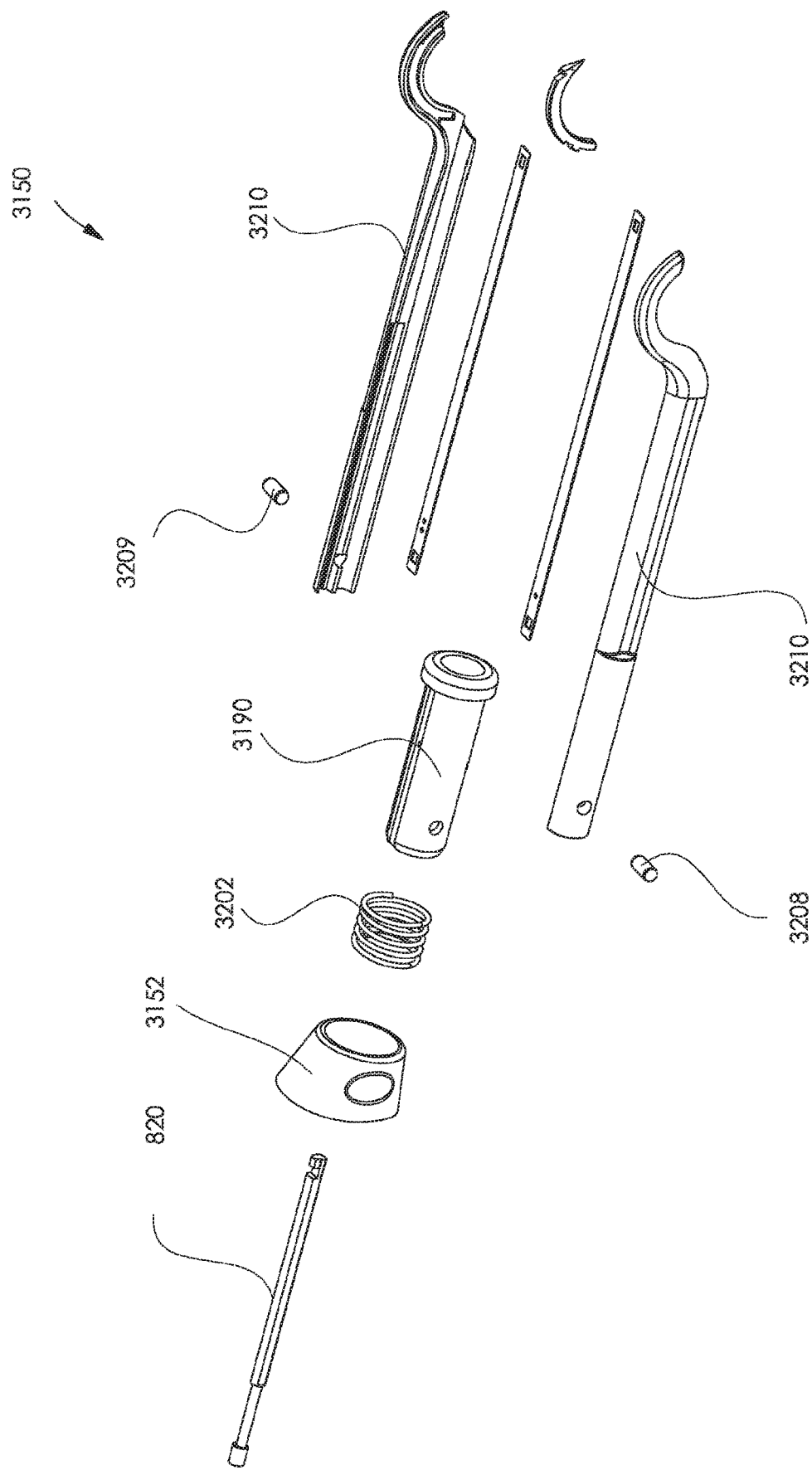
FIGS. 15C & 15D are simplified exploded view illustrations of the curved shaft assembly of FIGS. 15A & 15B, forming part of the arthroscopic surgical assembly of FIGS. 1A & 1B showing opposite views and corresponding to FIGS. 7C & 7D.
Figure 15D:
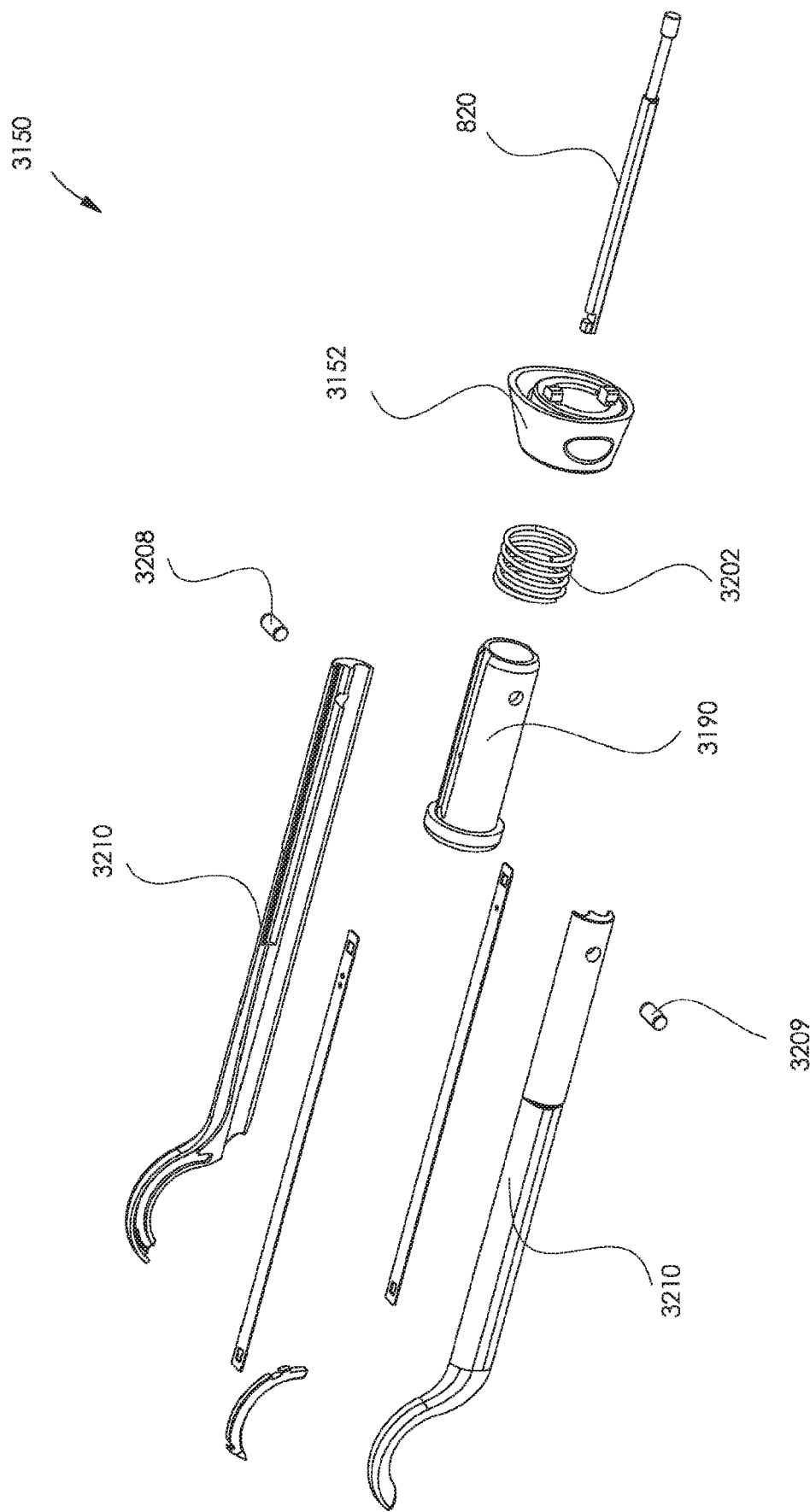

Reference is now made to FIGS. 15A-15F, 18A-18B and 19A-19B, which correspond generally to FIGS. 7A-7P described hereinabove. The detachable curved shaft assembly 3150, preferably includes a push rod 820 similarly to elongate push rod 820 shown in FIGS. 7A-7P, which includes a cylindrical rear portion 900, an intermediate rear portion 902 and a main portion 901. The readily detachable curved shaft assembly 3150 of FIGS. 15A-15F differs from that shown and described hereinabove with reference to FIGS. 7A-7P in at least the following respects:

As seen clearly in FIG. 15C, the readily detachable curved shaft assembly 3150 includes a generally hollow cylindrical element 3190, which is shown in FIGS. 16A and 16B. Generally hollow cylindrical element 3190 is formed with an elongate cylindrical bore 3192, an outer cylindrical surface 3193 and a pair of oppositely directed outwardly facing elongate slots 3194, formed in outer cylindrical surface 3193, as well as a pair of apertures 3196. Generally hollow cylindrical element 3190 has a first tapered outer facing edge 3198 at a first end thereof and at a second, opposite end thereof has a flange 3200 having an outer cylindrical surface 3201.

A compression spring 3202 is seated between generally conical mounting portion 3152 and flange 3200 of generally hollow cylindrical element 3190. The generally conical mounting portion 3152 is retained against disengagement from generally hollow cylindrical element 3190 by provision of protrusions 3204 formed on an outer surface of generally hollow cylindrical element 3190 at slot 3194 and corresponding protrusions 3206 at the interior of generally conical mounting portion 3152 as described hereinbelow with reference to FIGS. 17A-17D.

A pair of guiding and positioning pins 3208 and 3209 serve to guide the detachable curved shaft assembly 3150 during insertion thereof into and detachment thereof from the arthroscopic surgical device 3160. Preferably pins 3208 and 3209 are laser welded to respective curved shaft assembly elements 3210. It is seen particularly in an enlargement in FIG. 19B, that the radially outward extent of pins 3208 and 3209 is different. This is to obviate ambiguity during insertion of the detachable curved shaft assembly 3150 into the arthroscopic surgical device 3160.

Figure 15E:
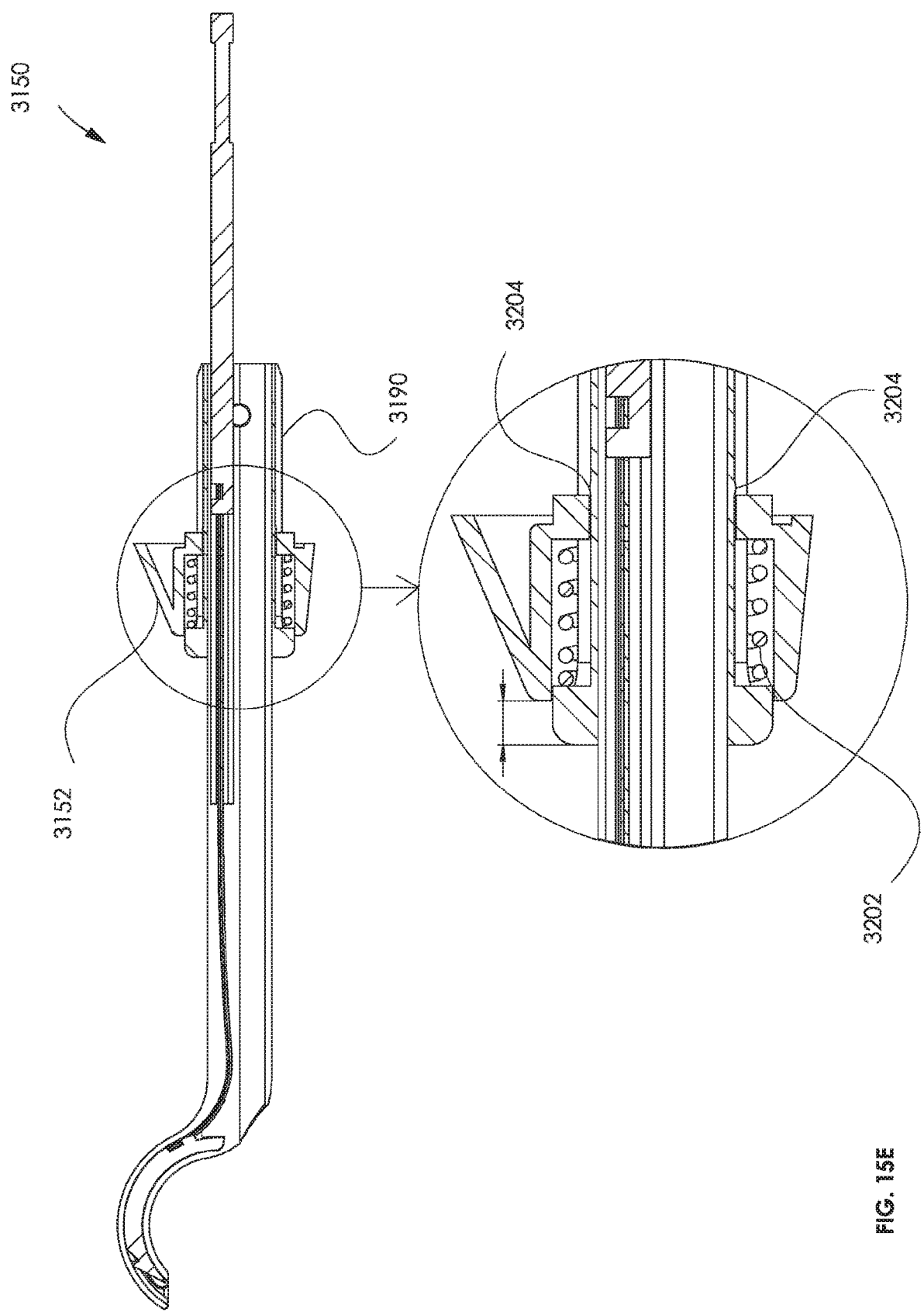
FIGS. 15E & 15F are simplified sectional illustrations of the curved shaft assembly of FIGS. 15A-15D, forming part of the arthroscopic surgical assembly of FIGS. 1A & 1B showing opposite views and corresponding to FIG. 7P.
Figure 15F:
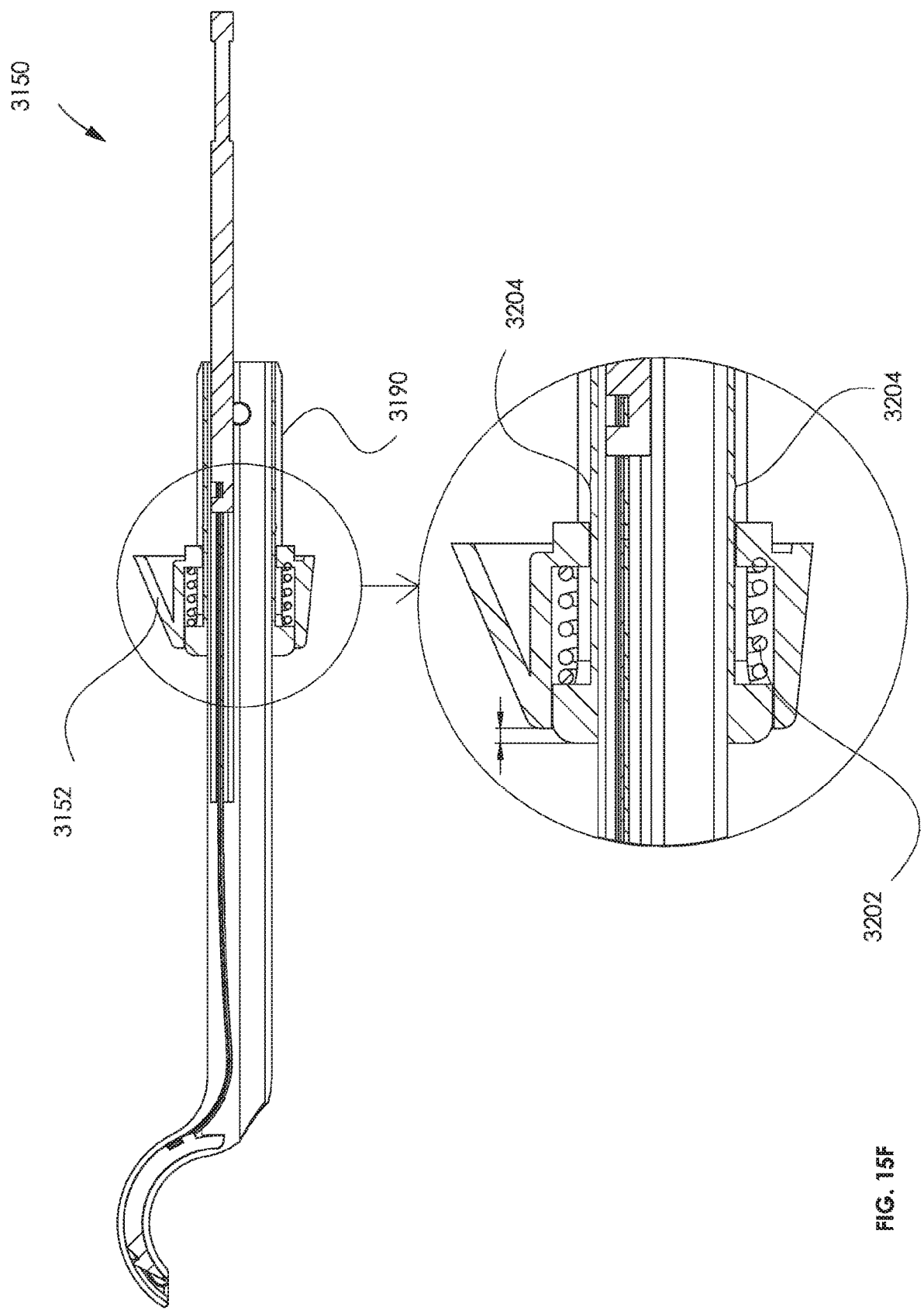
Figure 17A:
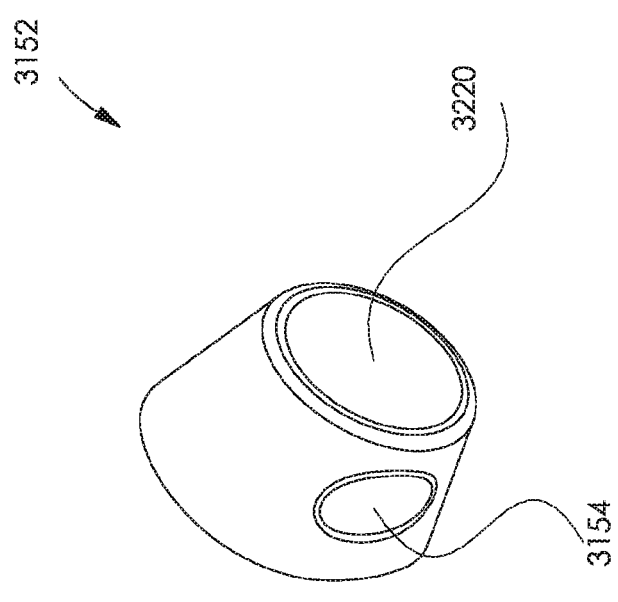
FIGS. 17A, 17B, 17C and 17D are pictorial illustrations taken in four different directions of a retaining cone, forming part of the curved shaft assembly of FIGS. 15A-15D and corresponding generally to FIGS. 8BN and 8BO.
Figure 17B:
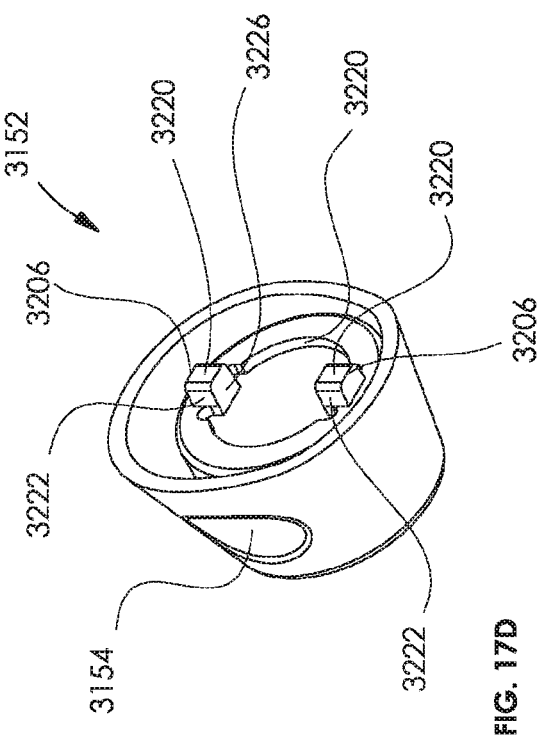
Figure 17C:
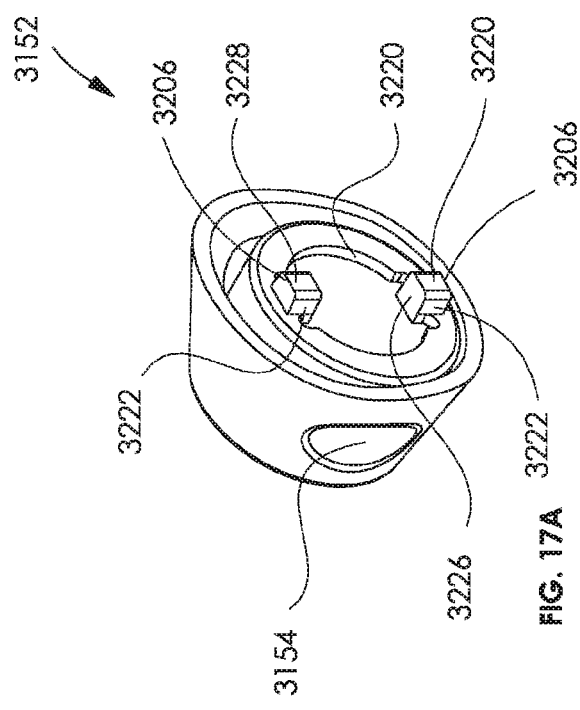
Figure 17D:
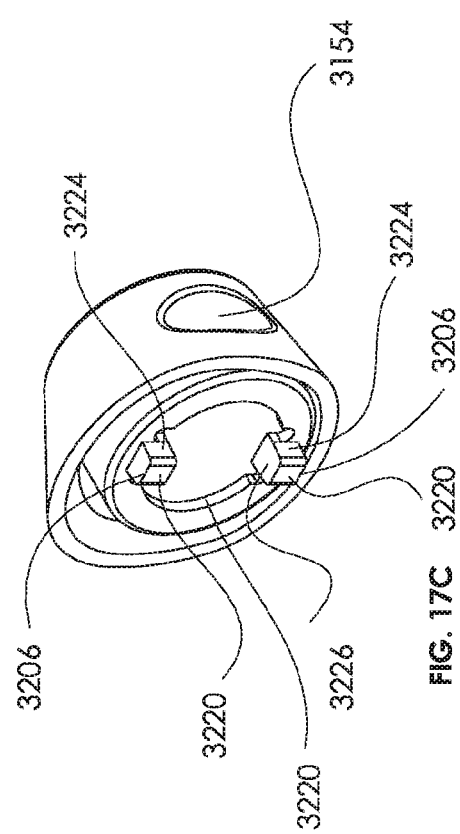
Figures 19A, 19B:
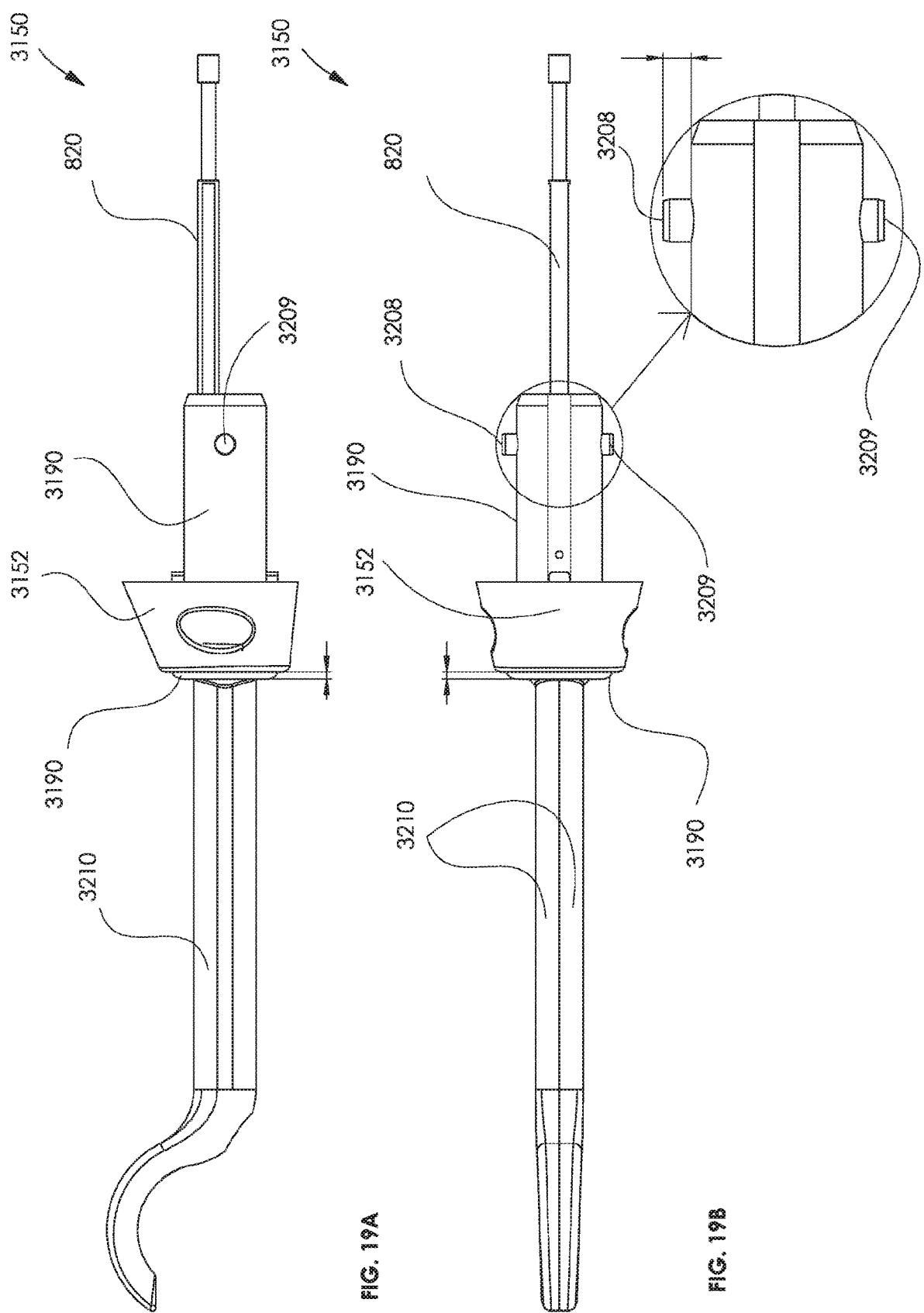
FIGS. 19A and 19B are simplified side view illustrations of the curved shaft assembly of FIGS. 15A-15F in a second operative orientation, showing opposite views.

As seen by comparing FIGS. 15E and 15F, compression spring 3202 permits forward relative axial displacement of generally conical mounting portion 3152 relative to generally hollow cylindrical element 3190 and thus relative to the readily detachable curved shaft assembly 3150, thereby permitting detachment of readily detachable curved shaft assembly 3150 from arthroscopic surgical device 3160.

Reference is now made to FIGS. 17A-17D, which correspond generally to FIGS. 8BN & 8BO described hereinabove. The generally conical mounting portion 3152 of FIGS. 17A-17D differs from that shown and described hereinabove with reference to FIGS. 8BN-8BO in at least the following respects, in addition to those described above:

Generally conical mounting portion 3152 includes a generally cylindrical stepped bore 3220 which is arranged for relative axial displacement relative to generally hollow cylindrical element 3190 and over outer cylindrical surface 3201 of flange 3200 thereof. Generally conical mounting portion 3152 also defines a flange 3220, which defines a spring seat for compression spring 3202. Protrusions 3206 extend rearwardly from flange 3220 and each define axial side surfaces 3222 and 3224 and a radially inwardly facing surface 3226 and a rearwardly-facing surface 3228.

Reference is now made to FIGS. 20A & 20B, which correspond generally to FIGS. 8BP, 8BQ and 8BR and to FIGS. 8BS, 8BT and 8BU respectively, described hereinabove. A first housing portion 3300 shown in FIG. 20A and a second housing portion 3302, shown in FIG. 20B, correspond generally to first housing portion 1002 and second housing portion 1004 of FIGS. 8BP, 8BQ and 8BR and to FIGS. 8BS, 8BT and 8BU, respectively, and differ from that shown and described hereinabove with reference to FIGS. 8BP, 8BQ and 8BR and to FIGS. 8BS, 8BT and 8BU respectively, and differ therefrom in at least the following respects:

First housing portion 3300, shown in FIG. 20A, and second housing portion 3302, shown in FIG. 20B, are provided with respective first and second bayonet-type connection socket portions, 3310 and 3320, respectively, which together constitute a bayonet-type connection socket.

First bayonet-type connection socket portion 3310 defines a generally semicircular cylindrical inner surface 3322 having a forward circumferential flange 3324 having a forward-facing edge 3326 for azimuthal displacement in sliding engagement therewith of one of protrusions 3206 at the interior of generally conical mounting portion 3152. Generally semicircular cylindrical inner surface 3322 is bounded by a pair of axially extending pin guiding edge surfaces 3334 and 3336. Pin guiding edge surface 3334 has a greater radial extent than does pin guiding edge surfaces 3336. Axially extending pin guiding edge surface 3334 is arranged for axial displacement in sliding engagement therewith of pin 3208 and axially extending pin guiding edge surface 3336 is arranged for axial displacement in sliding engagement therewith of pin 3209. An azimuthally directed slot 3338 is formed in semicircular cylindrical inner surface 3322 and communicates with axially extending pin guiding edge surface 3334, thereby permitting pin 3208 to initially move axially along surface 3334 and then move azimuthally in slot 3338 for bayonet-type locking engagement therewith.

Second bayonet-type connection socket portion 3320 defines a generally semicircular cylindrical inner surface 3342 having a forward circumferential flange 3344 having a forward-facing edge 3346 for azimuthal displacement in sliding engagement therewith of the other of protrusions 3206 at the interior of generally conical mounting portion 3152. Generally semicircular cylindrical inner surface 3342 is bounded by a pair of axially extending pin guiding edge surfaces 3354 and 3356. Pin guiding edge surface 3354 has a greater radial extent than does pin guiding edge surfaces 3356. Axially extending pin guiding edge surface 3354 is arranged for axial displacement in sliding engagement therewith of pin 3208 and axially extending pin guiding edge surface 3356 is arranged for axial displacement in sliding engagement therewith of pin 3209. An azimuthally directed slot 3358 is formed in semicircular cylindrical inner surface 3342 and communicates with axially extending pin guiding edge surface 3356, thereby permitting pin 3209 to initially move axially along surface 3356 and then move azimuthally in slot 3358 for bayonet-type locking engagement therewith.

When first housing portion 3300, shown in FIG. 20A, and second housing portion 3302 are joined together, axially extending pin guiding edge surfaces 3334 and 3354 are located in a mutually spaced parallel arrangement defining a first axial pin displacement slot 3360 and axially extending pin guiding edge surfaces 3336 and 3356 are located in a mutually spaced parallel arrangement defining a second axial pin displacement slot 3362. Slot 3360 has a greater radial extent than does slot 3362. Upon insertion of the detachable curved shaft assembly 3150 into operative engagement with the arthroscopic surgical device 3160, pin 3208 can only move axially in slot 3360, since its axial extent is too large to fit into slot 3362.

Preferably, when pin 3208 enters azimuthal slot 3338, simultaneously pin 3209 enters azimuthal slot 3358.

Reference is now made to FIGS. 21A & 21B, which correspond generally to FIGS. 8R, 8S, 8T and 8U, described hereinabove. An auxiliary chassis 3400, shown in FIGS. 21A and 21B, corresponds generally to auxiliary chassis 1110 described hereinabove with reference to FIGS. 8R-8T and differs therefrom, in at least the following respects:

As seen in FIGS. 21A and 21B, the auxiliary chassis 3400 includes an elongate curved retaining socket 3402 which receives and retains intermediate rear portion 902 of elongate push rod 820 of detachable curved shaft assembly 3150.

As also seen in FIGS. 21A and 21B, the auxiliary chassis 3400 also includes a stop protrusion 3404 which limits the rearward travel of elongate push rod 820 relative to auxiliary chassis 3400 by being engaged by a rearward surface of cylindrical rear portion 900 of push rod 820.

Figure 22A:
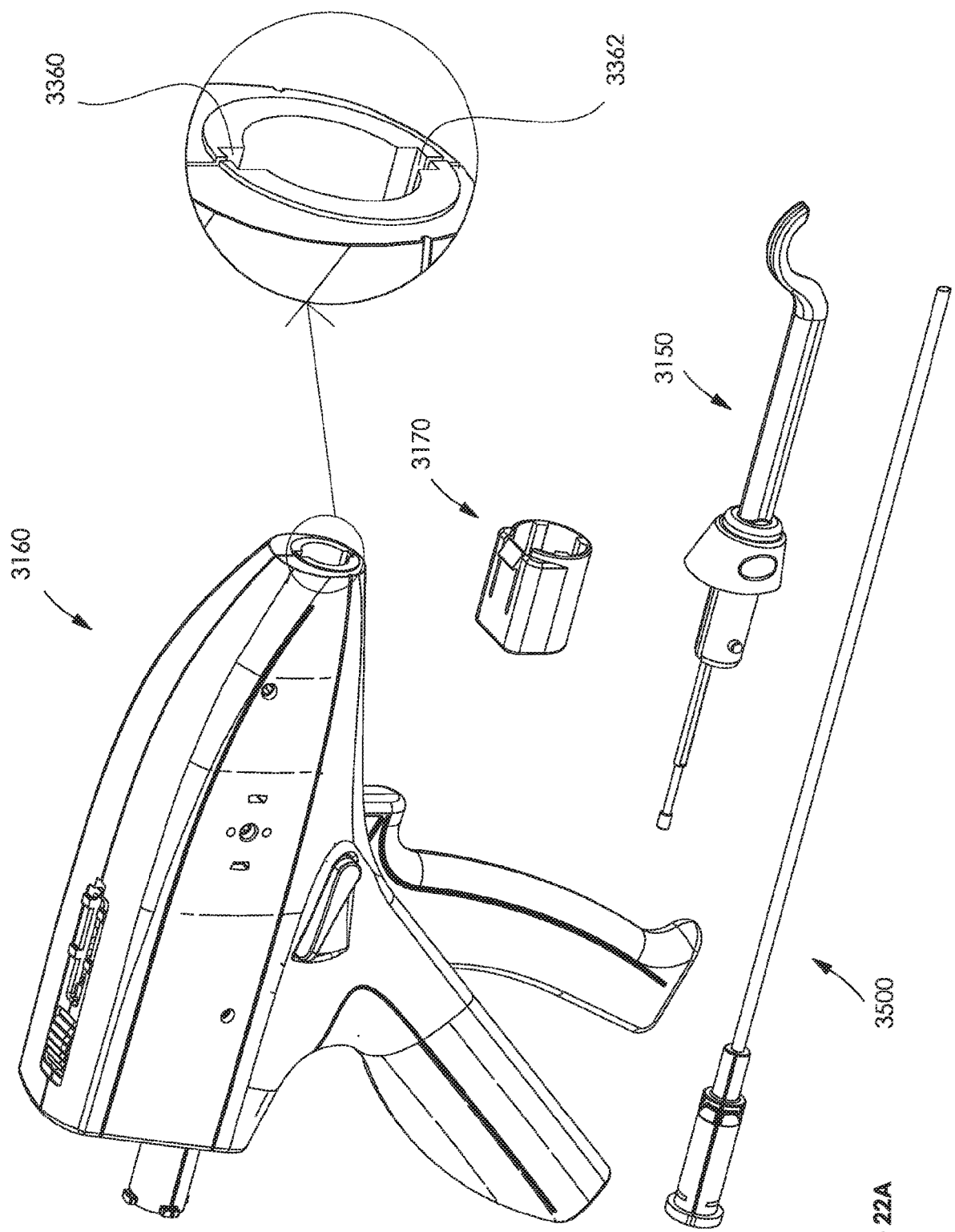
FIGS. 22A & 22B are simplified illustrations of the arthroscopic surgical assembly of FIGS. 12A-21B in a first operative orientation, showing opposite facing views.
Figure 22B:
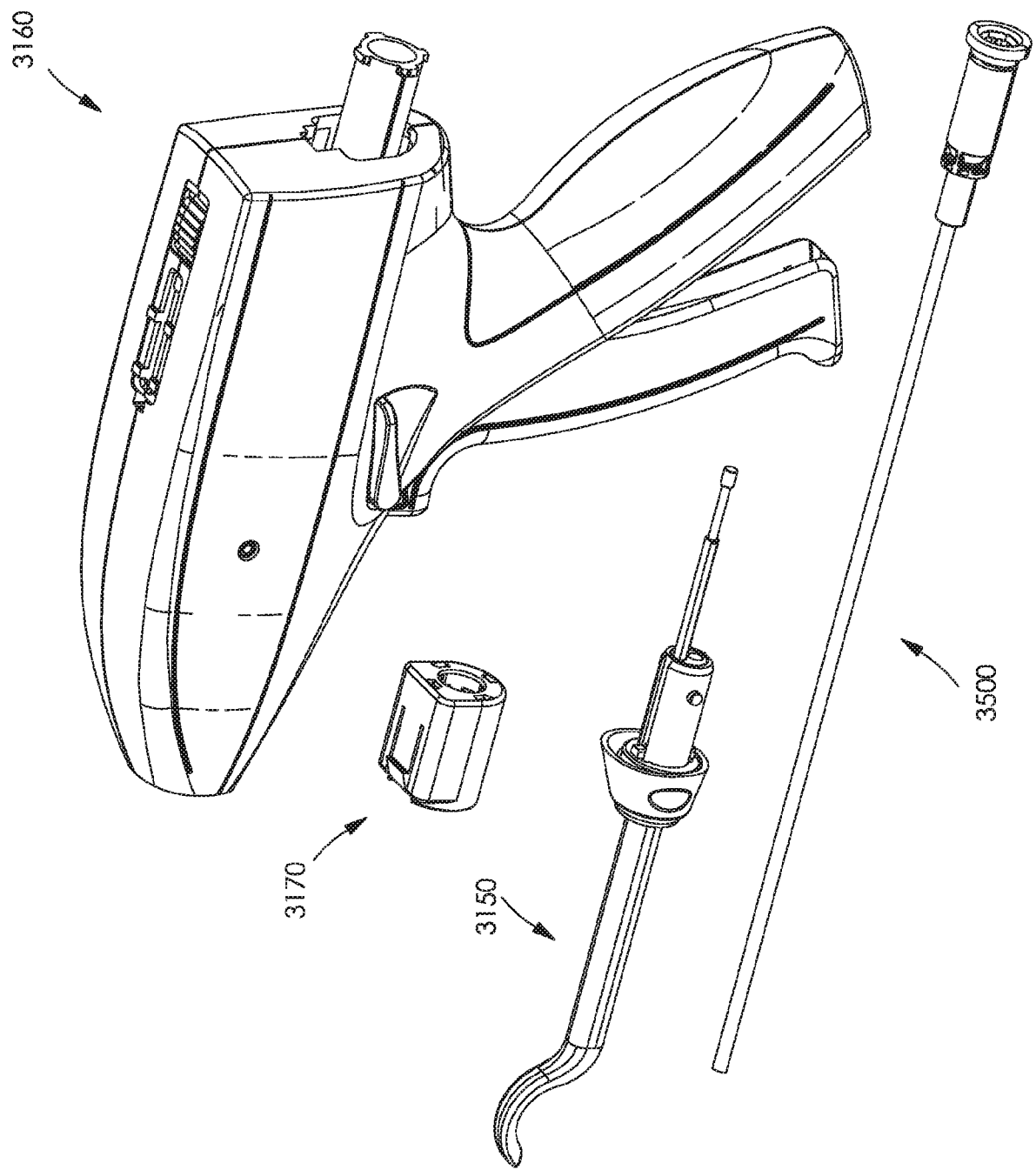

Reference is now made to FIGS. 22A & 22B, which are simplified illustrations of the arthroscopic surgical assembly of FIGS. 12A-21B in a first operative orientation, showing opposite facing views. As seen in FIGS. 22A-22B, a work channel assembly 3500 is provided in one assembled piece and corresponds generally to the work channel assembly 110 shown and described hereinabove with reference to FIGS. 3A & 3B. Work channel assembly 3500 as well as detachable curved shaft assembly 3150 and detachable retaining cap element 3170 are all shown separate and detached from the arthroscopic surgical device 3160.

Figure 23A:
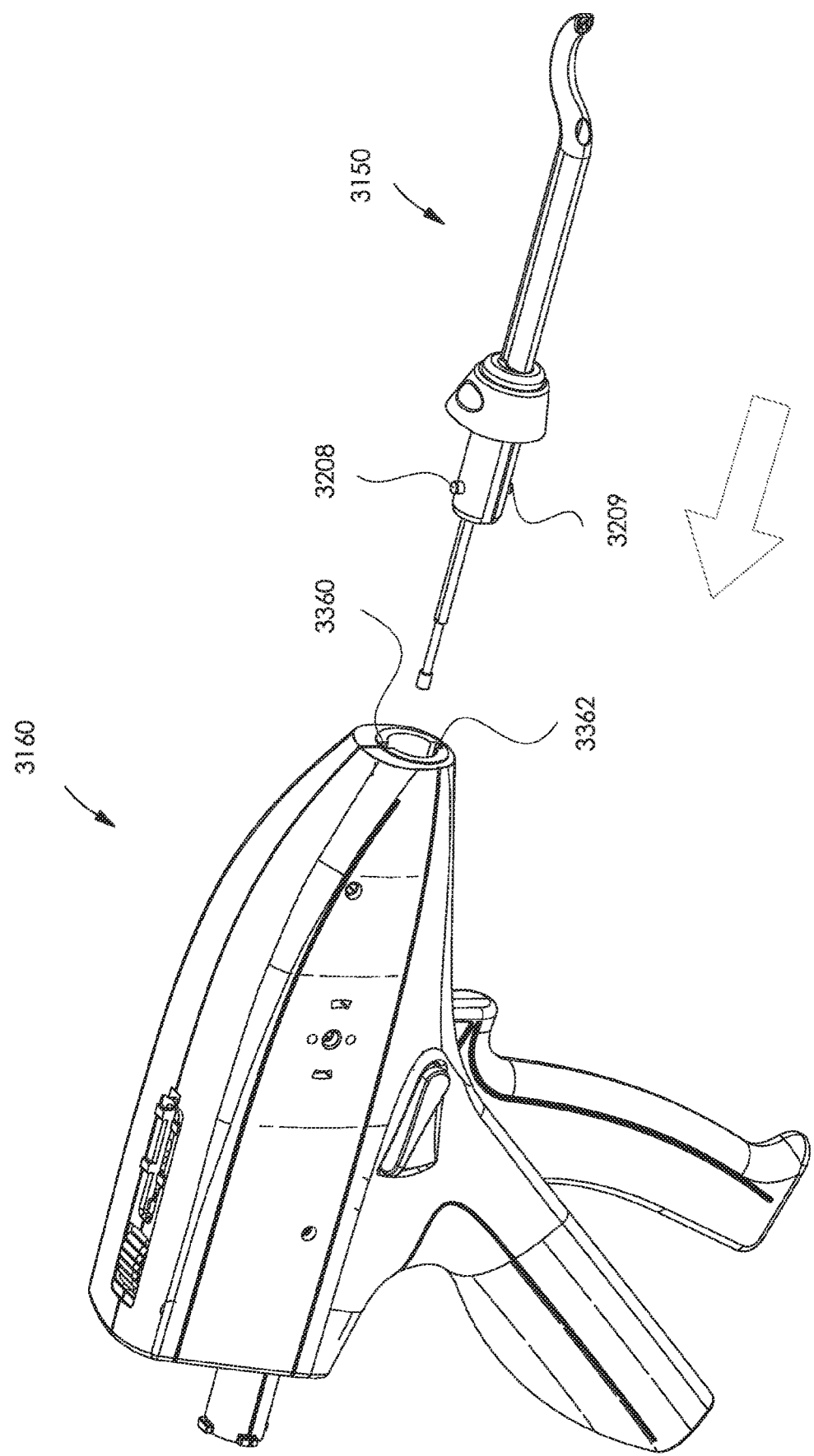
FIGS. 23A & 23B are simplified illustrations of the arthroscopic surgical assembly of FIGS. 12A-22B in a second operative orientation, showing opposite facing views.
Figure 23B:
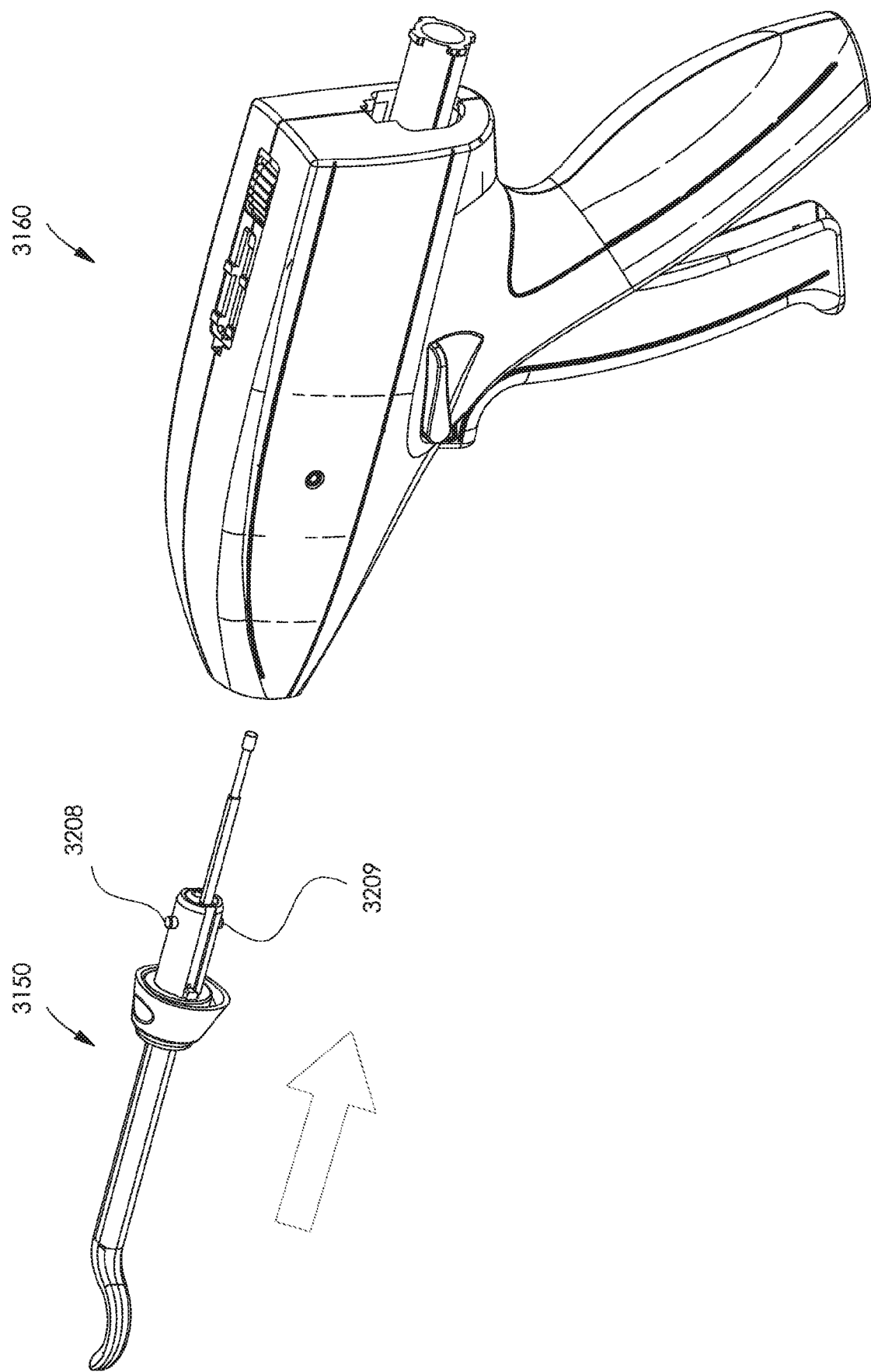

Reference is now made to FIGS. 23A & 23B, which are simplified illustrations of the arthroscopic surgical assembly of FIGS. 12A-22B in a second operative orientation, showing opposite facing views. FIGS. 23A & 23B show the mutual axial orientation of the detachable curved shaft assembly 3150 relative to the arthroscopic surgical device 3160 prior to insertion of the detachable curved shaft assembly 3150 into operative engagement with the arthroscopic surgical device 3160, wherein pin 3208 is aligned with slot 3360 and pin 3209 is aligned with slot 3362.

Figure 24A:
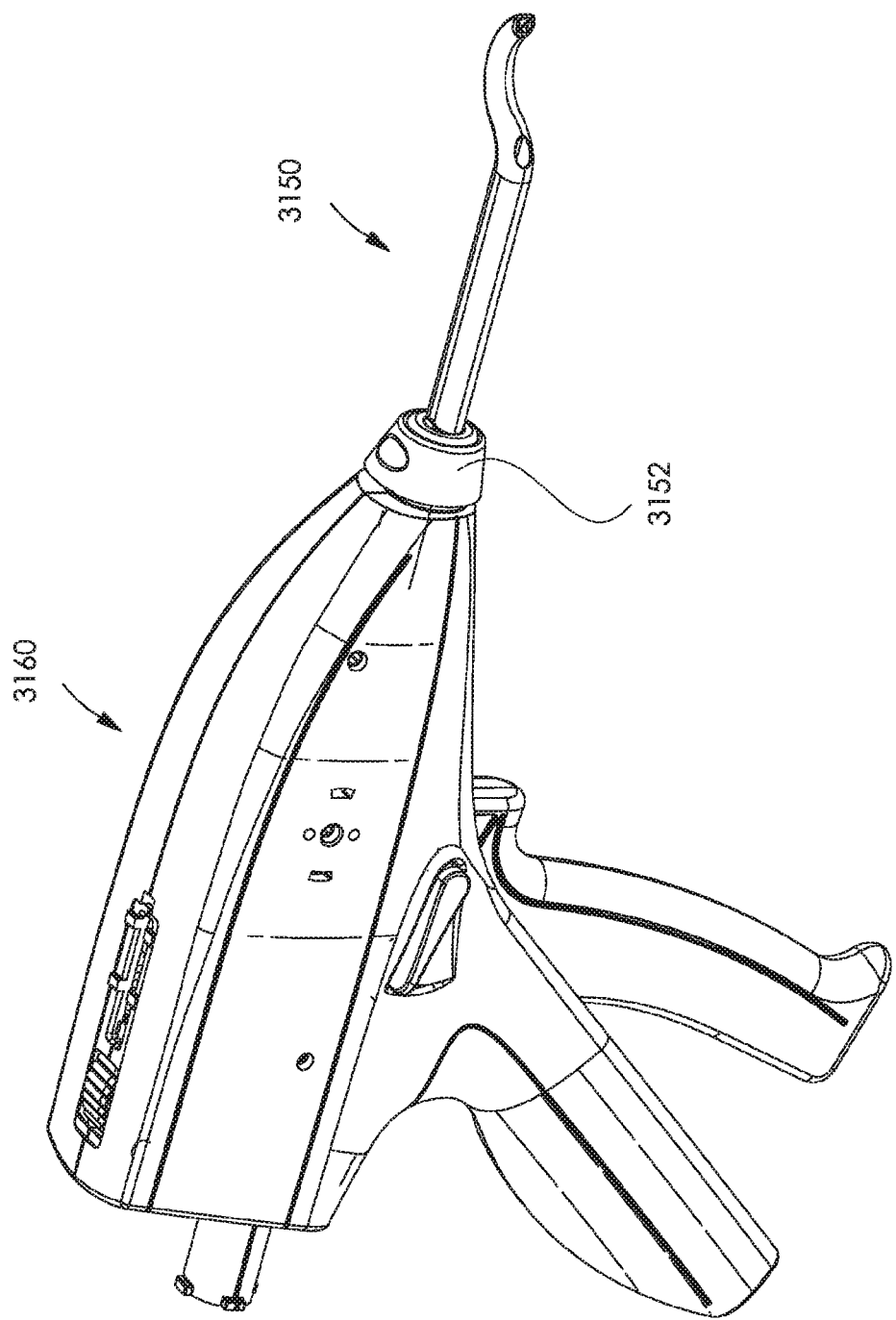
FIGS. 24A & 24B are simplified illustrations of the arthroscopic surgical assembly of FIGS. 12A-23B in a third operative orientation, showing opposite facing views.
Figure 24B:
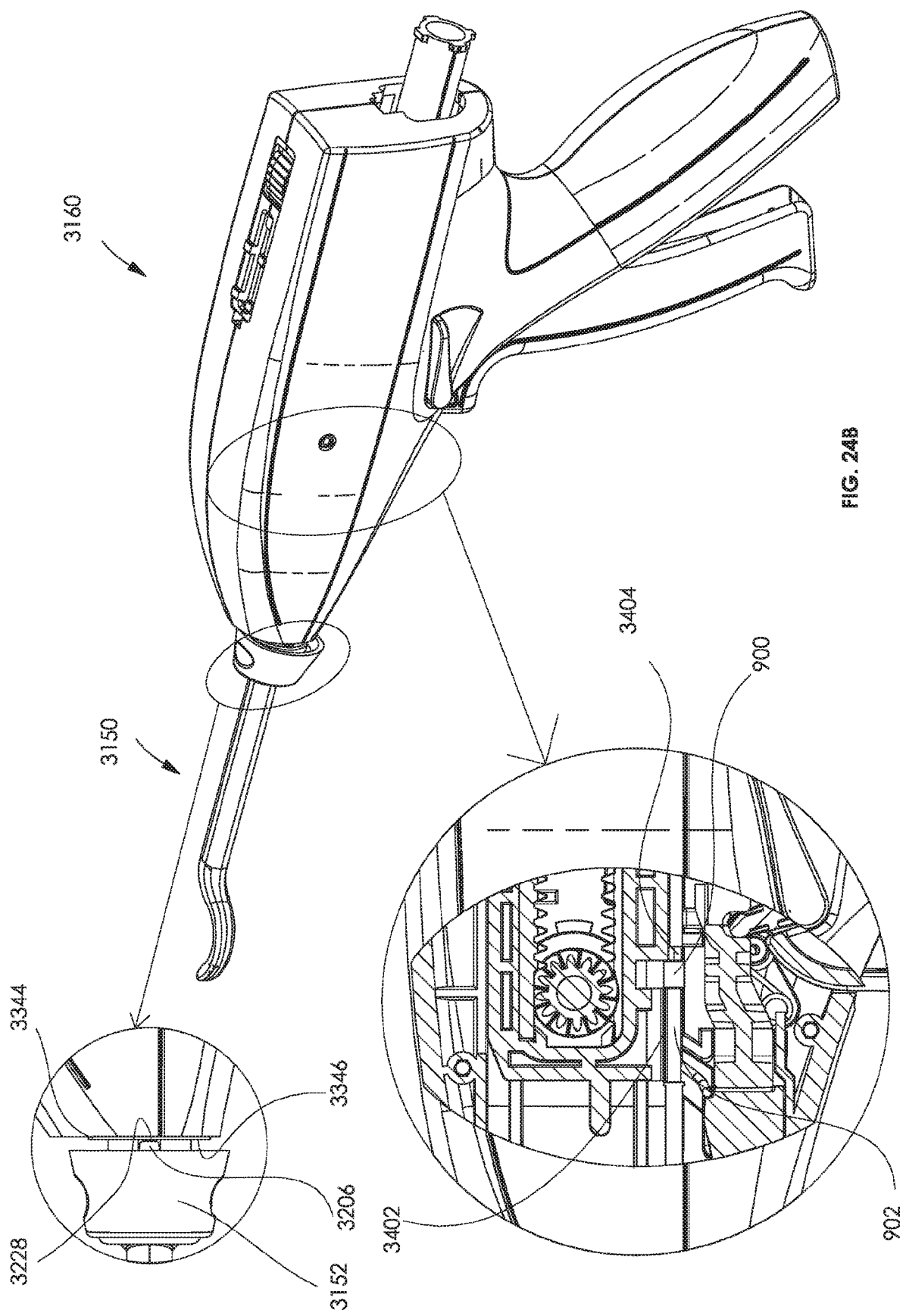

Reference is now made to FIGS. 24A & 24B, which are simplified illustrations of the arthroscopic surgical assembly of FIGS. 12A-23B in a third operative orientation, showing opposite facing views. FIGS. 24A & 24B show an initial step of insertion of the detachable curved shaft assembly 3150 into operative engagement with the arthroscopic surgical device 3160, wherein pin 3208 has travelled along slot 3360 and pin 3209 has travelled along slot 3362 and protrusions 3206 lie against forward-facing surfaces 3326 and 3346 and spring 3202 is compressed as seen in FIG. 15F.

Figure 25A:
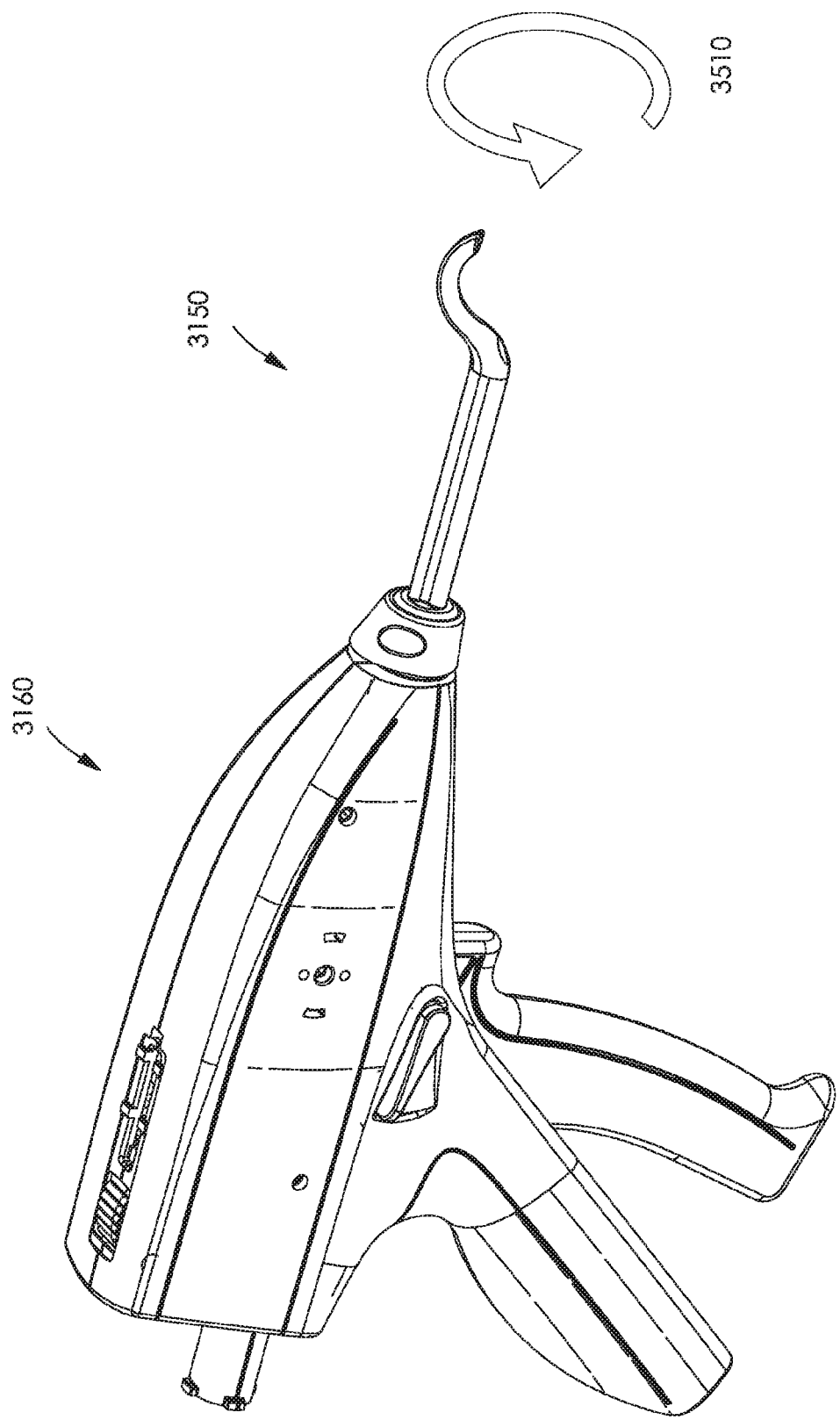
FIGS. 25A & 25B are simplified illustrations of the arthroscopic surgical assembly of FIGS. 12A-24B in a fourth operative orientation, showing opposite facing views.
Figure 25B:
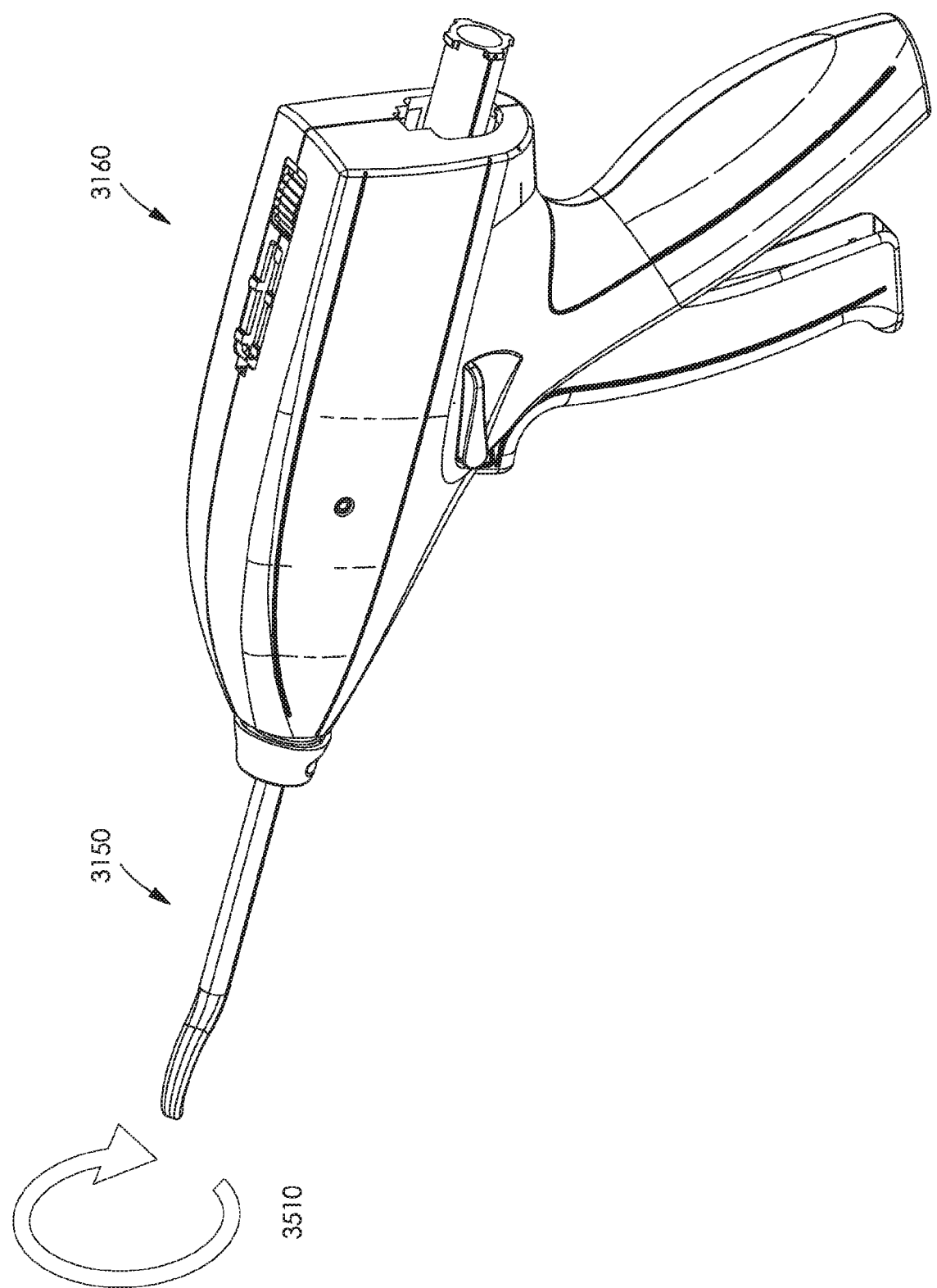

Reference is now made to FIGS. 25A & 25B, which are simplified illustrations of the arthroscopic surgical assembly of FIGS. 12A-24B in a fourth operative orientation, showing opposite facing views. FIGS. 25A & 25B show a rotation, preferably of about 22.5 degrees, as indicated by an arrow 3510, of the detachable curved shaft assembly 3150 relative to the arthroscopic surgical device 3160, such that pin 3208 has travelled partially along azimuthal slot 3338 and pin 3209 has travelled partially along azimuthal slot 3358 while protrusions 3206 lie against forward-facing surfaces 3326 and 3346 and spring 3202 is compressed as seen in FIG. 15F.

Figure 26A:
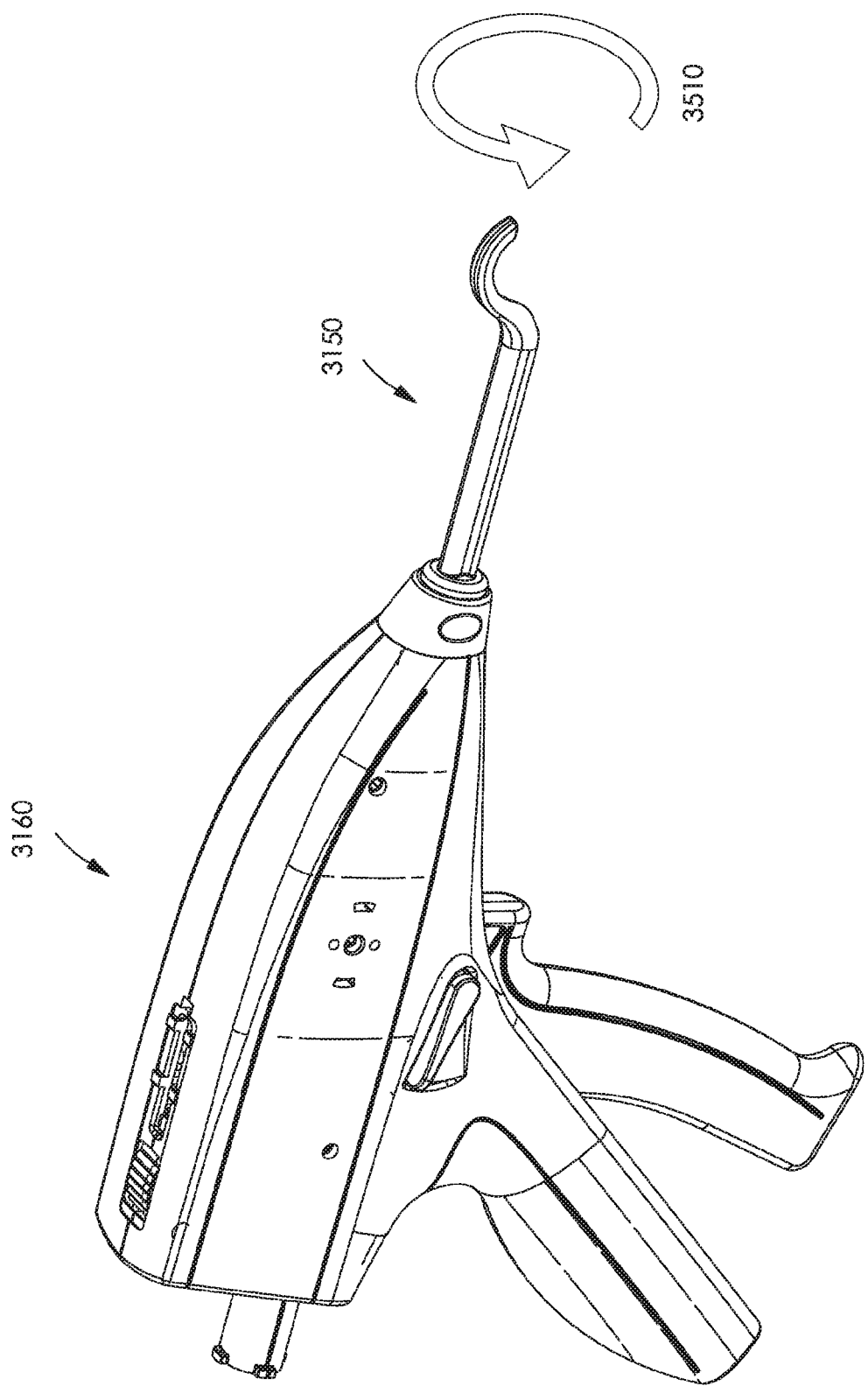
FIGS. 26A & 26B are simplified illustrations of the arthroscopic surgical assembly of FIGS. 12A-25B in a fifth operative orientation, showing opposite facing views.
Figure 26B:
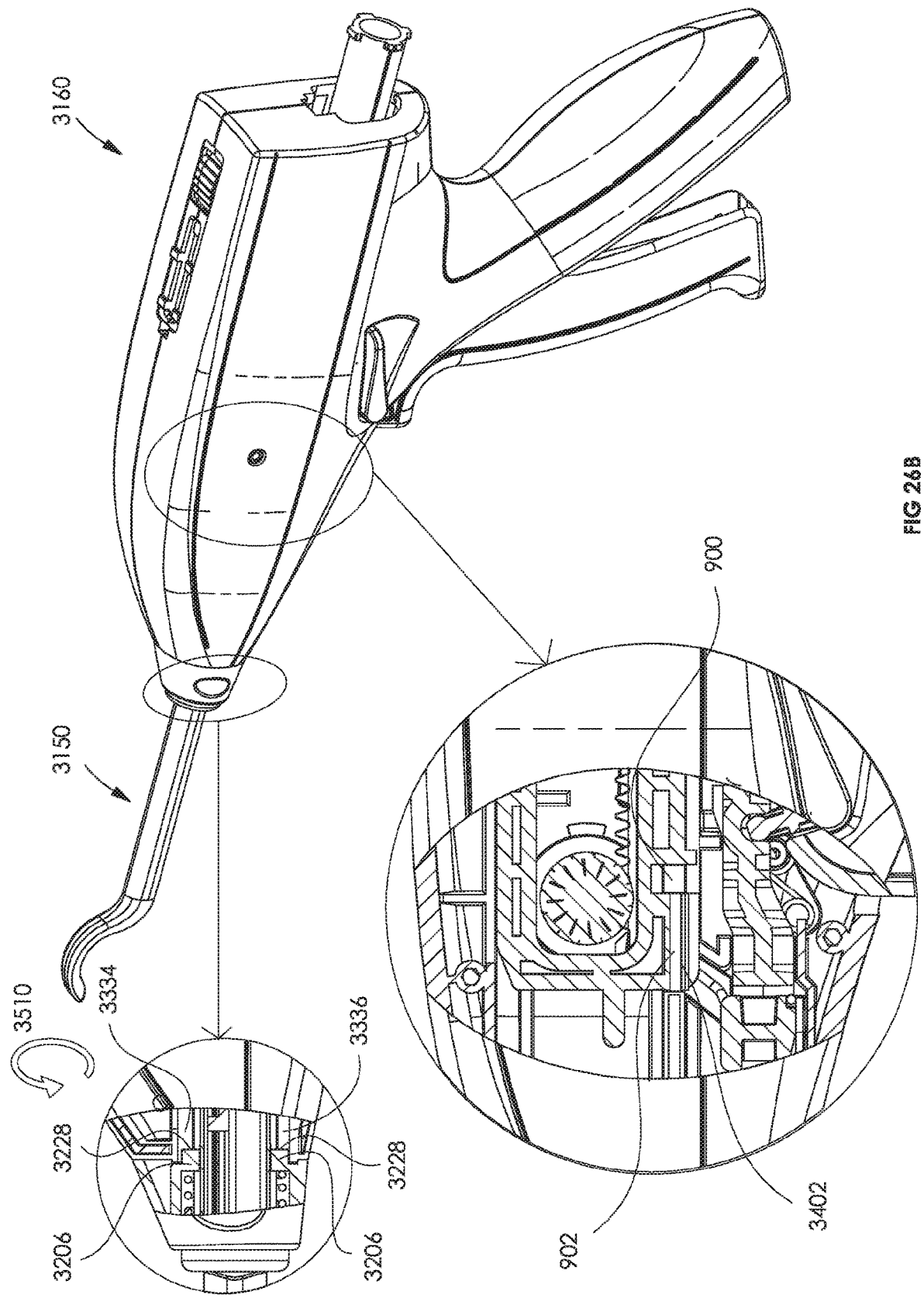

Reference is now made to FIGS. 26A & 26B, which are simplified illustrations of the arthroscopic surgical assembly of FIGS. 12A-24B in a fifth operative orientation, showing opposite facing views. FIGS. 26A & 26B show a further rotation, preferably of about 22.5 degrees, as indicated by an arrow 3510, of the detachable curved shaft assembly 3150 relative to the arthroscopic surgical device 3160, such that pin 3208 has travelled, fully along azimuthal slot 3338 and pin 3209 has travelled fully along azimuthal slot 3358 while protrusions 3206 lie in slots 3360 and 3362 as seen in FIG. 15E and thus prevent further azimuithal rotation of the detachable curved shaft assembly 3150 relative to the arthroscopic surgical device 3160. Pins 3208 and 3209 each fully reside in a corresponding azimuthal slot 3338 and 3358, thus preventing axial displacement of the detachable curved shaft assembly 3150 relative to the arthroscopic surgical device 3160.

Figure 27A:
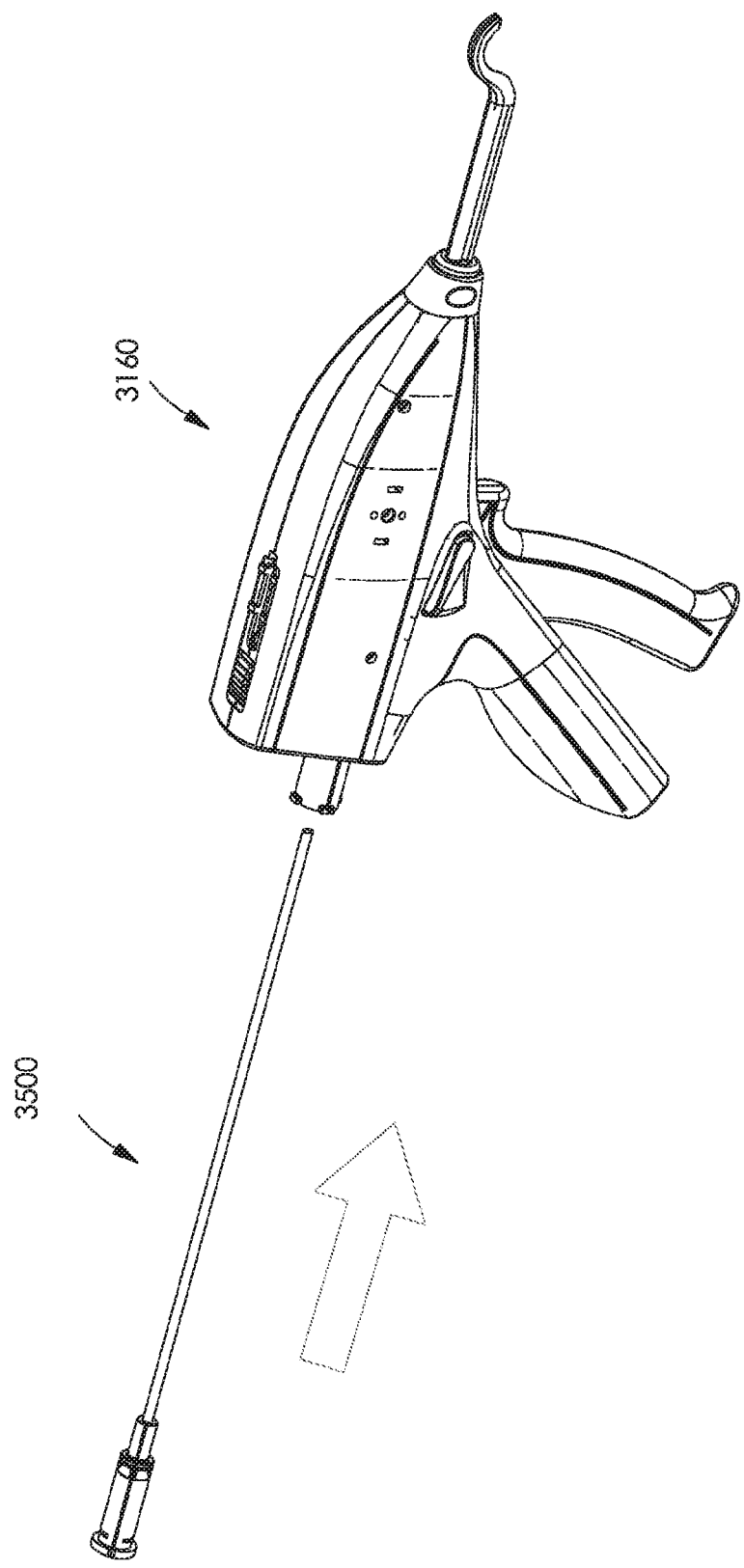

Reference is now made to FIGS. 27A & 27B, which are simplified illustrations of the arthroscopic surgical assembly of FIGS. 12A-26B in a sixth operative orientation, showing opposite facing views, wherein the working channel assembly 3500 is aligned for insertion into the arthroscopic surgical device 3160 having mounted therein the detachable curved shaft assembly 3150 as seen in FIGS. 26A & 26B.

Figure 28A:
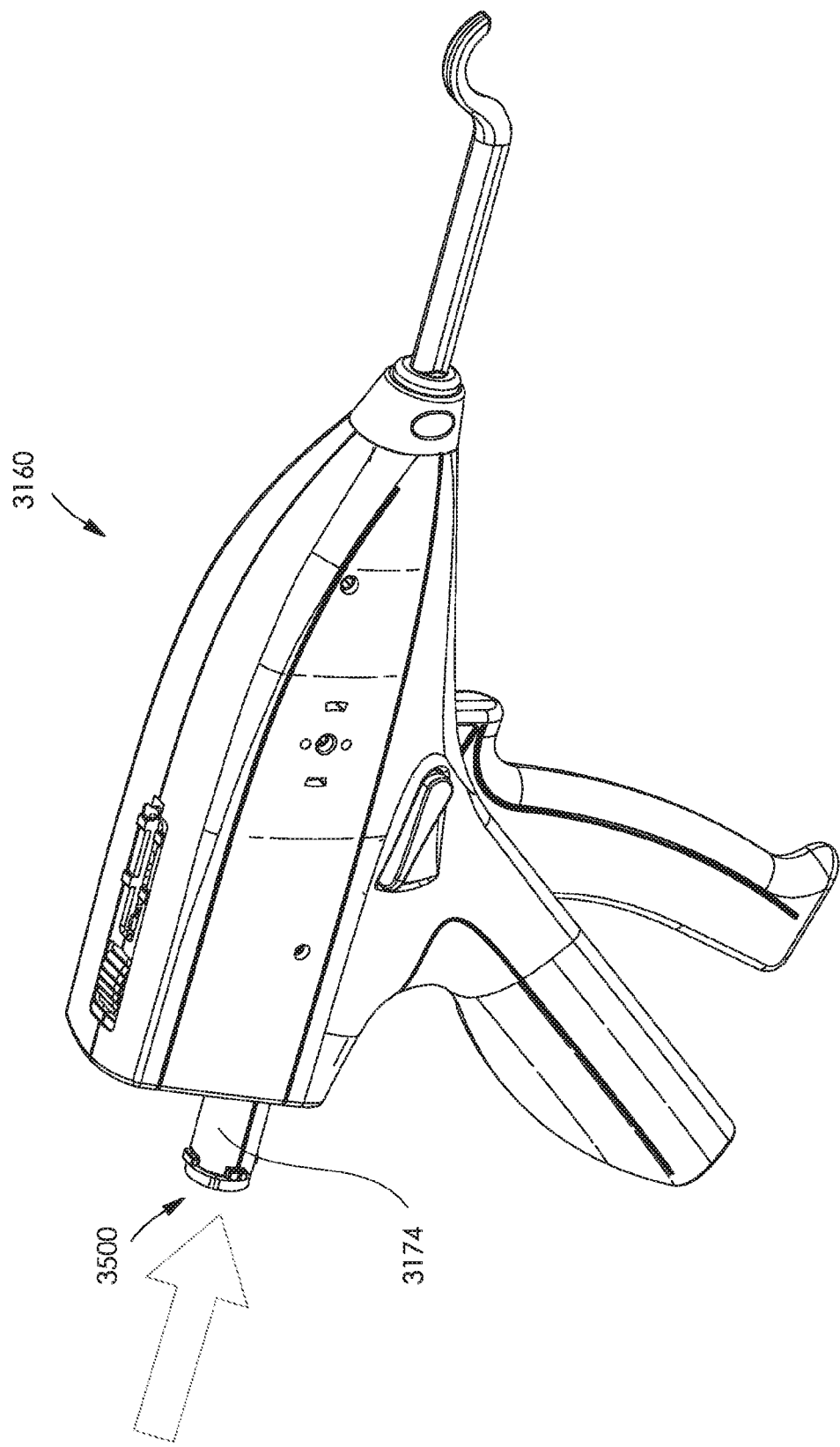
Figure 288:
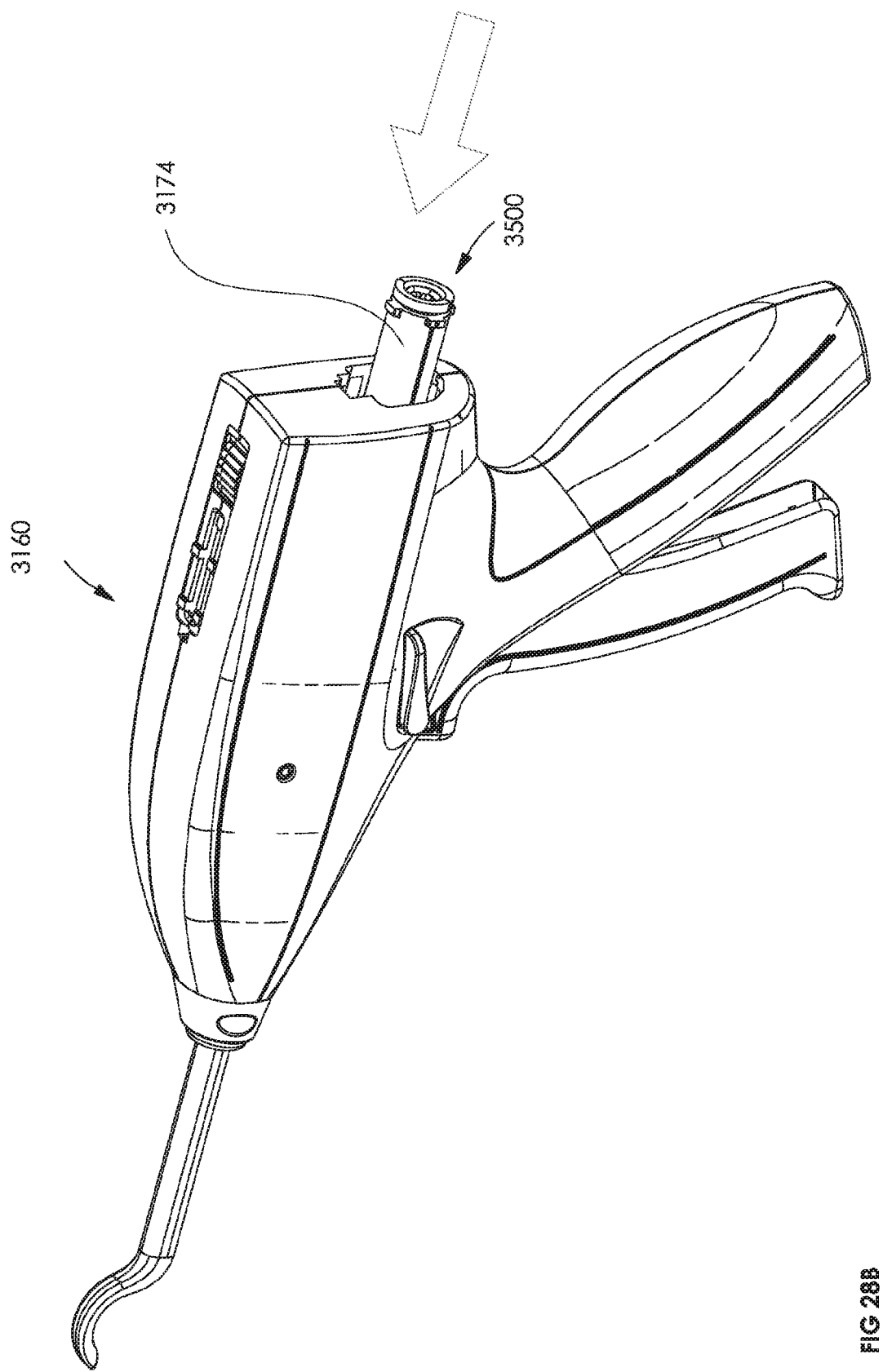

Reference is now made to FIGS. 28A & 28B, which are simplified illustrations of the arthroscopic surgical assembly of FIGS. 12A-27B in a seventh operative orientation, showing opposite facing views, wherein the working channel assembly 3500 is fully inserted into the arthroscopic surgical device 3160 having mounted therein the detachable curved shaft assembly 3150 as seen in FIGS. 26A & 26B.

Figure 29A:
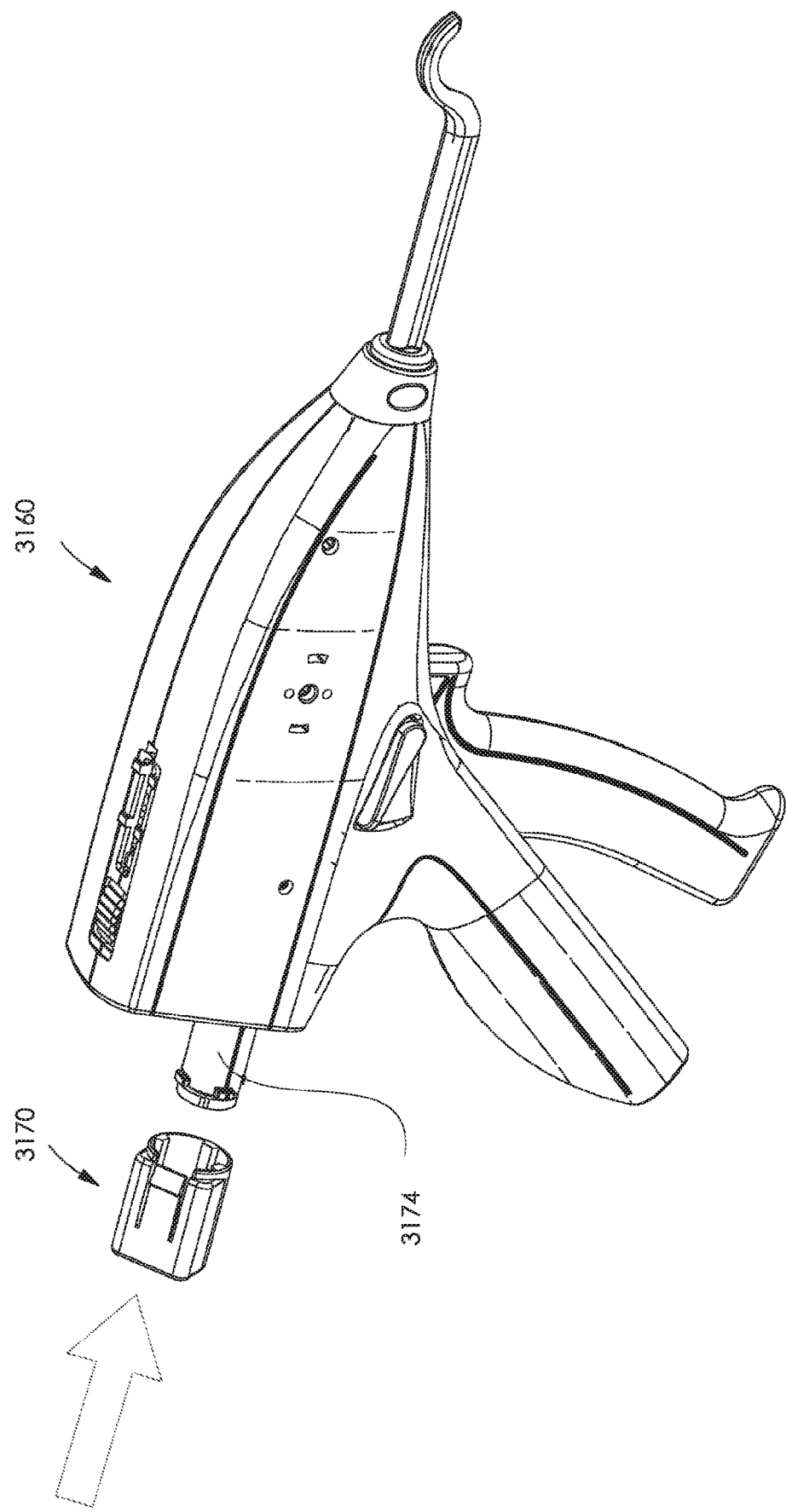
FIGS. 29A-29B are simplified illustrations of the arthroscopic surgical assembly of FIGS. 12A-28B in an eighth operative orientation, showing opposite facing views.
Figure 29B:
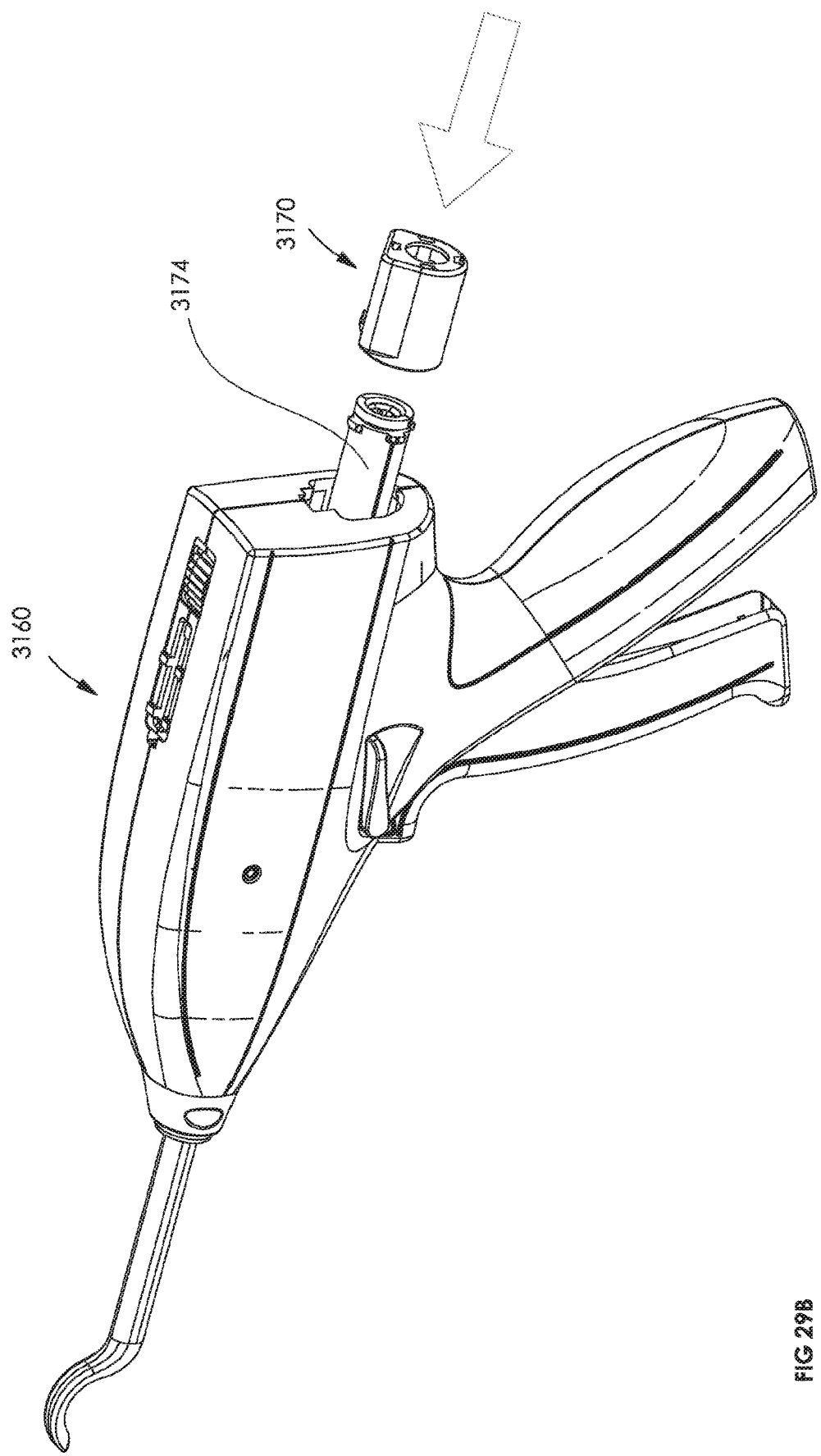

Reference is now made to FIGS. 29A & 29B, which are simplified illustrations of the arthroscopic surgical assembly of FIGS. 12A-28B in an eighth operative orientation, showing opposite facing views, wherein detachable retaining cap element 3170 is aligned for engagement with the arthroscopic surgical device 3160 having mounted therein the detachable curved shaft assembly 3150 as seen in FIGS. 26A & 26B.

Figure 30A:
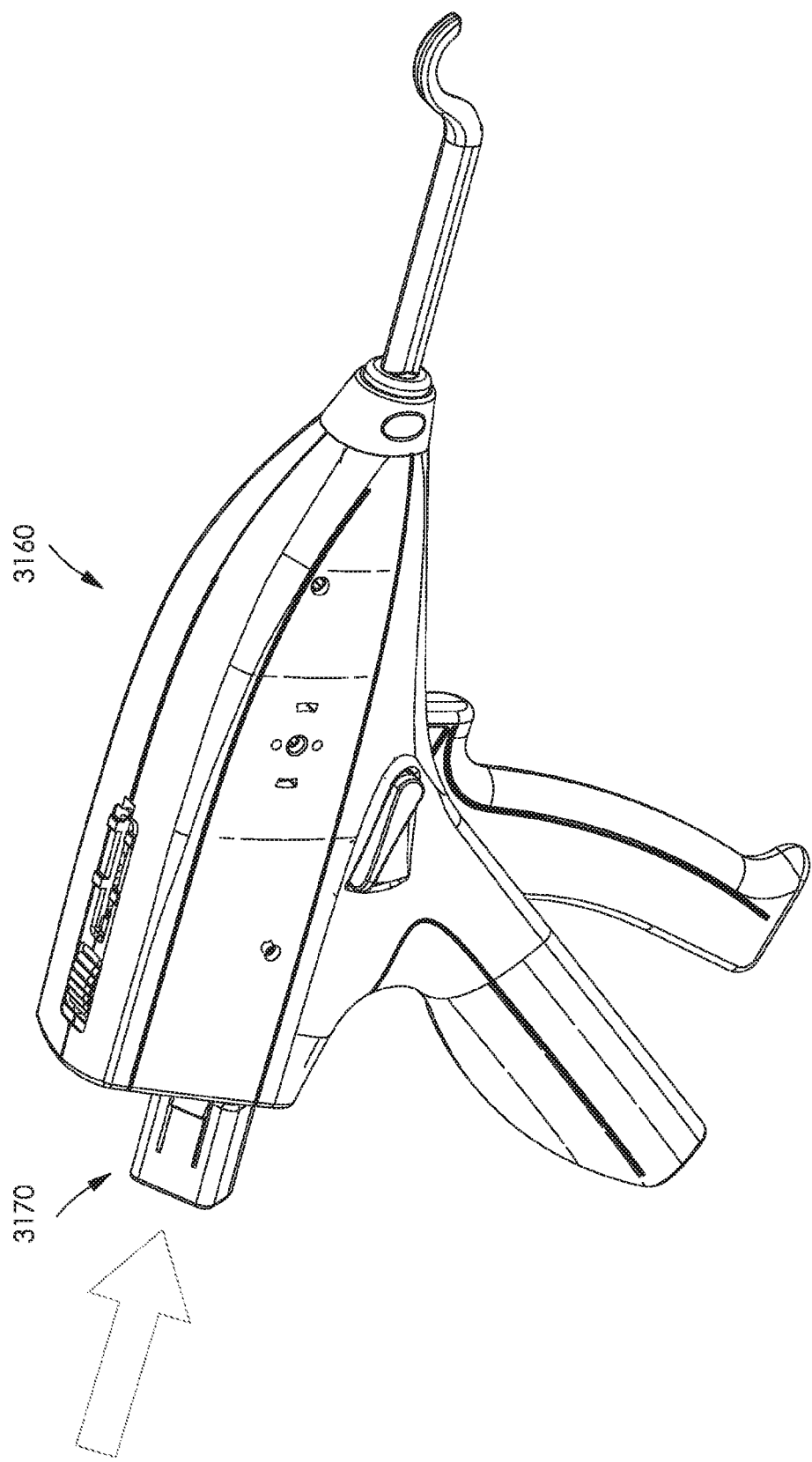

Reference is now made to FIGS. 30A & 30B, which are simplified illustrations of the arthroscopic surgical assembly of FIGS. 12A-29B in a ninth operative orientation, showing opposite facing views, wherein the detachable retaining cap element 3170 is about to be engaged in a bayonet-type detachable locking engagement between detachable retaining cap element 3170 and a rack-defining intermediate element 3174 of the arthroscopic surgical device 3160.

Figure 31A:
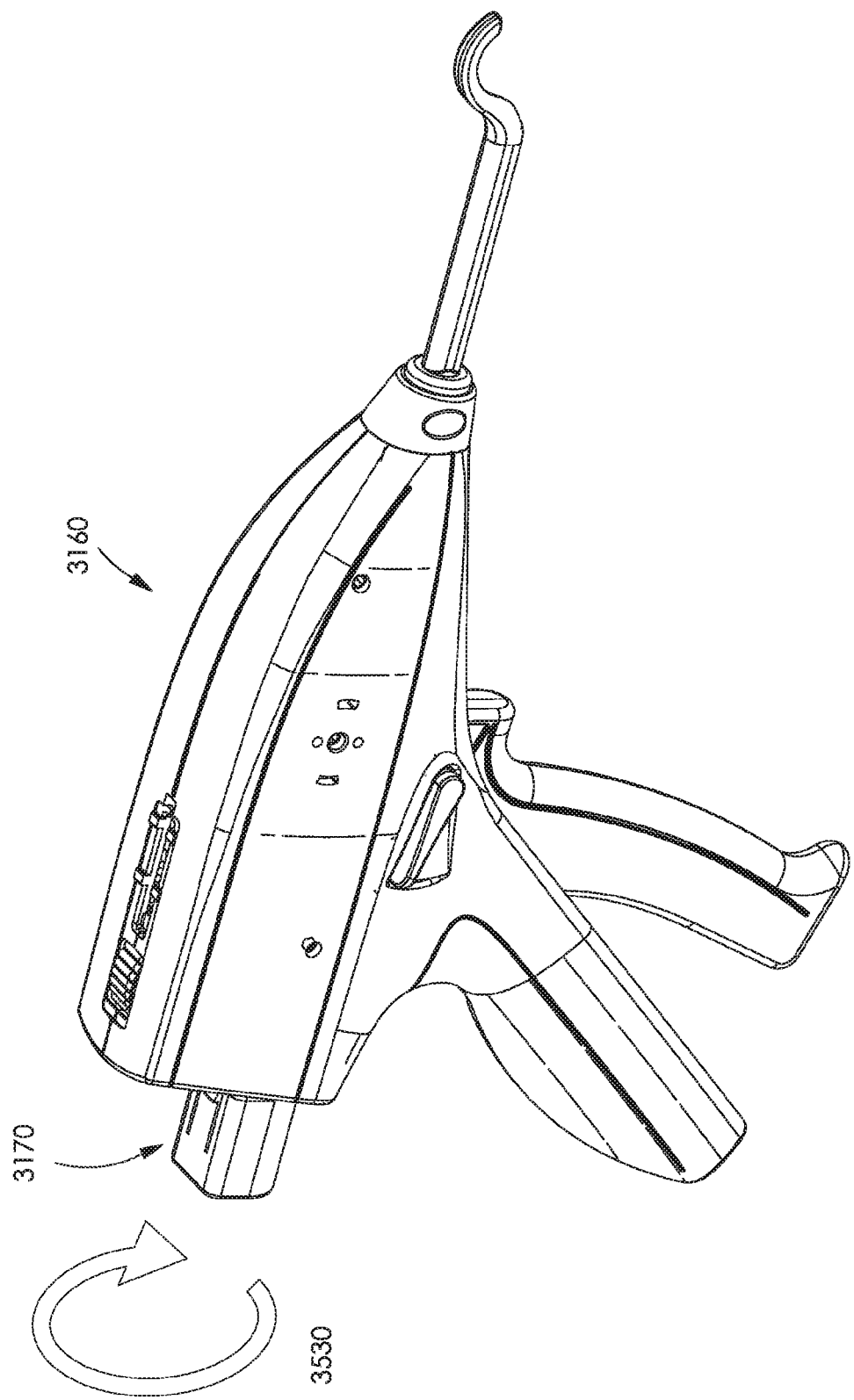
FIGS. 31A & 31B are simplified illustrations of the arthroscopic surgical assembly of FIGS. 12A-30B in a tenth operative orientation, showing opposite facing views.
Figure 31B:
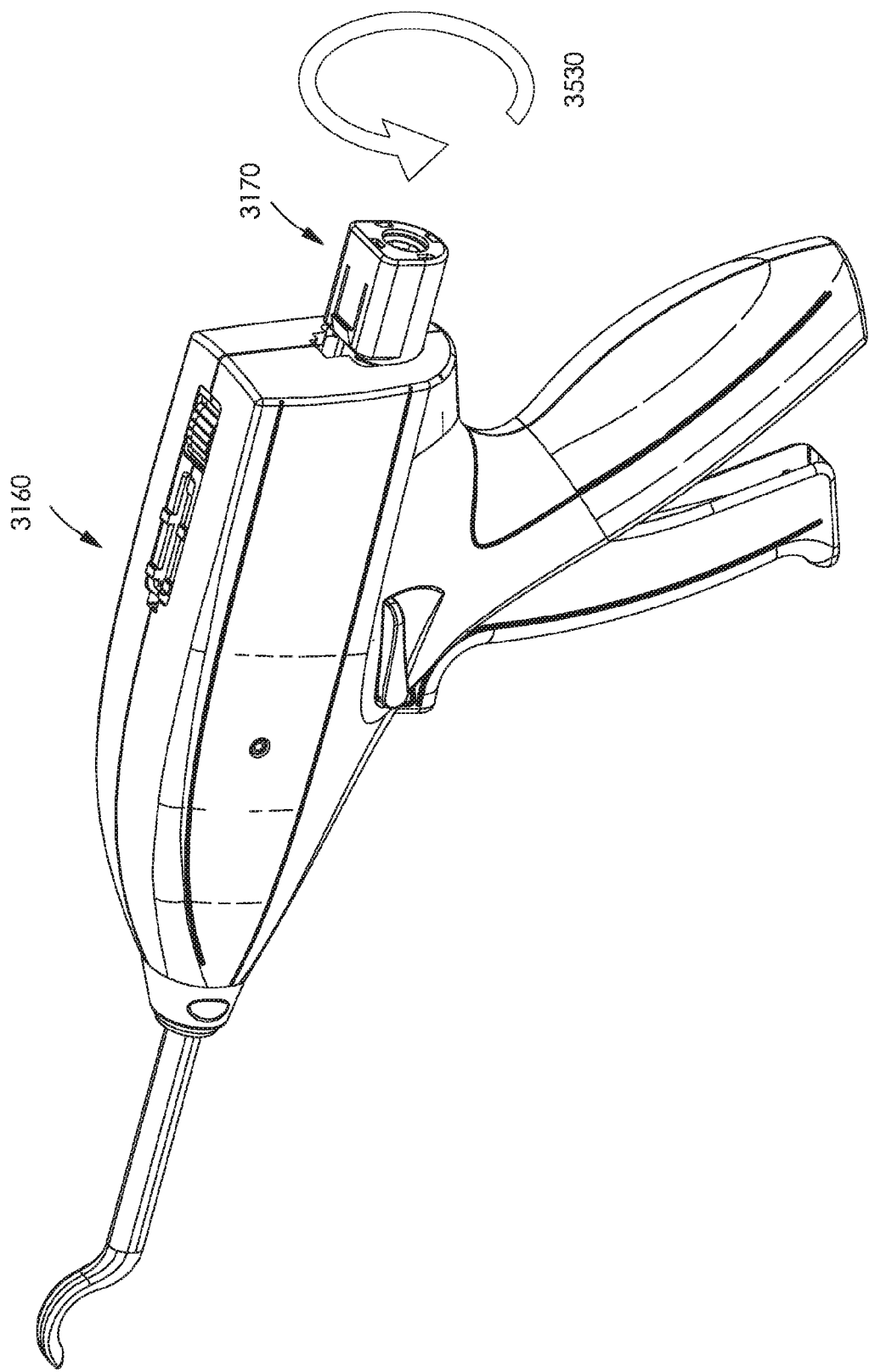

Reference is now made to FIGS. 31A & 31B, which are simplified illustrations of the arthroscopic surgical assembly of FIGS. 12A-30B in a tenth operative orientation, showing opposite facing views, wherein the detachable retaining cap element 3170 is rotated in a direction indicated by an arrow 3530, preferably through 22.5 degrees, so as to be fully engaged in a bayonet-type detachable locking engagement with a rack-defining intermediate element 3174 of the arthroscopic surgical device 3160 as described hereinabove with reference to FIG. 14.

It is appreciated that operation of the arthroscopic surgical device, as described hereinabove, is preliminary to other operative procedures. Typically, once a snare wire has been pulled through and exits through both of a pair of channels in a bone, the snare wire may be used to pull sutures into and through the two channels so the sutures extend through and outside both channels, in place of the snare wire. The sutures then may be used to tie tissue, such as a ligament or a tendon, to the bone and secure the tissue to the bone.

Provided along with the above described invention are kits that include at least the subject devices and/or components thereof which may be used according to the subject methods. The subject kits include at least bone punch assembly, drill bit assembly, snare wire cartridge assembly, curved shaft assembly, manual override gear shifter, work channel assembly, quick connection element, and at least one snare wire, e.g., as described above. The kits may further include one or more components to be employed in a given surgical procedure, e.g., additional snare wire cartridge assemblies, additional manual override gear shifters, drill, sutures, additional snare wires, one or more hexagonal wrenches, other replacement components and the like. The components of the kits may be present in sterile packaging, as desired, where various components may be combined in a given packaging or each component present in its own packaging.

In certain embodiments, the kits which are disclosed herein include instructions, such as instructions for using the devices. The instructions for using the devices are generally recorded on a suitable recording medium. For example, the instructions may be printed on a substrate, such as paper or plastic, etc. As such, the instructions may be present the kits as a package insert, in the labeling of the container of the kit or components thereof (i.e., associated with the packaging or subpackaging etc.). In other embodiments, the instructions are present as an electronic storage data file present on a suitable computer readable storage medium, e.g. Portable Flash drive, CD-ROM, diskette, etc. The instructions may take any form, including complete instructions for how to use the device or as a website address with which instructions posted on the worldwide web may be accessed.

In addition, embodiments of the disclosed kits or their components may be used according to any of the embodiments of the methods described herein or combinations thereof.

It is also appreciated that the arthroscopic surgical device of the present invention and components thereof, including, but not limited to, the bone punch assembly, the drill bit assembly, the snare wire cartridge assembly, the drill, the curved shaft assembly, the manual override gear shifter, the work channel assembly, the quick connection element, the snare wires or sutures and the allen wrenches, may be disposable and/or sterilizable so as to be reusable. Typically, the components are sterilizable and reusable, except for the snare wires and sutures which are typically disposable rather than reusable.

As noted above, it is appreciated that the terms 'tunneling' and 'channeling' are used interchangeably in the description of the present invention and refer to a method of forming a hollow bore, such as a cylindrically circular hollow bore, in a bone.

It will be appreciated by persons skilled in the art that the present invention is limited by what has been particularly shown and described hereinabove. Rather the scope of the present invention includes both combinations and subcombinations of the various features described hereinabove as well as modifications thereof which would occur to persons skilled the art upon reading the foregoing description and which are not in the prior art.

The invention claimed is:

1. An arthroscopic bone channel forming and suturing system useful with a punch configured to form a first generally straight channel in a bone and a drill configured to form a second generally straight channel in said bone, said second generally straight channel not intersecting said first generally straight channel, said system comprising:
   an arthroscopic surgical device; and
   a detachable curved shaft assembly, said detachable curved shaft assembly being detachably mounted onto a front end portion of said arthroscopic surgical device, said detachable curved shaft assembly including:
      a curved bone puncture needle configured to be insertable into said first generally straight channel; and
      a curved needle driving assembly configured to manipulate said curved needle to form a curved junction between said first generally straight channel and said second generally straight channel,
   said arthroscopic surgical device comprising a coordinated multi-function driving assembly operative to coordinate operation of said curved needle driving assembly and a snare wire cartridge assembly, said snare wire cartridge assembly being configured to insert a snare wire to a suture pick up location via said second generally straight channel in said bone, to cause said suture snare wire to be pulled from said suture pick up location and through said first generally straight channel via said junction.

2. An arthroscopic bone channel forming and suturing system according to claim 1 and wherein said coordinated multi-function driving assembly operates automatically in response to repeated manual actuations.

3. An arthroscopic bone channel forming and suturing system according to claim 1 and wherein said coordinated multi-function driving assembly includes an override subassembly which is selectably operative to withdraw said curved needle after said curved needle has begun to be inserted into said first generally straight channel but before said curved needle begins to pull said suture through said junction.

4. An arthroscopic bone channel forming and suturing system according to claim 1 and also comprising:
   a work channel assembly; and
   said snare wire cartridge assembly, said snare wire cartridge assembly being insertable into said work channel assembly.

5. An arthroscopic bone channel forming and suturing system according to claim 1 and also comprising a detachable retaining cap element.

6. An arthroscopic bone channel forming and suturing system according to claim 5 and wherein said detachable retaining cap element includes a cylindrical surface which is configured to rotate relative to said arthroscopic surgical device.

7. An arthroscopic bone channel forming and suturing system according to claim 5 and wherein said detachable retaining cap element is detachably locked to a rack-defining intermediate element by rotation of said detachable retaining cap element relative to said rack-defining intermediate element.

8. An arthroscopic bone channel forming and suturing system according to claim 1 and wherein said detachable curved shaft assembly includes:
- a generally conical mounting portion;
- a generally hollow cylindrical element;
- a compression spring; and
- a pair of curved shaft assembly elements.

9. An arthroscopic bone channel forming and suturing system according to claim 8 and wherein said generally conical mounting portion is formed with a pair of finger engagement recesses.

10. An arthroscopic bone channel forming and suturing system according to claim 8 and wherein said compression spring is seated between said generally conical mounting portion and a flange of said generally hollow cylindrical element.

11. An arthroscopic bone channel forming and suturing system according to claim 8 and wherein each of said pair of curved shaft assembly elements includes a guiding and positioning pin.

12. An arthroscopic bone channel forming and suturing system according to claim 11 and wherein a radially outward extent of said guiding and positioning pin of a first of said pair of curved shaft assembly elements is different from a radially outward extent of said guiding and positioning pin of a second of said pair of curved shaft assembly elements.

13. An arthroscopic bone channel forming and suturing system according to claim 8 and wherein said compression spring permits relative axial displacement of said generally conical mounting portion relative to said generally hollow cylindrical element.

14. An arthroscopic bone channel forming and suturing system according to claim 13 and wherein said relative axial displacement permits detachment of said detachable curved shaft assembly from said arthroscopic device.

15. An arthroscopic bone channel forming and suturing system according to claim 1 and wherein said arthroscopic surgical device comprises a first housing portion and a second housing portion.

16. An arthroscopic bone channel forming and suturing system according to claim 15 and wherein said first housing portion includes a first connection socket portion and said second housing portion include a second connection socket portion, said first connection socket portion and said second connection socket portion together forming a connection socket.

17. An arthroscopic bone channel forming and suturing system according to claim 15 and wherein said first housing portion and said second housing portion, when joined together, define a first axial pin displacement slot and a second axial pin displacement slot.

18. An arthroscopic bone channel forming and suturing system according to claim 17 and wherein a radial extent of said first axial pin displacement slot is greater than a radial extent of said second axial pin displacement slot.

* * * * *